(12) United States Patent
Zhang et al.

(10) Patent No.: US 12,312,347 B2
(45) Date of Patent: *May 27, 2025

(54) AZAINDOLE DERIVATIVE AND USE THEREOF AS FGFR AND C-Met INHIBITOR

(71) Applicant: Wuxi Life Fountain Biotech Co., Ltd, Wuxi (CN)

(72) Inventors: Yang Zhang, Shanghai (CN); Zhengxia Chen, Shanghai (CN); Yikai Wang, Shanghai (CN); Meibi Dai, Shanghai (CN); Jie Li, Shanghai (CN); Zhen Gong, Shanghai (CN); Jian Li, Shanghai (CN); Shuhui Chen, Shanghai (CN)

(73) Assignee: WUXI LIFE FOUNTAIN BIOTECH CO., LTD, Jiangsu Province (CN)

( * ) Notice: Subject to any disclaimer, the term of this patent is extended or adjusted under 35 U.S.C. 154(b) by 1080 days.

This patent is subject to a terminal disclaimer.

(21) Appl. No.: 17/261,460

(22) PCT Filed: Jul. 19, 2019

(86) PCT No.: PCT/CN2019/096841
§ 371 (c)(1),
(2) Date: Jan. 19, 2021

(87) PCT Pub. No.: WO2020/015744
PCT Pub. Date: Jan. 23, 2020

(65) Prior Publication Data
US 2021/0253571 A1    Aug. 19, 2021

(30) Foreign Application Priority Data

| Jul. 19, 2018 | (CN) | 201810798237.7 |
| Sep. 6, 2018 | (CN) | 201811039652.0 |
| Nov. 29, 2018 | (CN) | 201811445346.7 |

(51) Int. Cl.
C07D 471/04    (2006.01)
C07D 487/04    (2006.01)

(52) U.S. Cl.
CPC ......... C07D 471/04 (2013.01); C07D 487/04 (2013.01)

(58) Field of Classification Search
CPC .................. C07D 471/04; C07D 487/04
See application file for complete search history.

(56) References Cited

U.S. PATENT DOCUMENTS

| 7,872,018 | B2 | 1/2011 | Ibrahim et al. |
| 8,067,434 | B2 | 11/2011 | Ibrahim et al. |
| 8,470,818 | B2 | 6/2013 | Ibrahim et al. |
| 9,718,847 | B2 | 8/2017 | Zhang et al. |
| 2006/0003083 | A1 | 1/2006 | Kouda et al. |
| 2007/0049615 | A1 | 3/2007 | Ibrahim et al. |
| 2008/0221148 | A1 | 9/2008 | Ibrahim et al. |
| 2010/0036118 | A1 | 2/2010 | Arnold et al. |
| 2010/0249118 | A1 | 9/2010 | Ibrahim et al. |
| 2010/0324065 | A1 | 12/2010 | Ibrahim et al. |
| 2015/0133400 | A1 | 5/2015 | Zhang et al. |
| 2016/0075712 | A1 | 3/2016 | Shi et al. |
| 2017/0320899 | A1 | 11/2017 | Zhang et al. |

FOREIGN PATENT DOCUMENTS

| CN | 1925855 | A | 3/2007 |
| CN | 101027302 | A | 8/2007 |
| CN | 101243084 | A | 8/2008 |
| CN | 101641351 | A | 2/2010 |
| CN | 104710417 | A | 6/2015 |
| CN | 105073747 | A | 11/2015 |
| JP | 2007521334 | A | 8/2007 |
| JP | 2008546797 | A | 12/2008 |
| JP | 2010514695 | A | 5/2010 |
| JP | 2016514695 | A | 5/2016 |
| JP | 2017526726 | A | 9/2017 |
| WO | 2007002433 | A1 | 1/2007 |
| WO | 2008080001 | A2 | 7/2008 |
| WO | 2008124850 | A1 | 10/2008 |
| WO | 2010059771 | A1 | 5/2010 |
| WO | 2014145051 | A1 | 9/2014 |
| WO | 2016044067 | A1 | 3/2016 |

OTHER PUBLICATIONS

First Office Action issued in Chinese Patent Application No. 201980047115.7 mailed on Jan. 30, 2022, 12 pages.
Extended European Report issued in International Patent Application No. 19837159.3 mailed on Mar. 4, 2022, 20 pages.
First Office Action issued in Japanese Patent Application No. 2021502901 mailed on Mar. 8, 2022, 13 pages.
Registry (STN) [online], Jan. 18, 2012, Search date Feb. 21, 2022, CAS Registry No. 1353506-63-4.
Written Opinion of the International Searching Authority issued in International Patent Application No. PCT/CN2019/096841 mailed on Oct. 17, 2019,.
Jan. 11, 2023 European First Office Action issued in European Patent Application No. 19837159.3.

(Continued)

Primary Examiner — Marcos L Sznaidman
(74) Attorney, Agent, or Firm — MH2 Technology Law Group LLP

(57) ABSTRACT

A series of pyrazolopymidine derivatives, and use thereof in the preparation of a medicament for treating disease associated with FGFR and c-Met. The pyrazolopymidine derivative is a compound represented by formula (I), a tautomer, or a pharmaceutically acceptable salt thereof.

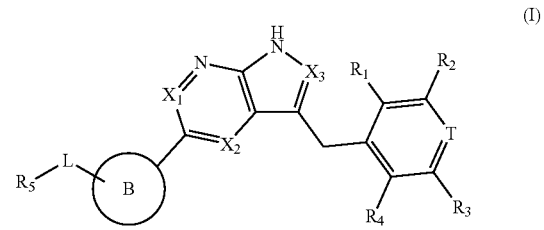

18 Claims, No Drawings

(56) References Cited

OTHER PUBLICATIONS

Feb. 7, 2023 Japanese Third Office Action issued in Japanese Patent Application No. 2021-502901.
Feb. 24, 2023 Korean First Office Action issued in Korean Patent Application No. 1020217004999.
Second Office Action issued in European Patent Application No. 19837159.3 dated Jul. 26, 2023, 5 pages.
Japanese Second Office Action dated Sep. 20, 2022, Japanese Patent Application No. 2021502901, 5 pages Including English translation.
McCoull, William et al. "Identification and Optimisation of 7-Azaindole PAK1 Inhibitors with Improved Potency and Kinase Selectivity" Med. Chem. Commun., vol. 5, Aug. 19, 2014 (Aug. 19, 2014), pp. 1533-1539, particularly see p. 1534, tables 1 and S3.
International Search Report and Written Opinion issued in International Patent Application No. PCT/CN2019/096841 dated Oct. 17, 2019 (with English language translation).
Lewis, Sara (Authorized Officer), Office Action issued in corresponding European Patent Application No. 19837159.3, mailed on May 14, 2024, 3 pages.

AZAINDOLE DERIVATIVE AND USE THEREOF AS FGFR AND C-Met INHIBITOR

CROSS-REFERENCE TO RELATED APPLICATIONS

This application is a U.S. National Stage application of PCT/CN2019/096841, filed 19 Jul. 2019, which claims the benefit of priority of Chinese Application No. 201810798237.7 filed on 19 Jul. 2019, Chinese Application No. 201811039652.0 filed on 6 Sep. 2018, and Chinese Application No. 201811445346.7 filed on 29 Nov. 2018, the entire disclosures of which are incorporated herein by reference in their entireties.

FIELD OF INVENTION

The present disclosure relates to a series of azaindole derivatives and uses thereof in the manufacture of medicaments for treating a disease associated with FGFR and c-Met. Specifically, the present disclosure relates to a compound represented by formula (I), a tautomer thereof or a pharmaceutically acceptable salt thereof.

BACKGROUND

FGFR is a type of biologically active substances that have functions of transmitting biological signals, regulating cell growth, participating in tissue repair, etc. In recent years, many members of the FGFR family have been found to play important roles in the occurrence and development process of tumors. Fibroblast growth factor receptor (FGFR) is a type of receptor proteins that can specifically bind to fibroblast growth factor (FGF). The FGFRs family includes the following types: FGFR1b, FGFR1c, FGFR2b, FGFR2c, FGFR3b, FGFR3c and FGFR4. Different subtypes of FGFR bind to different FGFs. The combination of FGFs and FGFRs leads to the autophosphorylation of multiple tyrosine residues in the cells. Phosphorylated FGFRs activate downstream signaling pathways including MEK/MAPK, PLCγ/PKC, PI3K/AKT, STATS, etc. In tumors, such as liver cancer, bladder cancer, lung cancer, breast cancer, endometrial cancer, glioma, prostate cancer, etc. FGFR activating mutations or ligand/receptor overexpression leads to its continuous constitutive activation, not only relates to the occurrence, development, and poor prognosis of tumors closely, but also plays an important role in tumor angiogenesis, tumor invasion and metastasis. Therefore, FGFR is considered as an important anti-tumor target.

c-Met protein (also known as the hepatocyte growth factor (HGF) receptor) is a transmembrane 190 kDa heterodimer with tyrosine kinase activity, encoded by c-Met oncogene. c-Met is the only known hepatocyte growth factor HGF receptor currently. The combination of HGF and c-MET can activate the downstream signal cascade, which phosphorylates cytoplasmic tyrosine kinases firstly, and then leads to autophosphorylation of MET. Various cytoplasmic effector proteins are recruited and phosphorylated, including GRB2, GABI, PLC and SOS. Once activated, GABI will form a binding site for downstream proteins (PI3K, etc.), and enter into the nucleus through RAS-MAPK and PI3K-AKT signaling pathways to affect gene expression and cell cycle progression. It has been shown that the HGF/c-Met signaling pathway demonstrates various cellular responses, including mitogenic activity, proliferative activity, morphogenetic activity, and angiogenic activity. About 5-10% of cancer patients have c-Met abnormalities, including liver cancer, stomach cancer, non-small cell lung cancer, bladder cancer, breast cancer, colorectal cancer, head and neck squamous cell carcinoma, hypopharyngeal cancer, ovarian cancer, etc. It has been clinically proven that inhibitors of the HGF/c-Met pathway have significant potential for the treatment of cancer. WO2010059771A1 reported a small molecule inhibitor with c-Met activity.

Both FGFR and c-Met are members of the receptor tyrosine kinase (RTK) family, and the signal pathways regulated by both include PI3K-AKT-mTOR and RAS-RAF-MEK-ERK, etc. Numerous studies have demonstrated that tumor escape occurs between FGFR and c-Met targets.

In terms of molecular mechanism, both c-Met and FGFR are members of the receptor tyrosine kinase (RTK) family, and the signal pathways regulated by both include PI3K-AKT-mTOR and RAS-RAF-MEK-ERK, etc. FGFR targets and c-Met targets can synergistically complement each other, and FGFR mutations and c-Met mutations are prone to play a signaling compensatory role when the other is inhibited, thereby leading to the resistant to the single inhibitor of tumor cells.

WO2010059771A1 disclosed Met and RON inhibitors: comparative example 1a and 1b; at present, no dual-target small molecule inhibitors with high activity against both FGFR and c-Met have been identified.

Content of the Present Invention

The present disclosure provides a compound represented by formula (1), a tautomer thereof or a pharmaceutically acceptable salt thereof.

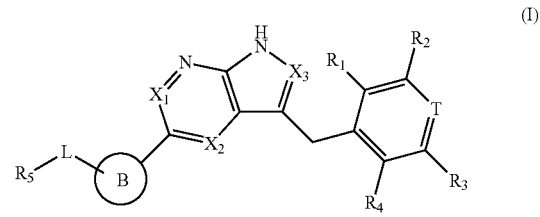

(I)

wherein, $X_1$, $X_2$ and $X_3$ are respectively independently selected from CH, C(CH$_3$) and N;

T is selected from CH and N;

$R_1$ and $R_4$ are respectively independently selected from H, F, Cl, Br, I, OH and NH$_2$;

$R_2$ and $R_3$ are respectively independently selected from H, F, Cl, Br, I, OH, NH$_2$, CN, COOH, C$_{1-6}$ alkyl and C$_{1-6}$ heteroalkyl, wherein the C$_{1-6}$ alkyl and C$_{1-6}$ heteroalkyl are optionally substituted by 1, 2 or 3 R$_a$;

$R_5$ is selected from H, C$_{1-6}$ alkyl, C$_{1-6}$ heteroalkyl, C$_{3-6}$ cycloalkyl, 4-6 membered heterocycloalkyl and 5-6 membered heterocycloalkenyl, wherein the C$_{1-6}$ alkyl, C$_{1-6}$ heteroalkyl, C$_{3-6}$ cycloalkyl, 4-6 membered heterocycloalkyl and 5-6 membered heterocycloalkenyl are optionally substituted by 1, 2 or 3 R$_b$;

ring B is selected from phenyl and 5-6 membered heteroaryl, wherein the phenyl and 5-6 membered heteroaryl are optionally substituted by 1, 2 or 3 R$_6$;

$R_6$ is respectively independently selected from H, F, Cl, Br, I, OH, NH$_2$, CN, COOH, C$_{1-3}$ alkyl and C$_{1-3}$ heteroalkyl, wherein the C$_{1-3}$ alkyl and C$_{1-3}$ heteroalkyl are optionally substituted by 1, 2 or 3R$_c$;

alternatively, two R$_6$ connected to adjacent carbon atoms and the C atoms to which they are connected together form a 4-6 membered heterocycloalkyl, which is optionally substituted by 1, 2 or 3 $R_c$;

L is selected from single bond and $—(CR_dR_e)_m—$;

m is selected from 1, 2, 3 and 4;

$R_a$ is respectively independently selected from H, F, Cl, Br, I, OH, $NH_2$, CN, COOH, $C_{1-3}$ alkyl and $C_{1-3}$ heteroalkyl, wherein the $C_{1-3}$ alkyl and $C_{1-3}$ heteroalkyl are optionally substituted by 1, 2 or 3 R;

$R_b$ is respectively independently selected from H, F, Cl, Br, I, OH, $NH_2$, CN, COOH, $C_{1-3}$ alkyl, $C_{1-3}$ heteroalkyl and 4-6 membered heterocycloalkyl, wherein the $C_{1-3}$ alkyl, $C_{1-3}$ heteroalkyl and 4-6 membered heterocycloalkyl are optionally substituted by 1, 2 or 3 R;

$R_c$ is respectively independently selected from H, F, Cl, Br, I, OH, $NH_2$, $CH_3$ and $CH_3CH_2$; alternatively, two $R_c$ connected to the same carbon atom and the C atom to which they are connected together form a 4-6 membered heterocycloalkyl, which is optionally substituted by 1, 2 or 3R;

$R_d$ and $R_e$ are respectively independently selected from H, F, Cl, Br, I, OH, $NH_2$, $CH_3$ and $CH_3CH_2$;

R is selected from F, Cl, Br, I, OH, CN, $NH_2$, CN, COOH, $CH_3$, $CH_3CH_2$, $CH_3CH_2CH_2$, $(CH_3)_2CH$, $CF_3$, $CHF_2$, $CH_2F$, $CH_3O$ and

wherein the $C_{1-6}$ heteroalkyl, $C_{1-3}$ heteroalkyl, 5-6 membered heteroaryl, 4-6 membered heterocycloalkyl and 5-6 membered heterocycloalkenyl respectively independently contain 1, 2, 3 or 4 heteroatoms or heteroatom groups independently selected from —NH—, —O—, —S—, —C(=O)—, S(=O)—, $S(=O)_2$—, and N.

In some embodiments of the present disclosure, the $R_a$ is respectively independently selected from H, F, Cl, Br, I, OH, $NH_2$, CN, COOH, $CH_3$, $CH_3CH_2$, $CH_3CH_2CH_2$, $(CH_3)_2CH$, $CF_3$, $CHF_2$, $CH_2F$,

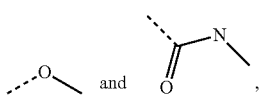

the other variables are as defined in the present disclosure.

In some embodiments of the present disclosure, the $R_b$ is respectively independently selected from H, F, Cl, Br, I, OH, $NH_2$, CN, COOH, $CH_3$, $CH_3CH_2$, $CH_3CH_2CH_2$, $(CH_3)_2CH$, $CF_3$, $CHF_2$, $CH_2F$,

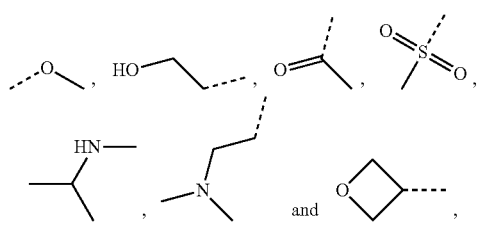

the other variables are as defined in the present disclosure.

In some embodiments of the present disclosure, the $R_2$ and $R_3$ are respectively independently selected from H, F, Cl, Br, I, OH, $NH_2$, CN, COOH, $C_{1-3}$ alkyl, $C_{1-3}$ alkyl-NC(=O)— and $C_{1-3}$ alkoxy, wherein $C_{1-3}$ alkyl, $C_{1-3}$ alkyl-NC(=O)— and $C_{1-3}$ alkoxy are optionally substituted by 1, 2 or 3 $R_a$, the other variables are as defined in the present disclosure.

In some embodiments of the present disclosure, the $R_2$ and $R_3$ are respectively independently selected from H, F, Cl, Br, I, OH, $NH_2$, CN, COOH, $CH_3$, $CH_2CH_3$, $CH_3CH_2CH_2$, $(CH_3)_2CH$,

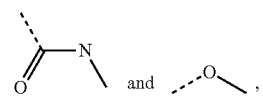

wherein the $CH_3$, $CH_2CH_3$, $CH_3CH_2CH_2$, $(CH_3)_2CH$,

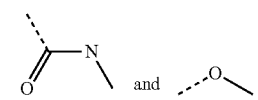

are optionally substituted by 1, 2 or 3 $R_a$, the other variables are as defined in the present disclosure.

In some embodiments of the present disclosure, the $R_2$ and $R_3$ are respectively independently selected from H, F, Cl, Br, I, OH, $NH_2$, CN, COOH, $CH_3$, $CH_2F$, $CHF_2$, $CF_3$, $CH_2CH_3$, $CH_3CH_2CH_2$, $(CH_3)_2CH$,

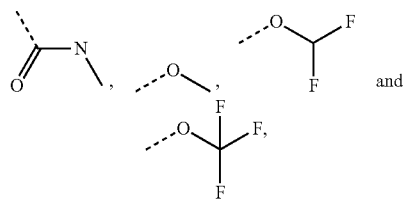

the other variables are as defined in the present disclosure.

In some embodiments of the present disclosure, the $R_5$ is selected from H, $C_{1-3}$ alkyl, $C_{1-3}$ alkoxy, $C_{1-3}$ alkyl-C(=O)—, $C_{1-3}$ alkyl-$S(=O)_2$—, $C_{1-3}$ alkyl-$S(=O)_2$—$C_{1-3}$ alkyl-, $C_{1-3}$ alkylamino, cyclohexyl, piperidinyl, morpholinyl, tetrahydropyranyl, tetrahydrofuranyl, 1,2,3,6-tetrahydropyridyl, azetidinyl, oxebutanyl, pyrrolidinyl and piperazinyl, wherein $C_{1-3}$ alkyl, $C_{1-3}$ alkoxy, $C_{1-3}$ alkyl-C(=O)—, $C_{1-3}$ alkyl-$S(=O)_2$—, $C_{1-3}$ alkyl-$S(=O)_2$—$C_{1-3}$ alkyl-, $C_{1-3}$ alkylamino, cyclohexyl, piperidinyl, morpholinyl, tetrahydropyranyl, tetrahydrofuranyl, 1,2,3,6-tetrahydropyridyl, azetidinyl, oxebutanyl, pyrrolidinyl and piperazinyl are optionally substituted by 1, 2 or 3 $R_b$, the other variables are as defined in the present disclosure.

In some embodiments of the present disclosure, the $R_5$ is selected from H, $CH_3$, $CH_3CH_2$, $CH_3CH_2CH_2$, $(CH_3)_2CH$, $C(R_b)_3$, $CH(R_b)_2$, $CH_2(R_b)$,

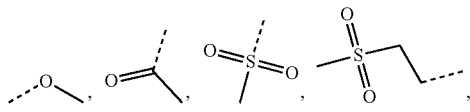

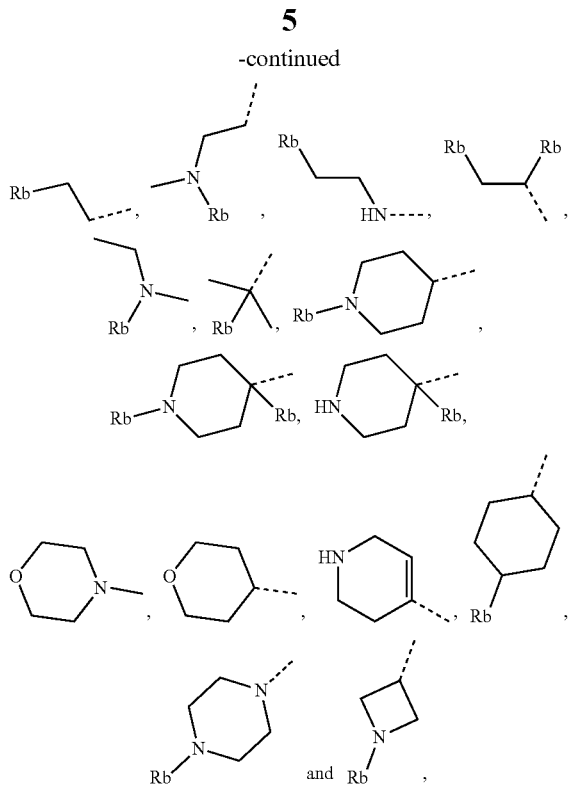

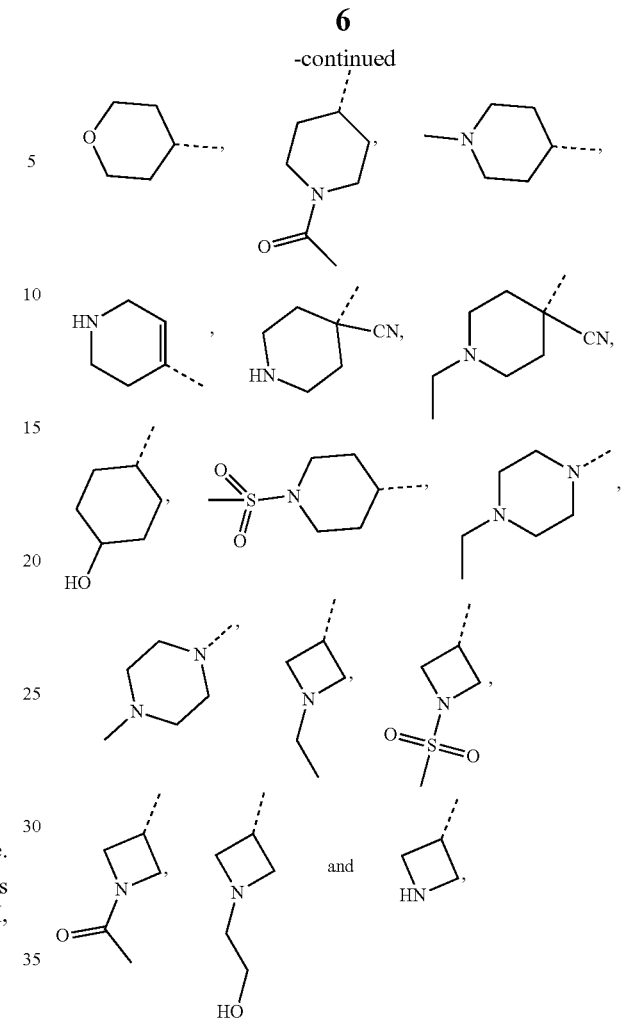

the other variables are as defined in the present disclosure.

In some embodiments of the present disclosure, the $R_5$ is selected from H, $CH_3$, $CH_3CH_2$, $CH_3CH_2CH_2$, $(CH_3)_2CH$, $CF_3$, $CHF_2$, $CH_2F$,

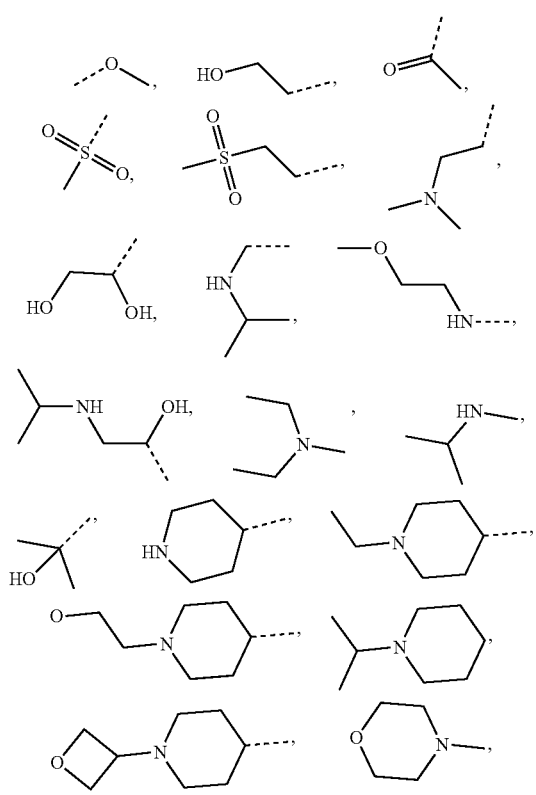

the other variables are as defined in the present disclosure.

In some embodiments of the present disclosure, the $R_6$ is respectively independently selected from H, F, Cl, Br, I, OH, $NH_2$, CN, COOH, $CH_3$, $CH_2CH_3$, $CH_3CH_2CH_2$, $(CH_3)_2CH$ and

wherein the $CH_3$, $CH_2CH_3$, $CH_3CH_2CH_2$, $(CH_3)_2CH$ and

are optionally substituted by 1, 2 or 3 $R_c$, the other variables are as defined in the present disclosure.

In some embodiments of the present disclosure, the $R_6$ is respectively independently selected from H, F, Cl, Br, I, OH, $NH_2$, CN, COOH, $CH_3$, $CH_3CH_2$, $CH_3CH_2CH_2$, $(CH_3)_2CH$, $CF_3$, $CHF_2$, $CH_2F$ and

the other variables are as defined in the present disclosure.

In some embodiments of the present disclosure, the two $R_e$ connected to the same carbon atom are linked together to form piperidinyl optionally substituted by 1, 2 or 3 R.

In some embodiments of the present disclosure, the two $R_e$ connected to the same carbon atom are linked together to form

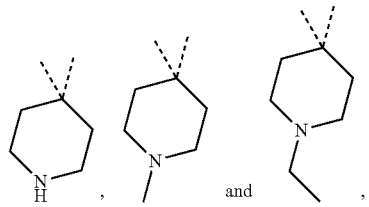

the other variables are as defined in the present disclosure.

In some embodiments of the present disclosure, the L is selected from a single bond, —CH$_2$— and —CH$_2$CH$_2$, the other variables are as defined in the present disclosure.

In some embodiments of the present disclosure, the ring B is selected from phenyl, pyrazolyl, imidazolyl, pyridyl and pyrazinyl, wherein the phenyl, pyrazolyl, imidazolyl, pyridyl and pyrazinyl are optionally substituted by 1, 2 or 3 $R_6$, the other variables are as defined in the present disclosure.

In some embodiments of the resent disclosure, the ring B is selected from

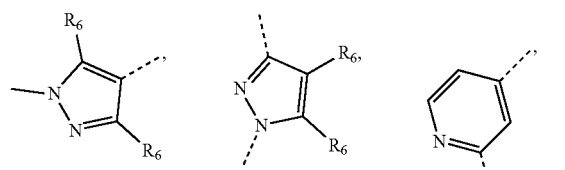

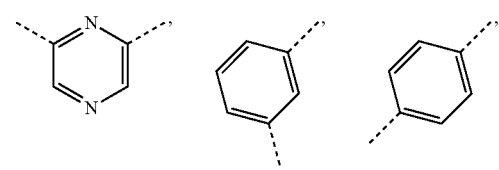

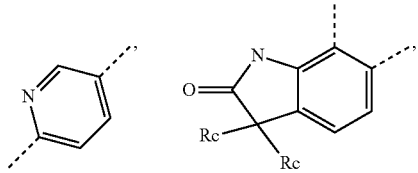

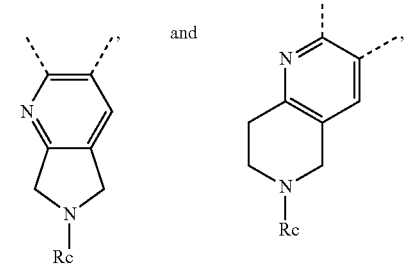

the other variables are as defined in the present disclosure.

In some embodiments of the present disclosure, the ring B is selected from,

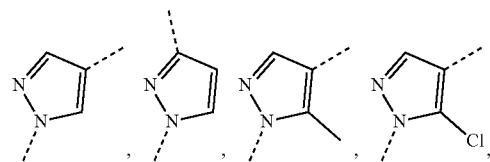

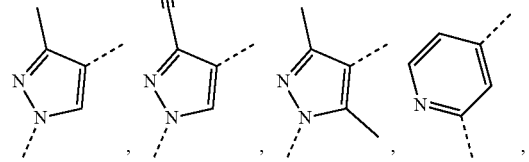

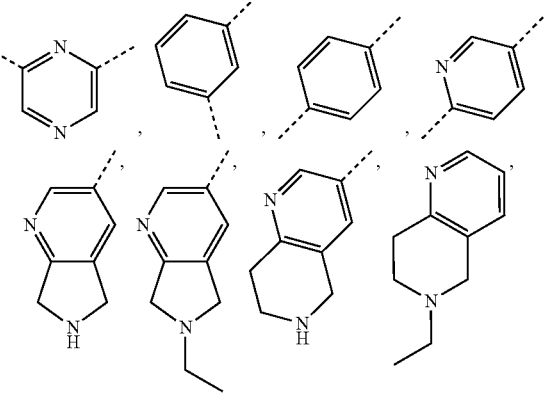

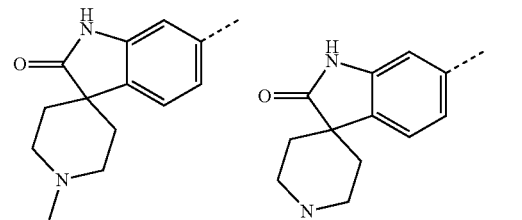

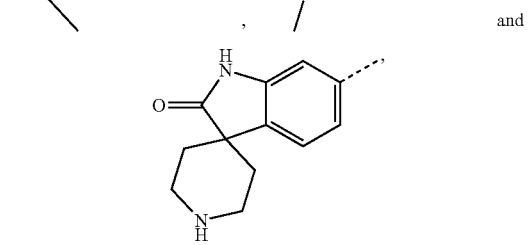

the other variables are as defined in the present disclosure.

In some embodiments of the present disclosure, the moiety

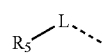

is selected from H, CH$_3$, CH$_3$CH$_2$, CH$_3$CH$_2$CH$_2$, (CH$_3$)$_2$CH, CF$_3$, CHF$_2$, CH$_2$F,

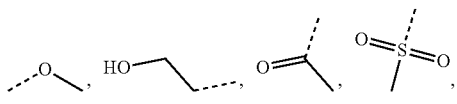

-continued

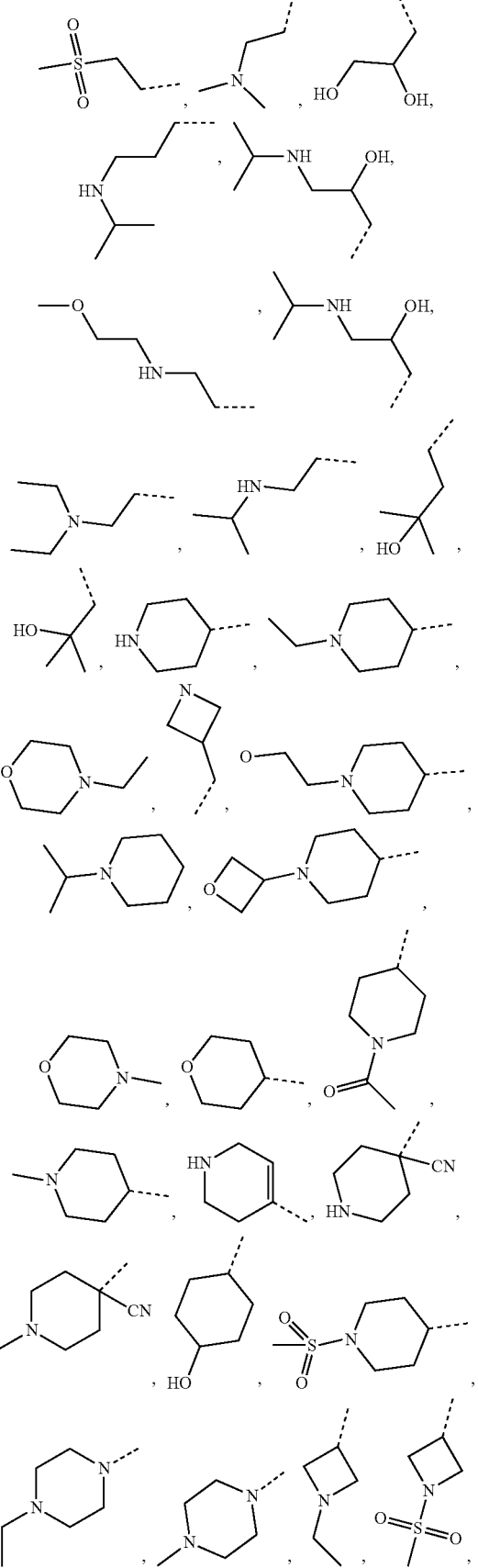

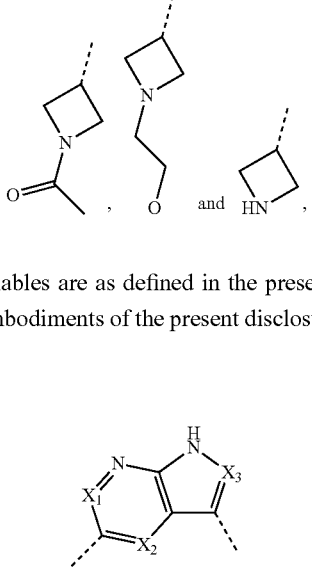

the other variables are as defined in the present disclosure.

In some embodiments of the present disclosure, the above moiety is selected from

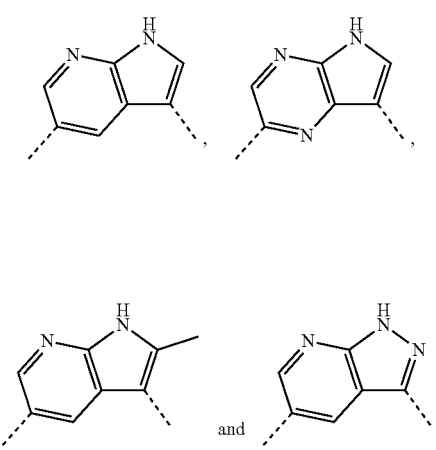

the other variables are as defined in the present disclosure.

The present disclosure also has some embodiments derived from any combination of the variables described above In some embodiments of the present disclosure, the compound, the tautomer thereof or the pharmaceutically acceptable salt thereof, is selected from

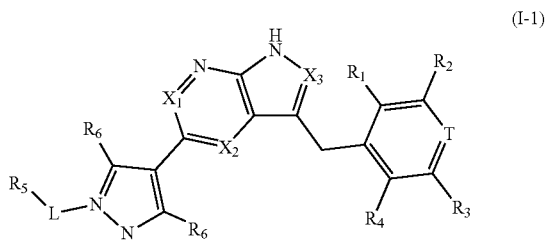

(I-1)

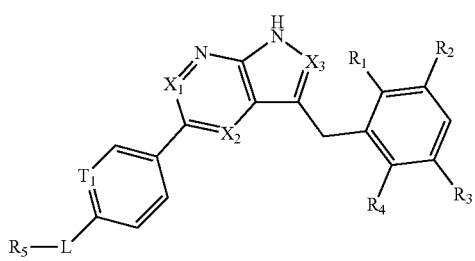
(I-2)
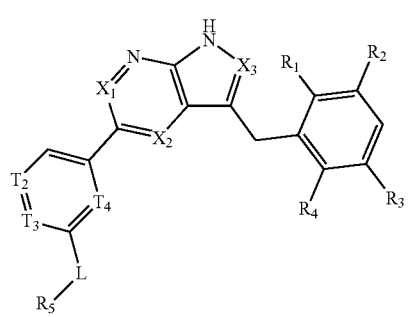
(I-3)
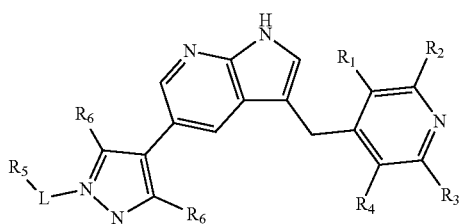
(I-1d)
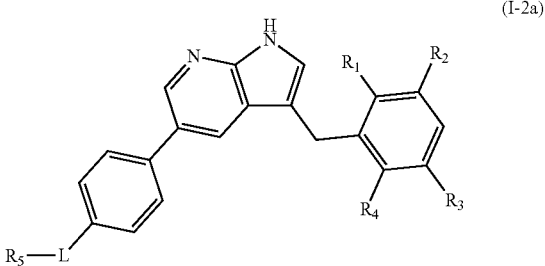
(I-2a)
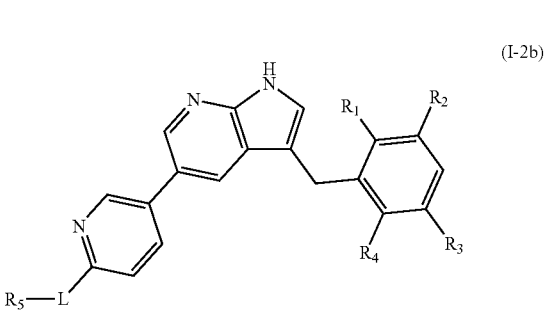
(I-2b)
wherein,
T₁, T₂, T₃ and T₄ are respectively independently selected from C(R₆) and N;
T, X₁, X₂, X₃, R₁, R₂, R₃, R₄, R₅, R₆ and L are as defined in the present disclosure.
In some embodiments of the present disclosure, the compound, the tautomer thereof or the pharmaceutically acceptable salt thereof, is selected from
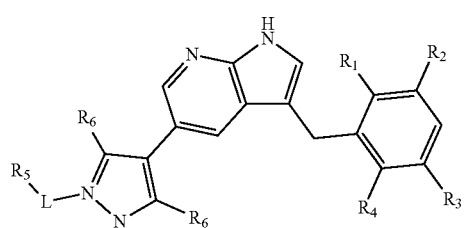
(I-1a)
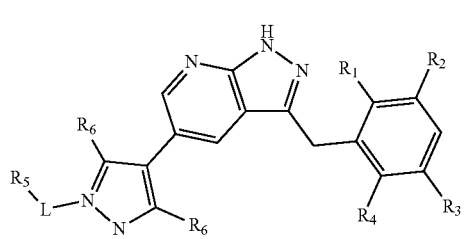
(I-1b)
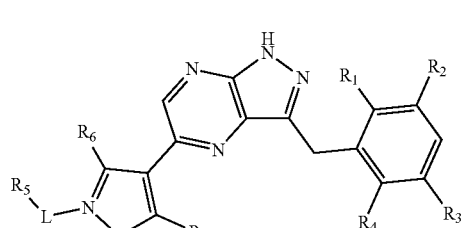
(I-1c)
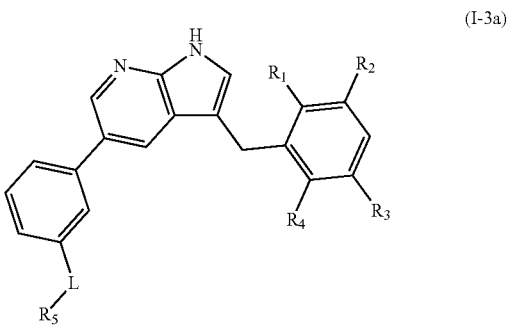
(I-3a)
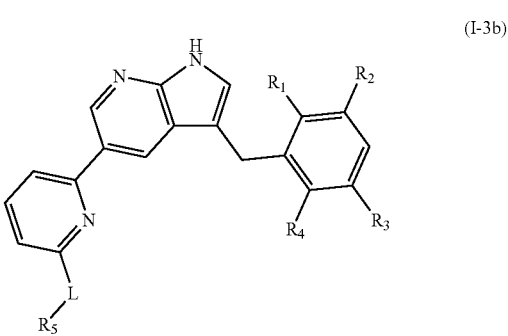
(I-3b)

(I-3c)
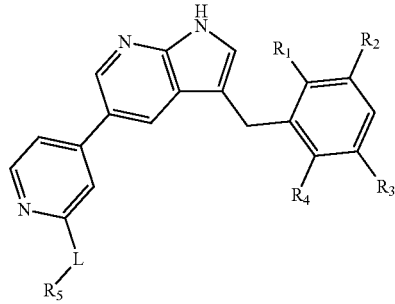
(I-3d)
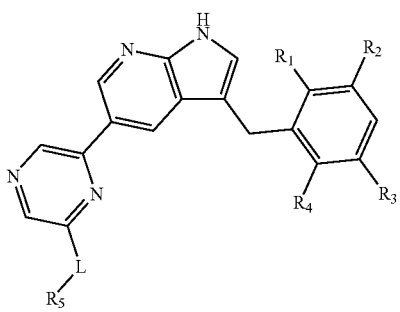
(I-3e)
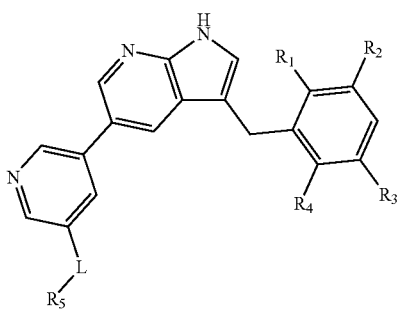
wherein,
R₁, R₂, R₃, R₄, R₅ and L are as defined in the present disclosure.
The present disclosure also provides a compound as shown below, a tautomer thereof or a pharmaceutically acceptable salt thereof, wherein the compound is selected from
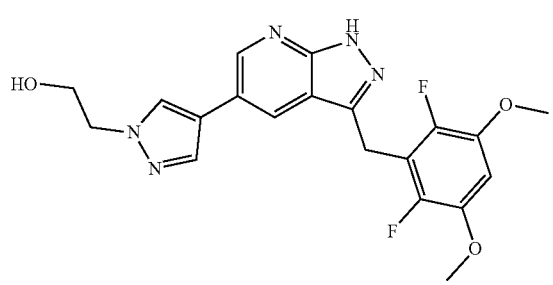
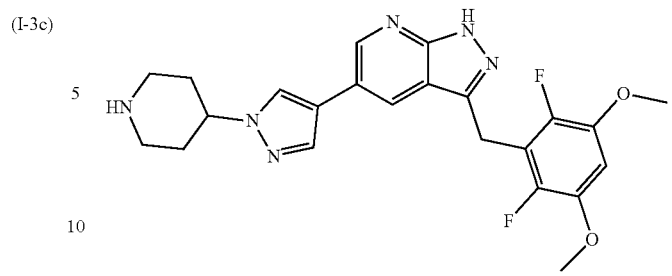
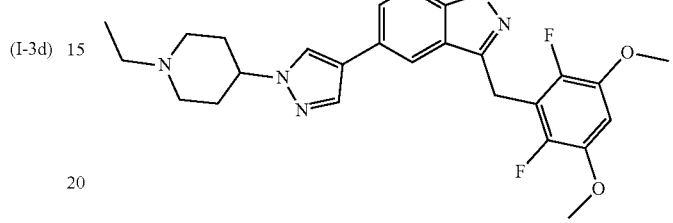
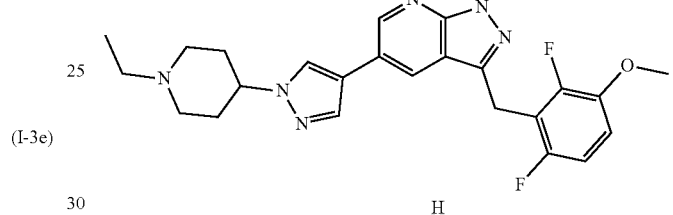
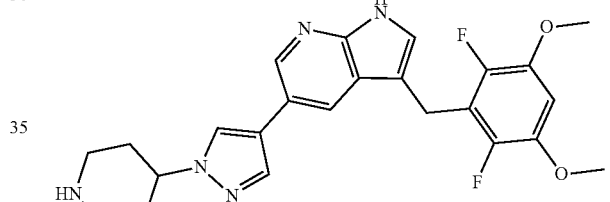
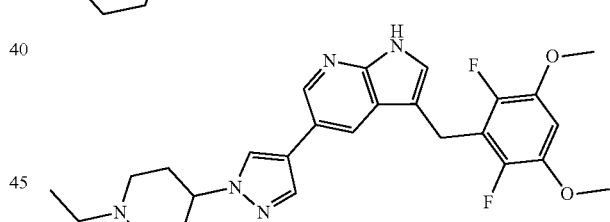
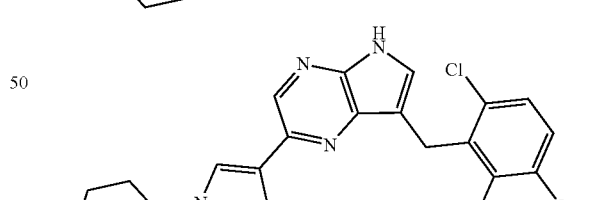
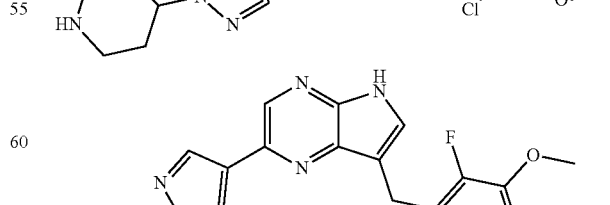

15
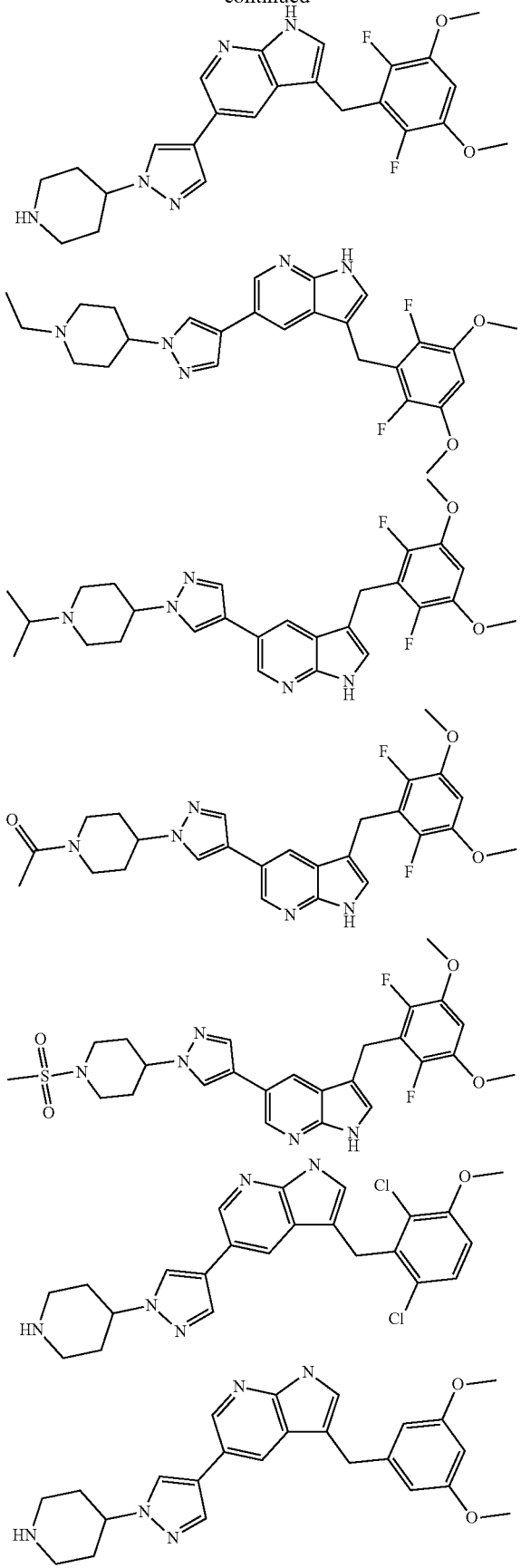
16
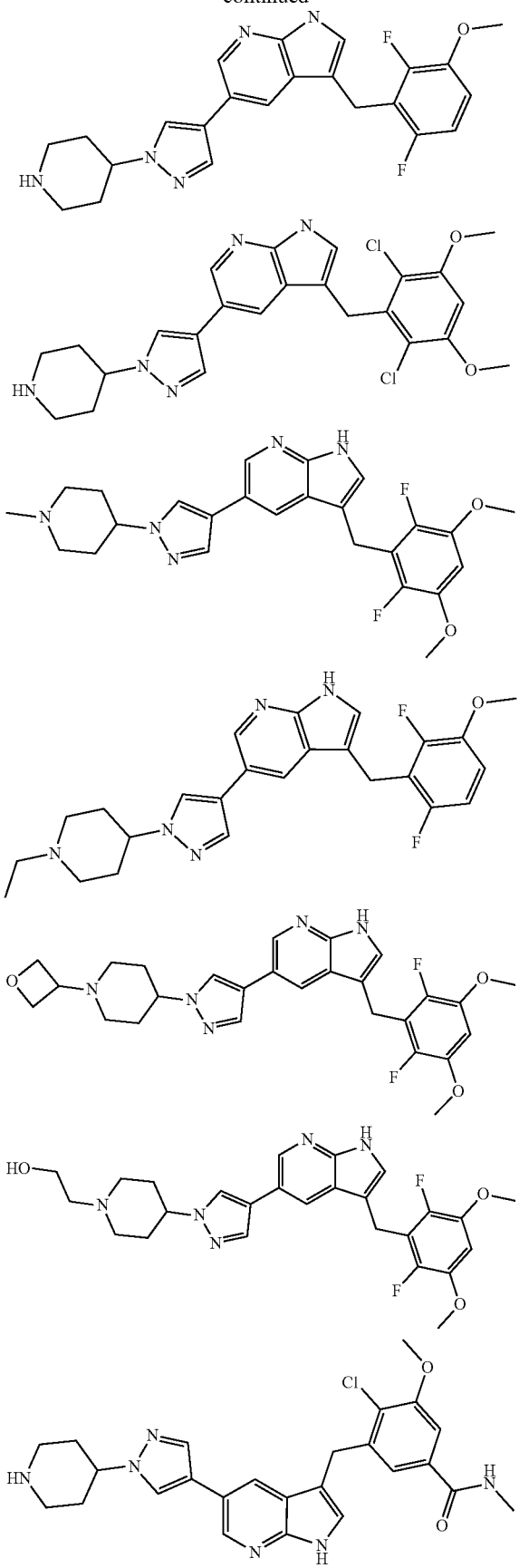

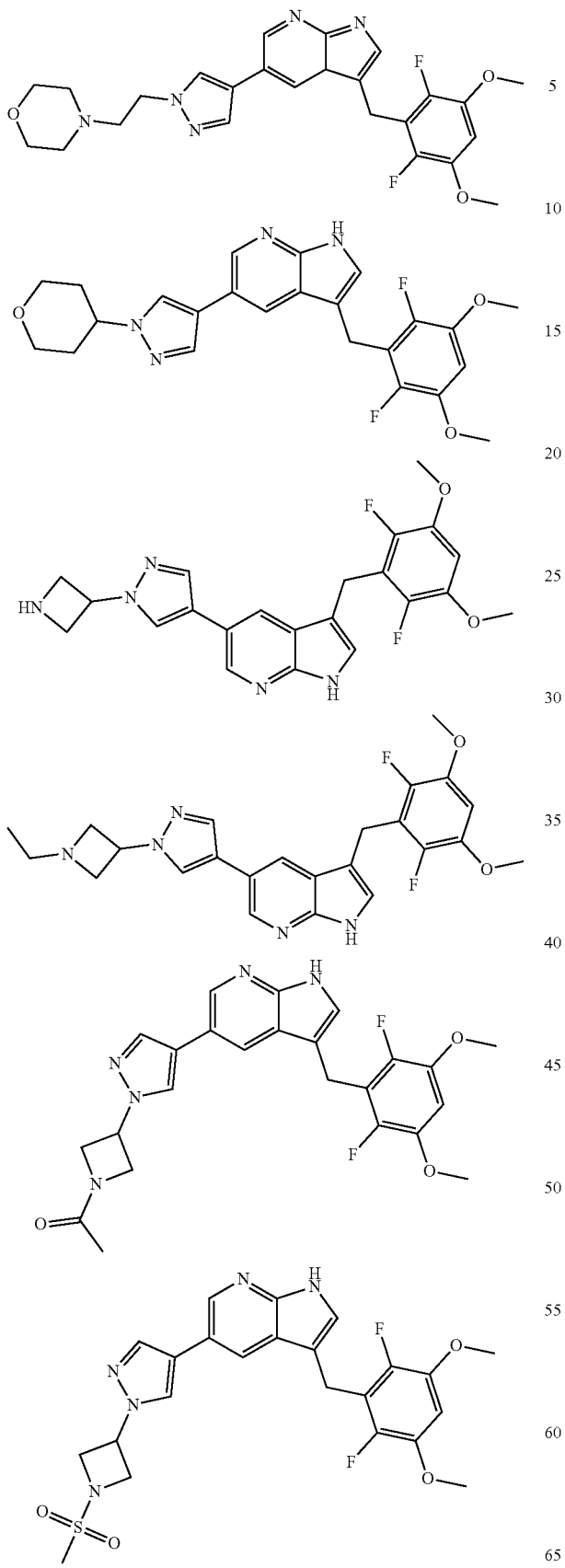
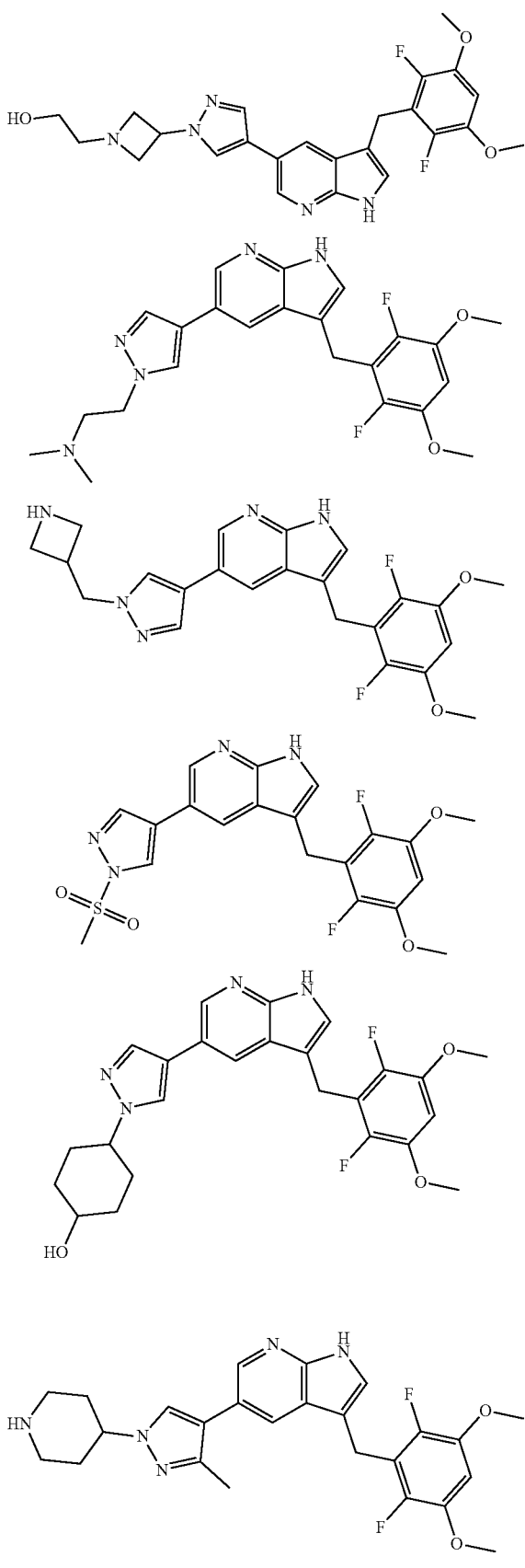

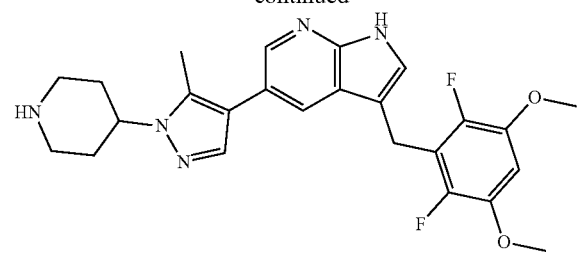
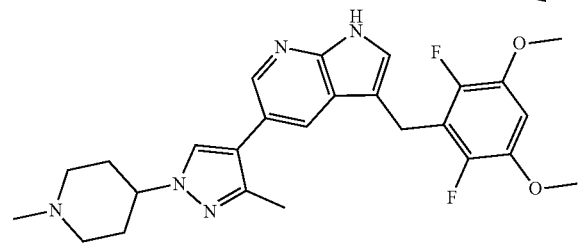
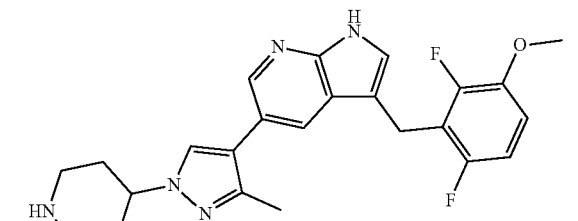
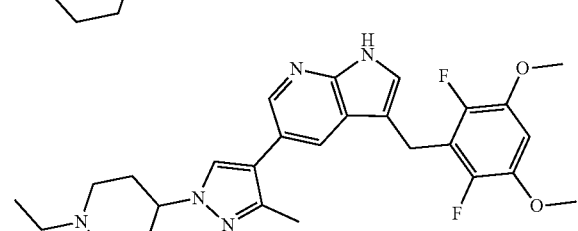
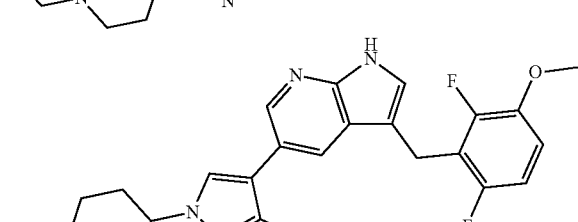
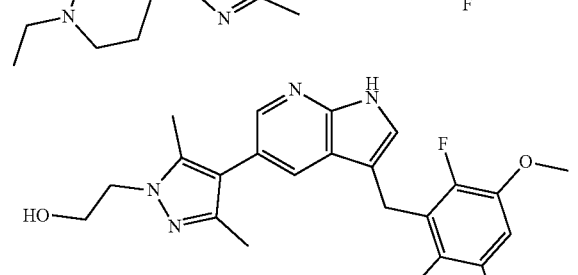
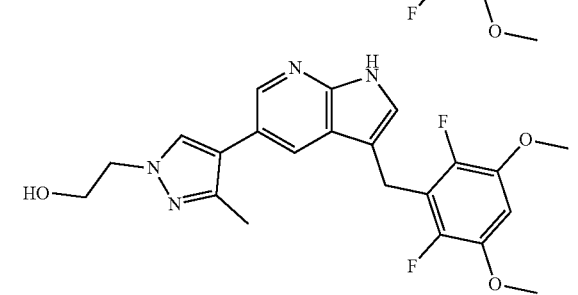
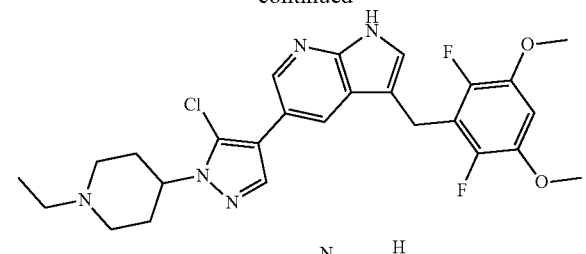
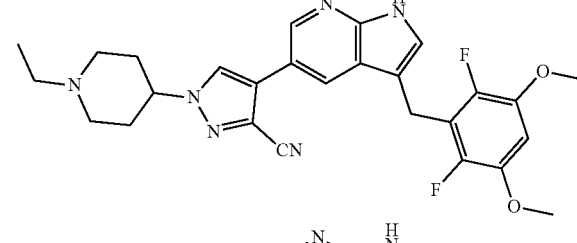
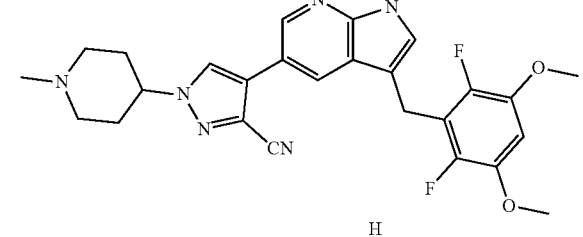
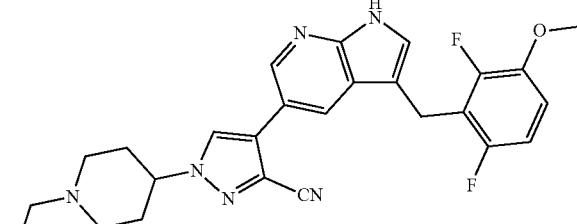
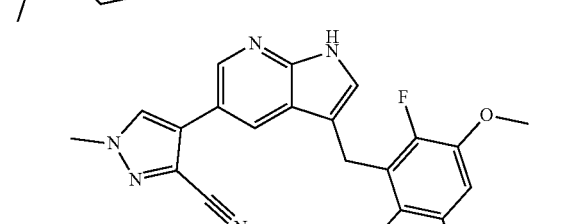
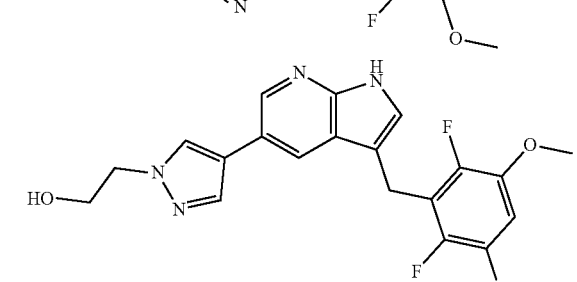
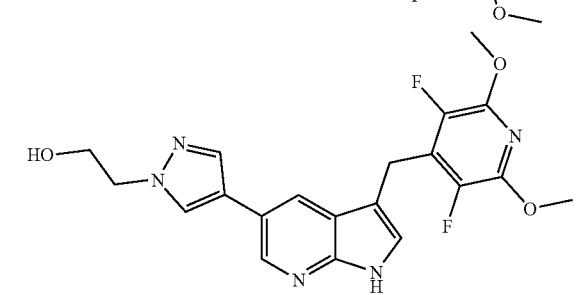

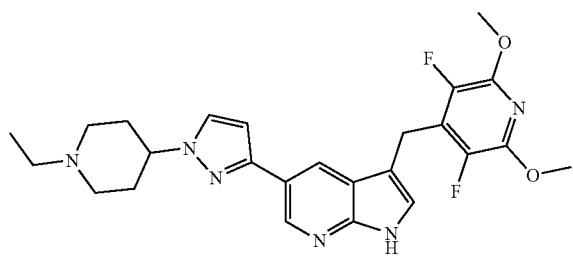
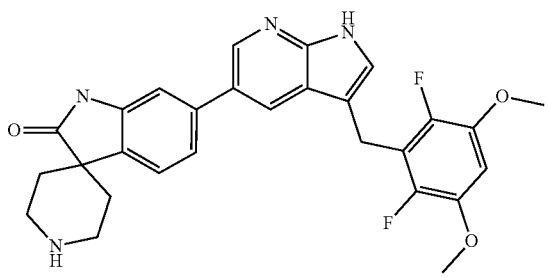
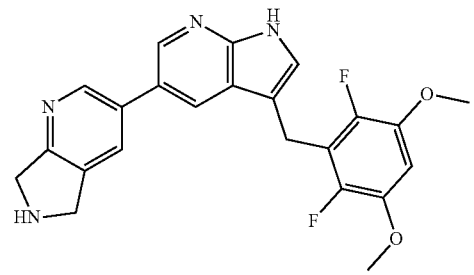
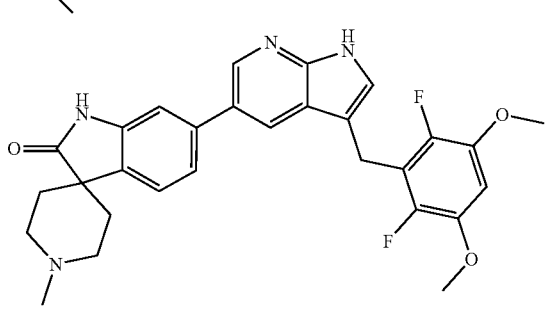
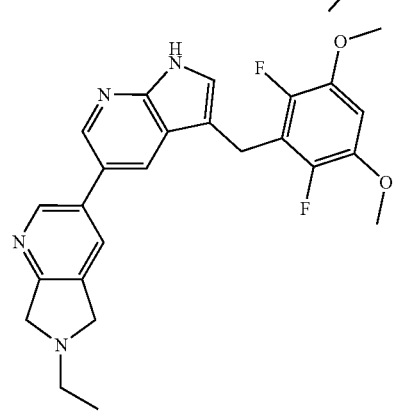
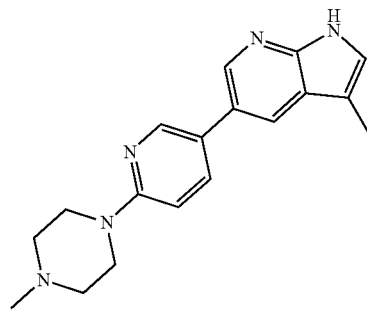
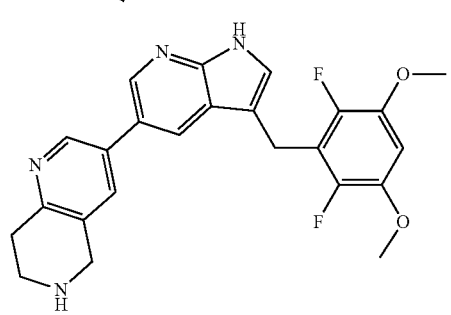
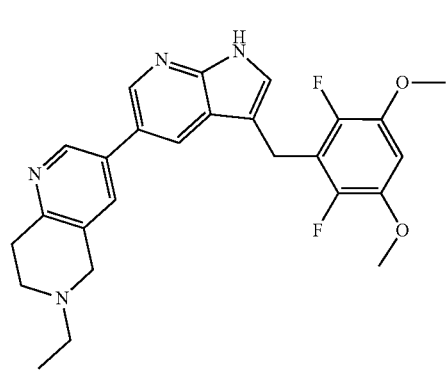
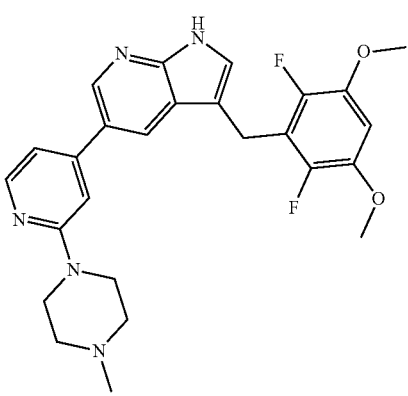

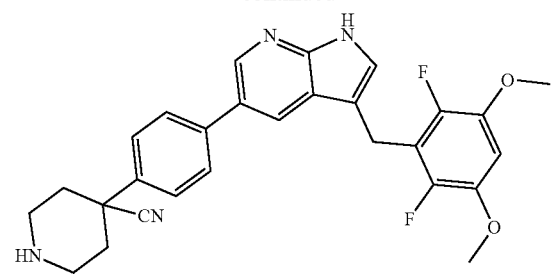
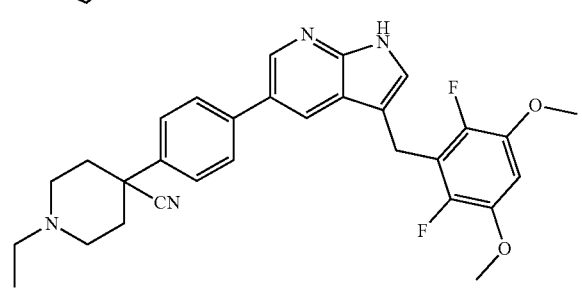
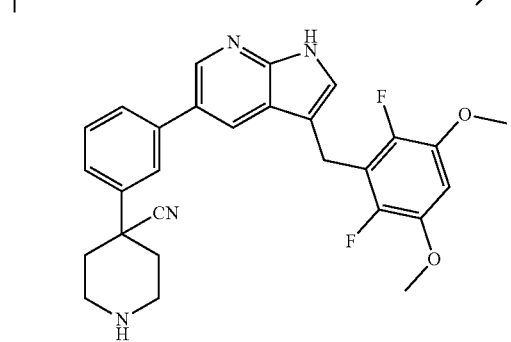
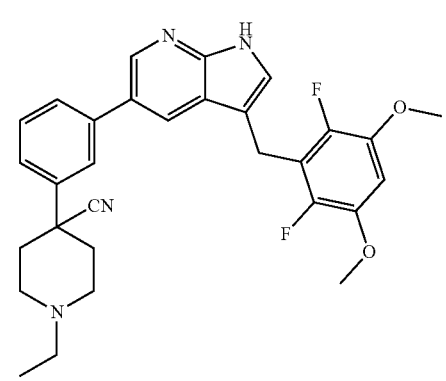
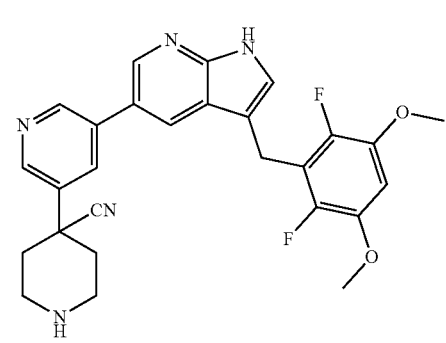
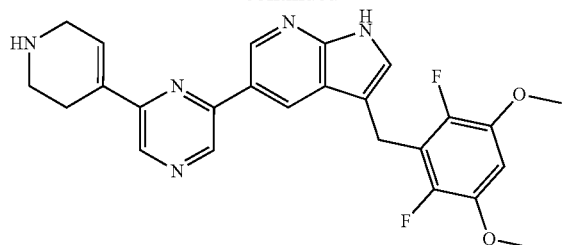
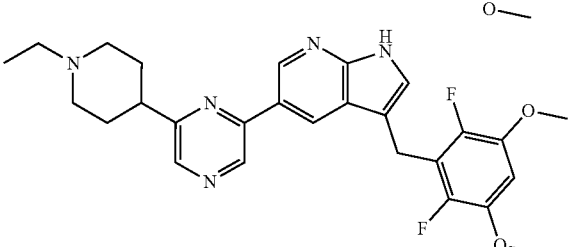
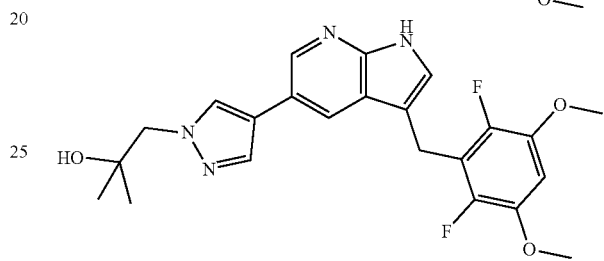
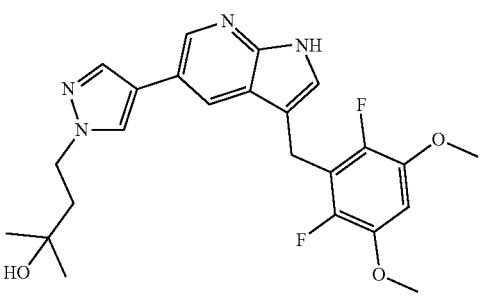
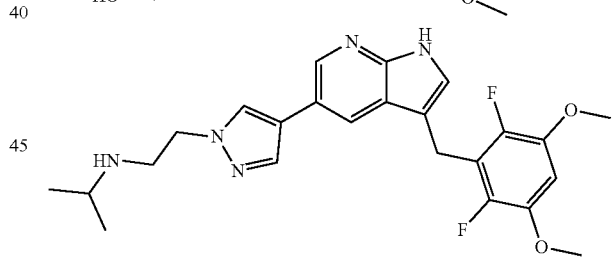
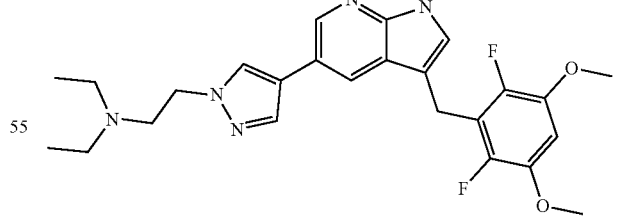
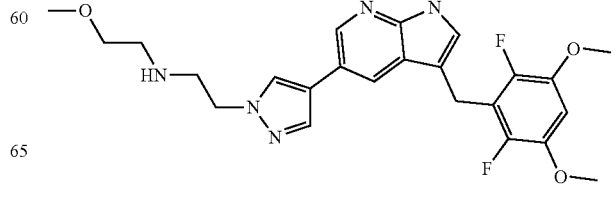

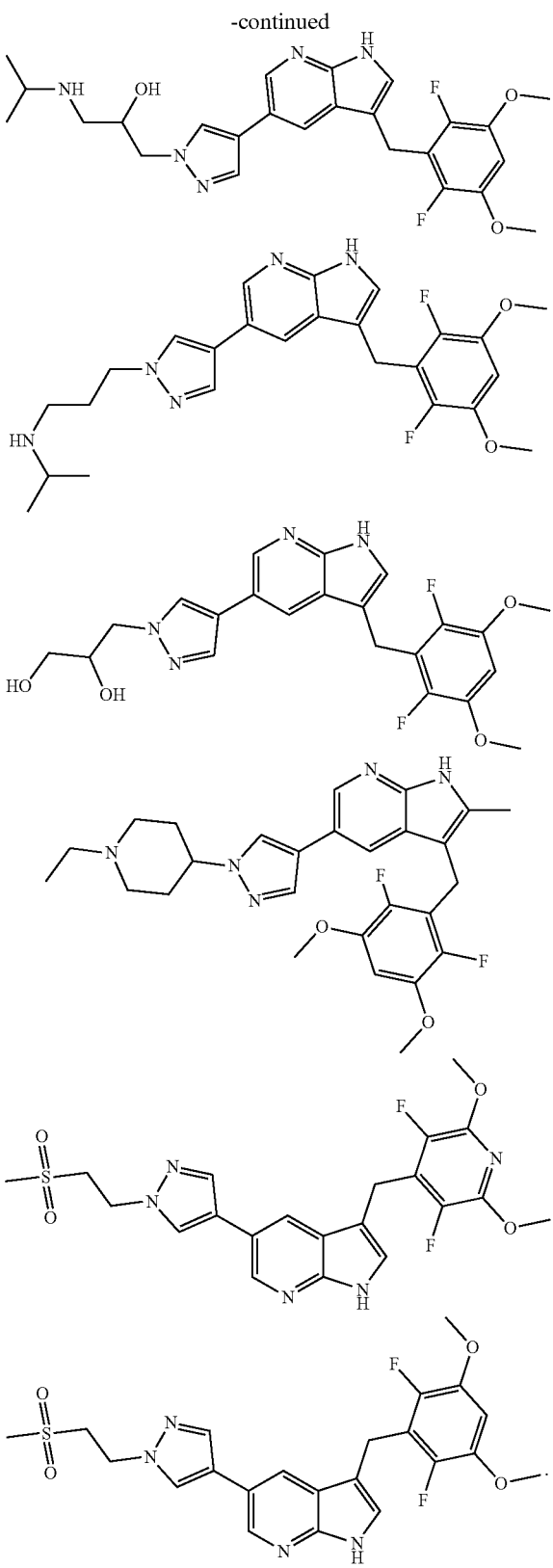

The present disclosure also provides a use of the compound, the tautomer thereof or the pharmaceutically acceptable salt thereof in the manufacture of medicaments for treating a disease associated with FGFR and c-Met.

DEFINITION AND DESCRIPTION

Unless otherwise indicated, the following terms and phrases used herein are intended to have the following meanings. A specific term or phrase should not be considered indefinite or unclear in the absence of a particular definition, but should be understood in the ordinary meaning. When a trade name appears herein, it is intended to refer to its corresponding commodity or active ingredient thereof.

The term "pharmaceutically acceptable" as used herein refers to those compounds, materials, compositions, and/or dosage forms that are suitable for use in contact with human and animal tissues within the scope of reliable medical judgment, with no excessive toxicity, irritation, allergic reaction or other problems or complications, commensurate with a reasonable benefit/risk ratio.

The term "pharmaceutically acceptable salt" refers to a salt of the compound of the present disclosure that is prepared by reacting the compound having a specific substituent of the present disclosure with a relatively non-toxic acid or base. When the compound of the present disclosure contains a relatively acidic functional group, a base addition salt can be obtained by contacting the neutral form of the compound with a sufficient amount of base in a pure solution or a suitable inert solvent. The pharmaceutically acceptable base addition salt includes a salt of sodium, potassium, calcium, ammonium, organic amine or magnesium or similar salts. When the compound of the present disclosure contains a relatively basic functional group, an acid addition salt can be obtained by contacting the neutral form of the compound with a sufficient amount of acid in a pure solution or a suitable inert solvent. Examples of the pharmaceutically acceptable acid addition salt includes an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; and an organic acid salt, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid, and the like; and an salt of amino acid (such as arginine and the like), and a salt of an organic acid such as glucuronic acid and the like. Certain specific compounds of the present disclosure that contain both basic and acidic functional groups can be converted to any base or acid addition salt.

The pharmaceutically acceptable salt of the present disclosure can be prepared from the parent compound that contains an acidic or basic moiety by conventional chemical methods. Generally, such salt can be prepared by reacting the free acid or base form of the compound with a stoichiometric amount of appropriate base or acid in water or an organic solvent or a mixture thereof.

The compounds of the present disclosure may exist in specific geometric or stereoisomeric forms. The present disclosure contemplates all such compounds, including cis- and trans-isomers, (−)- and (+)-enantiomers, (R)- and (S)-enantiomers, diastereomers, (D)-isomers, (L)-isomers, and racemic and other mixtures thereof, such as enantiomers or diastereomers enriched mixtures, all of which are within the scope of the present disclosure. Additional asymmetric carbon atoms may be present in substituents such as alkyl. All these isomers and their mixtures are included within the scope of the present disclosure.

Unless otherwise indicated, the term "enantiomers" or "optical isomers" refers to stereoisomers which are mirror images of each other.

Unless otherwise indicated, the term "cis/trans-isomer" or "geometric isomer" is caused by the inability of a double bond or a single bond of a ring-forming carbon atom to rotate freely.

Unless otherwise indicated, the term "diastereomer" refers to a stereoisomer in which a molecule has two or more chiral centers, and there is non-mirror image relationship between molecules.

Unless otherwise indicated, "(D)" or "(+)" refers to dextrorotation, "(L)" or "(−)" refers to levorotation, and "(DL)" or "(±)" refers to racemic.

Unless otherwise indicated, a wedged solid bond ( ) and a wedged dashed bond ( ) represent the absolute configuration of a stereo-center, a straight solid bond ( ) and a straight dashed bond ( ) represent the relative configuration of a stereo-center, a wave line ( ) represents a wedged solid bond ( ) or a wedged dashed bond ( ), or a wave line ( ) represents a straight solid bond ( ) or a straight dashed bond ( ).

Unless otherwise indicated, when double bond structure, such as carbon-carbon double bond, carbon-nitrogen double bond, and nitrogen-nitrogen double bond, exists in the compound, and each atom on the double bond is connected to two different substituents (including the condition where a double bond contains a nitrogen atom, the lone pair of electrons attached on the nitrogen atom is regarded as a substituent connected), if the atom on the double bond in the compound is connected to its substituent by a wave line ( ), this refers to the (Z) isomer, (E) isomer or a mixture of two isomers of the compound. For example, the following formula (A) means that the compound exists as a single isomer of formula (A-1) or formula (A-2) or as a mixture of two isomers of formula (A-1) and formula (A-2); the following formula (B) means that the compound exists in the form of a single isomer of formula (B-1) or formula (B-2) or in the form of a mixture of two isomers of formula (B-1) and formula (B-2). The following formula (C) means that the compound exists as a single isomer of formula (C-1) or formula (C-2) or as two a mixture of two isomers of formula (C-1) and formula (C-2).

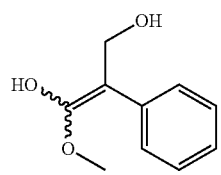

(A)

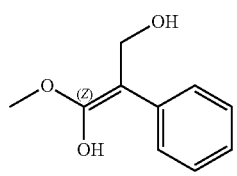

(A-1)

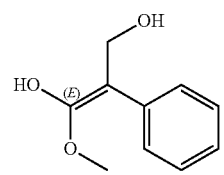

(A-2)

-continued

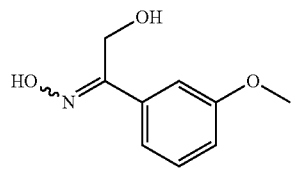

(B)

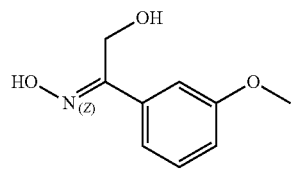

(B-1)

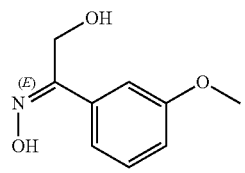

(B-2)

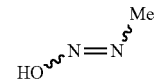

(C)

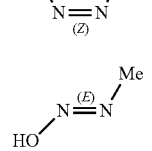

(C-1)

(C-2)

The compounds of the disclosure may be specific. Unless otherwise indicated, the term "tautomer" or "tautomeric form" means that at room temperature, the isomers of different functional groups are in dynamic equilibrium and can be transformed into each other quickly. If tautomers are possible (e.g. in solution), the chemical equilibrium of the tautomers can be reached. For example, proton tautomer (also known as prototropic tautomer) includes interconversions via proton migration, such as keto-enol isomerization and imine-enamine isomerization. Valence tautomer includes interconversion formed by recombination of some bonding electrons. A specific example of the keto-enol tautomerization is the interconversion between two tautomers of pentane-2,4-dione and 4-hydroxypent-3-en-2-one.

Unless otherwise indicated, the term "enriched in an isomer", "isomer enriched", "enriched in an enantiomer" or "enantiomer enriched" refers to that the content of the isomer or enantiomer is less than 100%, and the content of the isomer or enantiomer is 60% or more, or 70% or more, or 80% or more, or 90% or more, or 95% or more, or 96% or more, or 97% or more, or 98% or more, or 99% or more, or 99.5% or more, or 99.6% or more, or 99.7% or more, or 99.8% or more, or 99.9% or more.

Unless otherwise indicated, the term "isomer excess" or "enantiomer excess" refers to the difference between the relative percentages of two isomers or two enantiomers. For example, if the content of one isomer or enantiomer is 90%, and the content of the other isomer or enantiomer is 10%, the isomer or enantiomeric excess (ee value) is 80%.

The optically active (R)- and (S)-isomer, or D and L isomer can be prepared using chiral synthesis or chiral reagents or other conventional techniques. If one kind of enantiomer of certain compound of the present disclosure is to be obtained, the pure desired enantiomer can be obtained by asymmetric synthesis or derivative action of chiral auxiliary followed by separating the resulting diastereomeric mixture and cleaving the auxiliary group. Alternatively, when the molecule contains a basic functional group (such as amino) or an acidic functional group (such as carboxyl), the compound reacts with an appropriate optically active acid or base to form a salt of the diastereomeric isomer which is then subjected to diastereomeric resolution through the conventional method in the art to give the pure enantiomer. In addition, the enantiomer and the diastereoisomer are generally isolated through chromatography which uses a chiral stationary phase and optionally combines with a chemical derivative method (such as carbamate is generated from amine). The compound of the present disclosure may contain an unnatural proportion of atomic isotope on one or more than one atom(s) constituting the compound. For example, the compound can be radiolabeled with a radioactive isotope, such as tritium ($^3$H), iodine-125 ($^{125}$I) or C-14 ($^{14}$C). For another example, deuterated drugs can be formed by replacing hydrogen with deuterium, the bond formed by deuterium and carbon is stronger than that of ordinary hydrogen and carbon, compared with non-deuterated drugs, deuterated drugs have the advantages of reduced toxic and side effects, increased drug stability, enhanced efficacy, extended biological half-life of drugs, etc. All isotopic variations of the compound of the present disclosure, whether radioactive or not, are encompassed within the scope of the present disclosure. The term "optional" or "optionally" means that the subsequent event or condition may occur but not requisite, that the term includes the instance in which the event or condition occurs and the instance in which the event or condition does not occur.

The term "substituted" means one or more than one hydrogen atom(s) on a specific atom are substituted by the substituent, including deuterium and hydrogen variants, as long as the valence of the specific atom is normal and the substituted compound is stable. When the substituent is an oxygen (i.e. =O), it means two hydrogen atoms are substituted. Positions on an aromatic ring cannot be substituted by a ketone. The term "optionally substituted" means an atom can be substituted by a substituent or not, unless otherwise specified, the type and number of the substituent may be arbitrary as long as being chemically achievable.

When any variable (such as R) occurs in the constitution or structure of the compound more than once, the definition of the variable at each occurrence is independent. Thus, for example, if a group is substituted by 0-2 R, the group can be optionally substituted by up to two R, wherein the definition of R at each occurrence is independent. Moreover, a combination of the substituent and/or the variant thereof is allowed only when the combination results in a stable compound.

When the number of a linking group is 0, such as —(CRR)$_0$—, it means that the linking group is a single bond.

When one of the variables is a single bond, it means that the two groups linked by the single bond are connected directly. For example, when L in A-L-Z represents a single bond, the structure of A-L-Z is actually A-Z.

When a substituent is vacant, it means that the substituent does not exist. For example, when X is vacant in A-X, the structure of A-X is actually A. When a substituent is attachable to more than one atom on a ring, such substituent can be bonded to any atom of the ring. For example, when pyridyl acts as a substituent, it can be linked to the group to be substituted by any carbon atom on the pyridine ring.

When the enumerative linking group does not indicate the direction for linking, the direction for linking is arbitrary, for example, the linking group L contained in

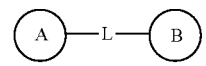

is -M-W—, then -M-W— can link ring A and ring B to form

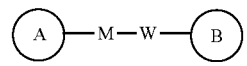

in the direction same as left-to-right reading order, and form

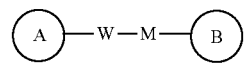

in the direction contrary to left-to-right reading order. A combination of the linking group, substituent and/or variants thereof is allowed only when such combination can result in a stable compound.

Unless otherwise specified, the term "$C_{1-6}$ alkyl" refers to a linear or branched saturated hydrocarbon group containing 1 to 6 carbon atoms. The $C_{1-6}$ alkyl includes $C_{1-5}$, $C_{1-4}$, $C_{1-3}$, $C_{1-2}$, $C_{2-6}$, $C_{2-4}$, $C_6$ and $C_5$ alkyl, etc. It can be monovalent (such as methyl), divalent (such as methylene) or multivalent (such as methine). Examples of $C_{1-6}$ alkyl include but are not limited to methyl (Me), ethyl (Et), propyl (including n-propyl and isopropyl), butyl (including n-butyl, isobutyl, s-butyl, and t-butyl), pentyl (including n-pentyl, isopentyl and neopentyl), hexyl, etc.

Unless otherwise specified, the term "$C_{1-3}$ alkyl" refers to a linear or branched saturated hydrocarbon group containing 1 to 3 carbon atoms. The $C_{1-3}$ alkyl includes $C_{1-2}$ and $C_{2-3}$ alkyl and the like; it can be monovalent (such as methyl), divalent (such as methylene) or multivalent (such as methine). Examples of $C_{1-3}$ alkyl include but are not limited to methyl (Me), ethyl (Et), propyl (including n-propyl and isopropyl), etc.

The term "heteroalkyl" by itself or in combination with another term refers to a stable linear chain, branched alkyl or a combination thereof which has a specified number of carbon atoms and at least one heteroatom. In some embodiments, a heteroatom is selected from B, O, N and S, wherein nitrogen and sulfur atoms are optionally oxidized and the nitrogen heteroatom is optionally quaternized. In other embodiments, the heteroatom group is selected from —C(=O)O—, —C(=O)—, —C(=S)—, —S(=O), —S(=O)$_2$—, —C(=O)N(H)—, —N(H)—, —C(=NH)—, —S(=O)$_2$N(H)— and —S(=O)N(H)—. In some embodiments, wherein the heteroalkyl is $C_{1-6}$ heteroalkyl. In other embodiments, wherein the heteroalkyl is $C_{1-3}$ heteroalkyl. The heteroatom or heteroatom group can be located at any internal position of a heteroalkyl including the position where the alkyl connects to the rest part of the molecule. However, the terms "alkoxy", "alkylamino" and "alkylthio" (or thioalkoxy) are used by the conventional expressions and refer to an alkyl group that is connected to the rest part of the molecule via an oxygen atom, an amino or a sulfur atom respectively. Examples include, but are not limited to, —OCH₃, —OCH₂CH₃, —OCH₂CH₂CH₃, —OCH₂(CH₃)₂, —CH₂—CH₂—O—CH₃, —NHCH3, —N(CH₃)₂, —NHCH2CH₃, —N(CH₃)(CH₂CH₃), —CH₂—CH₂—NH—CH₃, —CH₂—CH₂—N(CH₃)—CH₃, —SCH₃, —SCH₂CH₃, —SCH₂CH₂CH₃, —SCH₂(CH₃)₂, —CH₂—S—CH₂—CH₃, —CH₂—CH₂, —S(=O)—CH₃, —CH₂—CH₂—S(=O)₂—CH₃ Up to two consecutive heteroatoms can be present, such as, —CH₂—NH—OCH₃.

Unless otherwise specified, the term "$C_{1-3}$ alkoxy" refers to those alkyl containing 1 to 3 carbon atoms that are connected to the rest of the molecule by one oxygen atom. The $C_{1-3}$ alkoxy group includes $C_{1-2}$, $C_{2-3}$, $C_3$ and $C_2$ alkoxy. Examples of $C_{1-3}$ alkoxy include, but are not limited to, methoxy, ethoxy, propoxy (including n-propoxy and iso-propoxy) and the like.

Unless otherwise specified, "$C_{3-6}$ cycloalkyl" refers to a saturated cyclic hydrocarbyl consisting of 3 to 6 carbon atoms, which is a monocyclic and bicyclic system, and the $C_{3-6}$ cycloalkyl includes $C_{3-5}$, $C_{4-5}$ and $C_{5-6}$ cycloalkyl, etc; it can be monovalent, divalent or polyvalent. Examples of $C_{3-6}$ cycloalkyl include, but are not limited to, cyclopropyl, cyclobutyl, cyclopentyl, cyclohexyl, and the like.

Unless otherwise specified, the term "4-6 membered heterocycloalkyl" by itself or in combination with other terms, refers to a saturated cyclic group consisting of 4 to 6 ring atoms, respectively, of which 1, 2, 3 or 4 ring atoms are independently selected from O, S and N heteroatoms, the rest are carbon atoms, wherein the nitrogen atom is optionally quatemized, and the nitrogen and sulfur heteroatoms are optionally oxidized (i.e. NO and S(O)$_P$, p is 1 or 2). It includes both monocyclic and bicyclic systems, wherein the bicyclic system includes a spiro ring, a fused ring, and a bridge ring. In addition, for the "4-6 membered heterocycloalkyl", a heteroatom may occupy connection position of the heterocycloalkyl to the rest of the molecule. The 4-6 membered heterocycloalkyl includes 4-6 membered, 4 membered, 5-membered and 6-membered heterocycloalkyl. Examples of 4-6 membered heterocycloalkyl include, but are not limited to, azetidinyl, oxetanyl, thietanyl, pyrrolidinyl, pyrazolidinyl, imidazolidinyl, tetrahydrothiophenyl (including tetrahydrothiophen-2-yl and tetrahydrothiophen-3-yl, etc.), tetrahydrofuranyl (including tetrahydrofuran-2-yl, etc.), tetrahydropyranyl, piperidinyl (including 1-piperidinyl, 2-piperidinyl and 3-piperidinyl, etc.), piperazinyl (including 1-piperazinyl and 2-piperazinyl, etc.), morpholinyl (including 3-morpholinyl and 4-morpholinyl, etc.), dioxanyl, dithianyl, isoxazolidinyl, isothiazolidinyl, 1,2-oxazinyl, 1,2-thiazinyl, hexahydropyridazinyl, homopiperazinyl or homopiperidinyl and the like.

Unless otherwise specified, the term "5-6 membered heterocycloalkenyl" by itself or in combination with other terms, refers to a partially unsaturated cyclic group consisting of 5 to 6 ring atoms with at least one carbon-carbon double bond, respectively, of which 1, 2, 3 or 4 ring atoms are independently selected from O, S and N heteroatoms, the rest are carbon atoms, wherein the nitrogen atom is optionally quatemized, and the nitrogen and sulfur heteroatoms are optionally oxidized (i.e. NO and S(O)$_P$, p is 1 or 2). It includes both monocyclic and bicyclic systems, wherein the bicyclic system includes a spiro ring, a fused ring, and a bridge ring, and any ring in the systems is non-aromatic. In addition, for the "5-6 membered heterocycloalkenyl", a heteroatom may occupy connection position of the heterocycloalkenyl to the rest of the molecule. The 5-6 membered heterocycloalkyl includes 5-membered and 6-membered heterocycloalkenyl. Examples of 5-6 membered heterocycloalkenyl include, but are not limited to

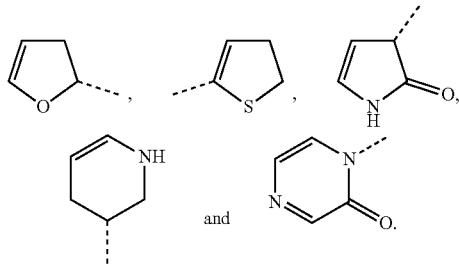

Unless otherwise specified, the terms "5-10 membered heteroaryl ring" and "5-10 membered heteroaryl" of the present disclosure can be used interchangeably. The term "5-10 membered heteroaryl" refers to a cyclic group consisting of 5 to 10 ring atoms with a X-conjugated electron system, wherein 1, 2, 3 or 4 ring atoms are heteroatoms respectively selected from O, S and N, the rest are carbon atoms. It can be monocyclic, fused bicyclic, or fused tricyclic system, wherein each ring is aromatic. The nitrogen atom is optionally quatemized, and the nitrogen and sulfur heteroatoms are optionally oxidized (i.e. NO and S(O)$_P$, p is 1 or 2). The 5-10 membered heteroaryl can be connected to the rest part of the molecule via heteroatom or carbon atom. The 5-10 membered heteroaryl includes 5-8 membered, 5-7 membered, 5-6membered, 5 membered, and 6 membered heteroaryl. Examples of the 5-10 membered heteroaryl include, but are not limited to, pyrrolyl (including N-pyrrolyl, 2-pyrrolyl and 3-pyrrolyl etc.), pyrazolyl (including 2-pyrazolyl and 3-pyrazolyl etc.), imidazolyl (including N-imidazolyl, 2-imidazolyl, 4-imidazolyl and 5-imidazolyl, etc.), oxazolyl (including 2-oxazolyl, 4-oxazolyl and 5-oxazolyl, etc.), triazolyl (1H-1,2,3-triazolyl, 2H-1,2,3-triazolyl, 1H-1,2,4-triazolyl and 4H-1,2,4-triazolyl, etc.), tetrazolyl, isoxazolyl (3-isoxazolyl, 4-isoxazolyl and 5-isoxazolyl, etc.), thiazolyl (including 2-thiazolyl, 4-thiazolyl and 5-thiazolyl, etc.), furanyl (including 2-furanyl and 3-furanyl, etc.), thienyl (2-thienyl and 3-thienyl, etc.), pyridyl (including 2-pyridyl, 3-pyridyl, 4-pyridyl, etc.), pyrazinyl, pyrimidinyl (including 2-pyrimidinyl and 4-pyrimidinyl, etc.), benzthiazolyl (including 5-benzothiazolyl, etc.), purinyl, benzimidazolyl (including 2-benzimidazolyl, etc.), benzoxazolyl, indolyl (including 5-indolyl, etc.), isoquinolinyl (including 1-isoquinolinyl and 5-isoquinolinyl, etc.), quinoxalinyl (including 2-quinoxalinyl and 5-quinoxalinyl, etc.) or quinolinyl (including 3-quinolinyl and 6-quinolinyl, etc.).

Unless otherwise specified, $C_{n-n+m}$ or $C_n$-$C_{n+m}$ includes any specific case of n to n+m carbons, for example, $C_{1-12}$ includes $C_1$, $C_2$, $C_3$, $C_4$, $C_5$, $C_6$, $C_7$, $C_8$, $C_9$, $C_{10}$, $C_{11}$, and $C_{12}$, also includes any range from n to n+m, for example, $C_{1-12}$ includes $C_{1-3}$, $C_{1-6}$, $C_{1-9}$, $C_{3-6}$, $C_{3-9}$, $C_{3-12}$, $C_{6-9}$, $C_{6-12}$, and $C_{9-12}$, etc.; in the same way, n to n+m means that the number of atoms in the ring is n to n+m, for example, 3-12 membered rings include 3 member ring, 4-membered ring, 5-membered ring, 6-membered ring, 7-membered ring, 8-membered ring, 9-membered ring, 10-membered ring, 11-membered ring, and 12-membered ring, also includes any range from n to n+m, for example, 3-12 membered rings include 3-6 member ring, 3-9 member ring, 5-6 member ring, 5-7 member ring, 6-7 member ring, 6-8 member ring, and 6-10 member ring, and the like.

The term "leaving group" refers to a functional group or atom that can be replaced by another functional group or atom through a substitution reaction (e.g., an affinity substitution reaction). For example, representative leaving groups include triflate; chlorine, bromine, and iodine; sulfonate group such as mesylate, tosylate, p-bromobenzenesulfonate, and p-toluenesulfonate, and the like; acyloxy, such as acetoxy, trifluoroacetoxy, and the like.

The term "protecting group" includes, but is not limited to "amino protecting group", "hydroxy protecting group" or "thio protecting group". The term "amino protecting group" refers to a protecting group suitable for blocking the side reaction on the nitrogen of an amino. Representative amino protecting groups include, but are not limited to: formyl; acyl, such as alkanoyl (e.g, acetyl, trichloroacetyl or trifluoroacetyl); alkoxycarbonyl, such as tert-butoxycarbonyl (Boc); arylmethoxycarbonyl such as benzyloxycarbonyl (Cbz) and 9-fluorenylmethoxycarbonyl (Fmoc); arylmethyl such as benzyl (Bn), trityl (Tr), 1,1-bis-(4'-methoxyphenyl)methyl; silyl such as trimethylsilyl (TMS) and tert-butyldimethylsilyl (TBS) and the like. The term "hydroxy protecting group" refers to a protecting group suitable for blocking the side reaction on hydroxy. Representative hydroxy protecting groups include, but are not limited to: alkyl such as methyl, ethyl and tert-butyl; acyl such as alkanoyl (e.g, acetyl); arylmethyl such as benzyl (Bn), p-methoxybenzyl (PMB), 9-fluorenylmethyl (Fm), and diphenylmethyl (DPM); silyl such as trimethylsilyl (TMS) and tert-butyl dimethyl silyl (TBS) and the like.

The compounds of the present disclosure can be prepared by a variety of synthetic methods well known to those skilled in the art, including the following enumerative embodiment, the embodiment formed by the following enumerative embodiment in combination with other chemical synthesis methods and the equivalent replacement well known to those skilled in the art. The preferred embodiments include, but are not limited to, the embodiments of the present disclosure.

The solvents used in the present disclosure are commercially available. The present disclosure employs the following abbreviations: aq stands for water; HATU stands for O-(7-azabenzotriazol-1-yl)-N,N,N',N'-tetramethyluronium hexafluorophosphate; EDC stands for N-(3-dimethylaminopropyl)-N'-ethylcarbodiimide hydrochloride; m-CPBA stands for 3-chloroperoxybenzoic acid; eq stands for equivalent; CDI stands for carbonyldiimidazole; DCM stands for dichloromethane; PE stands for petroleum ether; DIAD stands for diisopropyl azodicarboxylate; DMF stands for N,N-dimethylformamide; DMSO stands for dimethyl sulfoxide; EtOAc stands for ethyl acetate, EtOH stands for ethanol; MeOH stands for methanol; CBz stands for benzyloxycarbonyl, which is an amine protecting group; BOC stands for tert-butoxycarbonyl, which is an amine protecting group; HOAc stands for acetic acid; NaCNBH$_3$ stands for sodium cyanoborohydride; r.t. stands for room temperature; O/N stands for overnight; THF stands for tetrahydrofuran; Boc$_2$O stands for di-tert-butyldicarbonate; TFA stands for trifluoroacetic acid; DIPEA stands for diisopropylethylamine; SOCl$_2$ stands for thionyl chloride, CS$_2$ stands for carbon disulfide; TsOH stands forp-toluenesulfonic acid; NFSI stands for N-fluoro-N-(phenylsulfonyl)benzenesulfonamide; NCS stands for 1-chloropyrrolidine-2,5-dione; n-Bu$_4$NF stands for tetrabutylammonium fluoride; iPrOH stands for 2-propanol; mp stands for melting point; LDA stands for lithium diisopropylamide; Pd(dppf)Cl$_2$ stands for [1,1'-Bis(diphenylphosphino)ferrocene]dichloropalladium (II).

The compounds are named manually or by ChemDraw® software, and commercially available compounds use their vendor directory names.

Technical Effect

Based on the analysis of c-Met and FGFR dual kinase proteins, a highly active small molecule core that inhibits both c-Met and FGFR was found. This dual-target inhibitor will potentially reduce tumor cell-dependent escape and greatly improve the effectiveness of tumor therapy, meanwhile is expected to act on these targets.

Specific Embodiment

The following embodiments further illustrate the present disclosure, but the present disclosure is not limited thereto. The present disclosure has been described in detail herein, and its specific embodiments are also disclosed. It is obvious for those skilled in the art to make various changes and improvements to the specific embodiments of the present disclosure without departing from the spirit and scope of the present disclosure.

Process A1

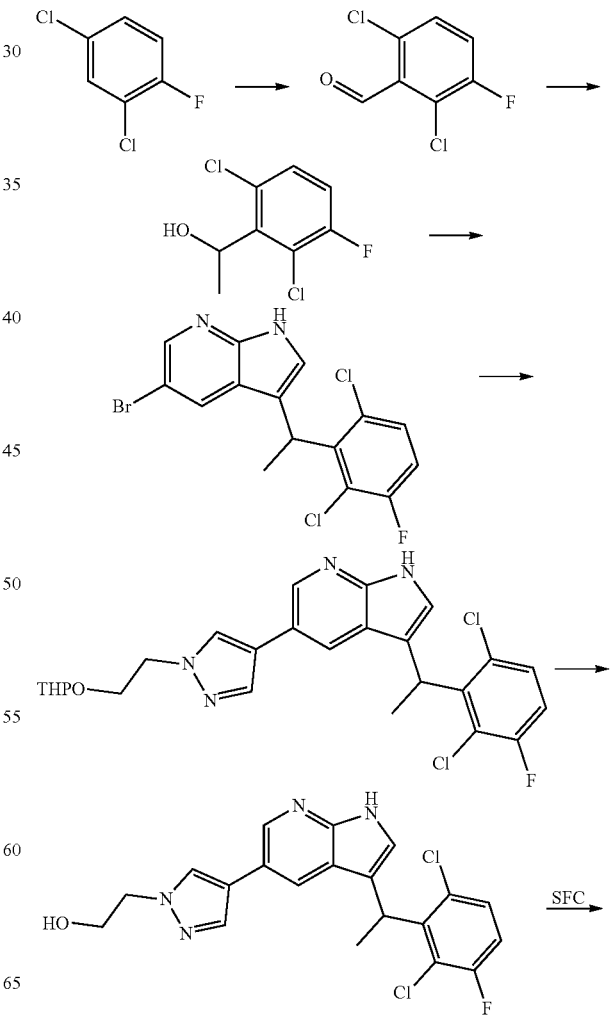

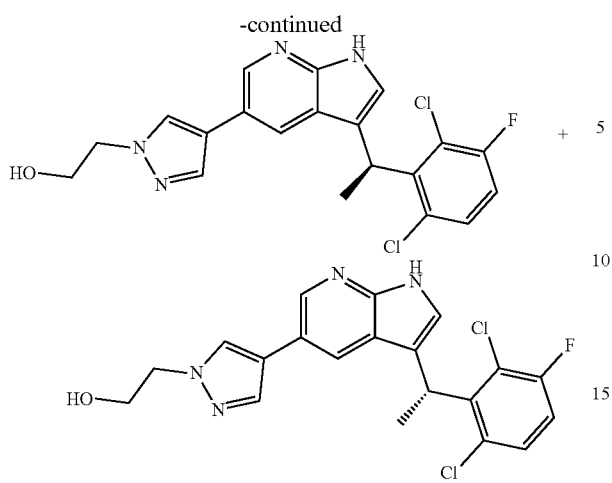

Comparative Embodiment 1a, 1b

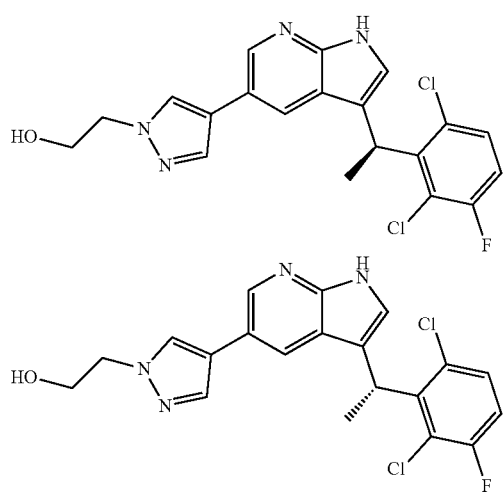

Comparative Embodiment 1A

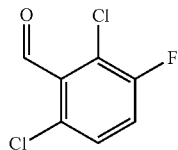 [SMILES: O=Cc1c(Cl)ccc(F)c1Cl]

n-Butyllithium (2.5 M, 2.91 mL) was added dropwise to a solution of 2,4-dichloro-1-fluorobenzene (1 g, 6.06 mmol) in tetrahydrofuran (10 mL) at −78° C. under nitrogen protection. After stirring for one hour, methyl formate (436.76 mg, 7.27 mmol) was added dropwise to the reaction solution under stirring. Finally, the reaction was allowed to run under nitrogen protection at 10-15° C. for 16 hours, 5 mL of saturated ammonium chloride aqueous solution was added to quench the reaction. The mixture was stirred for 10 minutes and then partitioned directly, and the aqueous phase was extracted with 10 mL of ethyl acetate. The combined organic phase was rotary-evaporated to dryness to obtain a crude product. The crude product was slurried with n-hexane (5 mL), and then filtered. The filtrate was rotary-evaporated to dryness to obtain comparative embodiment 1A as a white solid (1 g, yield: 85.49%).

$^1$H NMR (400 MHz, CHLOROFORM-d) δ 10.46 (s, 1H), 7.38-7.42 (m, 1H), 7.29-7.33 (m, 1H).

Comparative Embodiment 1B

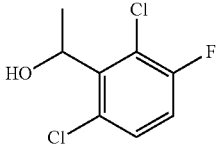

Methyl Grignard reagent (2.5 M, 6.22 mL) was added dropwise slowly to a solution of comparative embodiment LA (2 g, 10.36 mmol) in tetrahydrofuran (10 mL) at 0° C. The reaction was allowed to run under nitrogen protection at 15-20° C. for 16 hours, 2 mL of dilute hydrochloric acid (0.5 M) was added to quench the reaction, then 20 mL of water and 20 mL of ethyl acetate were added to extract the mixture. The aqueous phase was then extracted with 20 mL of ethyl acetate. The combined organic phase was dried over anhydrous sodium sulfate, and rotary-evaporated to dryness to obtain a crude product. The crude product was purified by chromatography on a silica gel column (petroleum ether/ethyl acetate=5/1) to obtain comparative example 1B as a yellow oil (1 g, yield: 46.16%).

$^1$H NMR (400 MHz, CHLOROFORM-d) δ 7.25-7.29 (m, 1H), 7.01-7.05 (m, 1H), 5.56-5.62 (m, 1H), 2.89-2.92 (d, J=10.4 Hz, 1H), 1.65-1.66 (d, J=6.8 Hz, 3H).

Comparative Embodiment 1C

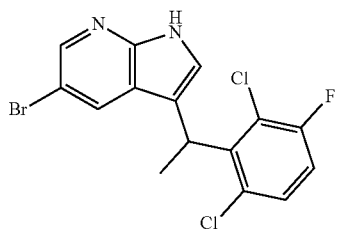 [SMILES: CC(c1c(Cl)ccc(F)c1Cl)c1c[nH]c2ncc(Br)cc12]

The product of comparative example 1B (900 mg, 4.31 mmol), 5-bromo-7-azaindole (424.14 mg, 2.15 mmol) and trifluoromethanesulfonic acid (1.94 g, 12.92 mmol) were added to dichloromethane (20 mL). The reaction was allowed to run at 10-20° C. for 16 hours under nitrogen protection. 20 mL of water and 20 mL of dichloromethane were added to extract the reaction solution. The aqueous phase was then extracted with 20 mL of dichloromethane. The combined organic phase was dried over anhydrous sodium sulfate, and rotary-evaporated to dryness to obtain a crude product. The crude product was purified by chromatography on a silica gel column (petroleum ether/ethyl acetate=5/1) to obtain the comparative embodiment 1C as yellow solid (400 mg, yield: 23.94%).

LCMS (ESI) m/z: 386.9 388.9 (M+1)$^+$

Comparative Embodiment 1D

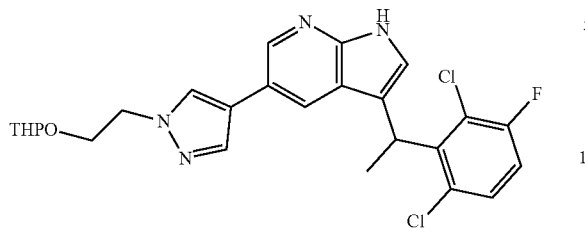

The product of comparative embodiment 1C (400 mg, 1.03 mmol), the product of embodiment 1I (398.54 mg, 1.24 mmol), Pd(dppf)Cl$_2$ (75.42 mg, 103.08 μmol) and potassium phosphate (712.10 mg, 3.09 mmol) were added to water (3 mL) and dioxane (6 mL), then the reaction solution was heated to 100° C. in a microwave synthesizer and reacted for 0.5 hour under nitrogen protection. 10 mL of water and 10 mL of ethyl acetate were added to extract the reaction solution. The aqueous phase was then extracted with 10 mL of ethyl acetate. The combined organic phase was dried over anhydrous sodium sulfate, and rotary-evaporated to dryness to obtain comparative embodiment 1D (300 mg, yield: 57.82%).

LCMS (ESI) m/z: 503.2 (M+1)$^+$

Comparative Embodiment 1E

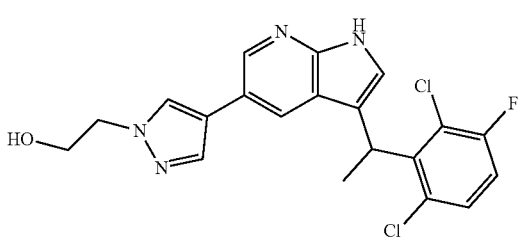 [SMILES: CC(c1c(Cl)ccc(F)c1Cl)c1c[nH]c2ncc(-c3cnn(CCO)c3)cc12]

The product of comparative embodiment 1D (30 mg, 59.60 μmol) and hydrogen chloride/ethyl acetate (4 M, 0.1 mL) were added to methanol (2 mL). The reaction solution was stirred at 20° C. for 16 hours under nitrogen protection. The reaction solution was directly rotary-evaporated at a low temperature to dryness to obtain a crude product. The crude product was separated by preparative chromatograph (μm column: YMC-Actus Triart C18 100*30 mm*5 μm; mobile phase: [water (0.05% hydrochloric acid)-ACN]; B %: 40%-60%, 7 min) to obtain the product. Finally, comparative embodiment 1E was obtained as a yellow oil (10 mg, yield: 40.02%).

LCMS (ESI) m/z: 419.1 (M+1)$^+$ $^1$H NMR (400 MHz, METHANOL-d$_4$) δ 8.60 (s, 1H), 8.04 (s, 1H), 8.01 (s, 1H), 7.78 (s, 1H), 7.73 (m, 1H), 7.03-7.26 (m, 1H), 5.37-5.43 (m, 1H), 4.30 (t, J=5.6 Hz, 2H), 3.93 (t, J=5.0 Hz, 2H), 1.96 (d, J=7.2 Hz, 3H).

Comparative Embodiment 1a, 1b

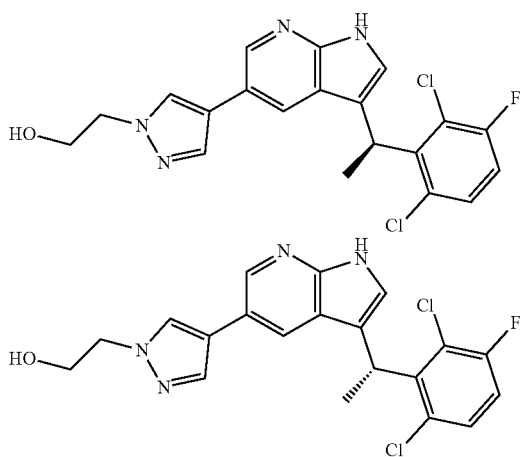

The product of comparative embodiment 1E (100 mg, 238.50 μmol) was treated with SFC chiral separation. SFC condition (column: YMC CHIRAL Amylose-C (250 mm*30 mm, 10 μm; mobile phase: [0.1% NH$_3$H$_2$O EtOH]; B %: 55%-55%, min). After chiral separation, the eluents were rotary-evaporated to dryness, two products were obtained: comparative embodiment 1a (relative retention time thereof was 4.20 min) and comparative embodiment 1b (relative retention time thereof was 11.30 min).

Comparative Embodiment 1a

LCMS (ESI) m/z: 419.1 (M+1)$^+$ $^1$H NMR (400 MHz, METHANOL-d$_4$) δ 8.32 (m, 1H), 7.84 (s, 1H), 7.61 (s, 1H), 7.50-7.32 (m, 3H), 7.19 (m, 1H), 5.25-5.30 (m, 1H), 5.25 (t, J=5.2 Hz, 2H), 3.91 (t, J=5.6 Hz, 2H), 1.88 (d, J=7.2 Hz, 3H).

Comparative Embodiment 1 b

LCMS (ESI) m/z: 419.1 (M+1)$^+$ $^1$H NMR (400 MHz, METHANOL-d$^4$) δ 8.20 (m, 1H), 7.72 (s, 1H), 7.49 (s, 1H), 7.25-7.28 (m, 3H), 7.05-7.09 (m, 1H), 5.13-5.19 (m, 1H), 4.13 (t, J=5.6 Hz, 2H), 3.79 (t, J=5.2 Hz 2H), 1.76 (d, J=7.2 Hz, 3H).

Process B

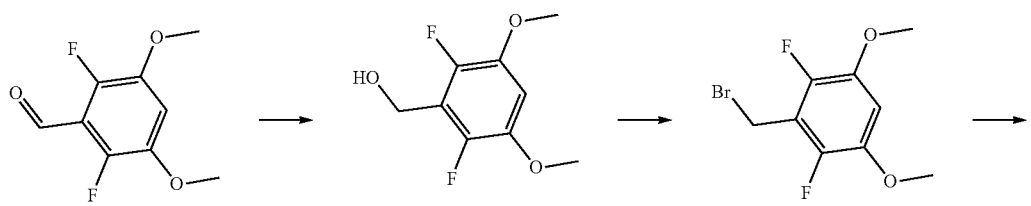

-continued
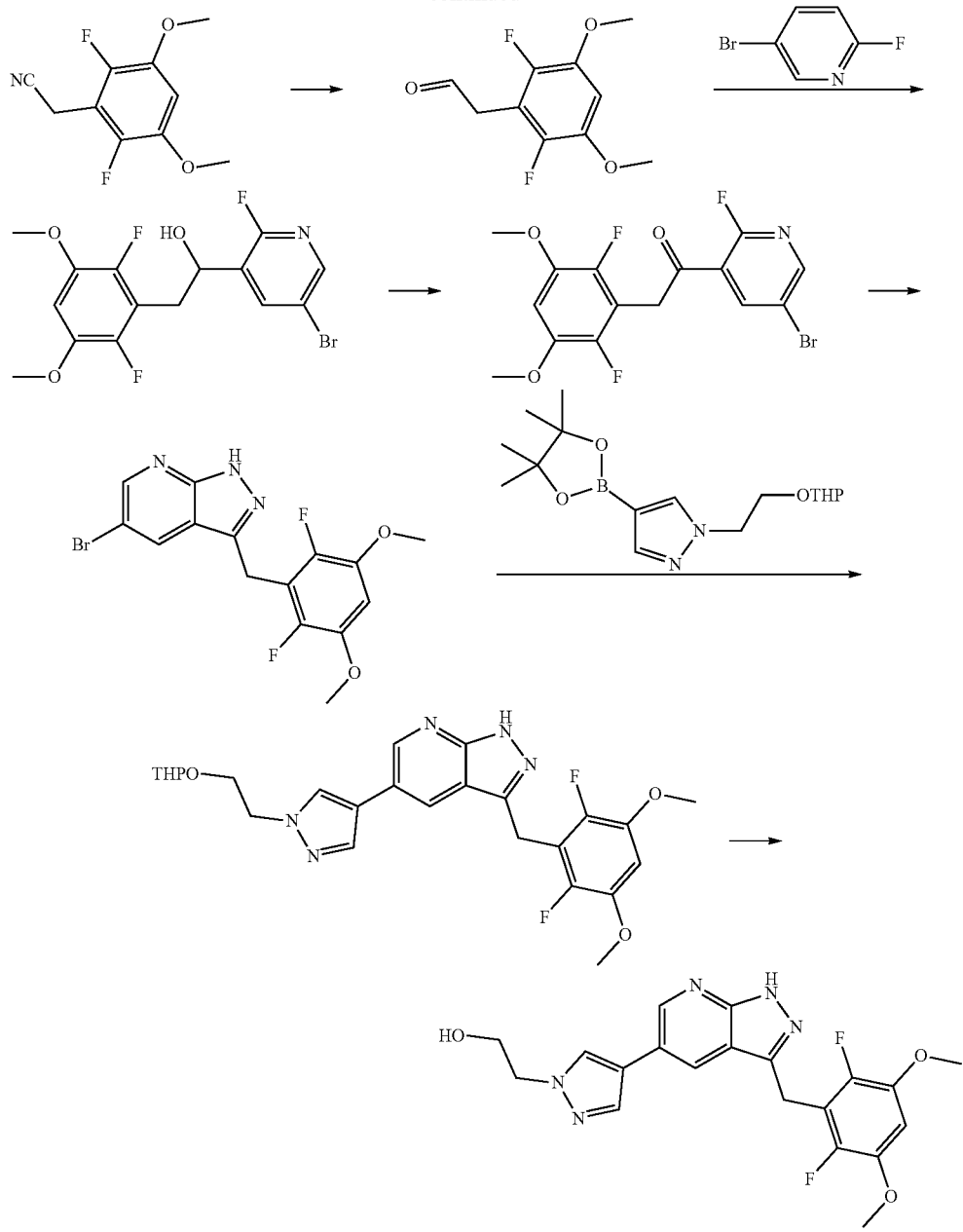
Embodiment 1
Embodiment 1A
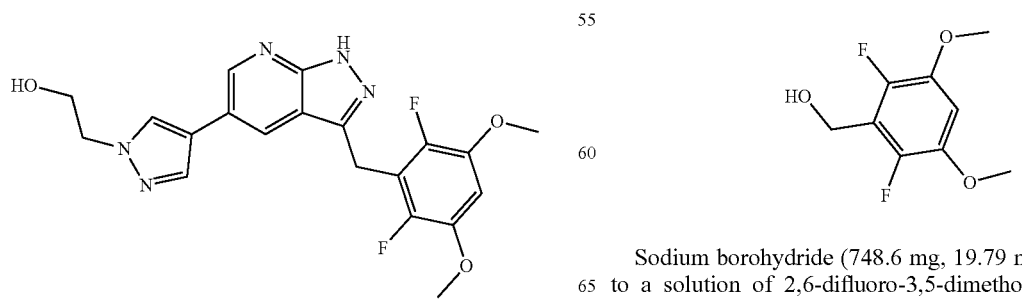
Sodium borohydride (748.6 mg, 19.79 mmol) was added to a solution of 2,6-difluoro-3,5-dimethoxy-benzaldehyde (2.0 g, 9.89 mmol) in tetrahydrofuran (20 mL) at 0° C. in batches. After the addition was completed, the reaction solution was slowly warmed to 20° C. and the reaction was allowed to stir for 6 hours. Dilute hydrochloric acid (5 mL, 2 M) was added to quench the reaction, then water (15 mL), and ethyl acetate (15 mL×2) was added to extract the reaction solution. The organic phase was washed with saturated brine (15 mL), dried over anhydrous sodium sulfate, filtered, and the filtrate was directly rotary-evaporated to dryness to obtain embodiment 1A, which was directly used in the next step.

LCMS (ESI) m/z: 204.2 (M+1)$^+$

Embodiment 1B

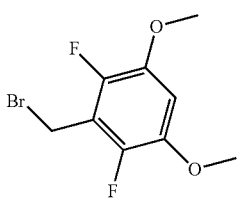

Phosphorus tribromide (3.82 g, 14.11 mmol, 1.2 eq) was slowly added to a solution of the product of embodiment 1A (2.4 g, 11.75 mmol) in tetrahydrofuran (30 mL) at 0° C. The reaction solution was stirred at 0° C. for 2 hours. The reaction solution was added with water (20 mL) and extracted with ethyl acetate (20 mL×2). The combined organic phase was washed with saturated sodium bicarbonate solution (15 mL) and brine (15 mL), dried over anhydrous sodium sulfate, and filtered. The filtrate was rotary-evaporated to dryness, and separated by flash chromatography on a silica gel column (petroleum ether/ethyl acetate=1/0 to 10/1) to obtain the product of embodiment 1B.

Embodiment 1C

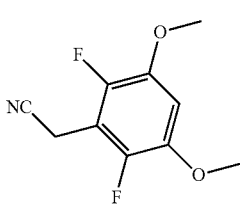

Sodium cyanide (330.30 mg, 6.74 mmol) was added to a solution of the product of embodiment 1B (1.5 g, 5.62 mmol) in EtOH (10 mL) and H$_2$O (10 mL), and the reaction solution was stirred at 80° C. for 4 hours. The reaction solution was cooled to room temperature, added with water (20 mL), extracted with ethyl acetate (20 mL×2), washed with saturated brine (20 mL), dried, and filtered. The filtrate was rotary-evaporated to dryness to obtain the product of embodiment 1C.

Embodiment 1D

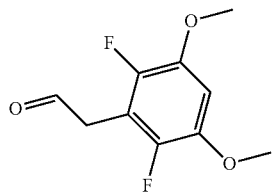

A solution of diisobutylaluminum hydride (DIBAL-H) in toluene (1 M, 9.38 mL) was slowly added dropwise to a solution of the product of embodiment 1C (1 g, 4.69 mmol) in toluene (10 mL) at −50° C. After the completion of addition, the reaction solution was stirred at −50° C. for 2 hours. The reaction solution was heated to room temperature. Dilute hydrochloric acid (1 M, 30 mL) aqueous solution was added to quench the reaction, then the mixture was stirred for 30 min, added with water (20 mL), and extracted with ethyl ester (30 mL×2). The combined organic phase was washed with saturated brine (20 mL), dried over anhydrous sodium sulfate, filtered, and concentrated in vacuo. The residue was separated and purified by flash chromatography on a silica gel column (petroleum ether:ethyl acetate=5:1) to obtain the product of embodiment 1D.

Embodiment 1E

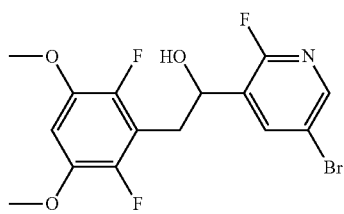 [SMILES: COc1cc(OC)c(F)c(CC(O)c2cc(Br)cnc2F)c1F]

Lithium diisopropylamide (LDA) (2 M, 2.68 mL) was slowly added to a solution of 2-fluoro-5-bromopyridine (708.24 mg, 4.02 mmol) in tetrahydrofuran (10 mL) at −78° C. After the completion of addition, the reaction solution was stirred at −78° C. for 30 minutes, and then a solution of the product of embodiment 1D (580 mg, 2.68 mmol) in tetrahydrofuran (10 mL) was slowly added dropwise to the above solution. The reaction solution was stirred for 1.5 hours at −78° C. The reaction solution was warmed to 0° C. The reaction was quenched with ammonium chloride aqueous solution (10 mL), and the resulting mixture was added with water (10 mL), and extracted with ethyl ester (15 mL*2). The combined organic phase was washed with saturated brine (15 mL), dried over anhydrous sodium sulfate, filtered, and concentrated in vacuo. The residue was separated and purified by flash chromatography on a silica gel column (petroleum ether:ethyl acetate=10:1) to obtain the product of embodiment 1E.

LCMS (ESI) m/z: 392.1 (M+1)$^+$

Embodiment 1F

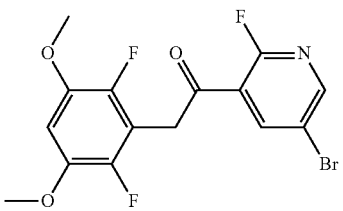 [SMILES: COc1cc(OC)c(F)c(CC(=O)c2cc(Br)cnc2F)c1F]

Dess-Martin reagent (DMP) (973.38 mg, 2.29 mmol) was added to a solution of the product of embodiment 1E (450 mg, 1.15 mmol) in dichloromethane (5 mL). The reaction solution was stirred at 26° C. for 16 hours. The reaction solution was filtered, and the filtrate was directly rotary-evaporated to dryness. The residue was separated and purified by flash chromatography on a silica gel column (petroleum ether:ethyl acetate=5:1) to obtain the product of embodiment 1F.

LCMS (ESI) m/z: 389.9 (M+1)$^+$

Embodiment 1G

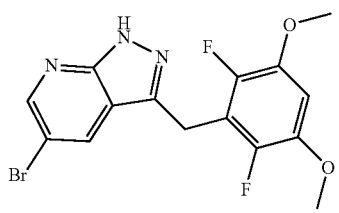 [SMILES: COc1cc(OC)c(F)c(Cc2n[nH]c3ncc(Br)cc23)c1F]

Hydrazine hydrate (294.59 mg, 5.77 mmol, 85% purity) was added to a solution of the product of embodiment 1F (450 mg, 1.15 mmol) in ethanol (6 mL), and the reaction solution was stirred at 100° C. for 1 hour. The reaction solution was directly rotary-evaporated to dryness to obtain the product of embodiment 1G.

LCMS (ESI) m/z: 384.1 (M+1)$^+$

Embodiment 1H

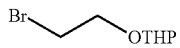

Methanesulfonic acid (1.15 g, 12.00 mmol) and 3,4-dihydropyran (7.40 g, 88.03 mmol) were added to a solution of 2-bromoethanol (10 g, 80.02 mmol) in dichloromethane (100 mL) at 0° C., and the reaction solution was stirred at 0° C. for 4 hours. Water (10 mL) was added to quench the reaction, and the resulting mixture was neutralized to pH of 7-8 with sodium bicarbonate aqueous solution. The mixture was added with water (50 mL), extracted with dichloromethane (100 mL×2), washed with saturated brine (100 mL), dried, filtered, and concentrated to obtain the product of embodiment 1H.

$^1$H NMR (400 MHz, CHLOROFORM-d) δ 4.68 (t, J=3.51 Hz, 1H), 3.98-4.06 (m, 1H), 3.85-3.94 (m, 1H), 3.73-3.82 (m, 1H), 3.45-3.57 (m, 3H), 1.41-1.91 (m, 8H).

Embodiment 1I

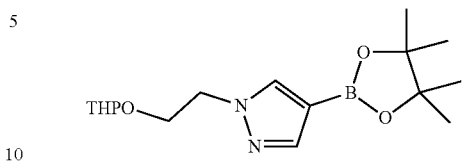

4-Pyrazoleboronic acid pinacol ester (25 g, 128.84 mmol), the product of embodiment 1H (53.88 g, 257.68 mmol) and potassium carbonate (35.61 g, 257.68 mmol) were weighed, and added to N,N-dimethylformamide (100 mL). The reaction solution was stirred at 60° C. for 16 hours. The reaction solution was added with 700 mL of water, and extracted with ethyl acetate (300 mL×3). The combined organic phase was dried over anhydrous sodium sulfate, filtered, and concentrated under reduced pressure to obtain a crude product. The crude product was separated by flash chromatography on a silica gel column (petroleum ether/ethyl acetate=1/0 to 1/1) to obtain the product of embodiment 1I.

$^1$H NMR (400 MHz, CHLOROFORM-d) δ 7.77 (s, 1H), 7.76 (s, 1H), 4.49-4.51 (m, 1H), 4.31-4.33 (m, 2H), 4.03-4.10 (m, 2H), 3.60-3.75 (m, 2H), 1.45-1.68 (m, 6H), 1.30 (s, 12H).

Embodiment 1J

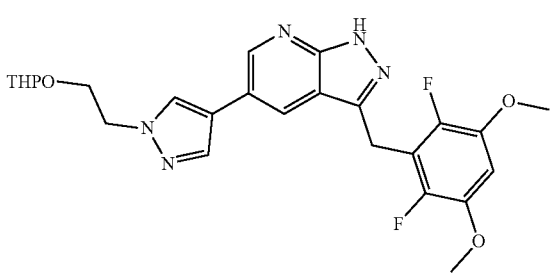

A suspension of the product of embodiment 1G (60 mg, 156.18 μmol), the product of embodiment 1I (55.35 mg, 171.80 μmol), Pd(dppf)Cl$_2$ (5.71 mg, 7.81 μmol) and potassium carbonate (43.17 mg, 312.36 μmol) in dioxane (2 mL) and water (1 mL) was heated to 100° C. under nitrogen protection and the reaction was allowed to run for 2 hours. The reaction solution was cooled, added with water (5 mL), and extracted with ethyl acetate (5 mL×2). The combined organic phase was washed with saturated brine (5 mL), dried over anhydrous sodium sulfate, filtered, and rotary-evaporated to dryness. The residue was separated and purified by preparative chromatography plate (petroleum ether:ethyl acetate=1:1) to obtain the product of embodiment 1J.

LCMS (ESI) m/z: 500.2 (M+1)$^+$

Embodiment 1

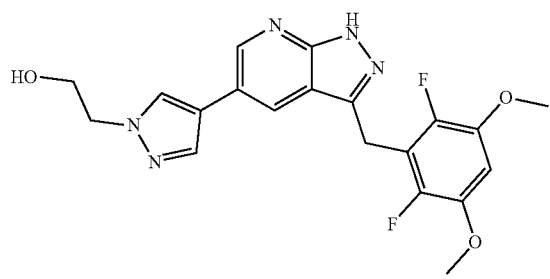 [SMILES: COc1cc(OC)c(F)c(Cc2n[nH]c3ncc(-c4cnn(CCO)c4)cc23)c1F]

Acetyl chloride (0.5 mL) was slowly added to methanol (2 mL) at 0° C. After the completion of the addition, the reaction solution was stirred at 16° C. for 30 min, and then the above solution was added to a solution of the product of embodiment 1J (50 mg, 100.10 μmol) in methanol (1 mL). The reaction solution was stirred at 40° C. for 30 min. The reaction solution was directly rotary-evaporated in vacuo to dryness, and the residue was purified by preparative HPLC (TFA system) to obtain trifluoroacetate salt of embodiment 1. The free base of embodiment 1 can be obtained by washing a solution of the trifluoroacetate salt of embodiment 1 in dichloromethane with 1N sodium bicarbonate, followed by separating and concentrating the organic phase.

LCMS (ESI) m/z: 416.2 (M+1)+

$^1$H NMR (400 MHz, DMSO-$d_6$) δ 13.29 (s, 1H), 8.78 (d, J=2.01 Hz, 1H), 8.28 (d, J=1.76 Hz, 1H), 8.22 (s, 1H), 7.93 (s, 1H), 6.93 (t, J=8.28 Hz, 1H), 4.30 (s, 2H), 4.19 (t, J=5.65 Hz, 2H), 3.85 (s, 6H), 3.79 (br t, J=5.52 Hz, 2H).

Process C

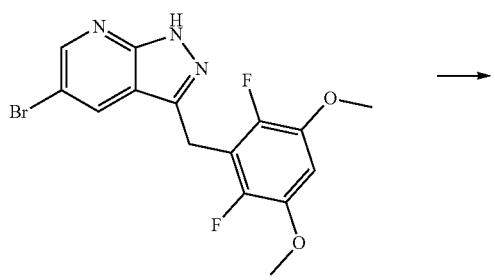

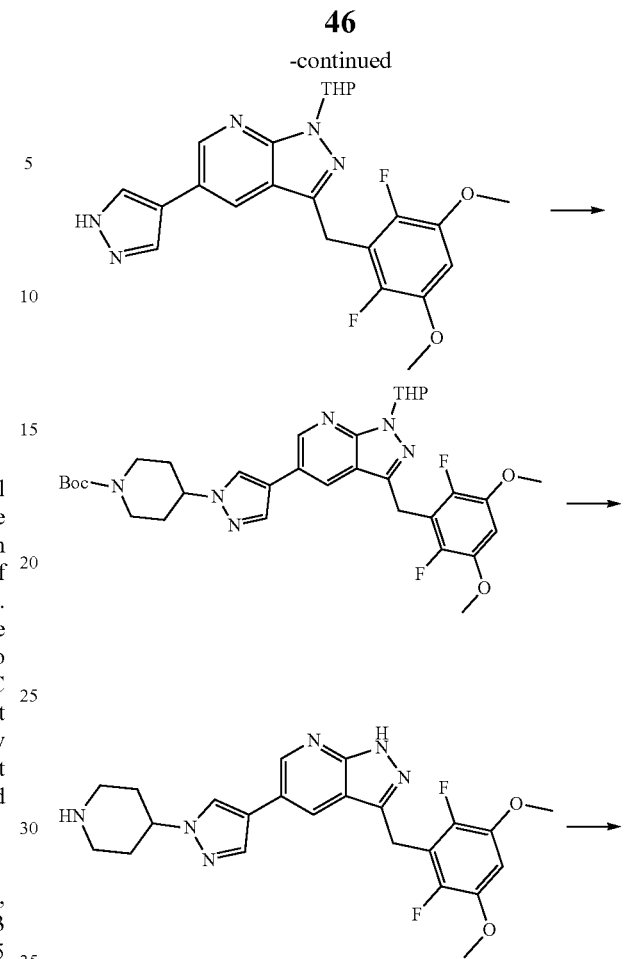

Embodiment 2

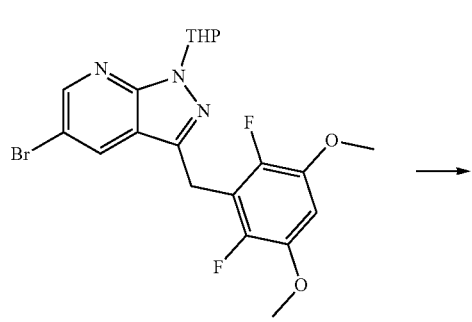

Embodiment 2A

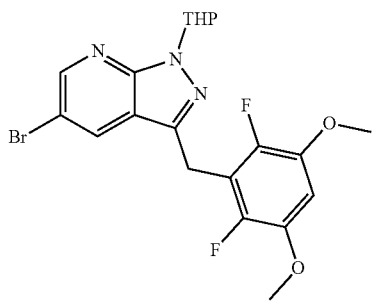

Methanesulfonic acid (3.75 mg, 39.04 μmol) was added to a solution of the product of embodiment 1G (100 mg, 260.30 μmol) and 2,3-dihydropyran (24.08 mg, 286.33 μmol) in dichloromethane (2 mL) at 0° C., and the reaction solution was stirred for 1 hour at 0° C. The reaction solution was added with dichloromethane (5 mL), washed with water (3 mL) and saturated brine (3 mL), dried over anhydrous sodium sulfate, and filtered. The filtrate was rotary-evaporated to dryness in vacuo to obtain the product of embodiment 2A.

LCMS (ESI) m/z: 468.2 (M+1)$^+$

Embodiment 2B

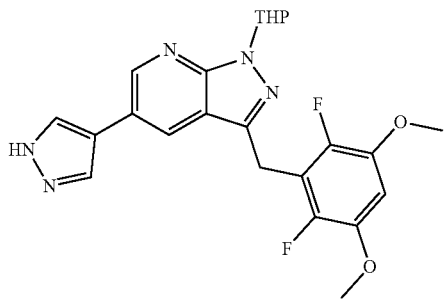

A mixture of the product of embodiment 2A (60 mg, 128.13 mol), 4-pyrazoleboronic acid pinacol ester (32.32 mg, 166.56 μmol) and Pd(dppf)Cl$_2$ (9.38 mg, 12.81 μmol), potassium carbonate (35.42 mg, 256.25 μmol) in dioxane (2 mL) and water (1 mL) was reacted at 100° C. under nitrogen protection and microwave conditions for 20 min. The reaction solution was untreated, and the upper layer of the reaction solution was directly separated by preparative chromatography plate (dichloromethane:methanol=10:1) to obtain the product of embodiment 2B.

LCMS (ESI)$_m$/z: 456.1 (M+1)$^+$

Embodiment 2C

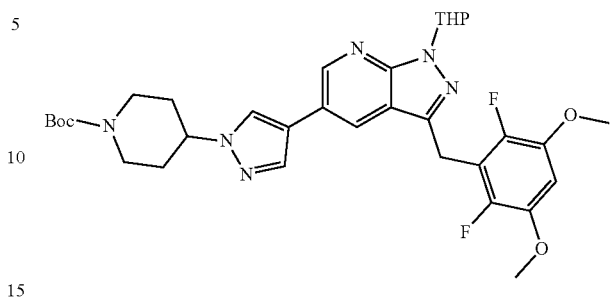

A suspension of the product of embodiment 2B (30 mg, 65.87 μmol) and 1-(1-Boc-4-piperidinyl)pyrazole-4-yl methanesulfonate (27.60 mg, 98.80 μmol), cesium carbonate (42.92 mg, 131.74 μmol) in N,N-dimethylformamide (2 mL) was stirred at 100° C. for 3 hours. The reaction solution was filtered, and the filtrate was directly rotary-evaporated to dryness. The residue was separated and purified by preparative chromatography plate (petroleum ether:ethyl acetate=10:1) to obtain the product of embodiment 2C.

LCMS (ESI) m/z: 639.3 (M+1)$^+$

Embodiment 2

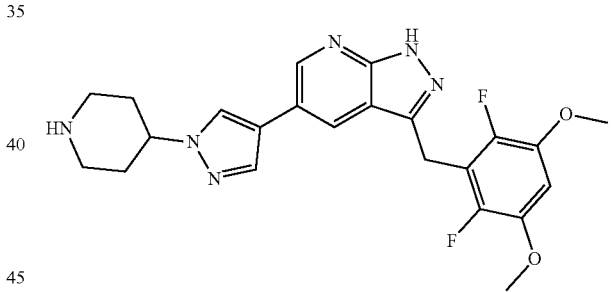

Acetyl chloride (2 mL) was slowly added to methanol (10 mL) at 0° C. After the completion of the addition, the reaction solution was stirred at 15° C. for 10 min. The product of embodiment 2C (40 mg, 62.63 μmol) was dissolved in methanol (2 mL), and then added with 3 ml of the above solution dropwise. The reaction solution was stirred at 40° C. for 20 min. The reaction solution was directly rotary-evaporated to dryness, and purified by preparative HPLC (hydrochloric acid system) to obtain hydrochloric salt of embodiment 2. The free base of embodiment 2 can be obtained by washing a solution of the hydrochloric salt of embodiment 2 in dichloromethane with 1N sodium bicarbonate, followed by separating and concentrating the organic phase.

LCMS (ESI) m/z: 455.2 (M+1)$^+$ $^1$H NMR (400 MHz, METHANOL-<4) δ 9.02 (s, 1H), 8.85 (d, J=1.50 Hz, 1H), 8.35 (s, 1H), 8.05 (s, 1H), 6.87 (t, J=8.32 Hz, 1H), 4.64-4.74 (m, 1H), 4.54 (s, 2H), 3.89 (s, 6H), 3.61-3.64 (m, 2H), 3.23-3.31 (m, 2H), 2.32-2.47 (m, 4H).

Embodiment 3

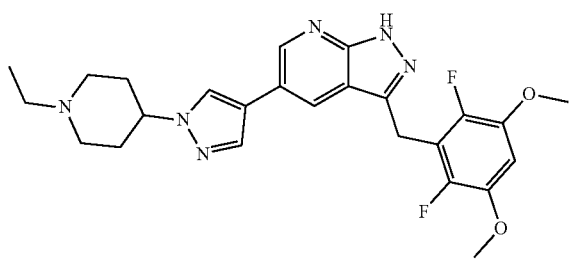 [SMILES: CCN1CCC(n2cc(-c3cnc4[nH]nc(Cc5c(F)c(OC)cc(OC)c5F)c4c3)cn2)CC1]

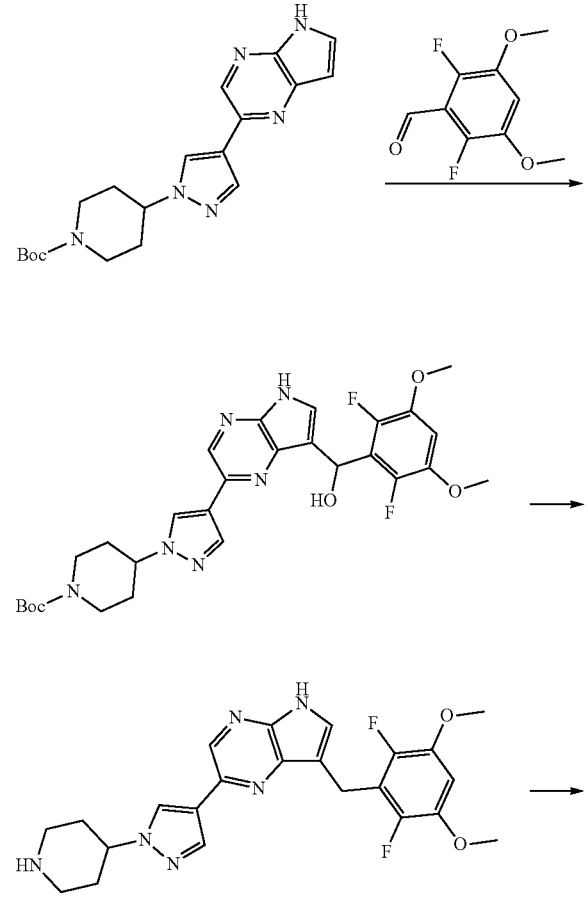

At 16° C. anhydrous acetaldehyde (24.47 mg, 244.43 μmol), and acetic acid (19.57 mg, 325.91 μmol) were added to a solution of the product of embodiment 2 (20 mg, 40.74 μmol) in dichloromethane (2 mL) and methanol (1 mL). After stirring for 20 min, sodium triacetoxyborohydride (12.95 mg, 61.11 μmol) was added, and the mixture was stirred for 40 min. The reaction solution was directly blow-dried with nitrogen. The residue was purified by preparative HPLC (hydrochloric acid system) to obtain hydrochloride salt of embodiment 3. In embodiment 3, the free base can be obtained by washing a solution of the hydrochloric salt of embodiment 3 in dichloromethane with 1N sodium bicarbonate, followed by separating and concentrating the organic phase.

LCMS (ESI) m/z: 483.2 (M+1)$^+$ $^1$H NMR (400 MHz, METHANOL-$d_4$) δ 9.05 (s, 1H), 8.89-8.96 (m, 1H), 8.38 (s, 1H), 8.05 (s, 1H), 6.85 (t, J=8.28 Hz, 1H), 4.62-4.74 (m, 1H), 4.54 (s, 2H), 3.87 (s, 6H), 3.78 (br d, J=12.55 Hz, 2H), 3.46-3.61 (m, 1H), 3.19-3.30 (m, 3H), 2.36-2.50 (m, 4H), 1.38-1.46 (m, 3H).

The following embodiment 4 and hydrochloride salt thereof were prepared by referring to the method as described in embodiment 3.

| Embodiment | Structure | NMR | LCMS (ESI) m/z: (M + 1) |
|---|---|---|---|
| Embodiment 4 | 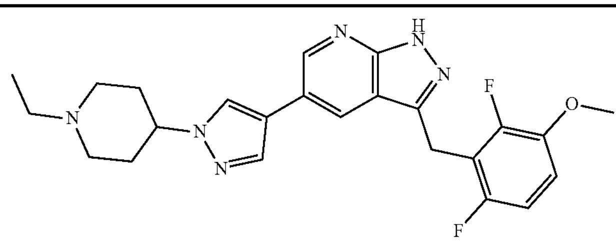 | $^1$H NMR (400 MHz, METHANOL-$d_4$) δ 8.62 (s, 1H), 8.11 (d, J = 2.01 Hz, 1H), 8.05 (s, 1H), 7.78 (s, 1H), 6.92 (dt, J = 5.14, 9.22 Hz, 1H), 6.77-6.85 (m, 1H), 4.24-4.38 (m, 3H), 3.75 (s, 3H), 3.27-3.37 (m, 3H), 2.77 (q, J = 7.28 Hz, 2H), 2.61 (br t, J = 9.66 Hz, 2H), 2.11-2.25 (m, 4H), 1.17-1.22 (m, 3H). | 453.1 |

Process D

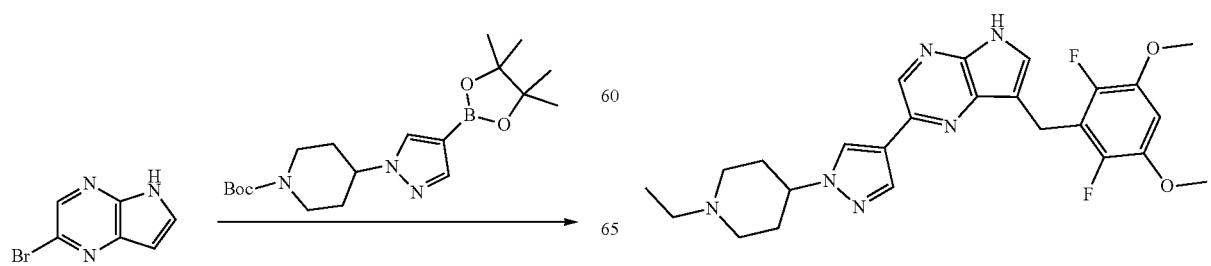

Embodiment 5

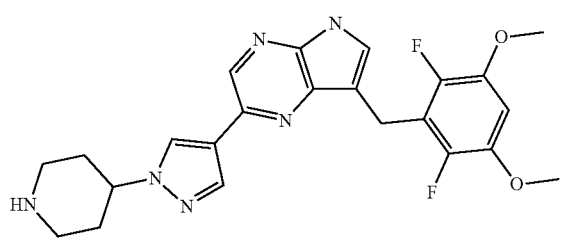 [SMILES: COc1cc(OC)c(F)c(Cc2c[nH]c3ncc(-c4cnn(C5CCNCC5)c4)nc23)c1F]

Embodiment 5A

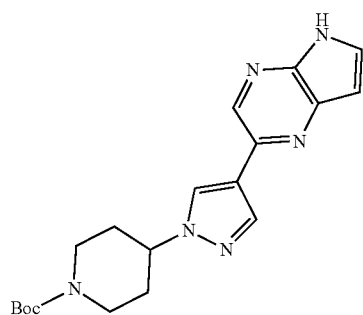 [SMILES: CC(C)(C)OC(=O)N1CCC(n2cc(-c3cnc4[nH]ccc4n3)cn2)CC1]

5-Bromo-4,7-diazaindole (500 mg, 2.52 mmol) was dissolved dioxane (10 mL)/water (5 mL) in a single-neck flask (50 mL), then added with 1-(1-Boc-4-piperidine)pyrazole-4-boronic acid pinacol ester (1.05 g, 2.78 mmol), Pd(dppf)Cl$_2$ (92.38 mg, 126.25 μmol), potassium carbonate (872.45 mg, 6.31 mmol). The reaction solution was purged with nitrogen three times, and then stirred at 100° C. for 14 hours under nitrogen protection. The reaction solution was added with water (30 mL), extracted with ethyl acetate (30 mL*2) twice. The combined organic phase was washed with saturated brine (20 mL), dried over anhydrous sodium sulfate, and filtered. The filtrate was concentrated under reduced pressure to give a crude product. The crude product was separated and purified by flash chromatography on a silica gel column (petroleum ether:ethyl acetate=1/0-1/1) to obtain the product of embodiment 5A.

$^1$H NMR (400 MHz, CHLOROFORM-d) δ 9.37 (br s, 1H), 8.50 (s, 1H), 8.06 (d, J=9.54 Hz, 2H), 7.59 (t, J=3.26 Hz, 1H), δ 71 (dd, J=2.01, 3.51 Hz, 1H), 4.20-4.40 (m, 3H), 2.81-3.01 (m, 2H), 2.20 (br d, J=12.55 Hz, 2H), 1.98 (dq, J=4.27, 12.30 Hz, 2H), 1.48 (s, 9H).

Embodiment 5B

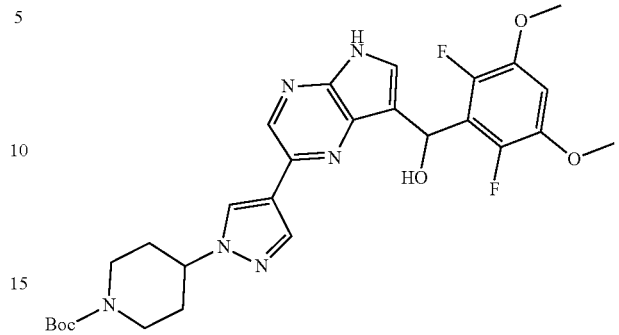

The product of embodiment 5A (100 mg, 271.42 μmol), 2,6-difluoro-3,5-dimethoxybenzaldehyde (109.74 mg, 542.84 μmol), potassium hydroxide (30.46 mg, 542.84 μmol) were dissolved in methanol (2 mL) in a single-neck flask (50 mL). The reaction solution was purged with nitrogen three times, and then stirred at room temperature of 30° C. for 16 hours under the protection of nitrogen. The reaction solution was concentrated under reduced pressure to obtain a crude product. The crude product was separated and purified by flash chromatography on a silica gel column (petroleum ether:ethyl acetate=1/0-0/1) to obtain the product of embodiment 5B.

LCMS (ESI) m/z: 571.3 (M+1)$^+$

Embodiment 5

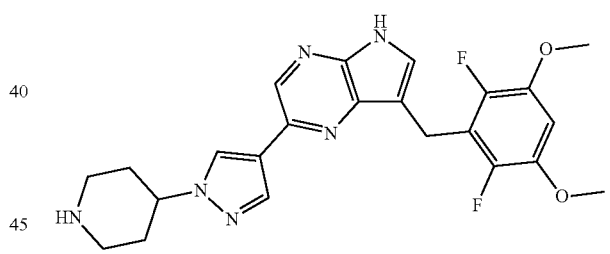

The product of embodiment 5B (150 mg, 262.89 μmol) was dissolved in dichloromethane (3.00 mL) in a single-neck flask (50 mL), and then added with triethylsilane (335.92 μL, 2.10 mmol) and trifluoroacetic acid (6.00 mL, 81.04 mmol). The reaction solution was stirred at 30° C. for 14 hours. The reaction solution was concentrated under reduced pressure, separated and purified by preparative HPLC (TFA system) to obtain trifluoroacetate salt of embodiment 5. In embodiment 5, the free base can be obtained by washing a solution of the trifluoroacetate salt of embodiment 5 in dichloromethane with 1N sodium bicarbonate, followed by separating and concentrating the organic phase.

LCMS (ESI) m/z: 476.9 (M+1)$^+$ $^1$H NMR (400 MHz, DMSO-d$_6$) δ 11.76 (d, J=2.51 Hz, 1H), 8.74 (br s, 1H), 8.61 (s, 1H), 8.48 (br d, J=8.03 Hz, 1H), 8.36 (s, 1H), 8.12 (s, 1H), 7.43 (d, J=2.01 Hz, 1H), 6.89 (t, J=8.28 Hz, 1H), 4.50-4.68 (m, 1H), 4.10 (s, 2H), 3.85 (s, 6H), 3.47 (br s, 2H), 3.02-3.23 (m, 2H), 2.03-2.37 (m, 4H).

Embodiment 6

Process E

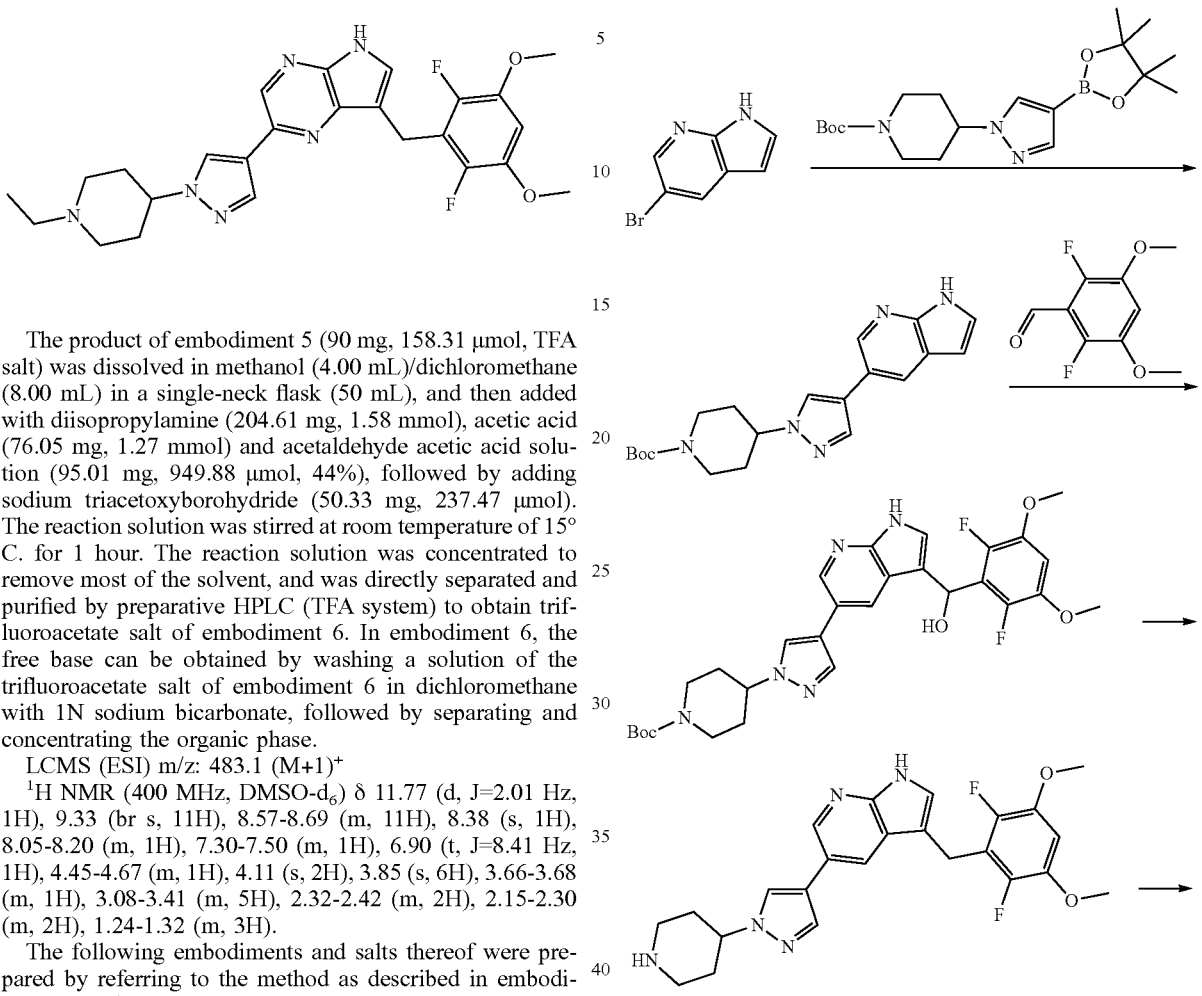

The product of embodiment 5 (90 mg, 158.31 μmol, TFA salt) was dissolved in methanol (4.00 mL)/dichloromethane (8.00 mL) in a single-neck flask (50 mL), and then added with diisopropylamine (204.61 mg, 1.58 mmol), acetic acid (76.05 mg, 1.27 mmol) and acetaldehyde acetic acid solution (95.01 mg, 949.88 μmol, 44%), followed by adding sodium triacetoxyborohydride (50.33 mg, 237.47 μmol). The reaction solution was stirred at room temperature of 15° C. for 1 hour. The reaction solution was concentrated to remove most of the solvent, and was directly separated and purified by preparative HPLC (TFA system) to obtain trifluoroacetate salt of embodiment 6. In embodiment 6, the free base can be obtained by washing a solution of the trifluoroacetate salt of embodiment 6 in dichloromethane with 1N sodium bicarbonate, followed by separating and concentrating the organic phase.

LCMS (ESI) m/z: 483.1 (M+1)$^+$ $^1$H NMR (400 MHz, DMSO-$d_6$) δ 11.77 (d, J=2.01 Hz, 1H), 9.33 (br s, 11H), 8.57-8.69 (m, 11H), 8.38 (s, 1H), 8.05-8.20 (m, 1H), 7.30-7.50 (m, 1H), 6.90 (t, J=8.41 Hz, 1H), 4.45-4.67 (m, 1H), 4.11 (s, 2H), 3.85 (s, 6H), 3.66-3.68 (m, 1H), 3.08-3.41 (m, 5H), 2.32-2.42 (m, 2H), 2.15-2.30 (m, 2H), 1.24-1.32 (m, 3H).

The following embodiments and salts thereof were prepared by referring to the method as described in embodiments 5 and 6.

| Embodiments | Structure | NMR | LCMS (ESI) m/z: (M + 1) |
|---|---|---|---|
| Embodiment 7 | 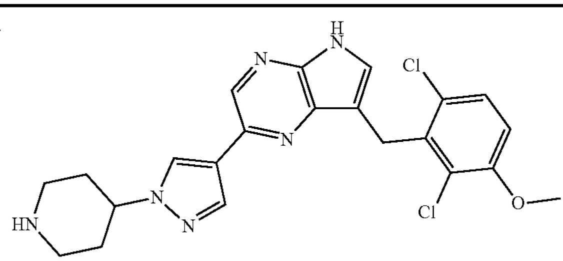 | $^1$H NMR (400 MHz, DMSO-$d_6$) δ 11.70 (br s, 1H), 8.59 (s, 1H), 8.35 (s, 1H), 8.07 (s, 1H), 7.47 (d, J = 9.03 Hz, 1H), 7.12-7.18 (m, 2H), 4.37 (s, 2H), 4.24-4.36 (m, 1H), 3.88 (s, 3H), 3.09-3.18 (m, 2H), 2.67-2.72 (m, 2H), 2.04-2.07 (m, 2H), 1.84-1.95 (m, 2H). | 456.9 |
| Embodiment 8 | 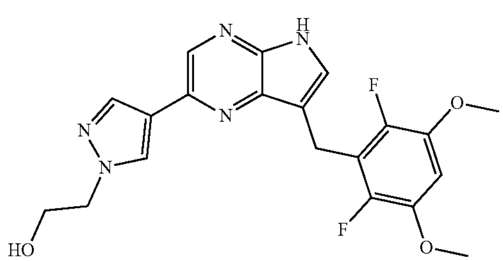 [SMILES: COc1cc(OC)c(F)c(Cc2c[nH]c3ncc(-c4cnn(CCO)c4)nc23)c1F] | $^1$HNMR (400 MHz, METHANOL-$d_4$) δ ppm 8.53 (s, 1 H), 8.31 (s, 1 H), 8.15 (s, 1 H), 7.30 (s, 1 H), 6.80 (t, J = 8.25 Hz, 1 H), 4.33 (t, J = 5.32 Hz, 2 H), 4.23 (s, 2 H), 3.98 (t, J = 5.32 Hz, 2 H), 3.89 (s, 6 H), 3.50 (s, 1 H). | 438.1 [M + 23]$^+$ |

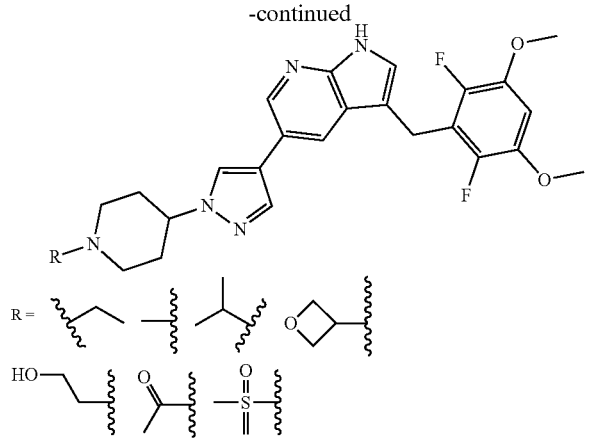

Embodiment 9

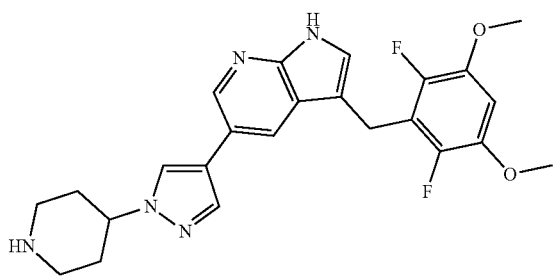 [SMILES: COc1cc(OC)c(F)c(Cc2c[nH]c3ncc(-c4cnn(C5CCNCC5)c4)cc23)c1F]

Embodiment 9A

5-Bromo-7-azaindole (3 g, 15.23 mmol), 1-(1-Boc-4-piperidine)pyrazole-4-boronic acid pinacol ester (6.32 g, 16.75 mmol), potassium carbonate (5.26 g, 38.06 mmol), Pd(dppf)Cl$_2$ (557.05 mg, 761.30 μmol) were added to a mixed solvent of dioxane (60 mL) and H$_2$O (30 mL). The reaction solution was purged with nitrogen, then heated to 100° C. and stirred for 1 hour. The reaction solution was added with water (40 mL), extracted with ethyl acetate (30 mL*2) twice. The combined organic phase was washed with saturated brine (30 mL), dried over anhydrous sodium sulfate, filtered, and concentrated under reduced pressure to obtain a crude product. The crude product was separated and purified by flash chromatography on a silica gel colunmn (petroleum ether:ethyl acetate=1/0-4/1) to obtain the product of embodiment 9A.

LCMS (ESI) m/z: 368.2 (M+1)$^+$

Embodiment 9B

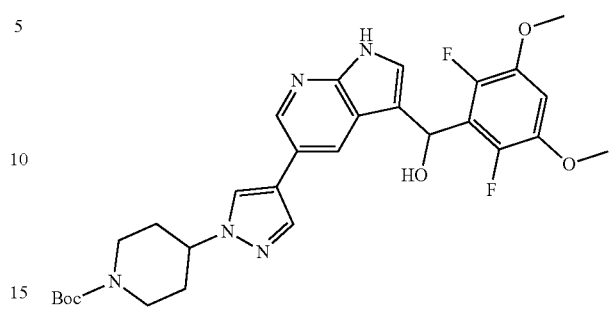

The product of embodiment 9A (1.00 g, 2.72 mmol), 2,6-difluoro-3,5-dimethoxybenzaldehyde (1.10 g, 5.44 mmol), potassium hydroxide (305.38 mg, 5.44 mmol) were dissolved in methanol (10 mL) in a single-neck flask (50 mL). The reaction solution was purged with nitrogen for three times, and then stirred at room temperature of 30° C. for 16 hours under the protection of nitrogen. The reaction solution was concentrated under reduced pressure to obtain a crude product. The crude product was separated and purified by chromatography on a silica gel column (petroleum ether:ethyl acetate=1/0-0/1) to obtain the product of embodiment 9A.

$^1$H NMR (400 MHz, CHLOROFORM-d) δ δ 9.59 (br s, 1H), 8.46 (d, J=2.01 Hz, 1H), 8.17 (d, J=1.51 Hz, 1H), 7.67-7.85 (m, 2H), 7.09 (s, 1H), 6.64 (t. J=8.28 Hz, 1H), 6.53 (br s, 1H), 4.20-4.48 (m, 3H), 3.83-3.95 (m, 6H), 2.93 (br s, 3H), 2.21 (br s, 2H), 1.89-2.04 (m, 2H), 1.49 (s, 9H).

Embodiment 9

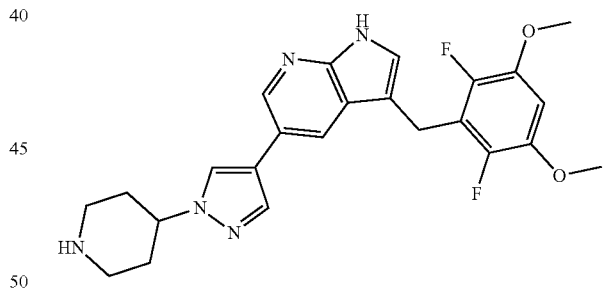

The product of embodiment 9B (100 mg, 175.56 μmol) was dissolved in dichloromethane (1.00 mL) in a single-neck flask (50 mL), and then added with triethylsilane (61.24 mg, 526.69 μmol) and trifluoroacetic acid (60.05 mg, 526.69 μmol). The reaction solution was stirred at 30° C. for 13 hours. Triethylsilane (0.14 mL) and trifluoroacetic acid (0.26 mL) were added additionally. The reaction solution was stirred at 30° C. for 3 hours. The reaction solution was concentrated under reduced pressure, added with water (5 mL), added with saturated aqueous sodium hydroxide solution to adjust pH to about 8, and extracted with dichloromethane three times (5 mL*3). The combined organic phase was washed with saturated brine (5 mL), dried over anhydrous sodium sulfate, filtered, and concentrated under reduced pressure to obtain the product of embodiment 9.

LCMS (ESI) m/z: 454.0 (M+1)$^+$

¹H NMR (400 MHz, METHANOL-d₄) δ 8.38 (d, J=2.01 Hz, 1H), 8.14 (d, J=2.01 Hz, 1H), 8.06 (s, 1H), 7.83 (s, 1H), 7.11 (s, 1H), 6.75 (t, J=8.28 Hz, 1H), 4.29-4.36 (m, 1H), 4.12 (s, 2H), 3.85 (s, 6H), 3.20 (br d, J=12.55 Hz, 2H), 2.76 (dt, J=2.51, 12.55 Hz, 2H), 2.14 (br d, J=12.55 Hz, 2H), 1.91-2.06 (m, 2H).

Embodiment 12

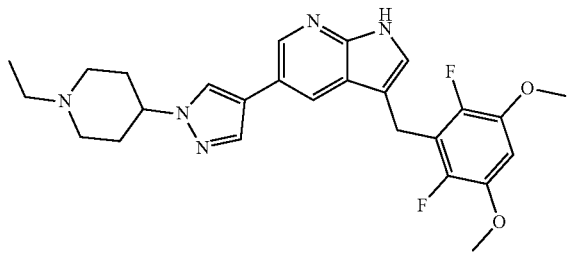 [SMILES: CCN1CCC(n2cc(-c3cnc4[nH]cc(Cc5c(F)c(OC)cc(OC)c5F)c4c3)cn2)CC1]

The product of embodiment 9 (50 mg, 88.10 μmol, TFA salt) was dissolved in 1,2-dichloroethane (1.00 mL) in a sample vial (5 mL), and then added with triethylamine (35.66 mg, 352.42 μmol), acetaldehyde (11.64 mg, 264.31 μmol), followed by acetic acid (10.58 mg, 176.21 μmol) to adjust pH to 5-6. The reaction solution was stirred at room temperature of 25° C. for 0.5 hour, and then added with sodium triacetoxyborohydride (37.35 mg, 176.21 μmol). The reaction solution was stirred for 12 hours at room temperature of 25° C. The reaction solution was filtered, and the filtrate was concentrated under reduced pressure to obtain a crude product. The crude product was separated and purified by preparative HPLC (TFA system) to obtain trifluoroacetate salt of embodiment 12. In embodiment 12, the free base can be obtained by washing a solution of the trifluoroacetate salt of embodiment 12 in dichloromethane with 1N sodium bicarbonate, followed by separating and concentrating the organic phase.

LCMS (ESI) m/z: 482.2 (M+1)⁺

¹H NMR (400 MHz, DMSO-d₆) δ 11.40 (s, 1H), 8.46 (d, J=2.01 Hz, 1H), 8.24 (s, 1H), 8.07 (d, J=1.76 Hz, 1H), 7.85 (s, 1H), 7.08 (s, 1H), 6.88 (t, J=8.41 Hz, 1H), 4.12-4.27 (m, 1H), 4.05 (s, 2H), 3.84 (s, 6H), 3.00 (br d, J=11.04 Hz, 2H), 2.38-2.65 (m, 4H), 1.97-2.12 (m, 4H), 1.04 (t, J=7.15 Hz, 3H).

Embodiment 14

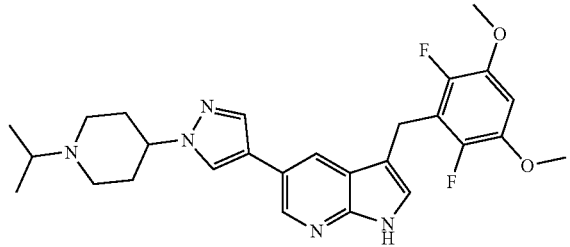 [SMILES: COc1cc(OC)c(F)c(Cc2c[nH]c3ncc(-c4cnn(C5CCN(C(C)C)CC5)c4)cc23)c1F]

The product of embodiment 9 (50 mg, 110.26 μmol, TFA salt) was dissolved in acetone (1.00 mL) in a single-neck flask (50 mL), and then added with 2-bromopropane (27.12 mg, 220.52 μmol) and potassium carbonate (45.71 mg, 330.78 μmol). The reaction solution was stirred at room temperature of 60° C. for 14 hours. The reaction solution was filtered, and the filtrate was concentrated under reduced pressure to obtain a crude product. The crude product was separated and purified by preparative HPLC (TFA system) to obtain trifluoroacetate salt of embodiment 14. In embodiment 14, the free base can be obtained by washing a solution of the trifluoroacetate salt of embodiment 14 in dichloromethane with 1N sodium bicarbonate, followed by separating and concentrating the organic phase.

LCMS (ESI) m/z: 496.2 (M+1)⁺

¹H NMR (400 MHz, METHANOL-d₄) δ 8.47 (br d, J=6.78 Hz, 1H), 8.32 (s, 1H), 8.14 (s, 1H), 7.95 (s, 1H), 7.20 (s, 1H), 6.79 (t, J=8.28 Hz, 1H), 4.55-4.71 (m, 1H), 4.16 (s, 2H), 3.88 (s, 6H), 3.57-3.73 (m, 3H), 2.33-2.58 (m, 4H), 1.37-1.49 (m, 6H).

Embodiment 17

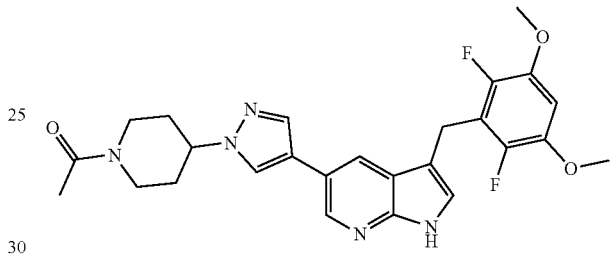

The product of embodiment 9 (50 mg, 88.10 μmol, TFA salt) was dissolved in N,N-dimethylformamide (1.00 mL) in a sample vial (5 mL), and then added with diisopropylamine (45.55 mg, 352.42 μmol), HATU (50.25 mg, 132.16 μmol), and acetic acid (10.58 mg, 176.21 μmol). The reaction solution was stirred at room temperature of 25° C. for 3 hours. The reaction solution was filtered, and the filtrate was separated and purified by preparative HPLC (TFA system) to obtain trifluoroacetate salt of embodiment 17. In embodiment 17, the free base can be obtained by washing a solution of the trifluoroacetate salt of embodiment 17 in dichloromethane with 1N sodium bicarbonate, followed by separating and concentrating the organic phase.

LCMS (ESI) m/z: 496.1 (M+1)⁺

¹H NMR (400 MHz, METHANOL-d₄) δ 8.67 (d, J=1.60 Hz, 1H), 8.57 (s, 1H), 8.26 (s, 1H), 7.98 (s, 1H), 7.33 (s, 1H), 6.81 (t, J=8.28 Hz, 1H), 4.70 (br d, J=13.40 Hz, 1H), 4.47-4.62 (m, 1H), 4.23 (s, 2H), 4.06-4.16 (m, 1H), 3.88 (s, 6H), 3.34-3.42 (m, 1H), 2.81-2.98 (m, 1H), 2.17-2.31 (m, 5H), 1.94-2.16 (m, 2H).

Embodiment 18

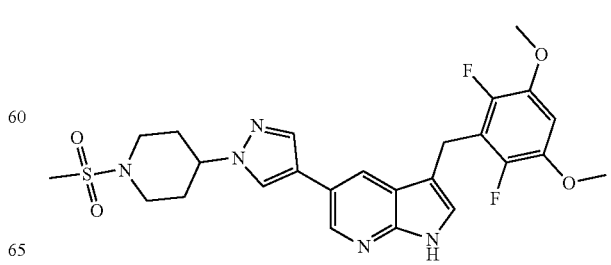

The product of embodiment 9 (50 mg, 110.26 μmol, TFA salt) was dissolved in acetone (1.00 mL) in a single-neck flask (50 mL), and then oxetanyl methanesulfonate (20.13 mg, 132.31 μmol) and potassium carbonate (30.48 mg, 220.52 μmol) were added. The reaction solution was stirred at room temperature 60° C. for 12 hours. The reaction solution was filtered, and the filtrate was concentrated under reduced pressure to obtain a crude product. The crude product was separated and purified by preparative HPLC (TFA system) to obtain trifluoroacetate salt of embodiment 18. In embodiment 18, the free base can be obtained by washing a solution of the trifluoroacetate salt of embodiment 18 in dichloromethane with 1N sodium bicarbonate, followed by separating and concentrating the organic phase.

LCMS (ESI) m/z: 532.1 (M+1)+

$^1$H NMR (400 MHz, CHLOROFORM-d) δ 8.26 (br s, 1H), 8.05 (s, 1H), 7.75 (s, 1H), 7.70 (s, 1H), 7.13 (s, 1H), 6.46 (t, J=8.03 Hz, 1H), 4.22-4.32 (m, 1H), 4.06 (s, 2H), 3.89 (br d, J=12.55 Hz, 2H), 3.79 (s, 6H), 2.92 (br t, J=11.04 Hz, 2H), 2.82 (s, 3H), 2.22-2.31 (m, 2H), 2.08-2.19 (m, 2H).

The following embodiments and salts thereof were obtained by referring to the methods described in embodiment 9 and embodiment 12.

| Embodiments | Structure | NMR | LCMS (ESI) m/z: (M + 1) |
|---|---|---|---|
| Embodiment 10 | 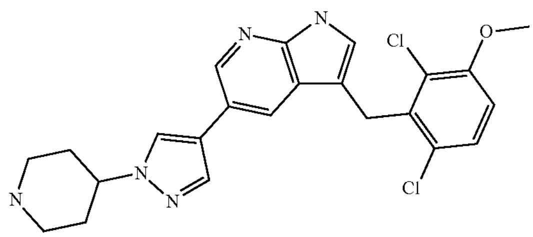 [SMILES: COc1ccc(Cl)c(Cc2c[nH]c3ncc(-c4cnn(C5CCNCC5)c4)cc23)c1Cl] | $^1$H NMR (METHANOL-d$_4$, 400 MHz): δ 8.75 (s, 1H), 8.60 (s, 1H), 8.29 (s, 1H), 8.02 (s, 1H), 7.41 (d, J = 8.0 Hz, 1H), 7.01-7.16 (m, 2H), 4.55-4.72 (m, 1H), 4.47 (s, 2H), 3.90 (s, 3H), 3.52-3.65 (m, 2H), 3.18-3.38 (m, 2H), 2.28-2.48 (m, 4H). | 456.3 |
| Embodiment 11 | 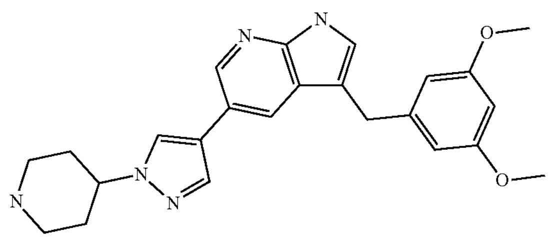 [SMILES: COc1cc(Cc2c[nH]c3ncc(-c4cnn(C5CCNCC5)c4)cc23)cc(OC)c1] | $^1$H NMR (METHANOL-d$_4$, 400 MHz): δ 8.27 (d, J = 2.0 Hz, 1H), 7.92 (s, 1H), 7.87 (d, J = 2.0 Hz, 1H), 7.70 (s, 1H), 7.06 (s, 1H), 6.36 (d, J = 2.0 Hz, 2H), 6.21 (t, J = 2.1 Hz, 1H), 4.19 (tt, J = 11.6, 4.0 Hz, 1H), 3.94 (s, 2H), 3.56-3.64 (m, 6H), 3.03-3.13 (m, 2H), 2.67 (td, J = 12.7, 2.5 Hz, 2H), 1.99-2.07 (m, 2H), 1.78-1.93 (m, 2H). | 418.2 |
| Embodiment 19 | 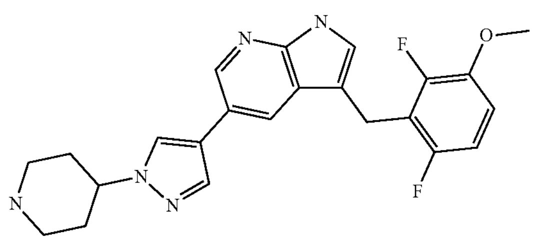 [SMILES: COc1ccc(F)c(Cc2c[nH]c3ncc(-c4cnn(C5CCNCC5)c4)cc23)c1F] | $^1$H NMR (400 MHz, METHANOL-d$_4$) δ 8.47 (d, J = 1.51 Hz, 1H), 8.38 (d, J = 1.76 Hz, 1H), 8.16 (s, 1H), 7.97 (s, 1H), 7.22 (s, 1H), 6.88-7.05 (m, 2H), 4.58-4.70 (m, 1H), 4.18 (s, 2H), 3.83-3.91 (m, 4H), 3.62 (br d, J = 13.30 Hz, 2H), 3.21-3.29 (m, 2H), 2.27-2.47 (m, 4H). | 423.5 |
| Embodiment 49 | 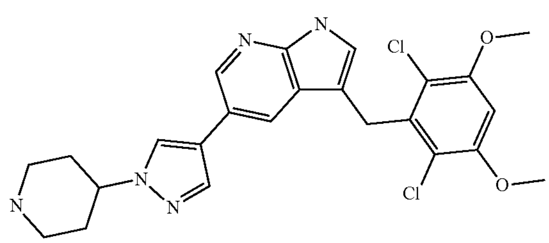 [SMILES: COc1cc(OC)c(Cl)c(Cc2c[nH]c3ncc(-c4cnn(C5CCNCC5)c4)cc23)c1Cl] | $^1$H NMR (400 MHz, METHANOL-d$_4$) δ 8.50 (d, J = 7.78 Hz, 2H), 8.19 (s, 1H), 7.98 (s, 1H), 6.98 (s, 1H), 6.80 (s, 1H), 4.55-4.69 (m, 1H), 4.47 (s, 2H), 3.94 (s, 6H), 3.60 (br d, J = 13.55 Hz, 2H), 3.18-3.28 (m, 3H), 2.25-2.44 (m, 4H). | 486.4 |
| Embodiment 13 | 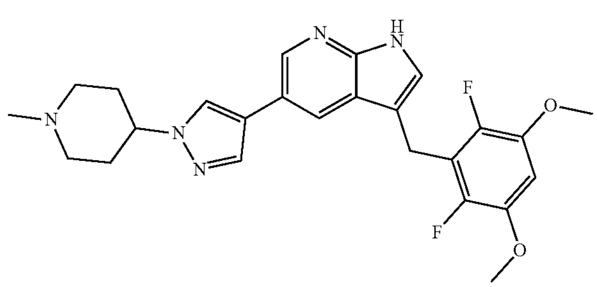 | $^1$H NMR (400 MHz, DMSO-d$_6$) δ 11.46 (s, 1H), 8.49 (d, J = 2.01 Hz, 1H), 8.21-8.27 (m, 1H), 8.07-8.15 (m, 1H), 7.94 (s, 1H), 7.10 (s, 1H), 6.89 (t, J = 8.28 Hz, 1H), 4.41-4.56 (m, 1H), 4.06 (s, 2H), 3.84 (s, 6H), 3.63 (br s, 3H), 3.11-3.26 (m, 2H), 2.85 (br d, J = 4.52 Hz, 2H), 2.33 (br d, J = 1.76 Hz, 2H), 2.12-2.26 (m, 2H). | 468.1 |

| Embodiments | Structure | NMR | LCMS (ESI) m/z: (M + 1) |
|---|---|---|---|
| Embodiment 38 | 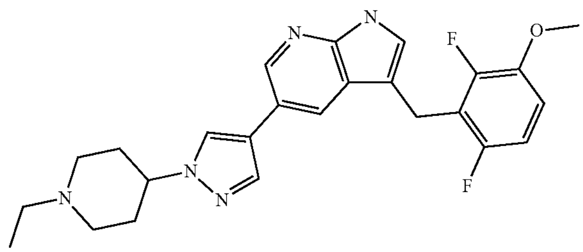 [SMILES: CCN1CCC(n2cc(-c3cnc4[nH]cc(Cc5c(F)ccc(OC)c5F)c4c3)cn2)CC1] | 1H NMR (400 MHz, CHLOROFORM-d) δ 12.78-13.07 (m, 1H), 12.63 (br s, 1H), 8.45 (br s, 1H), 8.25 (br s, 1H), 7.72-7.92 (m, 2H), 7.37 (br d, J = 11.2 Hz, 1H), 6.73-6.89 (m, 2H), 4.43-4.70 (m, 1H), 4.15 (s, 2H), 3.84-3.85 (m, 4H), 3.55 (br s, 2H), 3.15-3.18 (m, 2H), 2.86-2.88 (m, 1H), 2.48-2.69 (m, 2H), 2.26-2.56 (m, 2H), 1.39-1.42 (m, 3H). | 452.1 |
| Embodiment 15 | 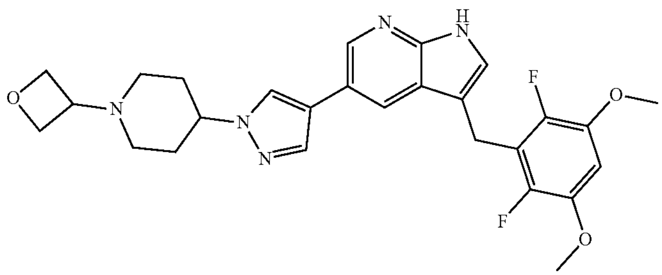 [SMILES: COc1cc(OC)c(F)c(Cc2c[nH]c3ncc(-c4cnn(C5CCN(C6COC6)CC5)c4)cc23)c1F] | ¹H NMR (400 MHz, METHANOL-d₄) δ 8.47 (br s, 1H), 8.32 (s, 1H), 8.15 (d, J = 4.52 Hz, 1H), 7.94-7.99 (m, 1H), 7.20 (s, 1H), 6.79 (t, J = 8.54 Hz, 1H), 4.92-5.01 (m, 2H), 4.84 (br d, J = 3.51 Hz, 1H), 4.45-4.74 (m, 2H), 4.17 (s, 2H), 3.88 (s, 6H), 3.61-3.74 (m, 2H), 3.07-3.31 (m, 3H), 2.32-2.51 (m, 4H). | 510.1 |

The following embodiment was obtained by referring to the method described in embodiment 14.

| Embodiment | Structure | NMR | LCMS (ESI) m/z: (M + 1) |
|---|---|---|---|
| Embodiment 16 | 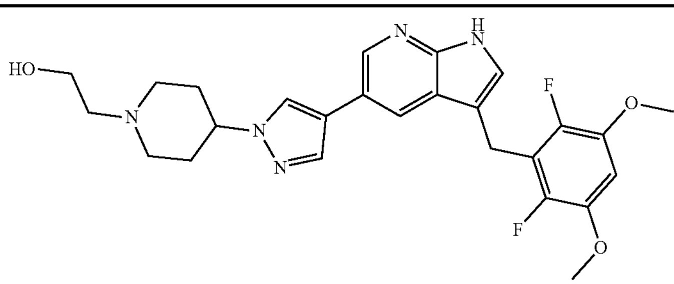 | ¹H NMR (400 MHz, METHANOL-d₄) δ 8.38 (s, 1H), 8.15 (s, 1H), 8.14 (s, 1H), 8.07 (s, 1H), 7.83 (s, 1H), 7.11 (s, 1H), 6.75 (t, J = 8.54 Hz, 1H), 4.60 (br s, 1H), 4.21-4.23 (m, 1H), 4.12 (s, 2H), 3.85 (s, 6H), 3.70-3.74 (m, 2H), 3.13-3.16 (m, 2H), 2.60-2.63 (m, 2H), 2.29-2.32 (m, 2H), 2.15-2.18 (m, 4H). | 498.2 |

Process F

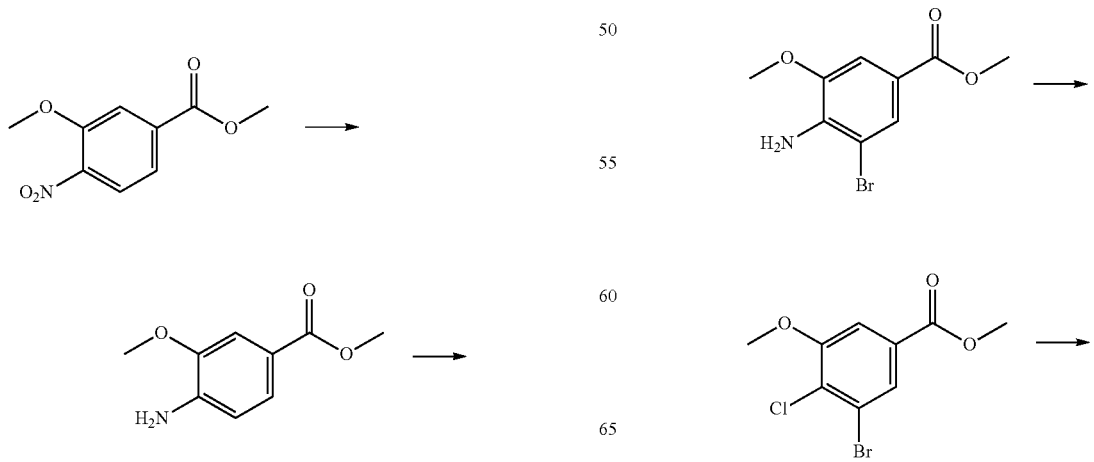

-continued

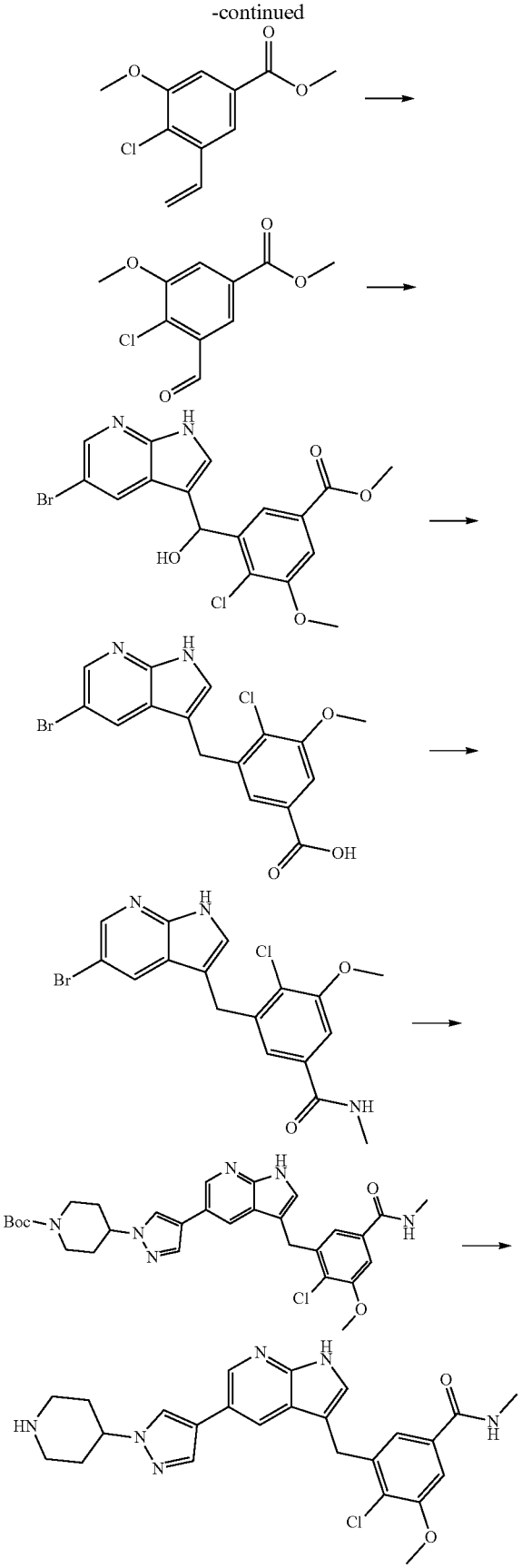

Embodiment 20

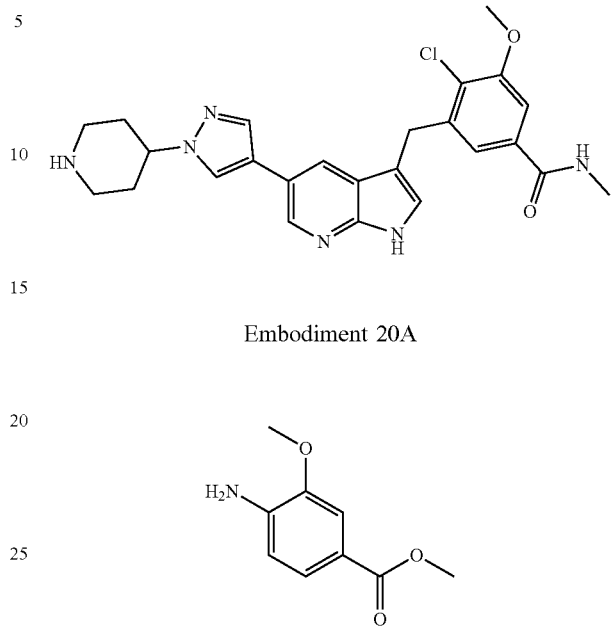

Embodiment 20A

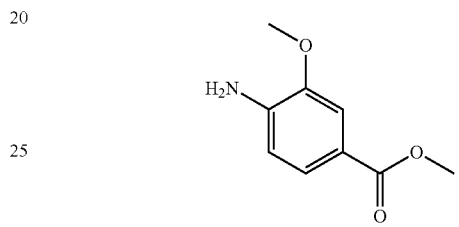

Palladium on carbon (dry, 10%, 0.1 g) was added to a solution of 2-methoxy-4-methoxycarbonyl-nitrobenzene (1 g, 4.74 mmol) in methanol (15 mL). The reaction solution was purged with nitrogen twice, purged with hydrogen twice, and then stirred at 30° C. for 3 hours under hydrogen stream (30 psi). The reaction solution was filtered, and the filtrate was concentrated in vacuo to obtain the product of embodiment 20A.

$^1$H NMR (400 MHz, CHLOROFORM-d) δ 7.56 (dd, J=1.76, 8.02 Hz, 1H), 7.46 (d, J=1.52 Hz, 1H), 6.67 (d, J=8.02 Hz, 1H), 4.23 (br s, 2H), 3.91 (s, 3H), 3.87 (s, 3H)

Embodiment 20B

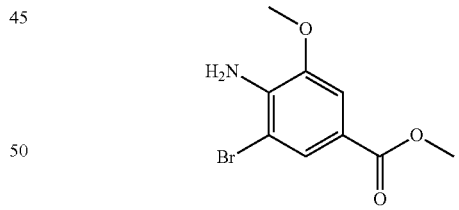

Bromosuccinimide (392.93 mg, 2.21 mmol) was added to a solution of the product of embodiment 20A (0.4 g, 2.21 mmol) in dichloromethane (5 mL) at 0° C. After completion of the addition, the reaction solution was heated to 30° C. and stirred for 2 hours. The reaction solution was added with sodium bisulfite aqueous solution (1 mL) dropwise, added with water (5 mL), and extracted with dichloromethane (2×5 mL). The combined organic phase was washed with saturated brine (5 mL), dried over anhydrous sodium sulfate, and filtered. The filtrate was rotary-evaporated to dryness in vacuo, and the residue was separated and purified by flash chromatography on a silica gel column to obtain the product of embodiment 20B.

LCMS (ESI) m/z: 260.1 (M+1)$^+$

¹H NMR (400 MHz, CHLOROFORM-d) δ 7.81 (d, J=1.51 Hz, 1H), 7.39 (d, J=1.51 Hz, 1H), 4.66 (br s, 2H), 3.92 (s, 3H), 3.88 (s, 3H).

Embodiment 20C

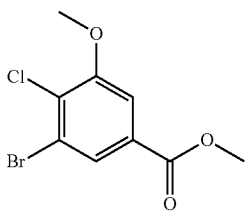

Copper chloride (2.15 g, 15.96 mmol), and tert-butyl nitrite (1.65 g, 15.96 mmol) were added to acetonitrile (25 mL), and the reaction solution was heated to 60° C. and stirred for 30 min. A solution of the product of embodiment 20B (4.15 g, 15.96 mmol) in acetonitrile (25 mL) was added to the above reaction solution. The reaction solution was stirred for 1.5 hours. The reaction solution was added with dilute hydrochloric acid (2 M, 10 mL) to quench the reaction, and then added with water (50 mL), extracted with ethyl acetate (100 mL×2), and washed with brine (30 mL). The organic phase was dried over anhydrous sodium sulfate, filtered and concentrated. The crude product was purified by flash chromatography on a silica gel column (petroleum ether/ethyl acetate=0/1 to 5/1) to obtain the product of embodiment 20C.

¹H NMR (400 MHz, CHLOROFORM-d) δ 7.93 (s, 1H), 7.54 (s, 1H), 3.97 (s, 3H), 3.94 (s, 3H).

Embodiment 20D

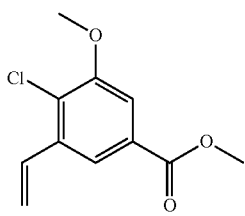

Vinylboronic acid pinacol ester (181.83 mg, 1.18 mmol), Pd(dppf)Cl₂ (392.66 mg, 536.64 μmol), and potassium phosphate (455.64 mg, 2.15 mmol) were added to a solution of the product of embodiment 20C (3M) mg, 1.07 mmol) in tetrahydrofuran (6 mL) and water (3 mL). The reaction solution was heated to 80° C. and reacted for 5 hours under the protection of nitrogen. The reaction solution was cooled to room temperature, added with water (5 mL), and extracted with ethyl acetate (5 mL×2). The combined organic phase was washed with saturated brine (5 mL×2), dried over anhydrous sodium sulfate, filtered, and rotary-evaporated to dryness in vacuo. The residue was separated by flash chromatography on a silica gel column to obtain the product of embodiment 20D.

LCMS (ESI) m/z: 227.2 (M+1)⁺

¹H NMR (400 MHz, CHLOROFORM-d) δ 7.89 (d, J=1.76 Hz, 1H), 7.50 (d, J=1.76 Hz, 1H), 7.14 (dd, J=10.92, 17.44 Hz, 1H), 5.85 (d, J=17.57 Hz, 1H), 5.48 (d, J=11.04 Hz, 1H), 3.96 (d, J=9.03 Hz, 6H)

Embodiment 20E

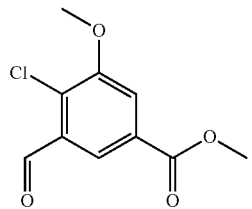

Ozone gas was introduced into a solution of the product of embodiment 20D (100 mg, 441.20 μmol) in dichloromethane (5 mL) at −78° C. for 5 minutes until the reaction solution turned blue, and then dimethyl sulfide (27.41 mg, 441.20 μmol) was added. The reaction solution was heated to room temperature and stirred for 2 hours. The reaction solution was directly concentrated to obtain the product of embodiment 20E.

¹H NMR (400 MHz, CHLOROFORM-d) δ δ 10.47-10.66 (m, 1H), 8.19 (d, J=2.01 Hz, 1H), 7.80 (d, J=1.76 Hz, 1H), 4.02 (s, 3H), 3.96 (s, 3H).

Embodiment 20F

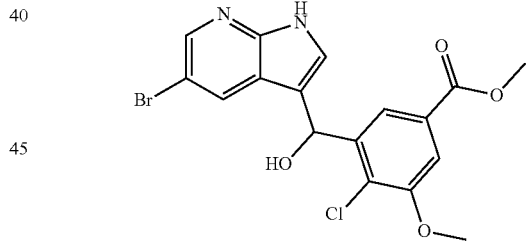

5-Bromo-7-azaindole (50 mg, 253.77 μmol), the product of embodiment 20E (63.82 mg, 279.14 μmol), and potassium hydroxide (28.48 mg, 507.53 μmol) were dissolved in methanol (1 mL) in a single-neck flask (50 mL). The reaction solution was purged with nitrogen three times, and then the reaction solution was stirred at room temperature of 30° C. for 14 hours under nitrogen protection. The reaction solution was added with water (2 mL), added with potassium hydroxide to adjust the pH to 8-9, stirred for 0.5 hour, extracted with ethyl acetate (5 mL), and then washed with water (5 mL*2) twice. The combined aqueous phase was added with HCl (6M) to adjust pH to 3-4, and then extracted with ethyl acetate (10 mL*2). The combined organic phase was dried over anhydrous sodium sulfate to obtain the product of embodiment 20F.

LCMS (ESI) m/z: 426.9 (M+1)⁺

Embodiment 20G

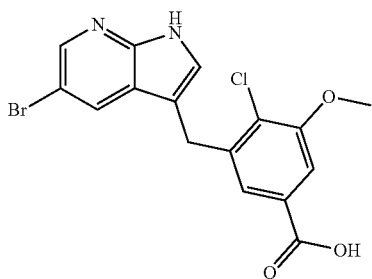 [SMILES: COc1cc(C(=O)O)cc(Cc2c[nH]c3ncc(Br)cc23)c1Cl]

The product of embodiment 20F (100 mg, 234.93 μmol) was dissolved in dichloromethane (2.00 mL) in a sample vial (5 mL), and then triethylsilane (218.54 mg, 1.88 mmol) and trifluoroacetic acid (2 mL, 27.01 mmol) were added. The reaction solution was stirred at a temperature of 30° C. for 3 hours. The reaction solution was concentrated under reduced pressure to obtain the product of embodiment 20G.

LCMS (ESI) m/z: 396.9 (M+1)$^+$

Embodiment 20H

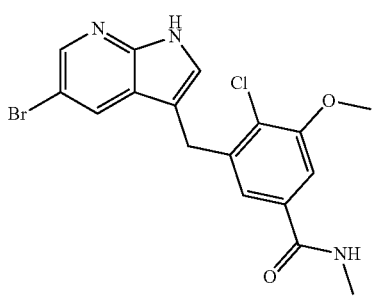 [SMILES: CNC(=O)c1cc(Cc2c[nH]c3ncc(Br)cc23)c(Cl)c(OC)c1]

The product of embodiment 20G (62 mg, 156.71 μmol) was dissolved in N,N-dimethylformamide (1 mL) in a single-neck flask (50 mL), and then diisopropylamine (81.01 mg, 626.84 μmol) and HATU (89.38 mg, 235.07 μmol) were added. The reaction solution was stirred at room temperature of 30° C. for 0.5 hour, and then added with methylamine hydrochloride (21.16 mg, 313.42 μmol). The reaction solution was stirred at room temperature of 30° C. for 12 hours. The reaction solution was quenched with water (10 mL), and extracted twice with ethyl acetate (10 mL*2). The combined organic phase was dried over anhydrous sodium sulfate to obtain the crude product. The crude product was separated and purified by preparative TLC plate (ethyl acetate) to obtain the product of embodiment 20H.

LCMS (ESI) m/z: 409.9 (M+1)$^+$

Embodiment 20I

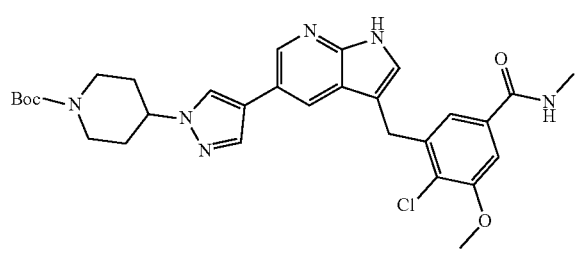 [SMILES: CNC(=O)c1cc(Cc2c[nH]c3ncc(-c4cnn(C5CCN(C(=O)OC(C)(C)C)CC5)c4)cc23)c(Cl)c(OC)c1]

The product of embodiment 20H (30 mg, 73.41 μmol) was dissolved in dioxane (0 mL)/water (0.5 mL) in a single-neck flask (50 mL), and then 1-(1-Boc-4-piperidinyl)pyrazole-4-boronic acid pinacol ester (30.47 mg, 80.75 μmol), Pd(dppf)Cl$_2$ (2.69 mg, 3.67 μmol), and potassium carbonate (25.36 mg, 183.52 μmol) were added. The reaction solution was purged with nitrogen three times, and then stirred at 100° C. for 14 hours under nitrogen protection. The reaction solution was added with water (10 mL), extracted with ethyl acetate (10 mL*2) twice. The combined organic phase was dried over anhydrous sodium sulfate to obtain a crude product. The crude product was separated by preparative chromatography plate (ethyl acetate) to obtain the product of embodiment 20I.

LCMS (ESI) m/z: 579.1 (M+1)$^+$

Embodiment 20

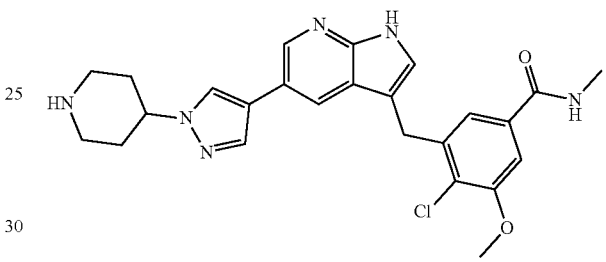

The product of embodiment 20I (30 mg, 51.81 μmol) was dissolved in hydrogen chloride/ethyl acetate (4 M, 2.00 mL) in a single-neck flask (50 mL), and the reaction solution was stirred at 30° C. for 1.5 hours. The reaction solution was directly concentrated under reduced pressure, and separated and purified by preparative HPLC (TFA system) (μm TFA) to obtain trifluoroacetate salt of embodiment 20. In embodiment 20, the free base can be obtained by washing a solution of the trifluoroacetate salt of embodiment 20 in dichloromethane with 1N sodium bicarbonate, followed by separating and concentrating the organic phase.

LCMS (ESI) m/z: 479.1 (M+1)$^+$ $^1$H NMR (400 MHz, DMSO-do) δ 11.45 (br s, 1H), 8.69 (br s, 1H), 8.48-8.52 (m 3H), 7.93-8.27 (m, 2H), 7.34-7.54 (m, 2H), 7.18 (s, 1H), 4.45-4.50 (m, 1H), 4.15-4.19 (n, 2H), 4.11 (br s, 1H), 3.89 (s, 3H), 3.10-3.15 (m, 4H), 2.75 (s, 3H), 2.15-2.33 (m, 4H).

Process G
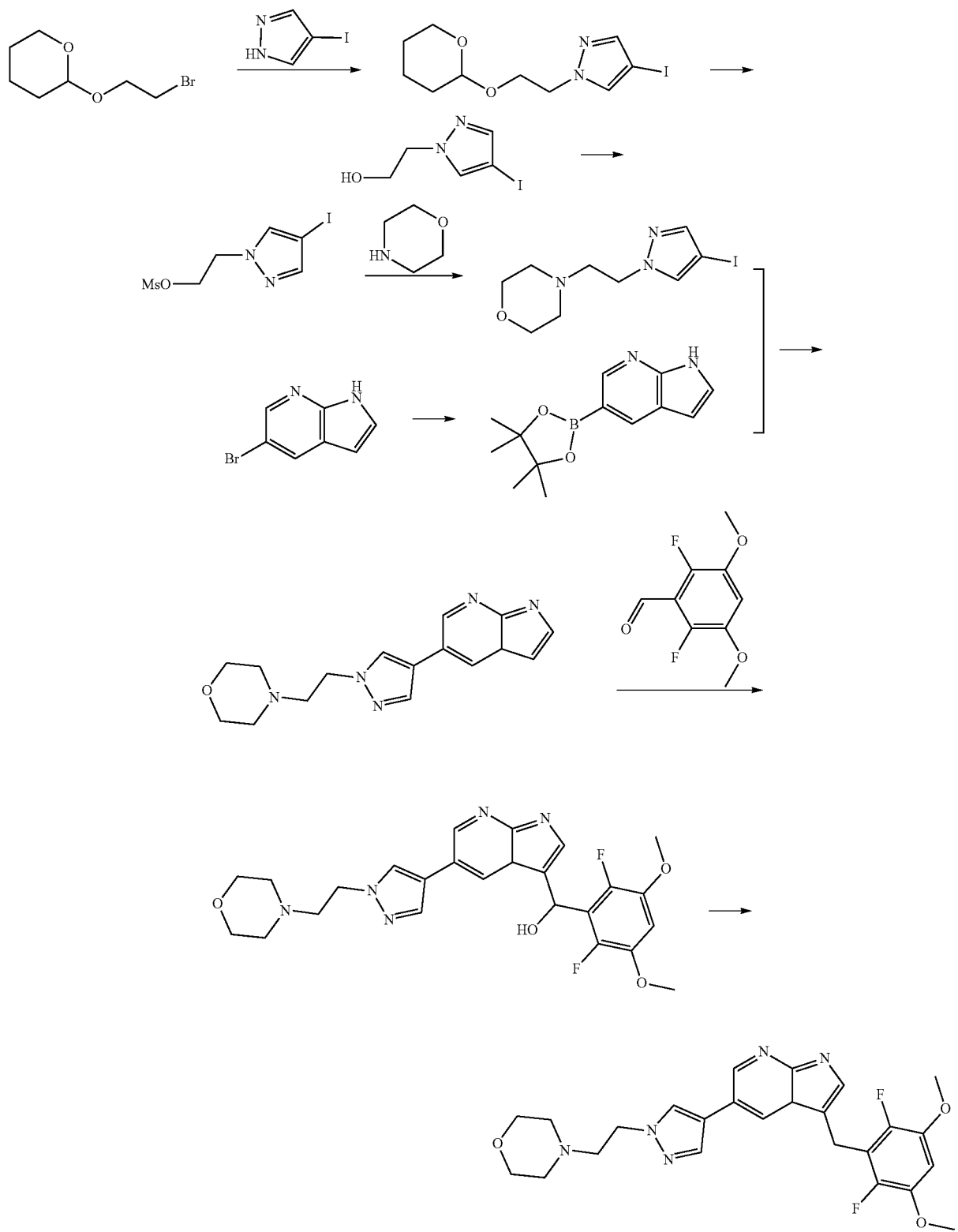

Embodiment 21

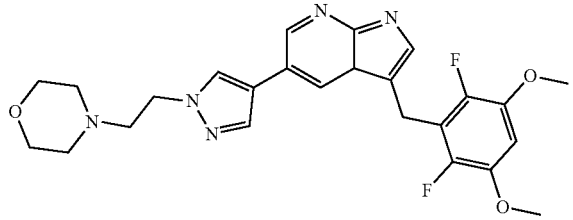 [SMILES: COc1cc(OC)c(F)c(CC2=CN=C3N=CC(c4cnn(CCN5CCOCC5)c4)=CC23)c1F]

Embodiment 21A

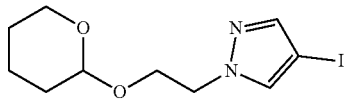 [SMILES: Ic1cnn(CCOC2CCCCO2)c1]

Cesium carbonate (18.70 g, 57.39 mmol) was added to a solution of the product of embodiment 1H (12 g, 57.39 mmol) and 4-iodopyrazole in acetonitrile (150 mL). The reaction solution was heated to 50° C. and maintained for 4 hours. The reaction solution was cooled, filtered, and concentrated. The residue was separated by flash chromatography on a silica gel column to obtain the product of embodiment 21A $^1$H NMR (400 MHz, CHLOROFORM-d) δ 7.53 (d, J=19.07 Hz, 2H), 4.52 (d, J=3.76 Hz, 1H), 4.33 (t, J=5.27 Hz, 2H), 4.03 (td, J=5.14, 10.79 Hz, 1H), 3.73 (td, J=5.33, 10.92 Hz, 1H), 3.57-3.66 (m, 1H), 3.41-3.50 (m, 1H), 1.72-1.83 (m, 1H), 1.42-1.68 (m, 5H).

Embodiment 21B

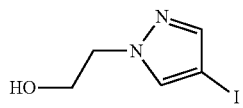

The product of embodiment 21A (1 g, 3.1 mmol) was added to a thumb flask containing hydrogen chloride/ethyl acetate (4 M, 10 mL) at 26° C. The reaction solution was stirred for 16 hours. The reaction solution was concentrated under reduced pressure to obtain the product of embodiment 21B.

$^1$H NMR (400 MHz, CHLOROFORM-d) δ ppm 7.51 (s, 1H), 7.47 (s, 1H), 4.19-4.26 (m, 2H), 3.90-3.96 (m, 2H).

Embodiment 21C

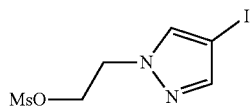

The product of embodiment 21B (370 mg, 1.55 mmol) and triethylamine (1.08 mL, 7.77 mmol) were added to dichloromethane (5 mL) at 0° C. firstly, then methanesulfonyl chloride (195.87 mg, 1.71 mmol) was added. The reaction solution was stirred for 2 hours. The reaction mixture was cooled to room temperature, quenched with water (3 mL), and then extracted with ethyl acetate (3 mL*3). The organic phase was washed with saturated brine, partitioned, dried over anhydrous sodium sulfate and concentrated under vacuum to obtain the product of embodiment 21C.

Embodiment 21D

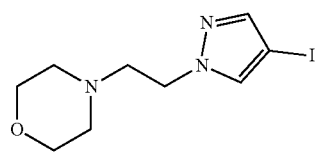 [SMILES: Ic1cnn(CCN2CCOCC2)c1]

The product of embodiment 21C (500 mg, 1.58 mmol) and morpholine (413.39 mg, 4.75 mmol) were added to acetonitrile (8 mL) at 25° C. under nitrogen atmosphere, then cesium carbonate (1.03 g, 3.16 mmol) was added. The reaction solution was heated to 80° C. in an oil bath and stirred for 16 hours. The reaction mixture was filtered and concentrated under reduced pressure. The reaction solution was separated and purified by flash chromatography on a silica gel column (petroleum ether/ethyl acetate=5/1) to obtain the product of embodiment 21D.

LCMS (ESI) m/z: 308.0 (M+1)$^+$ $^1$H NMR (400 MHz, CHLOROFORM-d) δ ppm 7.46 (s, 1H), 7.42 (s, 1H), 4.13-4.23 (m, 2H), 3.56-3.67 (m, 4H), 2.67-2.76 (m, 2H), 2.45-2.51 (m, 4H).

Embodiment 21E

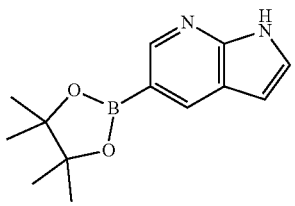 [SMILES: CC1(C)OB(c2cnc3[nH]ccc3c2)OC1(C)C]

Potassium acetate (996.21 mg, 10.15 mmol) and Pd(dppf)Cl$_2$·CH$_2$Cl$_2$ (414.47 mg, 507.53 μmol) were added to a solution of 5-bromo-7-azaindole (1 g, 5.08 mmol) and bis(pinacolato)diboron (1.55 g, 6.09 mmol) in dioxane (15 mL). The reaction solution was heated to 80° C. under nitrogen protection and reacted for 16 hours. The reaction solution was cooled, filtered, and the residue was separated by flash chromatography on a silica gel column to obtain the product of embodiment 21E.

$^1$H NMR (400 MHz, CHLOROFORM-d) δ 10.47 (br s, 1H), 8.68 (d, J=1.26 Hz, 1H), 8.41 (d, J=1.26 Hz, 1H), 7.31 (d, J=3.51 Hz, 1H), 6.52 (d, J=3.51 Hz, 1H), 1.30 (s, 12H).

Embodiment 21F

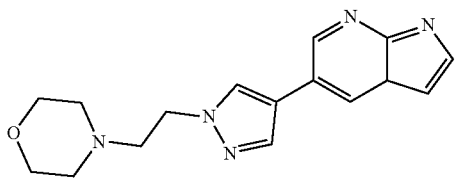 [SMILES: C1=CC2C=C(c3cnn(CCN4CCOCC4)c3)C=NC2=N1]

At 26° C., the product of embodiment 21E (119.21 mg, 0.48 mmol), the product of embodiment 21D (150 mg, 0.48 mmol) were added sequentially to tetrahydrofuran (3 mL), then water (1 mL) was added, Pd(dppf)Cl$_2$ (35.74 mg, 0.048 mmol) and potassium phosphate (207.34 mg, 0.96 mmol) were added lastly. The reaction solution was stirred at 100° C. for 6 hours under nitrogen atmosphere. The reaction mixture was cooled to room temperature firstly, quenched with water (10 mL), and extracted with ethyl acetate (10 mL*3). The organic phase was washed with saturated brine, partitioned, dried over anhydrous sodium sulfate and concentrated under vacuum. The crude product was purified by flash chromatography on a silica gel column (dichloromethane:methanol=5:1) to obtain the product of embodiment 21F.

LCMS (ESI) m/z: 298.2 (M+1)$^+$

Embodiment 21G

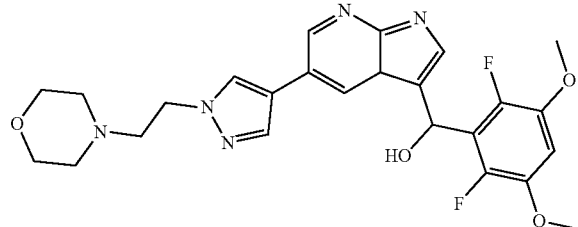

At 30° C., the product of embodiment 21F (50 mg, 0.17 mmol) and 2,6-difluoro-3,5-dimethoxybenzaldehyde (67.98 mg, 0.34 mmol) were added sequentially to methanol (5 mL), then potassium hydroxide (18.87 mg, 0.34 mmol) was added, and the reaction solution was stirred under nitrogen protection for 16 hours. The reaction solution was quenched with water (10 mL), and extracted with ethyl acetate (10 mL*3). The organic phase was washed with saturated brine, partitioned, dried over anhydrous sodium sulfate and concentrated under vacuum. The crude product was separated by preparative chromatography plate (dichloromethane/methanol=20/1) to obtain the product of embodiment 21G.

LCMS (ESI) m/z: 500.4 (M+1)$^+$

Embodiment 21

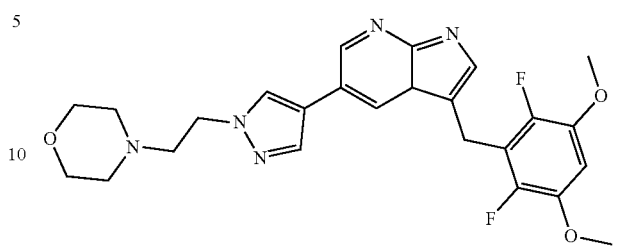

At 26° C., the product of embodiment 21G (50 mg, 0.1 mmol) was added to dichloromethane (3 mL), then triethylsilane (34.92 mg, 0.3 mmol) and trifluoroacetic acid (1 mL) were added, and the reaction solution was stirred for 3 hours. The reaction solution was concentrated directly under reduced pressure. The crude product was separated by preparative chromatography plate (dichloromethane:methanol=10:1) and then purified by preparative HPLC (TFA system) to obtain trifluoroacetate salt of embodiment 21. In embodiment 21, the free base can be obtained by washing a solution of the trifluoroacetate salt of embodiment 21 in dichloromethane with 1N sodium bicarbonate, followed by separating and concentrating the organic phase.

LCMS (ESI) m/z: 484.4 (M+1)$^+$ $^1$H NMR (400 MHz, DMSO-d$_6$) δ ppm 11.47 (s, 1H), 8.48 (d, J=2.01 Hz, 1H), 8.27 (s, 1H), 8.10 (s, 1H), 7.13 (s, 1H), 6.89 (t, J=8.41 Hz, 1H), 4.58-4.62 (m, 2H), 4.06 (s, 2H), 3.84 (s, 6H), 3.70-3.83 (m, 4H), 3.67-3.69 (m, 4H), 2.55-2.58 (m, 4H).

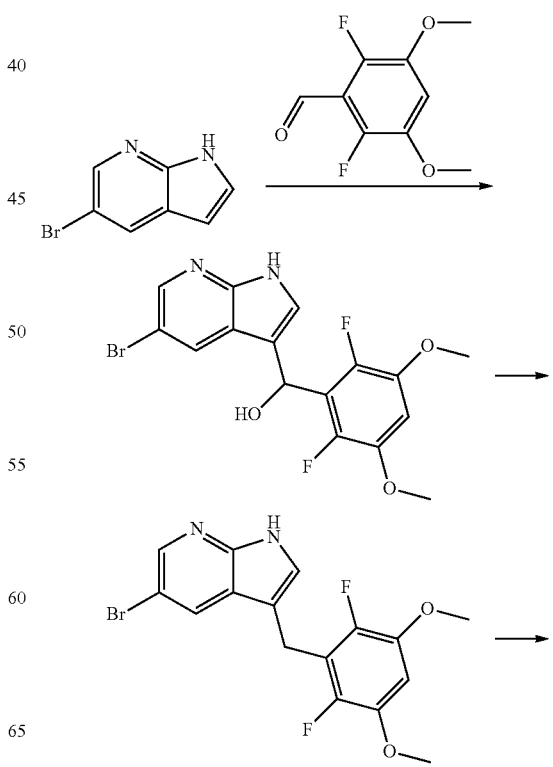

75

-continued

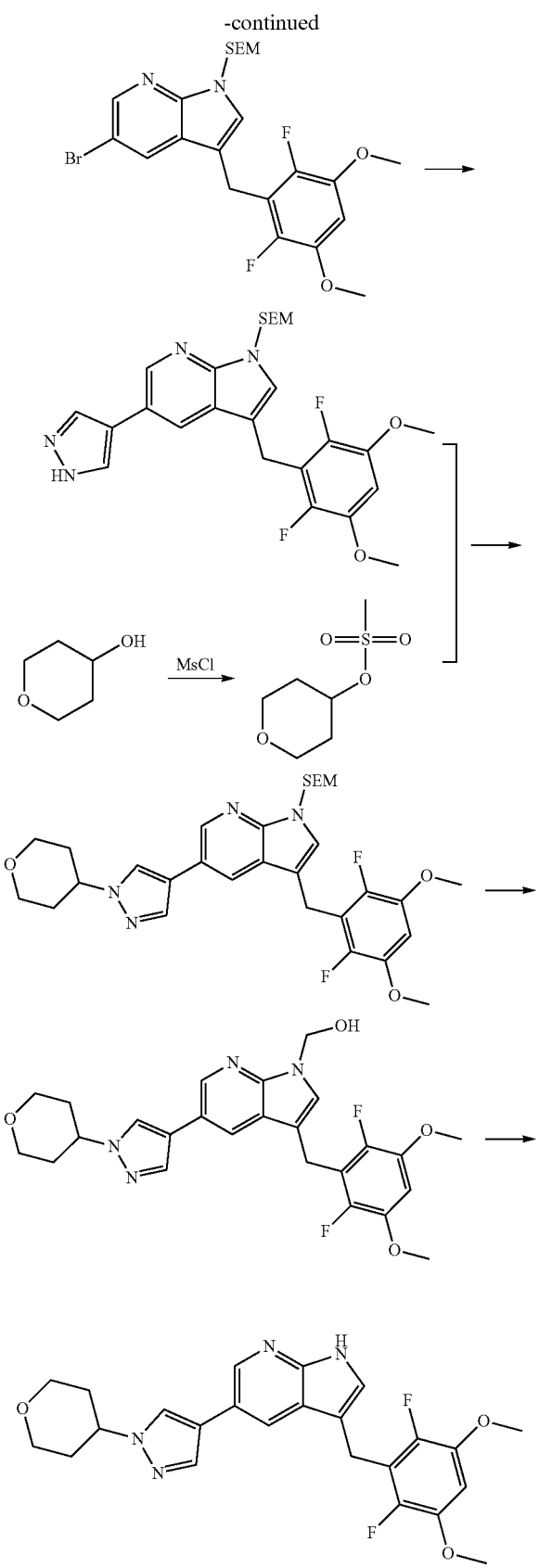

76

Embodiment 22

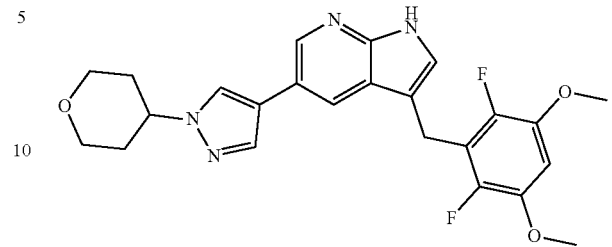

Embodiment 22A

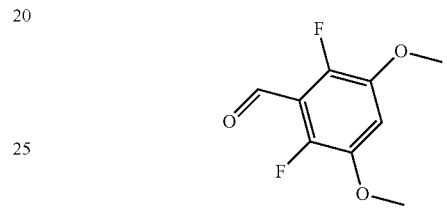

At 0° C., 3,5-dimethoxybenzaldehyde (300 g, 1.81 mol) was added to acetonitrile (4500 mL), then Select F (1.28 kg, 3.61 mol) was added to the reaction solution. The reaction solution was heated to 20° C. and stirred mechanically for 96 hours at this temperature. The reaction was stopped, added with 15 L of water under stirring, during which a precipitate occurred. The mixture was filtered, and the filter cake was dissolved in 1 L of dichloromethane, dried over anhydrous sodium sulfate, and concentrated under reduced pressure to obtain a crude product. The crude product was purified by chromatography column (petroleum ether:ethyl acetate=20/1-10/1) to obtain the product of embodiment 22A.

$^1$H NMR (400 MHz, CHLOROFORM-d) δ 10.38 (S, 1H) 6.91 (t, J=8.16 Hz, 1H) 3.94 (s, 6H).

Embodiment 22B

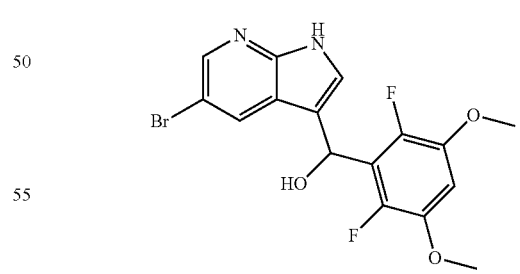

The product of embodiment 22A (10 g, 49.47 mmol) and 5-bromo-7-azaindole (8.12 g, 41.22 mmol) were added to methanol (80 mL), and potassium hydroxide (4.63 g, 82.44 mmol) was added to the reaction solution under stirring. The reaction solution was stirred at 15-20° C. for 16 hours, during which a large amount of white solid precipitated. The reaction solution was filtered, the filter cake was washed with 5 mL of methanol, and then the filtrate was rotary-evaporated to dryness at 50° C. under reduced pressure to obtain the product of embodiment 22B.

¹H NMR (400 MHz, DMSO-d₆) δ 8.36 (d, J=2.26 Hz, 1H), 8.12 (d, J=2.01 Hz, 1H), 7.40 (s, 1H), 7.05 (t, J=8.16 Hz, 1H), 6.41 (s, 1H), 6.15 (br s, 1H), 3.95 (s, 6H).

Embodiment 22C

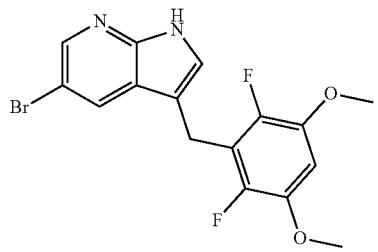 [SMILES: COc1cc(OC)c(F)c(Cc2c[nH]c3ncc(Br)cc23)c1F]

The product of embodiment 22B (10.00 g, 25.05 mmol), triethylsilane (14.56 g, 125.25 mmol) were added to dichloromethane (100 mL), and trifluoroacetic acid (14.28 g, 125.25 mmol) was added to the reaction solution under stirring. The reaction solution was stirred for 16 hours at 15-20° C. The reaction solution was directly rotary-evaporated to dryness at 40-50° C. under reduced pressure, and then dichloromethane (50 mL) was added. The mixture was rotary-evaporated again to obtain the product of embodiment 22C.

¹H NMR (400 MHz, DMSO-d₆) δ 11.74 (br s, 1H), 8.19-8.31 (m, 1H), 8.09 (d, J=2.01 Hz, 1H), 7.25 (d, J=2.01 Hz, 1H), 6.89 (t, J=8.41 Hz, 1H), 4.03 (s, 2H), 3.79-3.90 (m, 6H).

Embodiment 22D

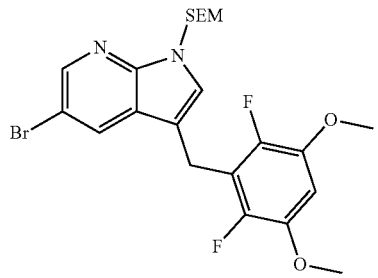 [SMILES: COc1cc(OC)c(F)c(Cc2cn(COCC[Si](C)(C)C)c3ncc(Br)cc23)c1F]

The product of embodiment 22C (10.00 g, 26.10 mmol) was dissolved in N,N-dimethylformamide (100 mL) and cooled to 0° C. Sodium hydride (2.09 g, 52.19 mmol, 60% purity) was added to the above reaction solution under stirring over 5 min and the reaction solution was stirred at 0° C. for 25 min. Chloromethyl trimethylsilylethyl ether (6.53 g, 39.15 mmol) was added to the reaction solution at 0° C., and the reaction solution was stirred for 30 min. The reaction solution was added with 100 mL of water, and extracted twice with ethyl acetate (100 mL*2). The combined organic phase was dried over anhydrous sodium sulfate, and rotary-evaporated to dryness at 40-50° C. under reduced pressure to obtain the product of embodiment 22D.

Embodiment 22E

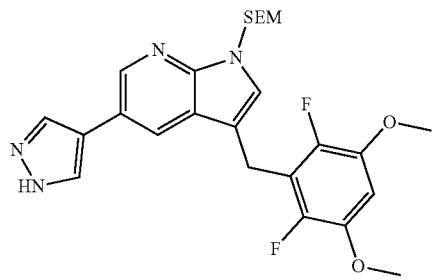 [SMILES: COc1cc(OC)c(F)c(Cc2cn(COCC[Si](C)(C)C)c3ncc(-c4cn[nH]c4)cc23)c1F]

100 mL single-neck flask was token, the product of embodiment 22D (2.1 g, 4.09 mmol), 4-pyrazoleboronic acid pinacol ester (1.59 g, 8.18 mmol), Pd(dppf)Cl₂ (149.63 mg, 204.50 μmol), potassium carbonate (1.41 g, 10.23 mmol) were added sequentially to the single-neck flask containing dioxane (20 mL) and H₂O (10 mL). The reaction solution was purged with nitrogen three times. The reaction solution was stirred for 14 hours under nitrogen protection at 100° C. The reaction solution was added with water (50 mL), and extracted three times with ethyl acetate (50 mL*3). The combined organic phase was washed with saturated brine (30 mL) once, dried over anhydrous sodium sulfate, and concentrated under reduced pressure. The crude product obtained was purified by column chromatography (petroleum ether/ethyl acetate=1/0-0/1) to obtain the product of embodiment 22E.

Embodiment 22F

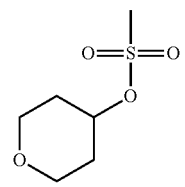

Tetrahydropyran-4-ol (200 mg, 1.96 mmol) was added to dichloromethane (3 mL) at 0° C., then methanesulfonyl chloride (269.18 mg, 2.35 mmol) and triethylamine (594.47 mg, 5.87 mmol) were added sequentially. The reaction solution was stirred at 20° C. for 2 hours. The reaction solution was added with water, and extracted with dichloromethane (10 mL*3). The organic phase was washed with saturated brine, partitioned, dried over anhydrous sodium sulfate, and concentrated under vacuum to obtain the product of embodiment 22F.

Embodiment 22G

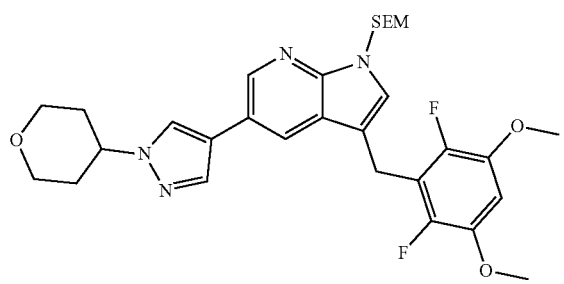 [SMILES: COc1cc(OC)c(F)c(Cc2cn(COCC[Si](C)(C)C)c3ncc(-c4cnn(C5CCOCC5)c4)cc23)c1F]

At 20° C. under nitrogen protection, the product of embodiment 22E (50.00 mg, 0.1 mmol) was added to N,N-dimethylformamide (2 mL), and then the product of embodiment 22F (36.00 mg, 0.2 mmol) and cesium carbonate (65.08 mg, 0.2 mmol) were added. The reaction mixture was heated to 100° C. continuously for 16 hours. The reaction solution was filtered and concentrated under vacuum. The mixture was separated by preparative chromatography plate (dichloromethane:methanol=1:1) to obtain the product of embodiment 22G.

LCMS (ESI) m/z: 585.5 (M+1)$^+$

Embodiment 22H

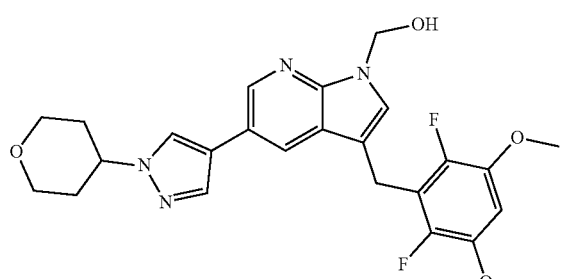

The product of embodiment 22G (25 mg, 43 μmol) was added to trifluoroacetic acid (1 mL) at 20° C. The reaction solution was stirred for 1 hour. The reaction solution was concentrated under reduced pressure to obtain the product of embodiment 22H.

LCMS (ESI) m/z: 485.4 (M+1)$^+$

Embodiment 22

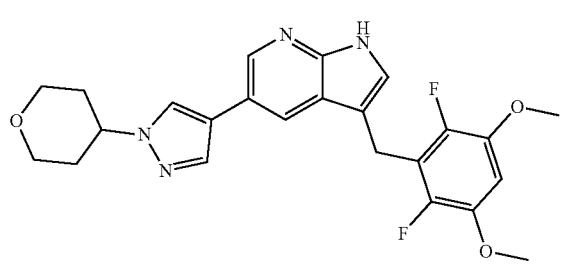 [SMILES: COc1cc(OC)c(F)c(Cc2c[nH]c3ncc(-c4cnn(C5CCOCC5)c4)cc23)c1F]

At 20° C., the product of embodiment 22H (20 mg, 0.04 mmol) was added to methanol (2 mL), then potassium carbonate (57.05 mg, 0.4 mmol) was added, and the reaction solution was stirred for 1 hour. The reaction solution was filtered and concentrated under vacuum. The residue was purified by preparative chromatography (TFA) to obtain the trifluoroacetate salt of embodiment 22. In embodiment 22, the free base can be obtained by washing a solution of the trifluoroacetate salt of embodiment 22 in dichloromethane with 1N sodium bicarbonate, followed by separating and concentrating the organic phase.

LCMS (ESI) m/z: 455.3 (M+1)$^+$ $^1$H NMR (400 MHz, METHANOL-d$_4$) δ 8.47 (s, 1H), 8.36 (s, 1H), 8.17 (s, 1H), 7.91 (s, 1H), 7.13-7.23 (m, 3H), δ 79 (t, J=8.53 Hz, 1H), 4.10-4.22 (m, 6H), 3.88 (s, 6H), 3.58-3.61 (m, 1H), 2.12-2.15 (m, 4H).

Process A

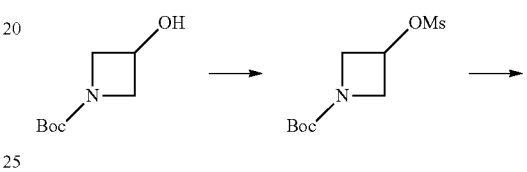

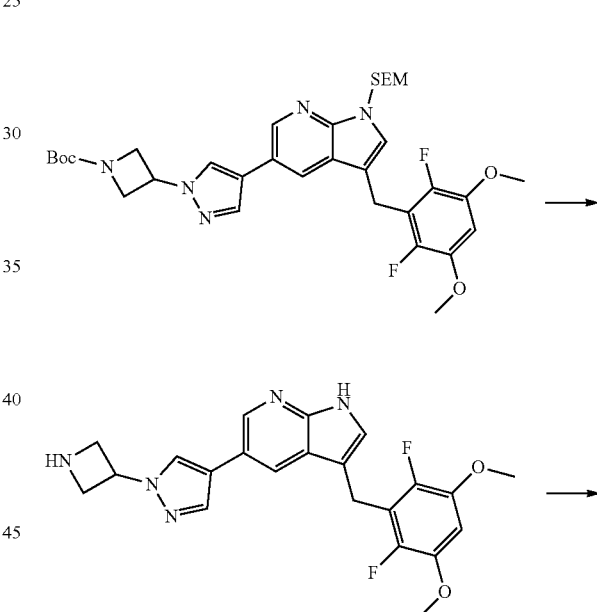

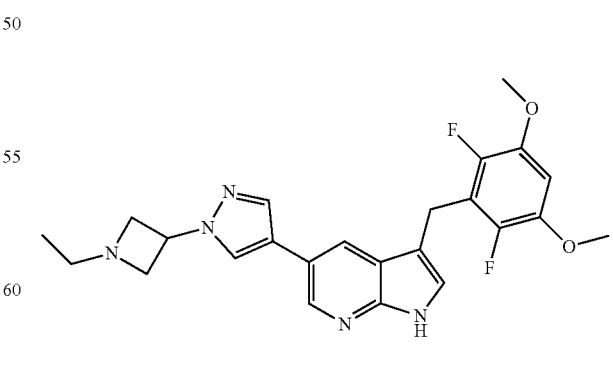

Embodiment 24

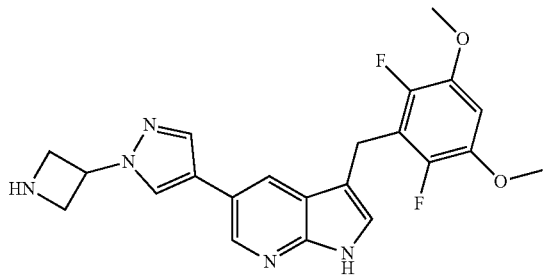 [SMILES: COc1cc(OC)c(F)c(Cc2c[nH]c3ncc(-c4cnn(C5CNC5)c4)cc23)c1F]

Embodiment 24A

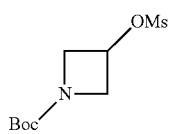 [SMILES: CC(C)(C)OC(=O)N1CC(OS(C)(=O)=O)C1]

N-Boc-3-hydroxyazetidine (500 mg, 2.89 mmol) was dissolved in dichloromethane (5 mL) in a single-neck flask (50 mL), then triethylamine (584.20 mg, 5.77 mmol) was added, followed by the slow addition of methanesulfonyl chloride (396.81 mg, 3.46 mmol) dropwise. The reaction solution was stirred for 2 hours at 0° C. The reaction solution was quenched with water (10 mL), and extracted with ethyl acetate (10 mL*2) twice. The combined organic phase was washed with saturated brine (10 mL), dried over anhydrous sodium sulfate, and concentrated under reduced pressure to obtain the product of embodiment 24A.

$^1$H NMR (400 MHz, CHLOROFORM-d) δ 5.09-5.17 (m, 1H), 4.21 (dd, J=6.53, 10.04 Hz, 2H), 4.03 (dd, J=4.27, 10.29 Hz, 2H), 3.00 (s, 3H), 1.37 (s, 9H).

Embodiment 24B

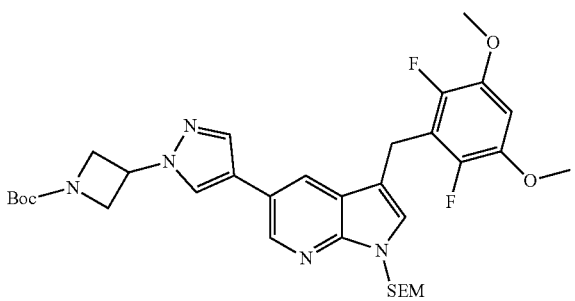 [SMILES: COc1cc(OC)c(F)c(Cc2cn(COCC[Si](C)(C)C)c3ncc(-c4cnn(C5CN(C(=O)OC(C)(C)C)C5)c4)cc23)c1F]

The product of embodiment 22E (50 mg, 99.88 μmol) was dissolved in N,N-dimethylformamide (1 mL)/water (0.5 mL) in a sample vial (5 mL), and then the product of embodiment 24A (25.10 mg, 99.88 μmol) and cesium carbonate (65.09 mg, 199.76 μmol) were added. The reaction solution was stirred at 100° C. for 14 hours. The reaction solution was added with water (10 mL), and extracted with ethyl acetate (10 mL*2) twice. The combined organic phase was washed with saturated brine (10 mL) three times, dried over anhydrous sodium sulfate, and concentrated under reduced pressure to obtain a crude product. The crude product was purified by preparative TLC (petroleum ether: ethyl acetate=1:1) to obtain the product of embodiment 24B.

LCMS (ESI) m/z: 656.3 (M+1)$^+$

Embodiment 24

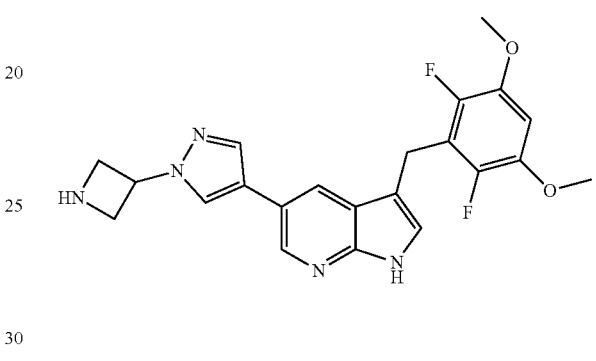

The product of embodiment 24B (50 mg, 76.24 μmol) was dissolved in dichloromethane (2.00 mL) in a single-neck flask (50 mL), and then trifluoroacetic acid (1.02 mL, 13.74 mmol) was added. The reaction solution was stirred at 25° C. for 2 hours. A small amount of raw material was shown to be remained and a major peak was generated as an intermediate. The reaction solution was directly concentrated under reduced pressure to obtain a crude product. The crude product was dissolved in MeOH (2 mL), and potassium carbonate (168.60 mg, 1.22 mmol) was added. The reaction solution was stirred at 25° C. for 16 hours, then the reaction solution was transferred to 50° C. and stirred for 1 hour. The reaction solution was filtered and the filtrate was purified by preparative HPLC (TFA system) to obtain trifluoroacetate salt of embodiment 24. In embodiment 24, the free base can be obtained by washing a solution of the trifluoroacetate salt of embodiment 24 in dichloromethane with 1N sodium bicarbonate, followed by separating and concentrating the organic phase.

LCMS (ESI) m/z: 426.0 (M+1)$^+$ $^1$H NMR (400 MHz, METHANOL-d$_4$) δ 8.45 (br s, 1H), 8.32 (d, J=2.01 Hz, 1H), 8.11 (d, J=13.55 Hz, 2H), 7.22 (s, 1H), 6.78 (t, J=8.28 Hz, 1H), 5.44-5.59 (m, 1H), 4.57-4.67 (m, 4H), 4.16 (s, 2H), 3.87 (s, 6H).

The following embodiments and salts thereof were prepared using embodiment 24 as the raw material, by referring to the methods described in embodiments 12, 17 and 18, respectively independently.

| Embodi-ments | Structure | NMR | LCMS (ESI) m/z: (M + 1) |
|---|---|---|---|
| Embodiment 25 | 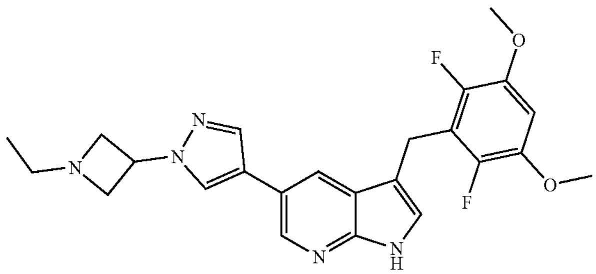 [SMILES: CCN1CC(n2cc(-c3cnc4[nH]cc(Cc5c(F)c(OC)cc(OC)c5F)c4c3)cn2)C1] | ¹H NMR (400 MHz, METHANOL-d₄) δ 8.46 (s, 1H), 8.38 (d, J =1.6 Hz, 1H), 8.15 (s, 1H), 8.10 (s, 1H), 7.23 (s, 1H), 6.77 (t, J = 8.32 Hz, 1H), 5.36-5.50 (m, 1H), 4.55-4.71 (m, 3H), 4.16 (s, 2 H), 3.85 (s, 6 H), 3.44-3.57 (m, 2 H), 1.30 (t, J = 7.2 Hz, 3H). | 454.0 |
| Embodiment 26 | 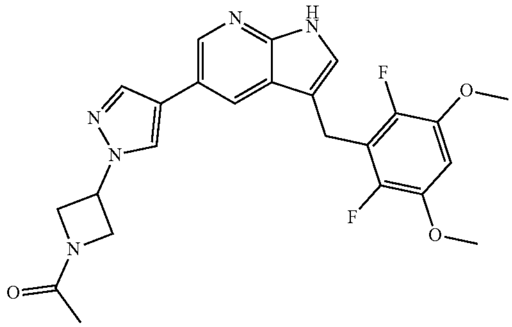 [SMILES: COc1cc(OC)c(F)c(Cc2c[nH]c3ncc(-c4cnn(C5CN(C(C)=O)C5)c4)cc23)c1F] | ¹H NMR (400 MHz, METHANOL-d₄) δ 8.86 (d, J = 1.6 Hz, 1H), 8.63 (d, J = 1.6 Hz, 1H), 8.34 (s, 1H), 7.40 (s, 1H), 6.80 (t, J = 8.32 Hz, 1H ), 5.34-5.39 (m, 1H), 4.69-4.78 (m, 1H), 4.63 (dd, J = 9.32, 5.19 Hz, 1H), 4.46-4.53 (m, 1H), 4.36-4.40 (m, 1 H), 4.24 (s, 2 H), 3.86 (s, 6 H), 1.97 (s, 3 H). | 468.1 |
| Embodiment 23 | 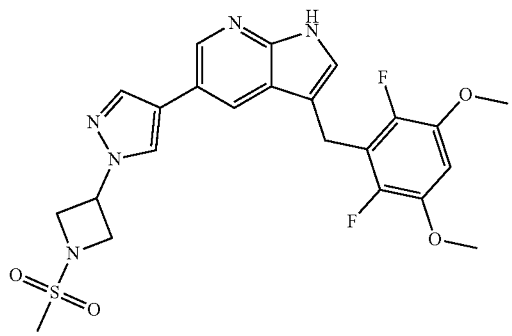 [SMILES: COc1cc(OC)c(F)c(Cc2c[nH]c3ncc(-c4cnn(C5CN(S(C)(=O)=O)C5)c4)cc23)c1F] | ¹H NMR (400 MHz, DMSO-d₆) δ 11.51 (br s, 1H), 8.49 (s, 1H), 8.35 (s, 1H), 8.14 (s, 1H), 8.04 (s, 1H), 7.12 (s, 1H), 6.89 (t, J = 8.28 Hz, 1H), 5.28-5.40 (m, 1H), 4.33 (d, J = 7.03 Hz, 4H), 4.07 (br s, 2H), 3.84 (s, 6H), 3.16 (s, 3H) | 526.1 (M + 23)⁺ |
Process B
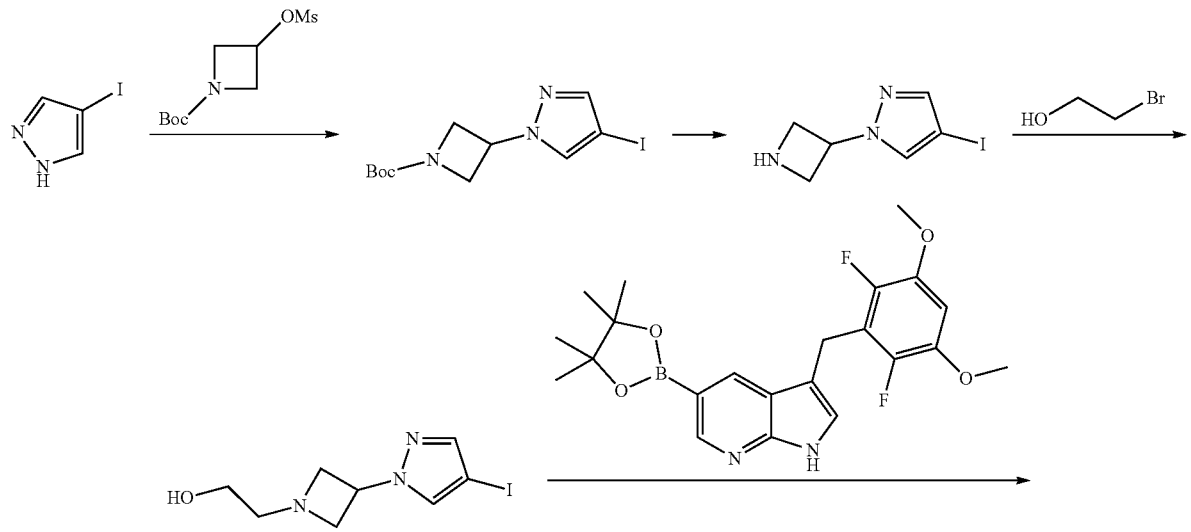

-continued

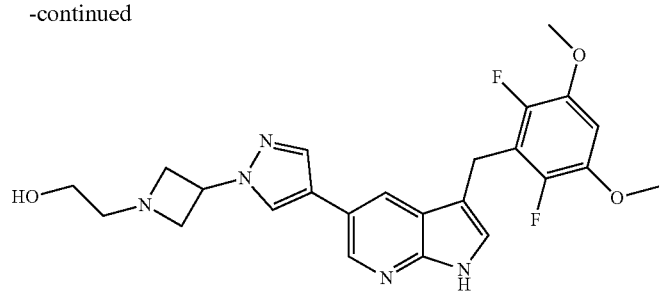

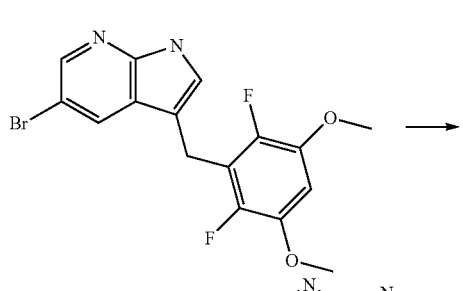

Embodiment 27

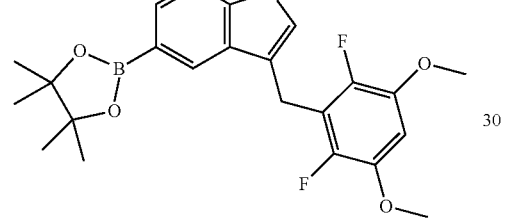

Embodiment 27A

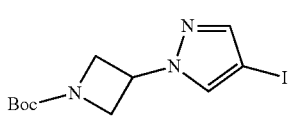 [SMILES: CC(C)(C)OC(=O)N1CC(n2cc(I)cn2)C1]

4-Iodopyrazole (463.13 mg, 2.39 mmol) was dissolved in N,N-dimethylformamide (6 mL) in a single-neck flask (50 mL), and then the product of embodiment 24A (600.00 mg, 2.39 mmol), cesium carbonate (1.56 g, 4.78 mmol) were added. The reaction solution was stirred at 100° C. for 14 hours. The reaction solution was added with water (20 mL), and extracted with ethyl acetate (20 mL*3) three times. The combined organic phase was washed with saturated brine (10 mL*3) three times, dried over anhydrous sodium sulfate, and concentrated under reduced pressure to obtain a crude product. The crude product was separated and purified by column chromatography (petroleum ether/ethyl acetate=1/0-3/1) to obtain the product of embodiment 27A.

$^1$H NMR (400 MHz, CHLOROFORM-d) δ 7.52-7.59 (m, 2H), 5.03 (tt, J=5.46, 7.84 Hz, 1H), 4.32-4.39 (m, 2H), 4.24-4.29 (m, 2H), 1.44 (s, 9H).

Embodiment 27B

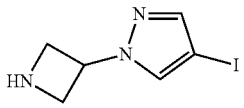

The product of embodiment 27A (800 mg, 2.29 mmol) was dissolved in trifluoroacetic acid (5 mL) in a single-neck flask (50 mL). The reaction solution was stirred at room temperature of 25° C. for 1 hour. The reaction solution was concentrated under reduced pressure to obtain the product of embodiment 27B.

LCMS (ESI) m/z: 249.9 (M+1)$^+$ $^1$H NMR (400 MHz, CHLOROFORM-d) δ 7.76 (s, 1H), 7.72 (s, 1H), 5.58-5.66 (m, 1H), 4.69-4.75 (m, 4H).

Embodiment 27C

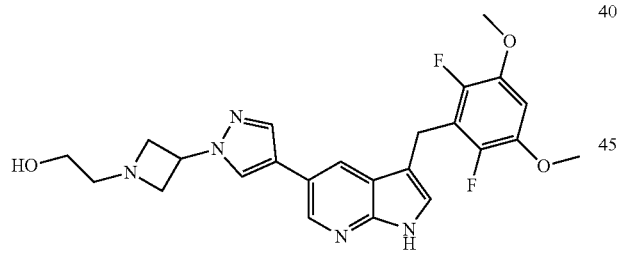

The product of embodiment 27B (500 mg, 1.38 mmol, TFA salt) was dissolved in acetone (5 mL) in a single-neck flask (50 mL), then 2-bromoethanol (344.18 mg, 2.75 mmol) and potassium carbonate (951.66 mg, 6.89 mmol) were added. The reaction solution was stirred at 60° C. for 14 hours. The reaction solution was filtered and the filtrate was concentrated under reduced pressure to obtain a crude product. The crude product was purified by column chromatography (dichloromethane:methanol=1:0 to 10:1) to obtain the product of embodiment 27C.

LCMS (ESI) m/z: 293.9 (M+1)$^+$ $^1$H NMR (400 MHz, CHLOROFORM-d) δ 7.54 (s, 1H), 7.50 (s, 1H), 4.92-5.07 (m, 1H), 4.30-4.44 (m, 4H), 4.16-4.21 (m, 2H), 3.73-3.78 (m, 2H).

Embodiment 27D

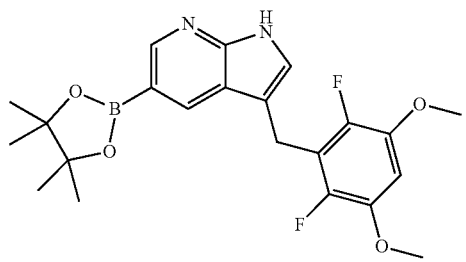

The product of embodiment 22C (4 g, 10.44 mmol) was added to dioxane (50 mL) firstly under nitrogen protection at 20° C., then bis(pinacolato)diboron (3.98 g, 15.66 mmol), Pd(dppf)Cl$_2$ (763.81 mg, 1.04 mmol) and potassium acetate (2.05 g, 20.88 mmol) were added sequentially. The reaction solution was stirred at 100° C. for 16 hours. The reaction solution was filtered and the filtrate was directly concentrated and rotary-evaporated to dryness under reduced pressure. The residue was separated by flash chromatography on a silica gel column (petroleum ether/ethyl acetate=0/1 to 3/1) to obtain the product of embodiment 27D.

LCMS (ESI) m/z: 431.3 (M+1)$^+$ $^1$H NMR (400 MHz, CHLOROFORM-d) δ 8.60 (d, J=1.00 Hz, 1H), 8.41 (d, J=1.26 Hz, 1H), 7.19 (s, 1H), 6.99 (s, 1H), 6.40-6.48 (m, 11H), 4.06 (s, 2H), 3.79 (s, 6H), 1.31 (s, 12H).

Embodiment 27

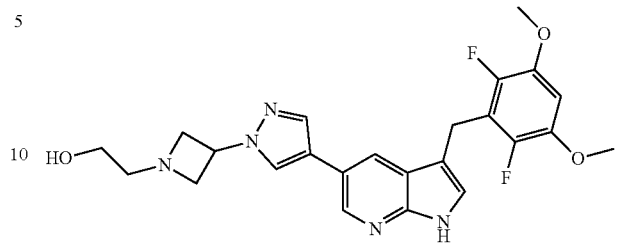

The product of embodiment 27C (102.19 mg, 348.63 μmol) was dissolved in dioxane (2 mL)/water (1 mL) in a single-neck flask (50 mL), and then the product of embodiment 27D (150 mg, 348.63 μmol), Pd(dppf)Cl$_2$ (12.75 mg, 17.43 μmol), potassium phosphate (68.33 mg, 679.27 μmol) were added. The reaction solution was purged with nitrogen three times, and stirred at 100° C. for 14 hours under nitrogen protection. The reaction solution was filtered, and the filtrate was added with water (10 mL), and extracted with ethyl acetate (10 mL*3) for three times. The combined organic phase was washed with saturated brine (10 mL), and dried over anhydrous sodium sulfate to obtain a crude product. The crude product was separated and purified by preparative HPLC (TFA system) to obtain trifluoroacetate salt of embodiment 27. In embodiment 27, the free base can be obtained by washing a solution of the trifluoroacetate salt of embodiment 27 in dichloromethane with 1N sodium bicarbonate, followed by separating and concentrating the organic phase.

LCMS (ESI) m/z: 514.0 (M+45)$^+$ $^1$H NMR (400 MHz, DMSO-d$_6$) δ 11.44 (s, 1H), 8.48 (d, J=2.01 Hz, 1H), 8.36 (s, 1H), 8.10 (d, J=1.76 Hz, 1H), 8.00 (s, 1H), 7.09 (s, 1H), 6.89 (t, J=8.53 Hz, 1H), 5.21-5.43 (m, 1H), 4.82 (t, J=5.65 Hz, 1H), 4.20-4.47 (m, 4H), 4.02-4.08 (m, 4H), 3.84 (s, 6H), 3.57 (q, J=5.52 Hz, 2H).

Process C

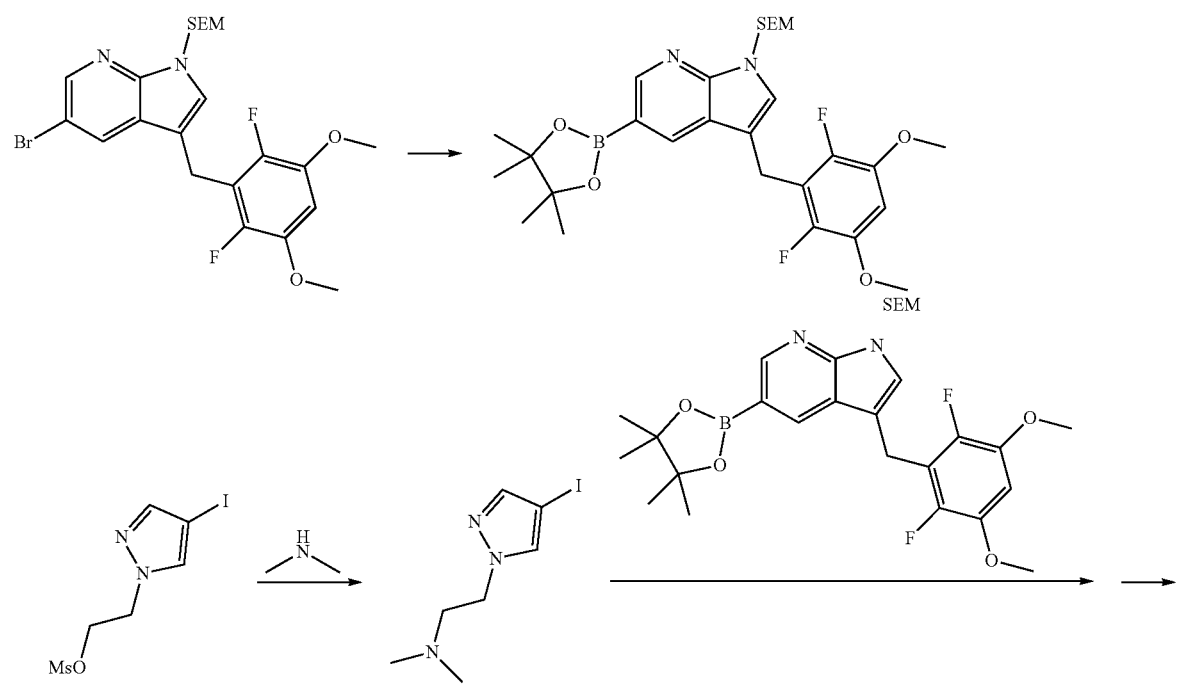

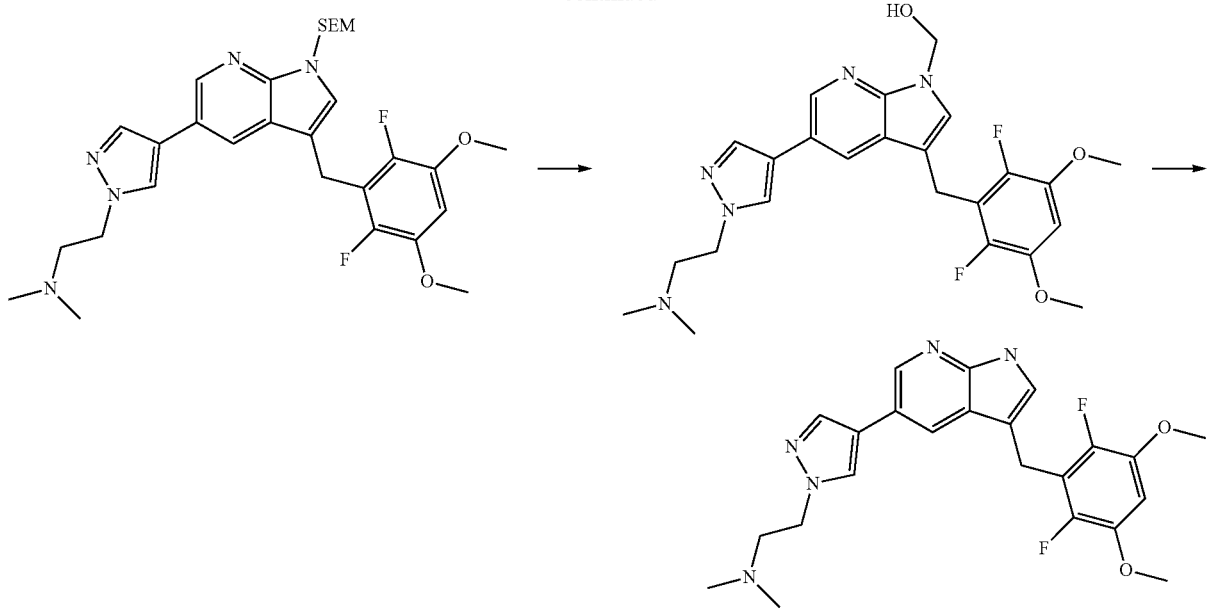

Embodiment 28

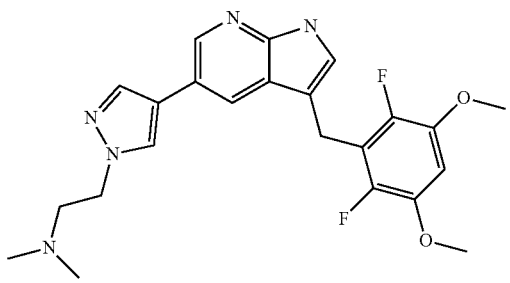

Embodiment 28A

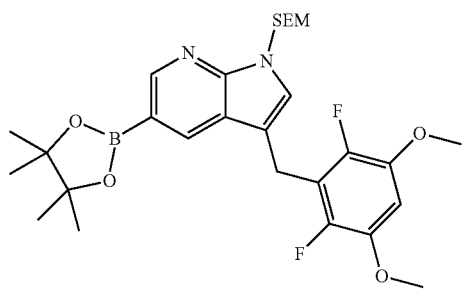

The product of embodiment 22D (10 g, 19.48 mmol) and bis(pinacolato)diboron (7.42 g, 29.21 mmol) were added to dioxane (100 mL) in a single-neck flask, then potassium carbonate (3.82 g, 38.95 mmol) and Pd(dppf)Cl$_2$ (712.54 mg, 973.81 μmol) were added to the flask. The reaction solution was purged with nitrogen three times. The reaction solution was heated to 90° C. and stirred for 16 hours. The reaction solution was cooled to 15-20° C., and filtered. The filtrate was rotary-evaporated to dryness under reduced pressure at 40-50° C. to obtain a crude product. The crude product was purified by column chromatography (petroleum ether/ethyl acetate=20/1-10/1 then dichloromethane/methanol=20/1-10/1) to obtain the product of embodiment 28A.

LCMS (ESI) m/z: 561.2 (M+1)$^+$ $^1$H NMR (400 MHz, CHLOROFORM-d) δ ppm 8.78 (d, J=1.51 Hz, 1H) 8.54 (d, J=1.26 Hz, 1H) 7.37 (s, 1H) 7.13 (s, 1H) 6.59-6.69 (m, 1H) 5.70 (s, 2H) 4.23 (br s, 2H) 3.98 (s, 6H) 3.55-3.61 (m, 2H) 2.15 (s, 3H) 1.48 (s, 12H) 0.93-0.99 (m, 2H) 0.00 (s, 8H), 8H).

Embodiment 28B

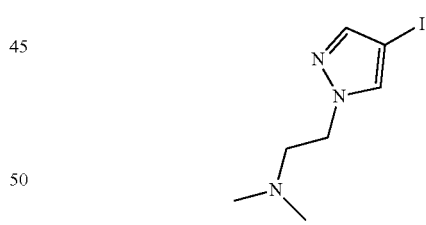

Cesium carbonate (680.26 mg, 2.09 mmol) was added to a solution of the product of embodiment 21C (220 mg, 695.95 μmol) and dimethylamine hydrochloride (113.50 mg, 1.39 mmol) in acetonitrile (5 mL). The reaction solution was stirred at 100° C. for 24 hours. The reaction solution was filtered and directly rotary-evaporated to dryness to obtain the product of embodiment 28B.

LCMS (ESI) m/z: 265.9 (M+1)$^+$ $^1$H NMR (400 MHz, CHLOROFORM-d) δ 7.54 (s, 1H), 7.50 (s, 1H), 4.22 (t, J=6.53 Hz 2H), 2.73 (t, J=6.53 Hz, 2H), 2.27 (s, 6H).

Embodiment 28C

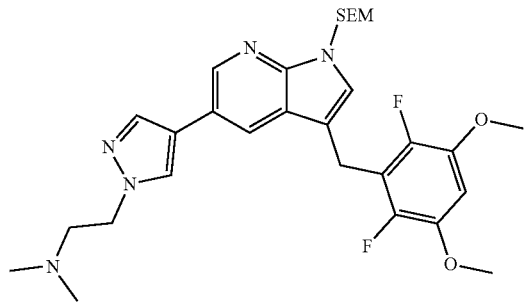

Pd(dppf)Cl$_2$ (13.05 mg, 17.84 μmol) and sodium carbonate (37.82 mg, 356.82 μmol) were added to a solution of the product of embodiment 28A (100 mg, 178.41 μmol) and the product of embodiment 28B (94.59 mg, 356.82 μmol) in H$_2$O (0.4 mL) and N,N-dimethylformamide (2 mL). The reaction solution was heated to 80° C. and reacted for 16 hours under nitrogen protection. The reaction solution was added with water (5 mL), and extracted with ethyl acetate (5 mL×2). The combined organic phase was washed with saturated brine (5 mL), dried over anhydrous sodium sulfate, and filtered. The filtrate was rotary-evaporated to dryness. The residue was purified by preparative chromatography plate (dichloromethane:methanol=10:1) to obtain the product of embodiment 28C.

LCMS (ESI) m/z: 572.3 (M+1)$^+$

Embodiment 28D

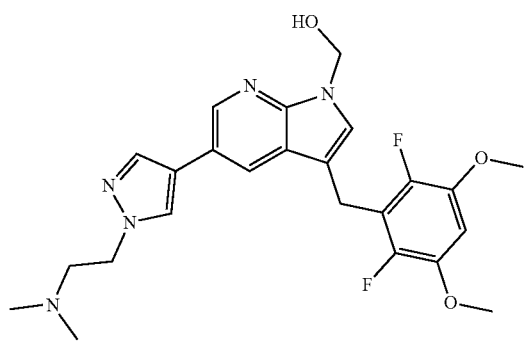

Trifluoroacetic acid (308.00 mg, 2.70 mmol, 0.2 mL) was added to a solution of the product of embodiment 28C (55 mg, 96.20 μmol) in dichloromethane (2 mL). The reaction solution was stirred at 20° C. for 16 hours. The reaction solution was directly rotary-evaporated to dryness to obtain the product of embodiment 28D.

LCMS (ESI) m/z: 472.2 (M+1)$^+$

Embodiment 28

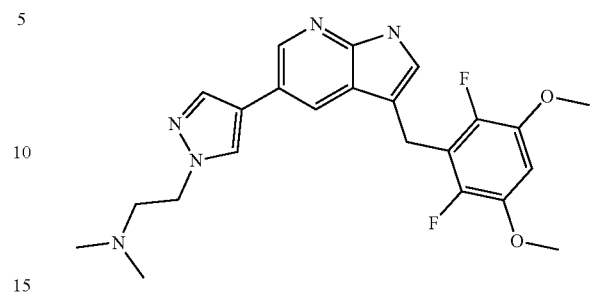

Potassium carbonate (28.32 mg, 204.95 μmol) was added to a solution of the product of embodiment 28D (60 mg, 102.47 μmol, TFA salt) in methanol (2 mL). The reaction was allowed to run at 22° C. for 30 min under nitrogen protection. The reaction solution was filtered, and the filtrate was rotary-evaporated to dryness. The residue was purified by preparative HPLC (hydrochloric acid system) to obtain hydrochloride salt of embodiment 28. In embodiment 28, the free base can be obtained by washing a solution of the hydrochloride salt of embodiment 28 in dichloromethane with 1N sodium bicarbonate, followed by separating and concentrating the organic phase.

LCMS (ESI) m/z: 442.0 (M+1)$^+$ $^1$H NMR (400 MHz, METHANOL-d$_4$) δ 8.83 (d, J=1.51 Hz, 1H), 8.65 (s, 1H), 8.33 (s, 1H), 8.10 (s, 1H), 7.41 (s, 1H), 6.80 (t, J=8.41 Hz, 1H), 4.67-4.76 (m, 2H), 4.24 (s, 2H), 3.86 (s, 6H), 3.76 (t, J=5.65 Hz, 2H), 3.02 (s, 6H).

Process L

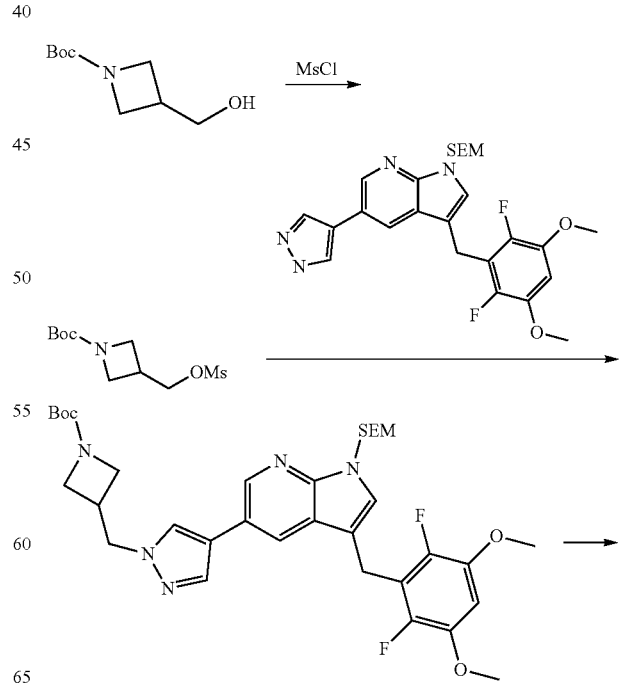

-continued

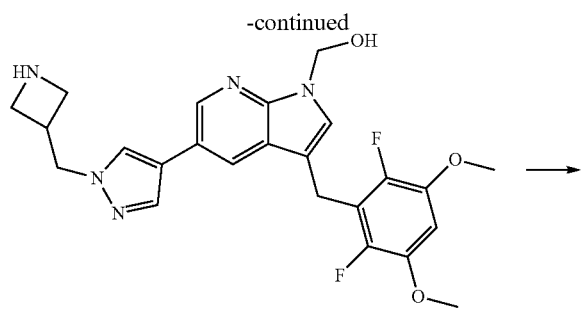

Embodiment 29

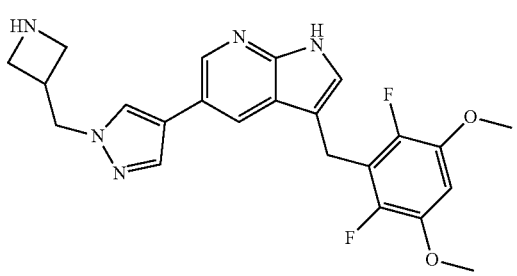

Embodiment 29A

At 0° C. under nitrogen protection, N-boc-3-hydroxymethylazetidine (200 mg, 1.07 mmol) was added to dichloromethane (5 mL) firstly, then triethylamine (216.18 mg, 2.14 mmol) and methanesulfonyl chloride (146.83 mg, 1.28 mmol) were added. The reaction solution was stirred for 3 hours at 20° C. The reaction solution was added with water (10 mL), and extracted with dichloromethane (10 mL*3). The organic phase was washed with saturated brine (10 mL), dried over anhydrous sodium sulfate, and concentrated under vacuum to obtain the product of embodiment 29A.

Embodiment 29B

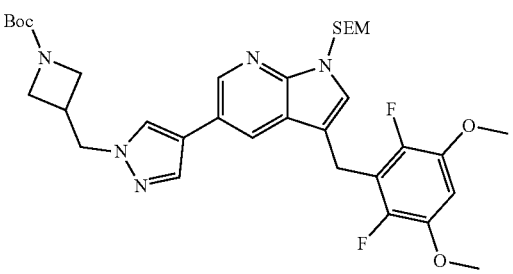 [SMILES: COc1cc(OC)c(F)c(Cc2cn(COCC[Si](C)(C)C)c3ncc(-c4cnn(CC5CN(C(=O)OC(C)(C)C)C5)c4)cc23)c1F]

At 20° C. under nitrogen protection, the product of embodiment 29A (50.00 mg, 0.1 mmol) was added to N,N-dimethylformamide (3 mL) firstly, and then the product of embodiment 22E (53.00 mg, 0.2 mmol) and cesium carbonate (65.09 mg, 0.2 mmol) were added. The reaction solution was heated continuously at 100° C. for 16 hours. The reaction solution was filtered, concentrated under vacuum and purified by chromatography on a silica gel plate (petroleum ether/ethyl acetate=1/2) to obtain the product of embodiment 29B.

LCMS (ESI) m/z: 670.5 (M+1)$^+$

Embodiment 29C

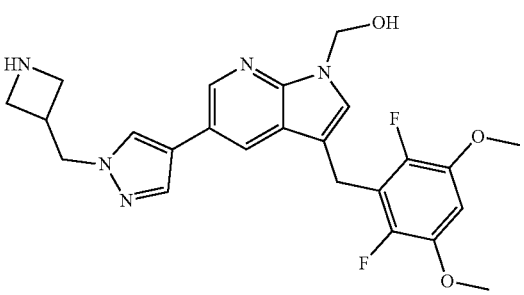 [SMILES: COc1cc(OC)c(F)c(Cc2cn(CO)c3ncc(-c4cnn(CC5CNC5)c4)cc23)c1F]

Trifluoroacetic acid (1 mL) was added to the product of embodiment 29B (59 mg, 0.088 mmol) at 20° C. The reaction solution was stirred continuously for 1 hour. The reaction solution was rotary-evaporated to dryness under vacuum to obtain the product of embodiment 29C, which was used directly in the next step.

LCMS (ESI) m/z: 470.3 (M+1)$^+$

Embodiment 29

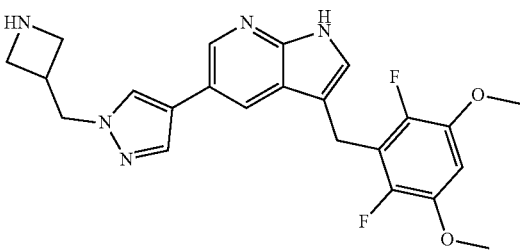 [SMILES: COc1cc(OC)c(F)c(Cc2c[nH]c3ncc(-c4cnn(CC5CNC5)c4)cc23)c1F]

At 20° C., potassium carbonate (58.88 mg, 0.43 mmol) and methanol (2 mL) were added sequentially to the product of embodiment 29C (40 mg, 0.085 mmol), and the reaction solution was stirred continuously for 1 hour. The reaction solution was rotary-evaporated to dryness under vacuum, and then purified by preparative chromatography (TFA) to obtain trifluoroacetate salt of embodiment 29. In embodiment 29, the free base can be obtained by washing a solution of the trifluoroacetate salt of embodiment 29 in dichloromethane with 1N sodium bicarbonate, followed by separating and concentrating the organic phase.

LCMS (ESI) m/z: 440.4 (M+1)+

$^1$H NMR (400 MHz, METHANOL-$d_4$) δ 8.40 (d, J=2.0 Hz, 11H), 8.18 (d, J=2.0 Hz, 1H), 8.07 (s, 1H), 7.92 (s, 1H), 7.15 (s, 1H), 6.78 (t, J=8.16 Hz, 1H), 4.62 (s, 2H), 4.48 (d, J=6.52 Hz, 2H), 4.07-4.20 (m, 6H), 3.87 (s, 6H), 3.52 (br d, J=7.78 Hz, 1H).

Process D

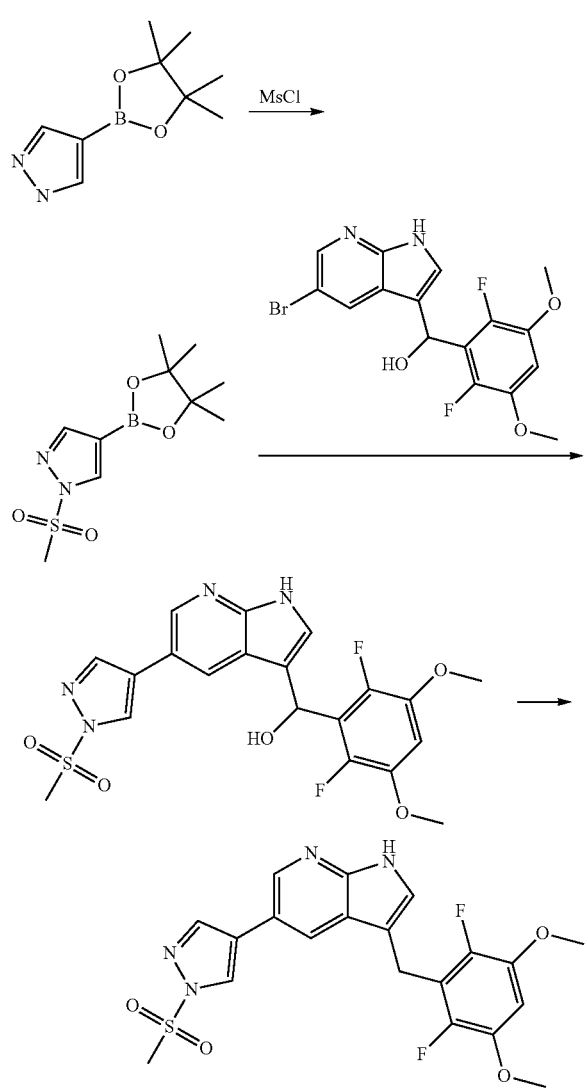

Embodiment 30

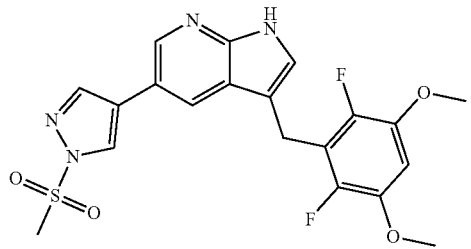 [SMILES: COc1cc(OC)c(F)c(Cc2c[nH]c3ncc(-c4cnn(S(C)(=O)=O)c4)cc23)c1F]

Embodiment 30A

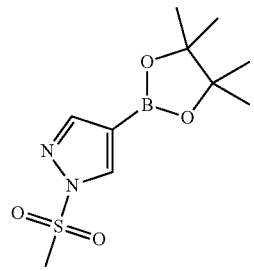 [SMILES: CC1(C)OB(c2cnn(S(C)(=O)=O)c2)OC1(C)C]

4-Pyrazoleboronic acid pinacol ester (100 mg, 515.36 μmol) was dissolved in dichloromethane (2 mL) in a single-neck flask (50 mL), then triethylamine (104.30 mg, 1.03 mmol) was added. Methanesulfonyl chloride (70.84 mg, 618.43 μmol) was added slowly dropwise to the above reaction solution at 0° C. The reaction solution was stirred for 2 hours at 0° C. The reaction solution was quenched with water (10 mL), and extracted with dichloromethane (10 mL*3) for 3 times. The combined organic phase was washed with saturated brine (10 mL) once, dried over anhydrous sodium sulfate, and concentrated under reduced pressure to obtain the product of embodiment 30A.

LCMS (ESI) m/z: 273.2 (M+1)+

$^1$H NMR (400 MHz, CHLOROFORM-d) δ 8.33 (s, 1H), 7.91-8.08 (m, 1H), 3.32 (s, 3H), 1.33 (s, 12H).

Embodiment 30B

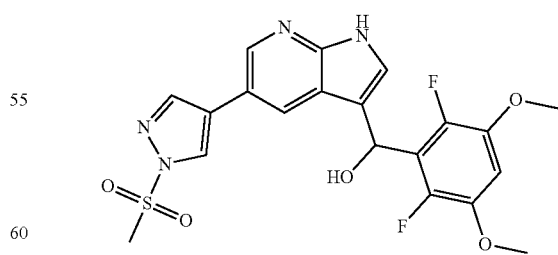

The product of embodiment 30A (120 mg, 300.61 μmol) was dissolved in dioxane (2 mL)/water (1 mL) in a single-neck flask (50 mL), and then the product of embodiment 22B (98.17 mg, 360.73 μmol), Pd(dppf)Cl$_2$ (11.00 mg, 15.03 μmol), potassium carbonate (103.87 mg, 751.53 μmol) were added. The reaction solution was purged with nitrogen three times, and then the reaction solution was stirred at 80° C. for 14 hours under nitrogen protection. The reaction solution was added with water (10 mL), and extracted with ethyl acetate (10 mL*3) three times. The combined organic phase was dried over anhydrous sodium sulfate to obtain a crude product. The crude product was separated and purified by preparative TLC (developing solvent: petroleum ether:ethyl acetate=1:1) to obtain the product of embodiment 30B.

LCMS (ESI) m/z: 464.9 (M+1)+

Embodiment 30

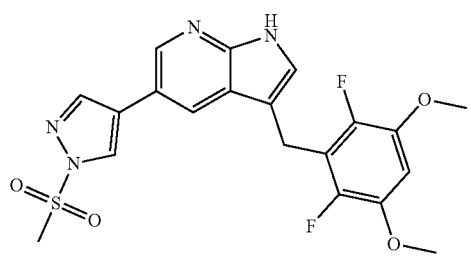 [SMILES: COc1cc(OC)c(F)c(Cc2c[nH]c3ncc(-c4cnn(S(C)(=O)=O)c4)cc23)c1F]

The product of embodiment 30B (90 mg, 193.78 µmol) was dissolved in dichloromethane (1.00 mL) in a single-neck flask (50 mL), and then triethylsilane (180.26 mg, 1.55 mmol) and trifluoroacetic acid (1.54 g, 13.51 mmol) were added. The reaction solution was stirred at 15° C. for 1 hour. The reaction solution was concentrated under reduced pressure and separated directly by preparative HPLC (TFA system) to obtain trifluoroacetate salt of embodiment 30. In embodiment 30, the free base can be obtained by washing a solution of the trifluoroacetate salt of embodiment 30 in dichloromethane with 1N sodium bicarbonate, followed by separating and concentrating the organic phase.

LCMS (ESI) m/z: 448.9 (M+1)+

$^1$H NMR (400 MHz, DMSO-d$_6$) δ 11.54 (br s, 1H), 8.77 (s, 1H), 8.63 (d, J=1.76 Hz, 1H), 8.49 (s, 1H), 8.33 (d, J=1.51 Hz, 1H), 7.09 (s, 1H), 6.78-6.97 (m, 1H), 4.08 (s, 2H), 3.85 (s, 6H), 3.61 (s, 3H).

Process E

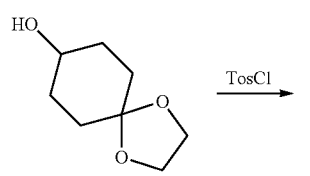

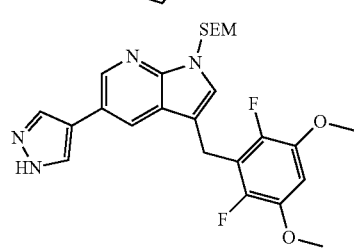

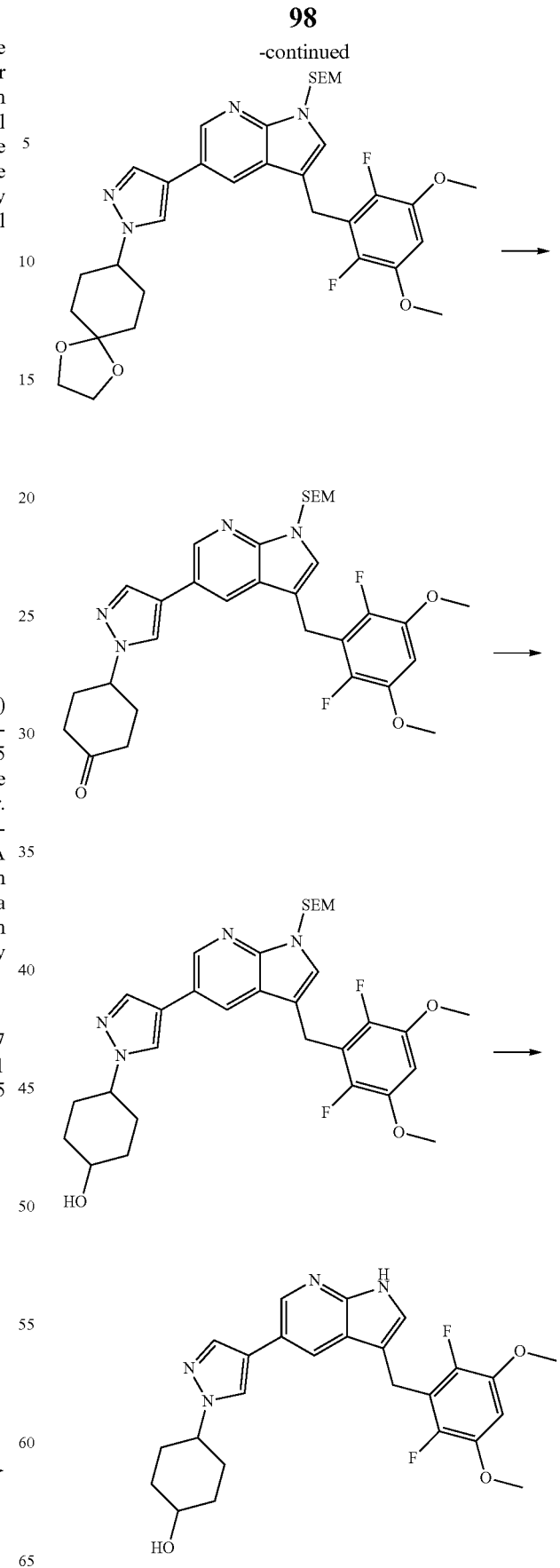

Embodiment 31

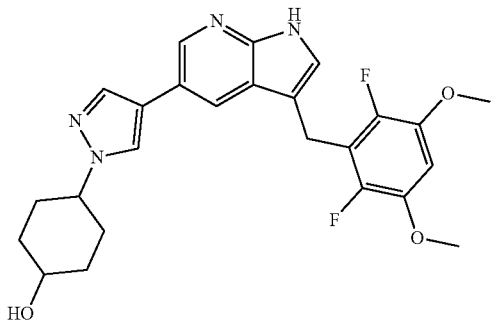 [SMILES: COc1cc(OC)c(F)c(Cc2c[nH]c3ncc(-c4cnn(C5CCC(O)CC5)c4)cc23)c1F]

Embodiment 31A

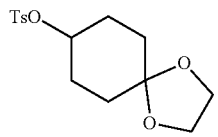

4-Hydroxycyclohexanone glycol acetal (500 mg, 3.16 mmol) was dissolved in dichloromethane (7 mL) in a single-neck flask (50 mL), then triethylamine (639.65 mg, 6.32 mmol) and 4-N,N-dimethylaminopyridine (77.23 mg, 632.12 μmol) were added. p-Toluenesulfonyl chloride (723.08 mg, 3.79 mmol) was added slowly dropwise to the above reaction solution at 0° C. The reaction solution was slowly returned to room temperature of 15° C. and stirred for 14 hours. The reaction solution was quenched with water (20 mL), and extracted with ethyl acetate (20 mL*3) three times. The combined organic phase was washed with saturated brine (20 mL*1) once, dried over anhydrous sodium sulfate, and concentrated under reduced pressure to obtain a crude product. The crude product was purified by column chromatography (petroleum ether/ethyl acetate=1/0-3/1 to obtain the product of embodiment 31 A.

$^1$H NMR (400 MHz, CHLOROFORM-d) δ 7.79 (d, J=8.28 Hz, 2H), 7.33 (d, J=8.03 Hz, 2H), 4.64 (tt, J=3.11, 6.05 Hz, 1H), 3.84-3.98 (m, 4H), 2.39-2.53 (m, 3H), 1.69-1.94 (m, 6H), 1.53-1.60 (n, 2H).

Embodiment 31B

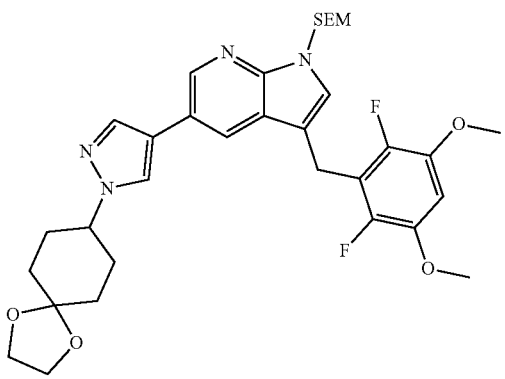 [SMILES: COc1cc(OC)c(F)c(Cc2cn(COCC[Si](C)(C)C)c3ncc(-c4cnn(C5CCC6(CC5)OCCO6)c4)cc23)c1F]

The product of embodiment 22E (100 mg, 199.76 μmol) was dissolved in N,N-dimethylformamide (2 mL) in a single-neck flask (50 mL), and then the product of embodiment 31A (124.80 mg, 399.51 μmol), and cesium carbonate (130.17 mg, 399.51 μmol) were added. The reaction solution was stirred at 100° C. for 14 hours. The reaction solution was added with water (20 mL), and extracted with ethyl acetate (20 mL*3) three times. The combined organic phase was washed with saturated brine (20 mL*3) for three times, dried over anhydrous sodium sulfate, and concentrated under reduced pressure to obtain a crude product. The crude product was separated and purified by column chromatography (petroleum ether/ethyl acetate=1/0-1/1 to obtain the product of embodiment 31B.

LCMS (ESI) m/z: 641.1 (M+1)$^+$

Embodiment 31C

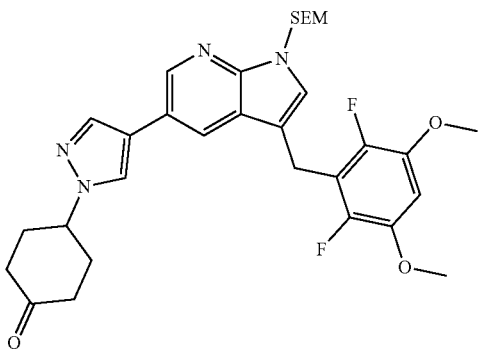 [SMILES: COc1cc(OC)c(F)c(Cc2cn(COCC[Si](C)(C)C)c3ncc(-c4cnn(C5CCC(=O)CC5)c4)cc23)c1F]

The product of embodiment 31B (200 mg, 312.11 μmol) was dissolved in acetone (2 mL) in a single-neck flask (50 mL), and then aqueous HCl solution (1.5 mL, 3M) was added and the reaction solution was stirred at room temperature of 15° C. for 14 hours. The reaction solution was added with aqueous sodium hydroxide (3M) to adjust the pH to 8, and then extracted with ethyl acetate (20 mL*3) for three times. The combined organic phase was washed with saturated brine (10 mL*3) once, dried over anhydrous sodium sulfate, and concentrated under reduced pressure to obtain the product of embodiment 31C.

LCMS (ESI) m/z: 597.1 (M+1)$^+$

Embodiment 31D

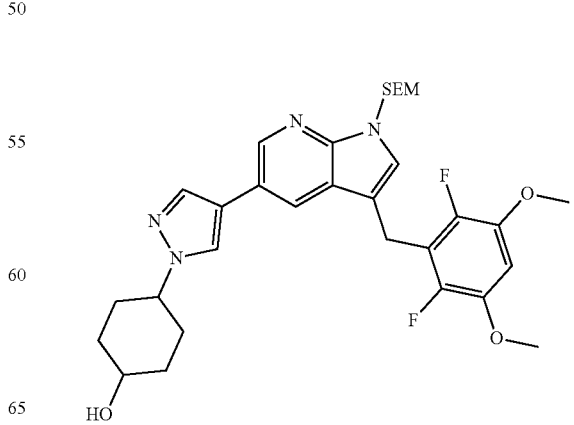

The product of embodiment 31C (160 mg, 268.12 μmol, crude product) was dissolved in methanol (2 mL) in a single-neck flask (50 mL), and then sodium borohydride (20.29 mg, 536.25 μmol) was added at 0° C. The reaction solution was slowly returned to 15° C. and stirred for 2 hours. The reaction solution was quenched with saturated aqueous ammonium chloride solution (10 mL), and then extracted with ethyl acetate (10 mL*3) for three times. The combined organic phase was washed with saturated brine (10 mL) once, dried over anhydrous sodium sulfate, and concentrated under reduced pressure to obtain the product of embodiment 31D.

LCMS (ESI)$_m$/z: 599.2 (M+1)$^+$

Embodiment 31

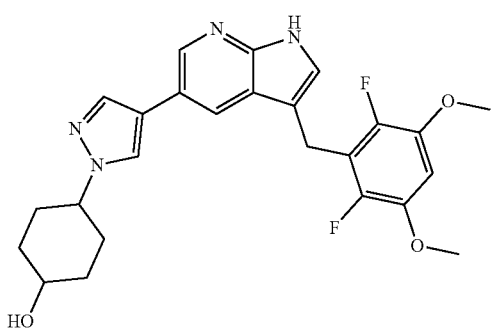

The product of embodiment 31D (120 mg, 200.42 μmol) was dissolved in dichloromethane (2.00 mL) in a single-neck flask (50 mL), and trifluoroacetic acid (3.08 g, 27.01 mmol) was added. The reaction solution was stirred at 15° C. for 2 hours. The reaction solution was directly concentrated under reduced pressure to obtain a crude product. The crude product was dissolved in methanol (2.00 mL), and potassium carbonate (553.97 mg, 4.01 mmol) was added. The reaction mixture was stirred at 15° C. for 14 hours. The reaction mixture was added with water (10 mL), and extracted with dichloromethane (10 mL*3) for three times. The combined organic phase was washed with saturated brine (10 mL) once, and dried over anhydrous sodium sulfate to obtain a crude product. The mixture was dissolved in MeOH (2 mL) and potassium carbonate (600 mg) was added, and the resulting mixture was stirred for 2 hours. The mixture was added with aqueous HCl (3M) solution to adjust the pH to about 5, and extracted with dichloromethane (10 mL*3) for 3 times. The combined organic phase was washed with saturated brine (10 mL) once, dried over anhydrous sodium sulfate, and concentrated under reduced pressure to obtain a crude product. The crude product was separated and purified by preparative HPLC (TFA system) to obtain trifluoroacetate salt of embodiment 31. In embodiment 31, the free base can be obtained by washing a solution of the trifluoroacetate salt of embodiment 31 in dichloromethane with 1N sodium bicarbonate, followed by separating and concentrating the organic phase.

LCMS (ESI) m/z: 469.2 (M+1)$^+$ $^1$H NMR (400 MHz, DMSO-d$_6$) δ 11.46 (br s, 1H), 8.46 (d, J=1.76 Hz, 1H), 8.20 (s, 1H), 8.10 (s, 1H), 7.83 (s, 1H), 7.09 (s, 1H), 6.89 (t, J=8.41 Hz, 1H), 4.11-4.24 (m, 1H), 4.06 (s, 2H), 3.84 (s, 6H), 2.06 (br d, J=10.79 Hz, 2H), 1.95 (br d, J=9.54 Hz, 2H), 1.77-1.89 (m, 2H), 1.32-1.44 (m, 2H).

Process F

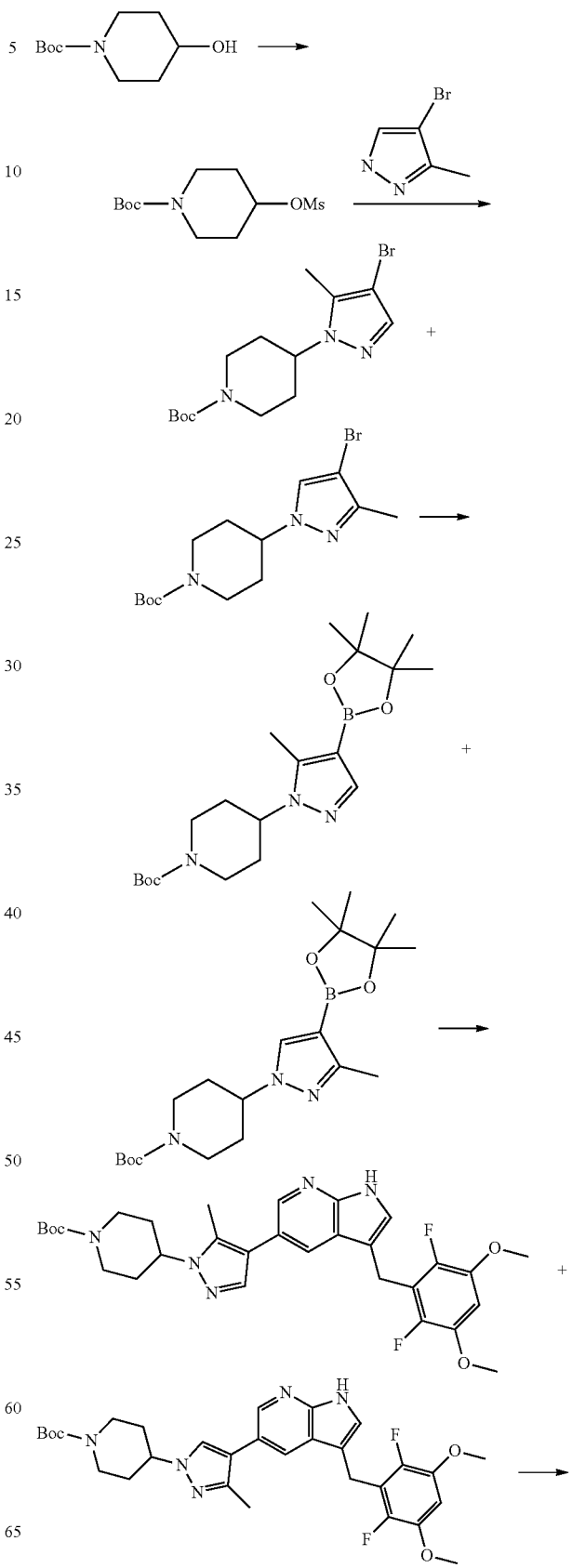

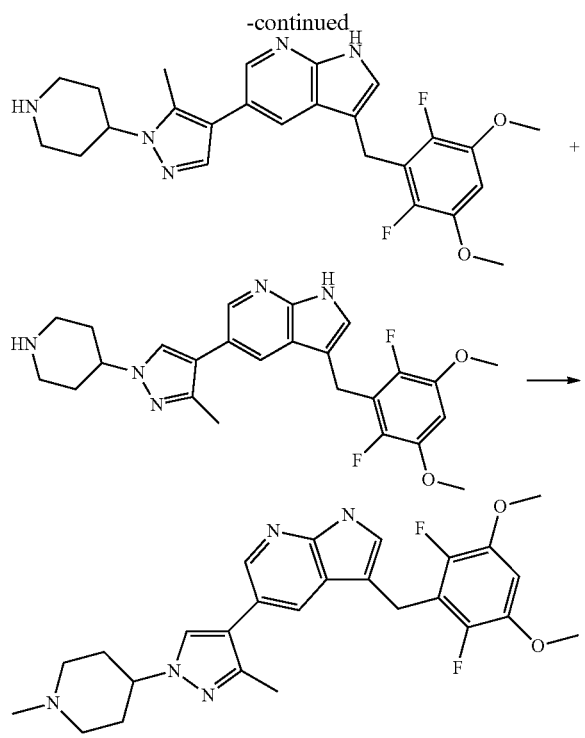

Embodiment 32

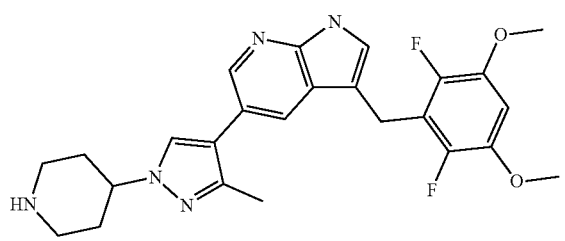 [SMILES: COc1cc(OC)c(F)c(Cc2c[nH]c3ncc(-c4cn(C5CCNCC5)nc4C)cc23)c1F]

Embodiment 32A

Triethylamine (43.22 mL, 310.54 mmol) was added to a solution of 4-hydroxy-N-boc-piperidine (25 g, 124.22 mmol) in dichloromethane (250 mL) at 0° C., and methanesulfonyl chloride (28.46 g, 248.43 mmol) was added dropwise at 0° C. The reaction solution was stirred for 1 hour at 0° C. The reaction solution was quenched with water (250 mL), partitioned and extracted with dichloromethane (250 mL) twice. The combined organic phase was washed with water (250 mL) twice, and the organic phase was dried over anhydrous sodium sulfate, and concentrated to obtain the product of embodiment 32A.

$^1$H NMR (400 MHz, CHLOROFORM-d) δ 4.86 (tt, J=3.70, 7.72 Hz, 1H), 3.61-3.76 (m, 2H), 3.28 (ddd, J=3.76, 8.16, 13.68 Hz, 2H), 2.97-3.07 (m, 3H), 1.89-2.01 (m, 2H), 1.75-1.86 (m, 2H), 1.38-1.50 (m, 9H).

Embodiment 32B

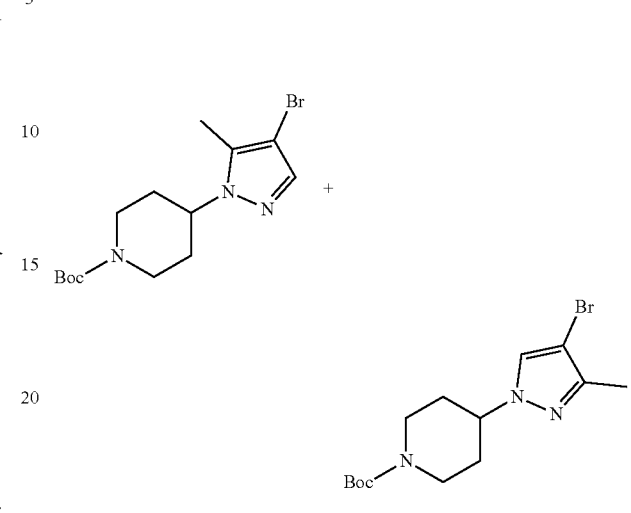

Sodium hydride (2.48 g, 62.11 mmol, 60% purity) was added to a solution of 4-bromo-3-methylpyrazole (5 g, 31.06 mmol) in N,N-dimethylformamide (150 mL) in portions at 0° C. The reaction solution was stirred at 0° C. for 1 hour. The product of embodiment 32A (9.54 g, 34.16 mmol) was added, and the reaction solution was stirred at 90° C. for 4 hours. The reaction was quenched with water (100 mL), and extracted with ethyl acetate (150 mL) three times. The combined organic phase was washed with water (150 mL) three times, and dried over anhydrous sodium sulfate to obtain a crude product. The crude product was separated by flash chromatography on a silica gel column (petroleum ether:ethyl acetate=3:1) to give an eluate. The eluate was concentrated to obtain the product of embodiment 32B. HNMR showed that the product was a mixture, which was used directly in the next step.

LCMS (ESI) m/z: 289.8 (M−56)$^+$ $^1$H NMR (400 MHz, CHLOROFORM-d) δ 7.41 (s, 1H), 7.34 (s, 1H), 4.24 (br s, 4H), 4.04-4.17 (m, 3H), 2.84 (br s, 4H), 2.27 (s, 3H), 2.21 (s, 3H), 2.04-2.16 (m, 4H), 1.73-1.90 (m, 4H), 1.45 (d, J=0.75 Hz, 18H).

Embodiment 32C

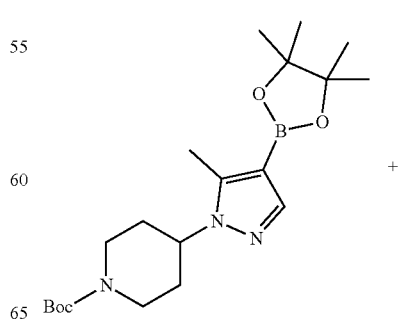

-continued

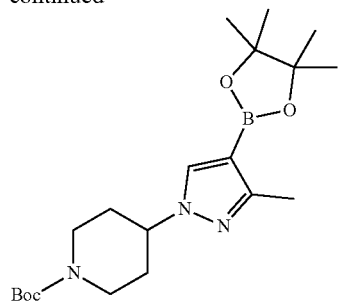

Bis(pinacolato)diboron (3.25 g, 12.78 mmol), Pd(dppf)Cl₂ (850.21 mg, 1.16 mmol), potassium acetate (2.85 g, 29.05 mmol) were added to a solution of the product of embodiment 32B (4 g, 11.62 mmol) in dioxane (40 mL). The reaction solution was purged with nitrogen three times and stirred at 100° C. for 16 hours under nitrogen protection. The reaction solution was added with water (150 mL), and extracted with ethyl acetate (150 mL*3). The combined organic phase was dried over anhydrous sodium sulfate, and concentrated to obtain a crude product. The crude product was separated by flash chromatography on a silica gel column (petroleum ether:ethyl acetate=3:1) to give an eluate. The eluate was rotary-evaporated to dryness to obtain the product of embodiment 32C as a mixture.

LCMS (ESI) m/z: 392.3 (M+1)⁺

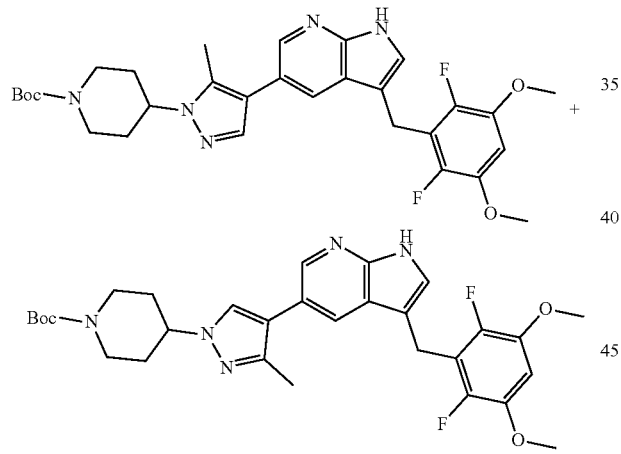

The product of embodiment 22C (490.48 mg, 1.28 mmol), Pd(dppf)Cl₂ (46.83 mg, 64.00 µmol), potassium phosphate (543.41 mg, 2.56 mmol) were added to a solution of the product of embodiment 32C in dioxane (5 mL)/water (2.5 mL). The reaction was allowed to run at 100° C. for 16 hours under nitrogen protection. The reaction solution was added with water (50 mL) and extracted with ethyl acetate (50 mL) twice. The combined organic phase was concentrated to obtain a crude product. The crude product was separated by flash chromatography on a silica gel column (petroleum ether:ethyl acetate=3:1) to give an eluate, which was concentrated under reduced pressure to obtain the product of embodiment 32D as a mixture.

LCMS (ESI) m/z: 568.2 (M+1)⁺

¹H NMR (400 MHz, CHLOROFORM-d) δ 8.24-8.32 (m, 1H), 7.97-8.03 (m, 1H), 7.50 (s, 1H), 7.22 (s, 1H), 6.49 (t, J=8.16 Hz, 1H), 4.18-4.41 (m, 3H), 4.10-4.15 (m, 2H), 3.84 (s, 6H), 2.90 (br s, 2H), 2.37-2.42 (m, 3H), 2.18 (br d J=10.79 Hz, 2H), 1.96 (dq, J=4.52, 12.30 Hz, 2H), 1.68 (s, 3H), 1.44-1.53 (m, 9H).

Embodiment 32, 33

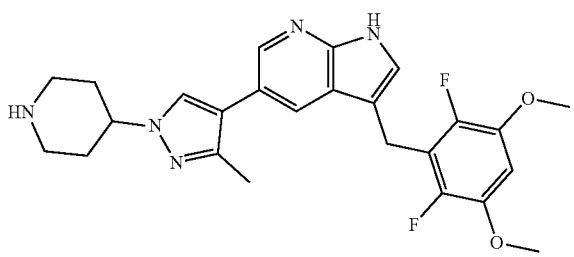

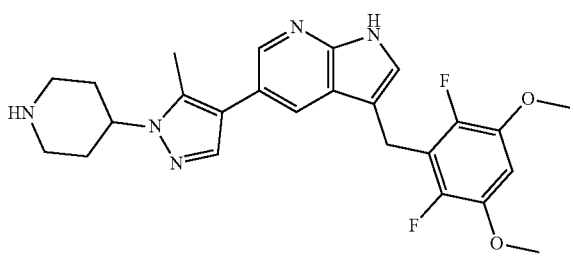

Trifluoroacetic acid (3.85 g, 33.76 mmol) was added to a solution of the product of embodiment 32D (250.00 mg, 440.43 µmol) in dichloromethane (2.5 mL). The reaction solution was stirred for 16 hours at 20° C. The reaction solution was concentrated and rotary-evaporated to dryness to obtain a crude product. The crude product was resolved by SFC (conditions: column: DAICEL CHIRALCEL OD (250 mm*30 mm, 10 µm); mobile phase: [0.1% NH₃H₂O EtOH]; B %: 45%-45%, min) to obtain the product of embodiment 32 (retention time of 4.29 min.) and the product of embodiment 33 (retention time of 4.29 min) respectively.

LCMS (ESI) m/z: 468.2 (M+1)⁺

Embodiment 32

¹H NMR (400 MHz, METHANOL-d₄) δ 8.15 (s, 1H), 7.94 (d, J=1.51 Hz, 1H), 7.58 (s, 1H), 7.20 (s, 1H), 6.71 (t, J=8.28 Hz, 1H), 4.28-4.42 (m, 1H), 4.09 (s, 2H), 3.82 (s, 6H), 3.20 (d, J=12.55 Hz, 2H), 2.77 (t, J=12.05 Hz, 2H), 2.39 (s, 3H), 2.04-2.14 (m, 2H), 1.87-1.99 (m, 2H).

Embodiment 33

¹H NMR (400 MHz, METHANOL-d₄) δ 8.19 (br s, 1H), 7.94 (s, 1H), 7.64 (s, 1H), 7.19 (br s, 1H), 6.57 (br t, J=8.03 Hz, 1H), 3.92-4.09 (m, 3H), 3.67-3.79 (m, 6H), 3.05 (br d, J=12.05 Hz, 2H), 2.56 (t, J=11.80 Hz, 2H), 2.28 (s, 3H), 1.90-1.94 (m, 2H), 1.70-1.85 (m, 2H).

Embodiment 35

Process G

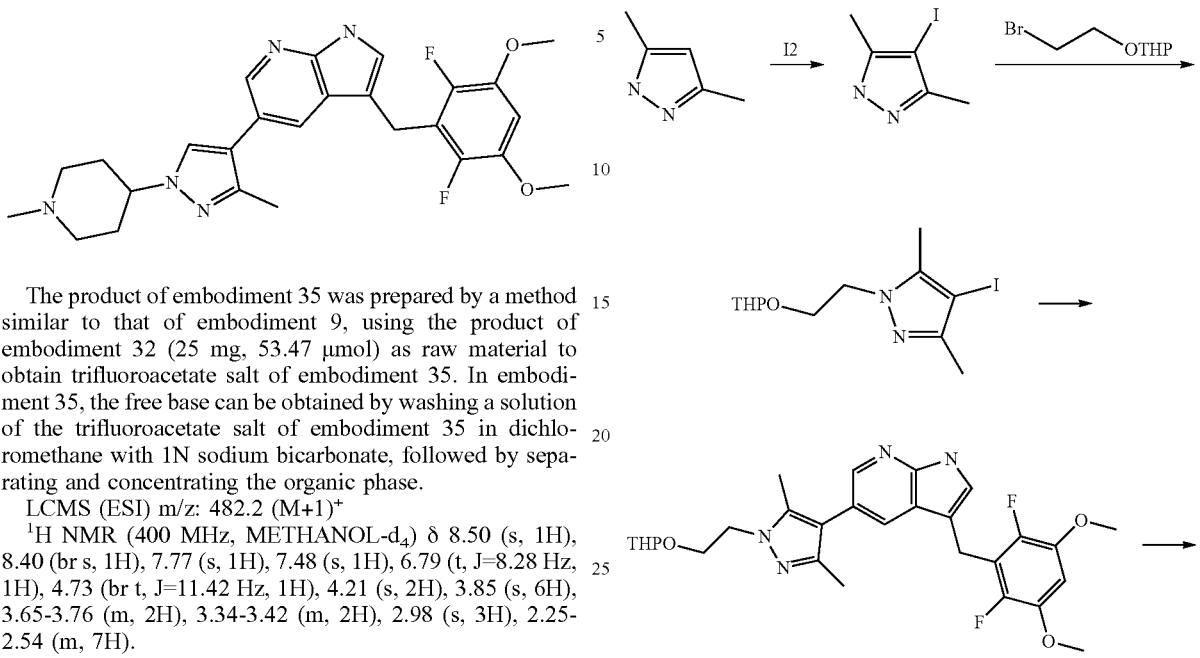

The product of embodiment 35 was prepared by a method similar to that of embodiment 9, using the product of embodiment 32 (25 mg, 53.47 μmol) as raw material to obtain trifluoroacetate salt of embodiment 35. In embodiment 35, the free base can be obtained by washing a solution of the trifluoroacetate salt of embodiment 35 in dichloromethane with 1N sodium bicarbonate, followed by separating and concentrating the organic phase.

LCMS (ESI) m/z: 482.2 (M+1)$^+$ $^1$H NMR (400 MHz, METHANOL-$d_4$) δ 8.50 (s, 1H), 8.40 (br s, 1H), 7.77 (s, 1H), 7.48 (s, 1H), 6.79 (t, J=8.28 Hz, 1H), 4.73 (br t, J=11.42 Hz, 1H), 4.21 (s, 2H), 3.85 (s, 6H), 3.65-3.76 (m, 2H), 3.34-3.42 (m, 2H), 2.98 (s, 3H), 2.25-2.54 (m, 7H).

The following embodiments and salts thereof were prepared by referring to the methods as described in embodiments 32 and 35 respectively.

| Embodiments | Structure | NMR | LCMS (ESI) m/z: (M + 1) |
|---|---|---|---|
| Embodiment 36 | 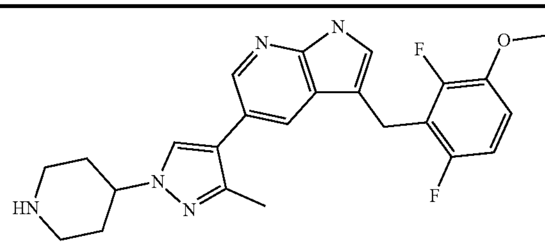 | $^1$H NMR (400 MHz, METHANOL-$d_4$) δ 8.72 (s, 1H), 8.51 (s, 1H), 8.15 (s, 1H), 7.55 (s, 1H), 6.92-7.03 (m, 2H), 4.60-4.62 (m, 1H), 4.27 (s, 2H), 3.86 (s, 3H), 3.61-3.63 (m, 2H), 3.27-3.31 (m, 2H), 2.38-2.43 (m, 7H), 2.03 (s, 3H). | 438.0 |
| Embodiment 37 | 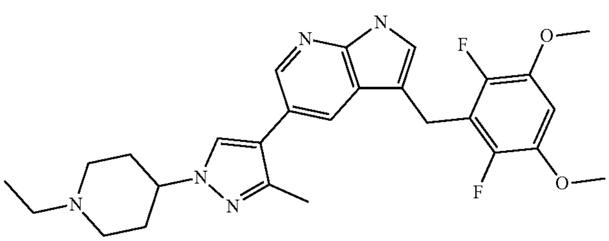 [SMILES: CCN1CCC(n2cc(-c3cnc4[nH]cc(Cc5c(F)c(OC)cc(OC)c5F)c4c3)c(C)n2)CC1] | $^1$H NMR (400 MHz, METHANOL-$d_4$) δ 8.64 (s, 1H), 8.46 (s, 1H), 7.82 (s, 1H), 7.55 (s, 1H), 6.79 (t, J = 8.28 Hz, 1H), 4.77 (br t, J = 11.67 Hz, 1H), 4.23 (s, 2H), 3.85 (s, 6H), 3.70-3.80 (m, 2H), 3.24-3.29 (m, 2H), 2.27-2.67 (m, 7H), 1.42 (t, J = 7.15 Hz, 3H). | 496.2 |
| Embodiment 39 | 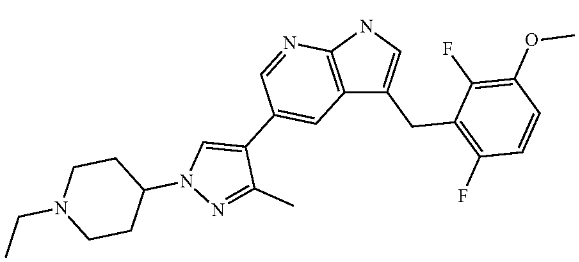 [SMILES: CCN1CCC(n2cc(-c3cnc4[nH]cc(Cc5c(F)ccc(OC)c5F)c4c3)c(C)n2)CC1] | $^1$H NMR (400 MHz, METHANOL-$d_4$) δ 8.28 (s, 1H), 8.27 (s, 1H), 8.14 (s, 1H), 7.31 (s, 1H), 6.88-7.01 (m, 2H), 4.13-4.17 (m, 2H), 3.85 (s, 3H), 3.77-3.81 (m, 2H), 3.45-3.56 (m, 1H), 3.20-3.29 (m, 4H), 2.67 (s, 2H), 2.46-2.55 (m, 4H), 2.33-2.47 (m, 7H), 1.38-1.44 (m, 3H). | 466.2 |

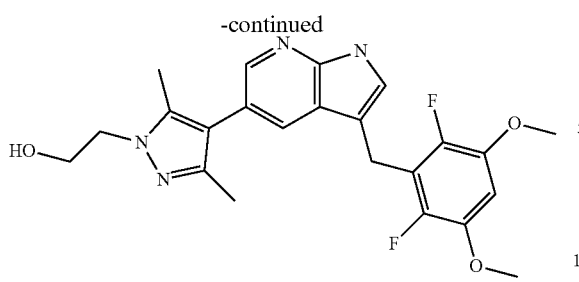

Embodiment 34

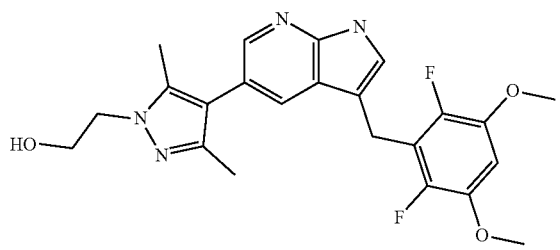 [SMILES: COc1cc(OC)c(F)c(Cc2c[nH]c3ncc(-c4c(C)nn(CCO)c4C)cc23)c1F]

Embodiment 34A

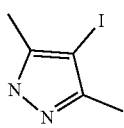

Iodine (3.17 g, 12.48 mmol) was added to a solution of 3,5-dimethylpyrazole (0.2 g, 2.08 mmol) in acetonitrile (40 mL), and ceric ammonium nitrate (684.35 mg, 1.25 mmol) was added. The reaction solution was stirred for 3 hours at 20° C. The reaction solution was quenched with saturated sodium thiosulfate solution (10 mL), and extracted with ethyl acetate (100 mL*2). The organic phase was rotary-evaporated under reduced pressure to obtain the product of embodiment 34A.

$^1$H NMR (400 MHz, CHLOROFORM-d) δ 2.27 (s, 6H).

Embodiment 34B

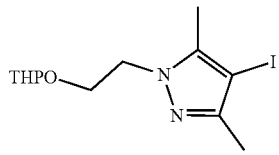

Cesium carbonate (1.12 g, 3.42 mmol) and the product of embodiment 34A (0.38 g, 1.71 mmol) were added to a solution of the product of embodiment 1H (393.63 mg, 1.88 mmol) in acetonitrile (10 mL). The reaction solution was stirred at 65° C. for 3 hours. The reaction solution was filtered through diatomaceous earth and the filtrate was rotary-evaporated to obtain the product of embodiment 34B.

LCMS (ESI) m/z: 266.9 (M+1)$^+$ $^1$H NMR (400 MHz, CHLOROFORM-d) δ 4.48 (t, J=3.51 Hz, 1H), 4.23 (t, J=5.52 Hz, 2H), 3.99 (td, J=5.08, 10.42 Hz, 1H), 3.37-3.72 (m, 3H), 2.31 (s, 3H), 2.20 (s, 3H), 1.41-1.78 (m, 8H).

Embodiment 34C

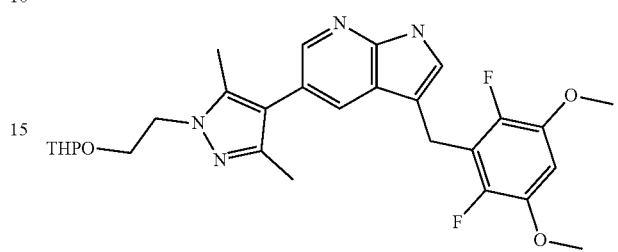

Pd(dppf)Cl$_2$ (6.27 mg, 8.57 μmol) and potassium phosphate (45.46 mg, 214.17 μmol) were added to a solution of the product of embodiment 34B (30 mg, 85.67 μmol) and the product of embodiment 27D (44.23 mg, 102.80 μmol) in dioxane (1 mL)/water (0.5 mL). The reaction solution was stirred at 100° C. for 3 hours. The dioxane layer was separated, and concentrated under reduced pressure to obtain a crude product, which was purified by preparative chromatography on a silica gel plate (dichloromethane:ethyl acetate=1:1) to obtain the product of embodiment 34C.

LCMS (ESI) m/z: 527.1 (M+1)$^+$

Embodiment 34

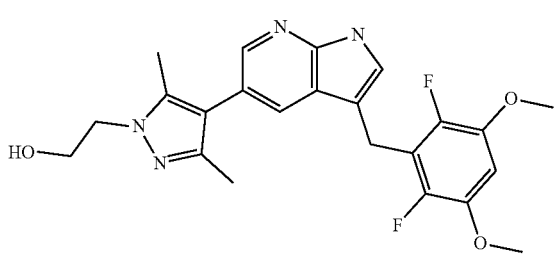 [SMILES: COc1cc(OC)c(F)c(Cc2c[nH]c3ncc(-c4c(C)nn(CCO)c4C)cc23)c1F]

Hydrochloric acid (2 M, 1 mL) was added to a solution of the product of embodiment 34C (10 mg, 18.99 μmol) in methanol (2 mL). The reaction solution was stirred at 20° C. for 0.5 hour. The reaction solution was concentrated under reduced pressure to obtain a crude product. The crude product was separated by preparative HPLC (hydrochloric acid system, HCl). The sample was lyophilized to obtain hydrochloride salt of embodiment 34. In embodiment 34, the free base can be obtained by washing a solution of the trifluoroacetate salt of embodiment 35 in dichloromethane with 1N sodium bicarbonate, followed by separating and concentrating the organic phase.

LCMS (ESI) m/z: 443.1 (M+1)$^+$ $^1$H NMR (400 MHz, METHANOL-d$_4$) δ 8.58 (s, 1H), 8.46 (s, 1H), 7.59 (s, 1H), 6.79 (t, J=8.28 Hz, 1H), 4.43 (br t, J=4.52 Hz, 2H), 4.25 (s, 2H), 3.96 (br t, J=4.27 Hz, 2H), 3.85 (s, 6H), 2.43 (s, 3H), 2.38 (s, 3H).

The following embodiments and salts thereof were prepared by referring to the method as described in embodiment 34.

| Embodiments | Structure | NMR | LCMS (ESI) m/z: (M + 1) |
|---|---|---|---|
| Embodiment 47 | 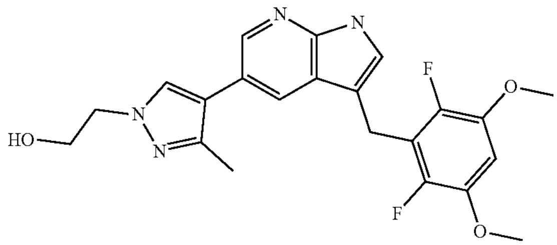 [SMILES: COc1cc(OC)c(F)c(Cc2c[nH]c3ncc(-c4cn(CCO)nc4C)cc23)c1F] | 1H NMR (400 MHz, DMSO-d<sub>6</sub>) δ 12.18 (br s, 1H), 8.38 (br s, 1H), 8.22 (br s, 1H), 8.03 (br s, 1H), 7.36 (br s, 1H), 6.88 (br t, J = 7.78 Hz, 1H), 4.11 (s, 2H), 3.72-3.84 (m, 10H), 2.30 (s, 3H). | 429.1 |

Process H

Embodiment 40

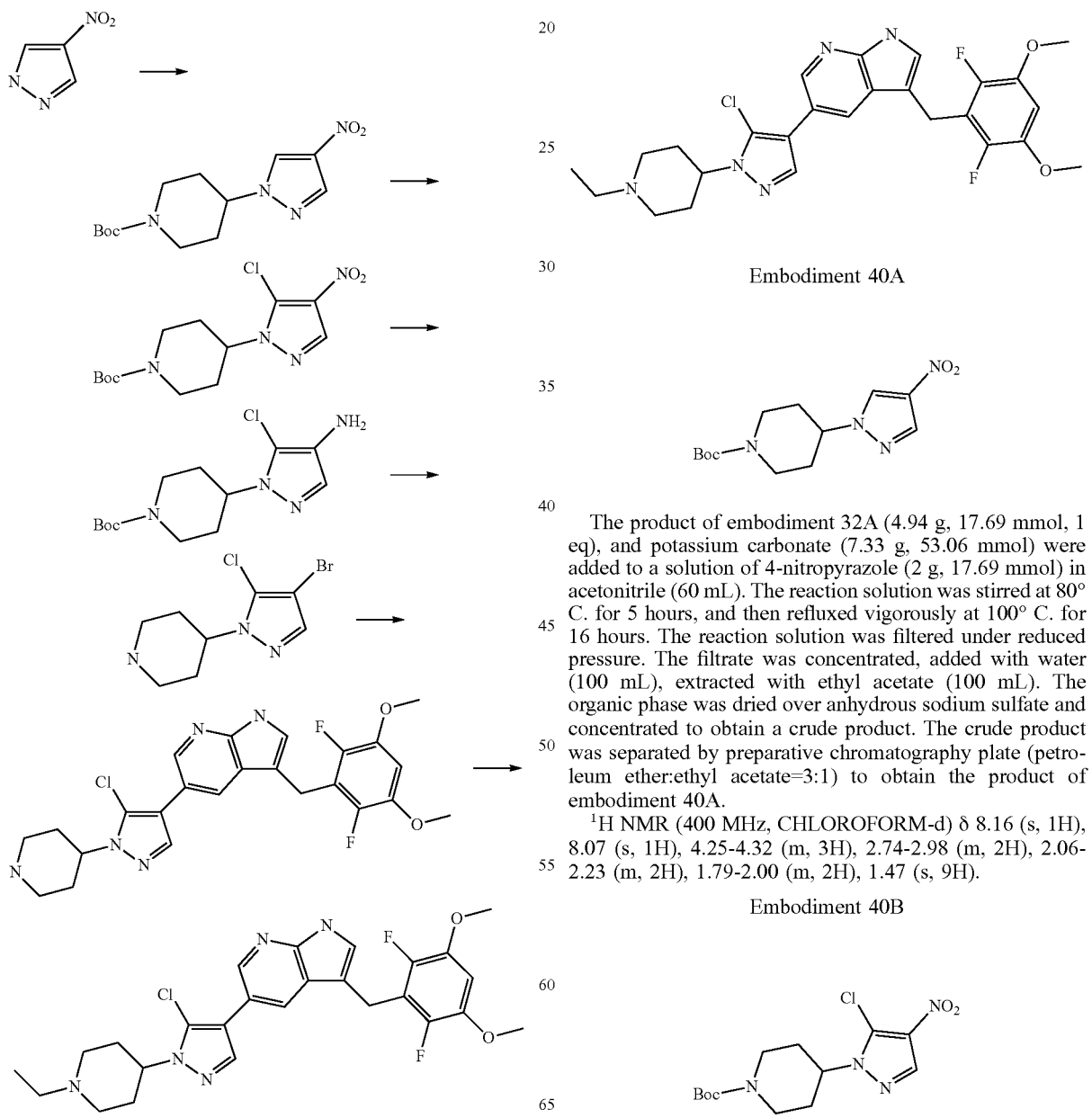

Embodiment 40A

The product of embodiment 32A (4.94 g, 17.69 mmol, 1 eq), and potassium carbonate (7.33 g, 53.06 mmol) were added to a solution of 4-nitropyrazole (2 g, 17.69 mmol) in acetonitrile (60 mL). The reaction solution was stirred at 80° C. for 5 hours, and then refluxed vigorously at 100° C. for 16 hours. The reaction solution was filtered under reduced pressure. The filtrate was concentrated, added with water (100 mL), extracted with ethyl acetate (100 mL). The organic phase was dried over anhydrous sodium sulfate and concentrated to obtain a crude product. The crude product was separated by preparative chromatography plate (petroleum ether:ethyl acetate=3:1) to obtain the product of embodiment 40A.

$^1$H NMR (400 MHz, CHLOROFORM-d) δ 8.16 (s, 1H), 8.07 (s, 1H), 4.25-4.32 (m, 3H), 2.74-2.98 (m, 2H), 2.06-2.23 (m, 2H), 1.79-2.00 (m, 2H), 1.47 (s, 9H).

Embodiment 40B

LiHMDS (1 M, 27.34 mL) was added dropwise to a solution of the product of embodiment 40A (2.7 g, 9.11 mmol) in THF (30 mL) at −78° C. under nitrogen protection. The reaction solution was stirred at −78° C. for 30 min. Hexachloroethane (4.31 g, 18.22 mmol) was added, and the reaction solution was stirred at −78° C. for 1.5 hours. The reaction solution was quenched with saturated ammonium chloride solution at 0° C., and extracted with ethyl acetate (100 mL) three times. The combined organic phase was concentrated to obtain a crude product. The crude product was separated by preparative chromatography plate (petroleum ether:ethyl acetate=3:1) to obtain the product of embodiment 40B.

$^1$H NMR (400 MHz, CHLOROFORM-d) δ 8.17 (s, 1H), 4.48 (tt, J=4.08, 11.36 Hz, 1H), 4.29 (br s, 2H), 2.89 (br s, 2H), 2.10 (dq, J=4.52, 12.30 Hz, 2H), 1.90-1.92 (m, 2H), 1.47 (s, 9H).

Embodiment 40C

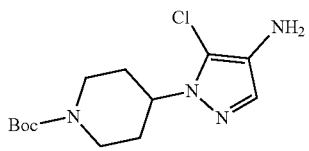 [SMILES: CC(C)(C)OC(=O)N1CCC(n2ncc([N+](=O)[O-])c2Cl)CC1]

Zinc powder (3.64 g, 55.63 mmol), and ammonium chloride solid (4.84 g, 90.40 mmol) were added to a solution of the product of embodiment 40B (2.30 g, 6.95 mmol) in tetrahydrofuran (21 mL)/methanol (14 mL)/water (7 mL). The reaction solution was stirred at 25° C. for 16 hours. The reaction solution was filtered by suction. The filtrate was added with water (50 mL), and extracted with ethyl acetate (50 mL). The combined organic phase was concentrated, dried over anhydrous sodium sulfate and concentrated to obtain the product of embodiment 40C.

LCMS (ESI) m/z: 245.0 (M−56)$^+$

Embodiment 40D

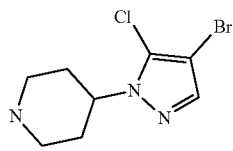 [SMILES: Clc1c(Br)cnn1C1CCNCC1]

Tert-butyl nitrite (190.28 mg, 1.85 mmol) was added to a solution of the product of embodiment 40C (370.00 mg, 1.23 mmol) in acetonitrile (10 mL). The reaction solution was stirred at 20° C. for 15 min. Copper bromide (357.18 mg, 1.60 mmol) was added then, and the reaction solution was stirred for 1 hour and then stirred at 60° C. for 16 hours. The reaction solution was filtered and concentrated to give a crude product, which was separated by preparative chromatography plate (dichloromethane:methanol=10:1) to obtain the product of embodiment 40D.

LCMS (ESI) m/z: 265.8 (M+1)$^+$ $^1$H NMR (400 MHz, CHLOROFORM-d) δ 7.51 (s, 1H), 4.51 (br s, 1H), 3.74-4.17 (m, 4H), 3.37-3.68 (m, 1H), 2.81-3.23 (m, 2H), 2.27 (br s, 3H), 2.17 (s, 2H), 2.00-2.03 (m, 1H), 1.14-1.29 (m, 2H).

Embodiment 40E

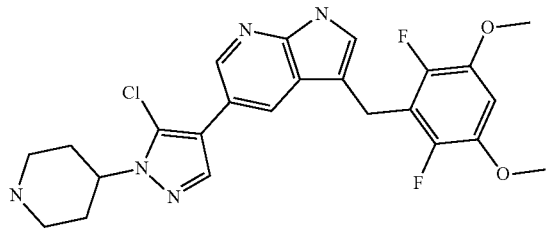 [SMILES: COc1cc(OC)c(F)c(Cc2c[nH]c3ncc(-c4cnn(C5CCNCC5)c4Cl)cc23)c1F]

Pd(dppf)Cl$_2$ (19.36 mg, 26.46 μmol) and potassium phosphate (112.33 mg, 529.20 μmol) were added to a solution of the product of embodiment 40D (70.00 mg, 264.60 μmol) and the product of embodiment 27D (125.23 mg, 291.06 μmol) in tetrahydrofuran/water (2 mL/1 mL). The reaction solution was stirred at 80° C. for 5 hours under nitrogen protection. The reaction solution was added with 2 mL of ethyl acetate and then partitioned. The organic phase was concentrated under reduced pressure and then separated by preparative chromatography plate (dichloromethane:methanol=10:1) to obtain the product of embodiment 40E.

LCMS (ESI) m/z: 488.1 (M+1)$^+$

Embodiment 40

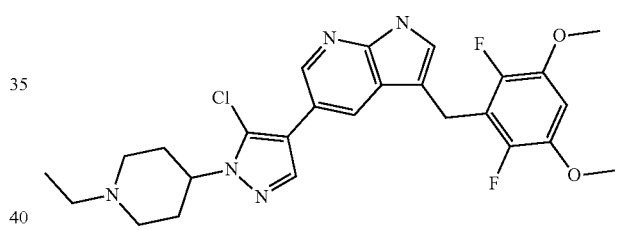

The product of embodiment 40 was prepared by a method similar to embodiment 9, using the product of embodiment 40E (50.00 mg, 102.47 μmol) as raw material to obtain hydrochloride salt of embodiment 40. In embodiment 40, the free base can be obtained by washing a solution of the hydrochloride salt of embodiment 40 in dichloromethane with 1N sodium bicarbonate, followed by separating and concentrating the organic phase.

LCMS (ESI) m/z: 516.2 (M+1)$^+$ $^1$H NMR (400 MHz, METHANOL-d$_4$) δ 8.82 (br s, 1H), 8.60 (br s, 1H), 8.04 (s, 1H), 7.54 (s, 1H), 6.79 (t, J=8.28 Hz, 1H), 4.23 (s, 2H), 3.85 (s, 6H), 3.76-3.79 (m, 2H), 3.22-3.29 (m, 3H), 2.39-2.58 (m, 2H), 2.31-2.35 (m, 2H), 1.42 (t, J=7.15 Hz, 3H).

Process I

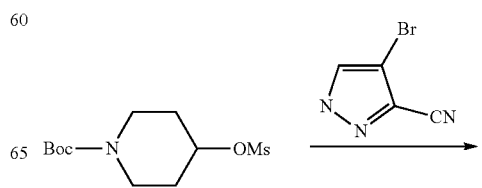

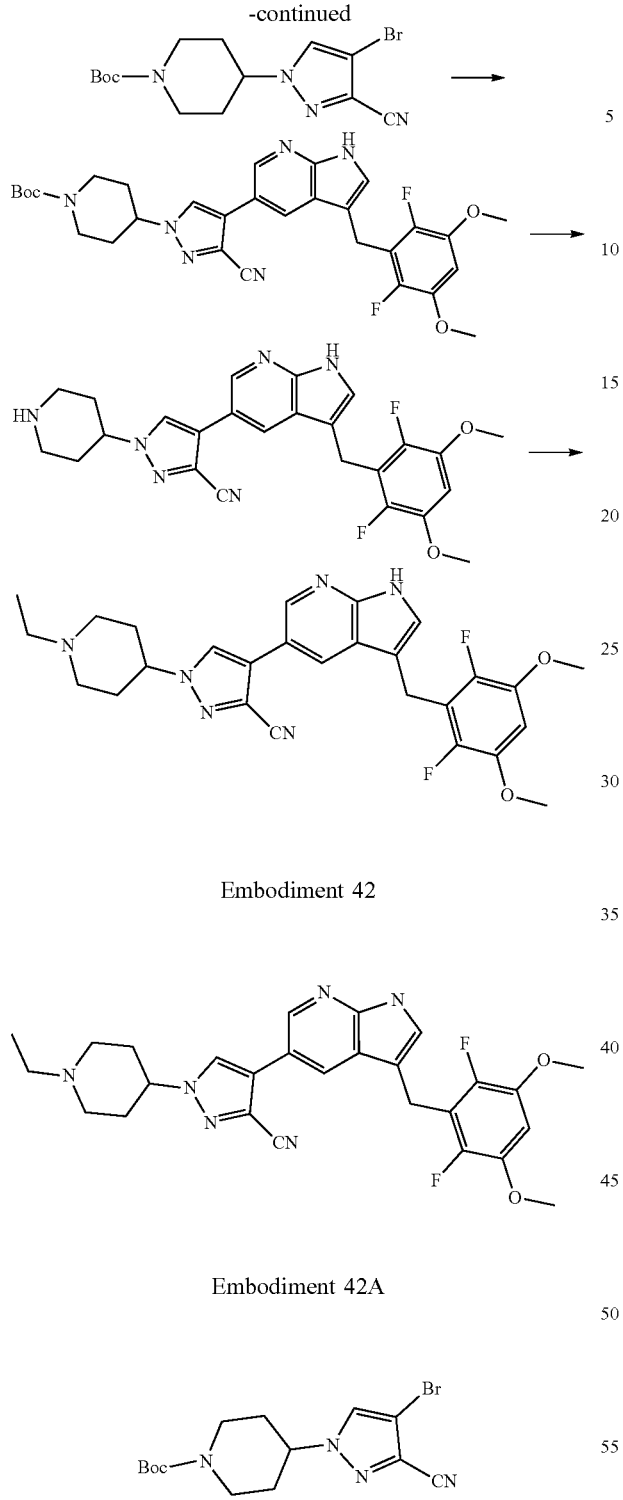

Embodiment 42

Embodiment 42A

Cesium carbonate (5.68 g, 17.44 mmol) was added to a solution of 3-cyano-4-bromopyrazole (1 g, 5.81 mmol) in acetonitrile (30 mL), and then the product of embodiment 32A (1.71 g, 6.11 mmol) was added. The reaction solution was heated to 90° C. and stirred for 3 hours. The reaction solution was filtered, and the filtrate was rotary-evaporated under reduced pressure to dryness to obtain a crude product. The crude product was separated by flash preparative chromatography on a silica gel column (petroleum ether:ethyl acetate=3:1) to give an eluate. The eluate was concentrated under reduced pressure to obtain the product of embodiment 42A.

$^1$H NMR (400 MHz, CHLOROFORM-d) δ 7.67 (s, 1H), 7.53 (s, 1H), 4.86-4.90 (m, 2H), 4.17-4.36 (m, 2H), 3.62-3.75 (m, 4H), 3.27-3.34 (m, 4H), 2.81-2.96 (m, 2H), 2.06-2.15 (m, 2H), 1.74-2.01 (m, 10H), 1.45 (s, 9H).

Embodiment 42B

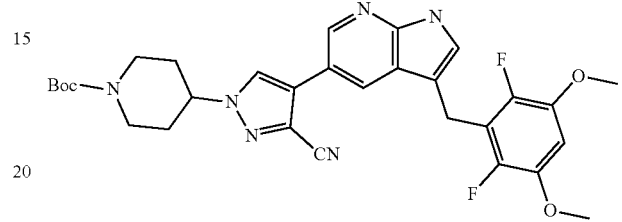

Pd(dppf)Cl$_2$ (123.59 mg, 168.90 μmol) and potassium phosphate (717.06 mg, 3.38 mmol) were added to a solution of the product of embodiment 42A (600 mg, 1.69 mmol, 1 eq) and the product of embodiment 27D (799.39 mg, 1.86 mmol) in THF (2 mL)/H$_2$O (1 mL). The reaction solution was stirred for 16 hours at 80° C. under nitrogen protection. The reaction solution was extracted with ethyl acetate (100 mL*2). The organic phases were combined to obtain a crude product. The crude product was separated by preparative chromatography with silica gel (petroleum ether:ethyl acetate=0:1) to obtain the product of embodiment 42B.

Embodiment 42C

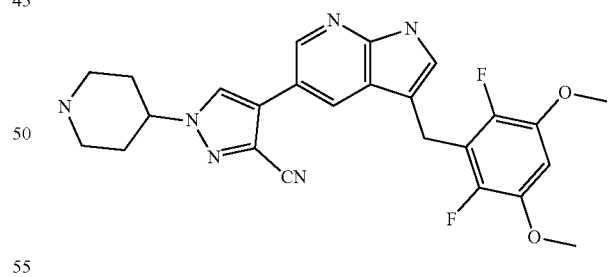

Hydrogen chloride/ethyl acetate (4N, 10 mL) was added to a single-neck flask containing the product of embodiment 42B (300 mg, 518.49 μmol). The reaction solution was stirred for 0.5 hour at 20° C. The reaction solution was rotary-evaporated under reduced pressure to dryness to obtain the product of embodiment 42C.

LCMS (ESI) m/z: 479.1 (M+1)$^+$

Embodiment 42

Process J

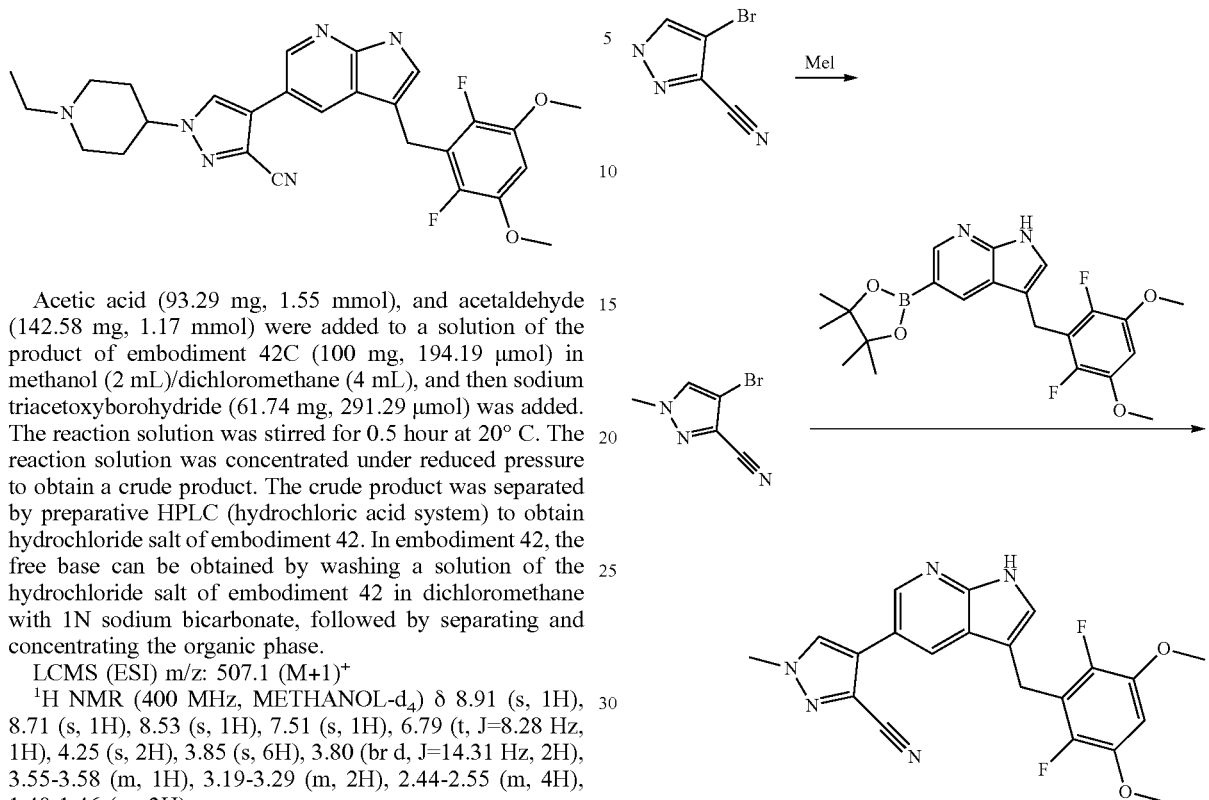

Acetic acid (93.29 mg, 1.55 mmol), and acetaldehyde (142.58 mg, 1.17 mmol) were added to a solution of the product of embodiment 42C (100 mg, 194.19 μmol) in methanol (2 mL)/dichloromethane (4 mL), and then sodium triacetoxyborohydride (61.74 mg, 291.29 μmol) was added. The reaction solution was stirred for 0.5 hour at 20° C. The reaction solution was concentrated under reduced pressure to obtain a crude product. The crude product was separated by preparative HPLC (hydrochloric acid system) to obtain hydrochloride salt of embodiment 42. In embodiment 42, the free base can be obtained by washing a solution of the hydrochloride salt of embodiment 42 in dichloromethane with 1N sodium bicarbonate, followed by separating and concentrating the organic phase.

LCMS (ESI) m/z: 507.1 (M+1)$^+$ $^1$H NMR (400 MHz, METHANOL-d$_4$) δ 8.91 (s, 1H), 8.71 (s, 1H), 8.53 (s, 1H), 7.51 (s, 1H), 6.79 (t, J=8.28 Hz, 1H), 4.25 (s, 2H), 3.85 (s, 6H), 3.80 (br d, J=14.31 Hz, 2H), 3.55-3.58 (m, 1H), 3.19-3.29 (m, 2H), 2.44-2.55 (m, 4H), 1.40-1.46 (m, 3H).

The following embodiments 43 and 45 and salts thereof were prepared by referring to the method as described in embodiment 42.

| Embodiments | Structure | NMR | LCMS (ESI) m/z: (M + 1) |
|---|---|---|---|
| Embodiment 43 | | $^1$H NMR (400 MHz, METHANOL-d$_4$) δ 8.75-8.93 (m, 1H), 8.64-8.72 (m, 1H), 8.54 (br d, J = 9.79 Hz, 1H), 7.50 (s, 1H), 6.77 (t, J = 8.16 Hz, 1H), 5.72 (s, 1H), 4.12-4.20 (m, 2H), 3.79-3.89 (m, 6H), 3.74 (br d, J = 11.80 Hz, 1H), 3.57-3.67 (m, 1H), 3.32-3.40 (m, 1H), 2.98 (s, 3H), 2.33-2.58 (m, 4H). | 493.0 (M + 1)$^+$ |
| Embodiment 45 | | $^1$H NMR (400 MHz, CHLOROFORM-d) Shift 11.29 (br s, 1H), 8.52 (d, J = 1.6 Hz, 1H), 8.38 (d, J = 1.2 Hz, 1H), 8.29 (s, 1H), 7.19 (s, 1H), 6.70-6.87 (m, 2H), 4.30-4.44 (m, 1H), 4.15 (s, 2H), 3.83 (s, 3H), 3.23 (d, J = 12.4 Hz, 2H), 2.47-2.67 (m, 4H), 2.13-2.31 (m, 4H), 1.74 ( s, 1H), 1.22 (t, J = 7.2 Hz, 3H). | 477.1 |

Embodiment 44

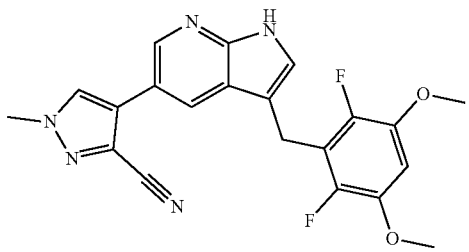

Embodiment 44A

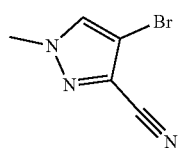

3-Cyano-4-bromopyrazole (200 mg, 1.16 mmol) was added to N,N-dimethylformamide (3 mL) firstly at 0° C., then sodium hydride (93.02 mg, 60% purity, 2.33 mmol) was added, and finally iodomethane (198.07 mg, 1.4 mmol) was slowly added. The reaction solution was stirred at 20° C. continuously for 2 hours. The reaction solution was quenched with water, and extracted with ethyl acetate (5 mL*3). The organic phase was added with saturated brine (5 mL), partitioned, dried over anhydrous sodium sulfate, and concentrated under vacuum. The crude product was mixed with silica gel and purified by flash chromatography on a silica gel column (petroleum ether/ethyl acetate=0/1-5/1) to obtain the product of embodiment 44B.

Embodiment 44

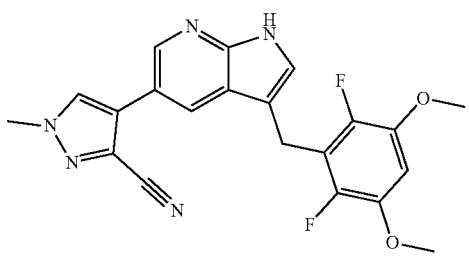

The product of embodiment 27D (277.57 mg, 0.65 mmol) was added to water (2 mL) and tetrahydrofuran (4 mL) at 20° C. firstly, then the product of embodiment 44B (100 mg, 0.54 mmol), potassium phosphate (228.23 mg, 1.08 mmol) and Pd(dppf)Cl$_2$ (39.34 mg, 0.054 mmol) were added. The reaction solution was stirred at 80° C. for 16 hours continuously. The reaction solution was quenched with water, and extracted with ethyl acetate (10 mL*3). The organic phase was washed with saturated brine and partitioned. The organic phase was dried over anhydrous sodium sulfate and concentrated under vacuum. The crude product was purified by chromatography on a silica gel plate (ethyl acetate) and then purified by preparative chromatography (TFA system) to obtain trifluoroacetate salt of embodiment 44. In embodiment 44, the free base can be obtained by washing a solution of the trifluoroacetate salt of embodiment 42 in dichloromethane with 1N sodium bicarbonate, followed by separating and concentrating the organic phase.

LCMS (ESI) m/z: 410.0 (M+1)$^+$ $^1$H NMR (400 MHz, METHANOL-d$_4$) δ 8.49 (s, 1H), 8.38 (d, J=2.0 Hz, 1H), 8.15 (s, 1H), 7.27 (s, 1H), 6.77 (t, J=8.4 Hz, 1H), 4.17 (s, 2H), 4.07 (s, 3H), 3.87 (s, 6H).

Process K

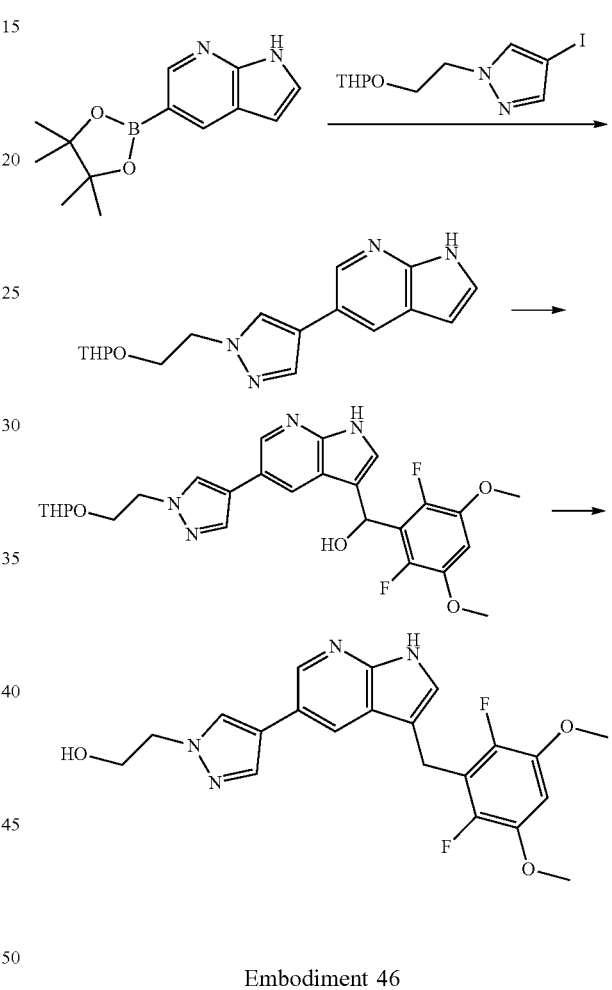

Embodiment 46

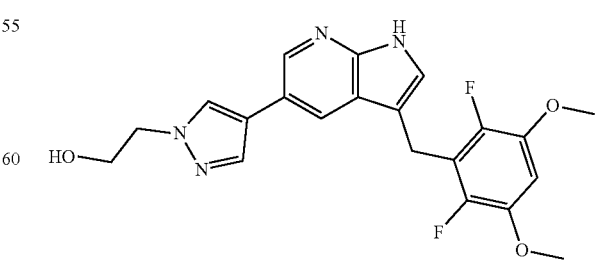

Embodiment 46A

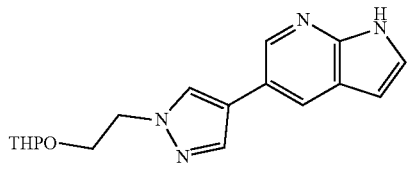

Pd(dppf)Cl$_2$ (45.43 mg, 62.08 µmol) and anhydrous potassium phosphate (263.57 mg, 1.24 mmol) were added to a solution of the product of embodiment 21A (200 mg, 620.84 µmol) and the product of embodiment 21E (197.01 mg, 807.10 µmol) in dioxane (4 mL) and water (1 mL). The reaction solution was heated to 100° C. for 6 hours under nitrogen protection. The reaction solution was cooled to room temperature, added with water (5 mL), and extracted with ethyl acetate (5 mL×2). The combined organic phase was washed with saturated brine (5 mL), dried over anhydrous sodium sulfate, filtered, and the filtrate was rotary-evaporated to dryness. The residue was separated by flash chromatography on a silica gel column to obtain the product of embodiment 46A.

LCMS (ESI) m/z: 313.4 (M+1)$^+$ $^1$H NMR (400 MHz, CHLOROFORM-d) δ 9.11 (br s, 1H), 8.45 (s, 1H), 8.02 (d, J=1.51 Hz, 1H), 7.81 (d, J=7.28 Hz, 2H), 7.33 (br s, 1H), 6.51 (d, J=2.01 Hz, 1H), 4.58 (br t, J=3.51 Hz, 2H), 4.40 (br t, J=5.14 Hz, 3H), 4.06-4.18 (m, 2H), 3.83 (td, J=5.24, 10.85 Hz, 1H), 3.62-3.73 (m, 2H), 3.40-3.52 (m, 2H), 1.39-1.64 (m, 10H).

Embodiment 46B

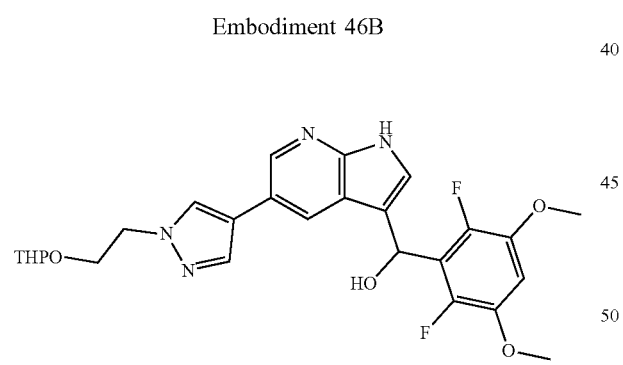

Potassium hydroxide (43.11 mg, 768.33 µmol) was added to a solution of the product of embodiment 46A (120 mg, 384.17 µmol) and 2,6-difluoro-dimethoxybenzaldehyde (0.32 mg, 768.33 µmol) in methanol (5 mL). The reaction solution was stirred at 30° C. for 16 hours.

The reaction solution was concentrated, separated and purified by chromatography plate to obtain the product of embodiment 46B.

LCMS (ESI) m/z: 514.5 (M+1)$^+$ $^1$H NMR (400 MHz, DMSO-d$_6$) δ 8.46 (s, 1H), 8.15 (s, 1H), 8.00 (s, 1H), 7.85 (s, 1H), 7.21 (s, 1H), 6.98 (s, 1H), 5.94-6.06 (m, 2H), 5.53 (s, 1H), 4.56 (s, 1H), 4.33 (br s, 2H), 3.85 (s, 7H), 3.67-3.83 (m, 5H).

Embodiment 46

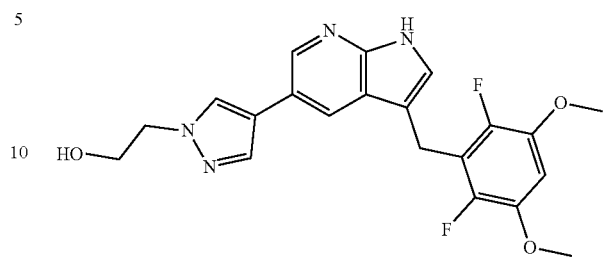

Trifluoroacetic acid (4.62 g, 40.52 mmol) was added to a solution of the product of embodiment 46B (100 mg, 194.36 µmol) and triethylsilane (180.79 mg, 1.55 mmol) in dichloromethane (3 mL). The reaction solution was stirred at 32° C. for 2 hours. The reaction solution was rotary-evaporated to dryness, directly purified by preparative chromatography (hydrochloric acid system) to obtain hydrochloride salt of embodiment 46. In embodiment 46, the free base can be obtained by washing a solution of the hydrochloride salt of embodiment 46 in dichloromethane with 1N sodium bicarbonate, followed by separating and concentrating the organic phase.

LCMS (ESI) m/z: 414.5 (M+1)$^+$ $^1$H NMR (400 MHz, METHANOL-d$_4$) δ 8.52 (s, 2H), 8.14 (s, 1H), 7.95 (s, 1H), 7.29 (s, 1H), 6.80 (t, J=8.53 Hz, 1H), 4.33 (t, J=5.27 Hz, 2H), 4.21 (s, 2H), 3.97 (t, J=5.40 Hz, 2H), 3.88 (s, 7H).

Process U

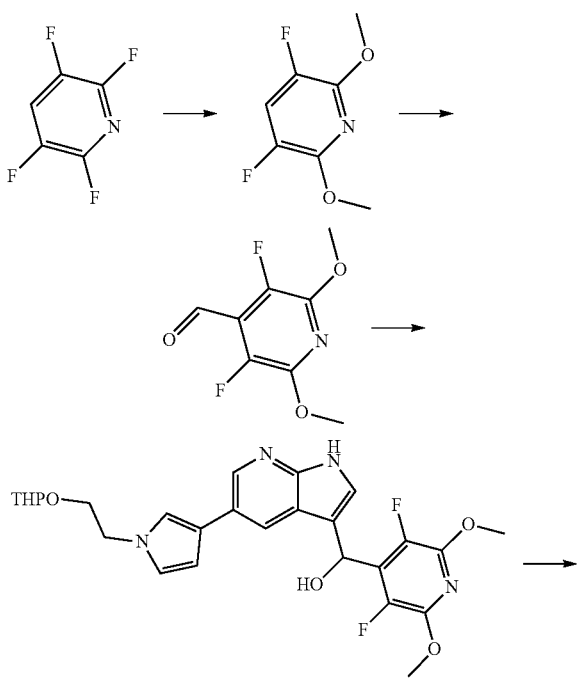

-continued

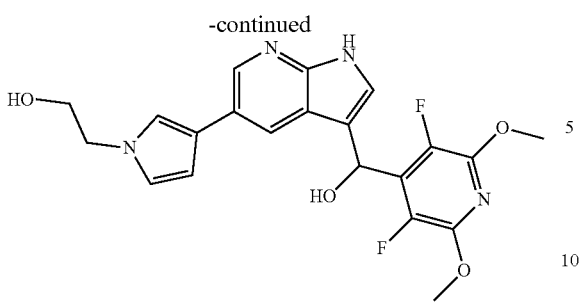

Embodiment 48

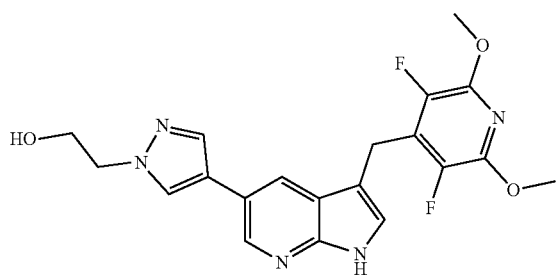 [SMILES: COc1nc(OC)c(F)c(Cc2c[nH]c3ncc(-c4cnn(CCO)c4)cc23)c1F]

Embodiment 48A

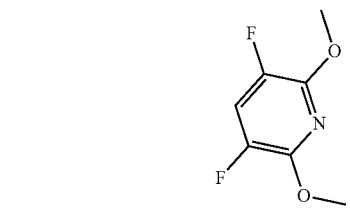

2,3,5,6-Tetrafluoropyridine (2 g, 13.24 mmol) was added to methanol (20 mL), and then a solution of sodium methoxide (2.86 g, 52.96 mmol) in methanol (10 mL) was added dropwise to the reaction solution. The reaction was allowed to run at 70° C. for 4 hours. The reaction solution was concentrated under reduced pressure, added with 60 mL of ethyl acetate, then added with 60 mL of water and partitioned. The organic phase was washed with saturated brine, dried over anhydrous sodium sulfate and concentrated under reduced pressure to obtain a crude product. The crude product was purified by column chromatography (petroleum ether/ethyl acetate=40/1-10/1) to obtain the product of embodiment 48A.

¹H NMR (400 MHz, CHLOROFORM-d) δ 7.15-7.19 (m, 1H) 3.92 (s, 6H)

Embodiment 48B

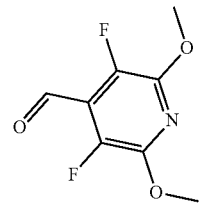

Diisopropylamine (462.23 mg, 4.57 mmol) was added to a reaction flask containing THF (5 mL), and cooled to −78° C. n-Butyllithium (2 M, 13.70 mL) was added dropwise to the reaction flask with stirring. The reaction solution was warmed to 0° C. and stirred at that temperature for 30 min. The reaction solution was cooled to −78° C. and a solution of the product of embodiment 48A (800 mg, 4.57 mmol) in THF (5 mL) was slowly added dropwise to the reaction flask over 10 min at −78° C. After the completion of the dropwise addition, the reaction solution was stirred at −78° C. for 1 hours. N,N-Dimethylformamide (667.78 mg, 9.14 mmol) was added dropwise to the reaction solution, and the reaction solution was heated to 15-20° C. and stirred at this temperature for 1 hour. The reaction solution was added with 10 mL of water, and extracted with ethyl acetate (10 mL*2). The combined organic phase was washed with saturated brine (10 mL) once, dried over anhydrous sodium sulfate, and concentrated under reduced pressure at 40-50° C., to obtain the product of embodiment 48B.

¹H NMR (400 MHz, CHLOROFORM-d) δ 10.33 (s, 1H) 3.96 (s, 6H).

Embodiment 48C

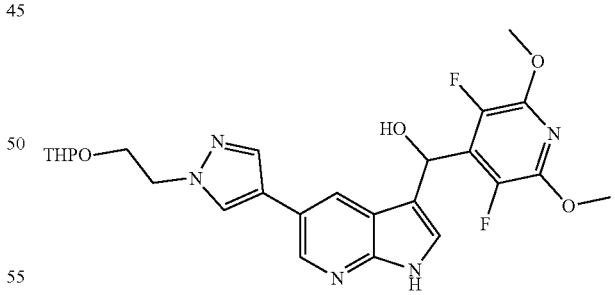

The product of embodiment 48B (200 mg, 0.98 mmol) and the product of embodiment 46A (256.28 mg, 0.82 mmol) were added to methanol (2 mL), and potassium hydroxide (92.07 mg, 1.64 mmol) was added to the reaction solution under stirring. The reaction solution was stirred at 15-20° C. for 16 hours. The reaction solution was added with 5 mL of water, and extracted with dichloromethane (10 mL*2). The combined organic phase was dried over anhydrous sodium sulfate, and concentrated under reduced pressure to obtain the product of embodiment 48C.

Embodiment 48

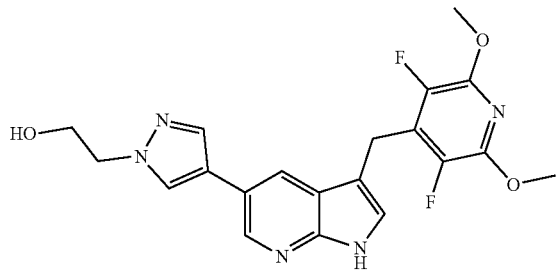 [SMILES: COc1nc(OC)c(F)c(Cc2c[nH]c3ncc(-c4cnn(CCO)c4)cc23)c1F]

The product of embodiment 48C (250 mg, 484.96 μmol), and triethylsilane (281.95 mg, 2.42 mmol) were added to dichloromethane (6 mL), and trifluoroacetic acid (276.47 mg, 2.42 mmol) was added to the reaction solution under stirring. The reaction solution was stirred at 15-20° C. for 16 hours. The reaction solution was directly rotary-evaporated to dryness under reduced pressure at 40-50° C., and dichloromethane (10 mL) was added. The mixture was rotary-evaporated to dryness again to obtain a crude product. The crude product was separated and purified by preparative HPLC (TFA system) to obtain trifluoroacetate salt of embodiment 48. In embodiment 48, the free base can be obtained by washing a solution of the trifluoroacetate salt of embodiment 48 in dichloromethane with 1N sodium bicarbonate, followed by separating and concentrating the organic phase.

LCMS (ESI) m/z: 415.9 (M+1)$^+$ $^1$H NMR (400 MHz, METHANOL-d$_4$) δ 8.54 (s, 2H) 8.15 (s, 1H) 7.96 (s, 1H) 7.34 (s, 1H) 4.33 (t, J=5.27 Hz, 2H) 4.25 (s, 2H) 3.98 (s, 6H) 3.95-3.97 (m, 2H).

The following embodiments and salts thereof were prepared by referring to the method as described in embodiment 48.

Embodiment 50

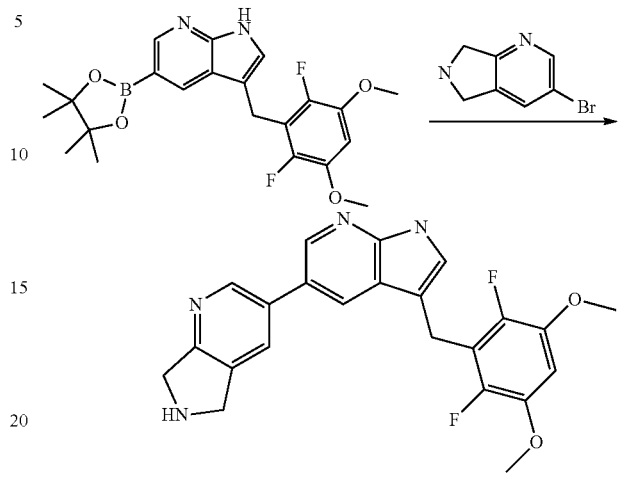

The product of embodiment 27D (0.1 g, 424.61 μmol, HCl) was dissolved in dioxane (4 mL) and water (1 mL), then the product of embodiment 27D (219.23 mg, 509.54 μmol), potassium phosphate (270.40 mg, 1.27 mmol) and Pd(dppf)Cl$_2$ (31.07 mg, 42.46 μmol) were added. The reaction was allowed to run at 100° C. for 16 hours. The reaction solution was filtered through diatomaceous earth to remove the inorganic salt and catalyst, and then added with 10 mL of water, extracted with 10 mL of ethyl acetate three times, dried over anhydrous sodium sulfate, filtered, and rotary-evaporated to dryness under reduced pressure to obtain a crude product. The crude product was separated and purified by preparative HPLC (TFA system) to obtain trifluoroacetate salt of embodiment 50. In embodiment 50, the free base can be obtained by washing a solution of the trifluoroacetate salt

| Embodiments | Structure | NMR | LCMS (ESI) m/z: (M + 1) |
|---|---|---|---|
| Embodiment 75 | 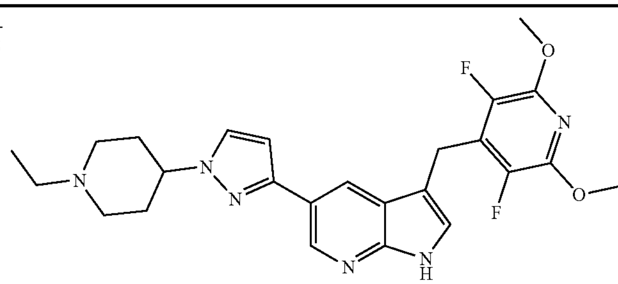 | N/A | 483.0 |
| Embodiment 77 | 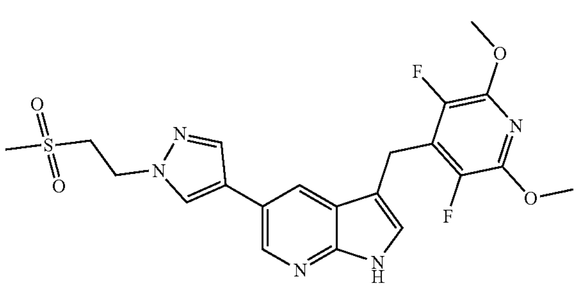 | $^1$H NMR (400 MHz, METHANOL-d$_4$) δ ppm 8.49 (s, 1 H) 8.40 (s, 1 H) 8.19 (s, 1 H) 7.98 (s, 1 H) 7.29 (s, 1 H) 4.74 (t, J = 6.65 Hz, 2 H) 4.23 (s, 2 H) 3.98 (s, 6 H) 3.79 (t, J = 6.27 Hz, 2 H) 2.85 (s, 3 H). | 478.0 |

N/A, indicates not measured.

of embodiment 50 in dichloromethane with 1N sodium bicarbonate, followed by separating and concentrating the organic phase.

$^1$H NMR (METHANOL-d$_4$, 400 MHz): δ 8.86 (s, 1H), 8.51 (br s, 1H), 8.38 (br s, 1H), 8.19 (s, 1H), 7.27 (s, 1H), 6.78 (t, J=8.2 Hz, 1H), 4.83 (s, 2H), 4.69 (s, 2H), 4.19 (s, 2H), 3.87 ppm (s, 6H).

Embodiment 51

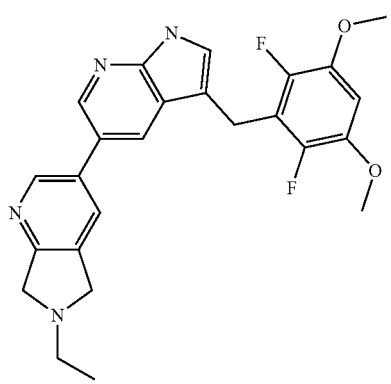 [SMILES: CCN1Cc2cc(-c3cnc4[nH]cc(Cc5c(F)c(OC)cc(OC)c5F)c4c3)cnc2C1]

The product of embodiment 51 was prepared by a method similar to that of embodiment 42, using the product of embodiment 50 (0.05 g, 118.36 μmol) as raw material to obtain trifluoroacetate salt of embodiment 51. In embodiment 51, the free base can be obtained by washing a solution of the trifluoroacetate salt of embodiment 51 in dichloromethane with 1N sodium bicarbonate, followed by separating and concentrating the organic phase.

$^1$H NMR (400 MHz, METHANOL-d$_4$) δ 8.87 (s, 1H), 8.50 (s, 1H), 8.35 (d, J=2.0 Hz, 1H), 8.18 (s, 1H), 7.27 (s, 1H), 6.78 (t, J=8.3 Hz, 1H), 4.19 (s, 2H), 3.83-3.90 (s, 6H), 3.62 (q, J=7.3 Hz, 2H), 1.51 (t, J=7.2 Hz, 3H).

The following embodiments and salts thereof were prepared by referring to the method as described in embodiments 50 and 51.

| Embodiments | Structure | NMR | LCMS (ESI) m/z: (M + 1) |
|---|---|---|---|
| Embodiment 52 | 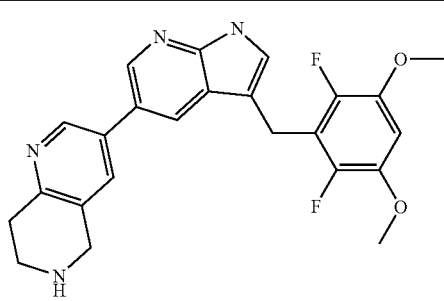 | $^1$H NMR (400 MHz, METHANOL-d$_4$) δ 8.85 (d, J = 2.0 Hz, 1H), 8.50-8.53 (m, 1H), 8.40 (d, J = 2.0 Hz, 1H), 8.09-8.11 (m, 1H), 7.28 (s, 1H), 6.78 (t, J = 8.3 Hz, 1H), 4.58 (s, 2H), 4.20 (s, 2H), 3.87 (s, 6H), 3.83-3.68 (m, 1H), 3.69-3.74 (m, 2H), 3.41 (br t, J = 6.1 Hz, 2H), 3.33-3.32 (m, 2H). | 437.1 |
| Embodiment 53 | 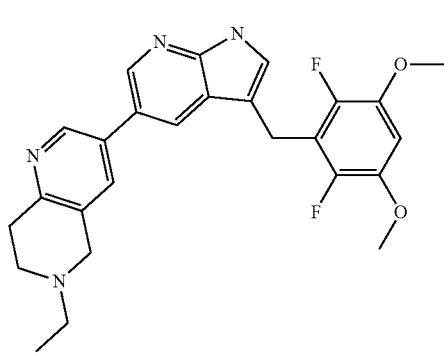 [SMILES: CCN1CCc2ncc(-c3cnc4[nH]cc(Cc5c(F)c(OC)cc(OC)c5F)c4c3)cc2C1] | $^1$H NMR (400 MHz, METHANOL-d$_4$) δ 8.86 (d, J = 2.0 Hz, 1H), 8.52 (d, J = 2.0 Hz, 1H), 8.40 (d, J = 2.0 Hz, 1H), 8.09 (d, J = 1.8 Hz, 1H), 7.28 (s, 1H), 6.78 (t, J = 8.4 Hz, 1H), 4.67 (br s, 2H), 4.20 (s, 2H), 3.87 (s, 6H), 3.83-3.68 (m, 1H), 3.48 (q, J = 7.2 Hz, 2H), 3.41 (br t, J = 6.2 Hz, 2H), 3.33-3.32 (m, 2H), 1.52 (t, J = 7.2 Hz, 3H). | 465.1 |

-continued

| Embodiments | Structure | NMR | LCMS (ESI) m/z: (M + 1) |
|---|---|---|---|
| Embodiment 54 | 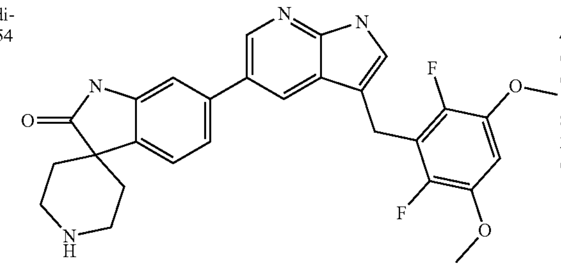 | ¹H NMR (METHANOL-d₄, 400 MHz): δ 8.89 (s, 1.0H), 8.66 (s, 1H), 7.44-7.55 (m, 2H), 7.32 (s, 1.1H), 6.80 (t, J = 8.4 Hz, 1H), 4.27 (s, 2H), 3.80-3.89 (m, 8H), 3.45 (d, J = 12.8 Hz, 2H), 2.21-2.32 (m, 2H), 2.08-2.11 (m, 2H). | 505.1 |
| Embodiment 55 | 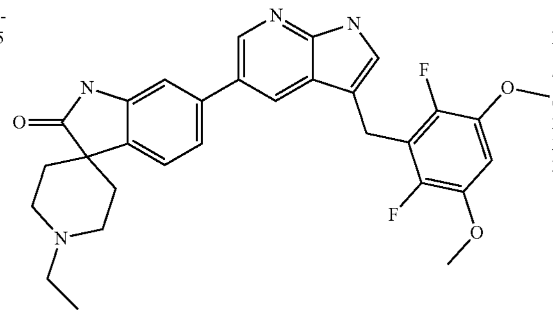 | ¹H NMR (400 MHz, METHANOL-d₄) δ 8.49 (s, 1H), 8.43 (d, J = 1.8 Hz, 1H), 7.39 (s, 2H), 7.25-7.32 (m, 2H), 6.78 (t, J = 8.4 Hz, 1H), 4.20 (s, 2H), 3.83-3.90 (m, 8H), 3.36-3.62 (m, 4H), 2.25-2.45 (m, 2H), 1.97-2.18 (m, 2H), 1.38-1.52 (m, 3H). | 533.1 |
| Embodiment 56 | 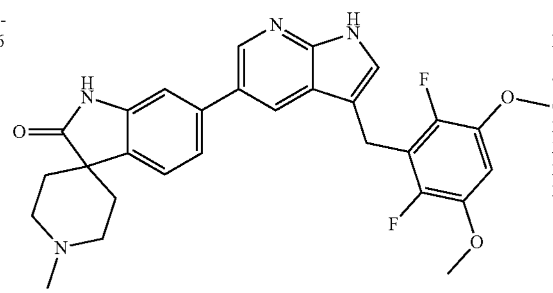 | ¹H NMR (400 MHz, METHANOL-d₄) δ 8.49 (s, 1H), 8.44 (d, J = 1.8 Hz, 1H), 7.42 (s, 2H), 7.22-7.37 (m, 2H), 6.78 (t, J = 8.4 Hz, 1H), 4.20 (s, 2H), 3.86-3.93 (m, 8H), 3.51-3.57 (m, 2H), 3.05 (s, 3H), 2.25-2.45 (m, 2H), 1.97-2.18 (m, 2H). | 519.1 |
| Embodiment 62 | 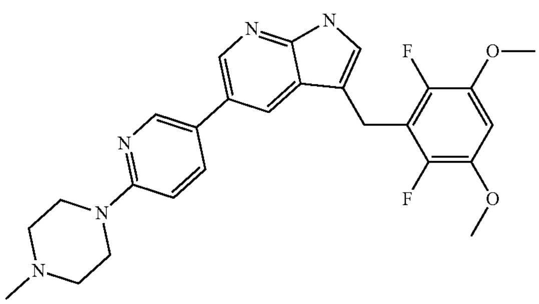 | ¹H NMR (400 MHz, METHANOL-d₄) δ 8.45-8.52 (m, 3H), 8.04 (d, J = 1.8 Hz, 1H), 7.35 (s, 1H), 7.17 (d, J = 4.0 Hz, 2H), 6.78 (t, J = 8.4 Hz, 1H), 4.21 (s, 2H), 3.87 (s, 6H), 3.45-3.68 (m, 8H), 3.00 (s, 3H). | 480.1 |
| Embodiment 78 | 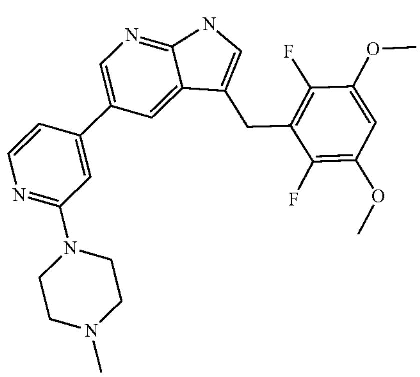 [SMILES: COc1cc(OC)c(F)c(Cc2c[nH]c3ncc(-c4ccnc(N5CCN(C)CC5)c4)cc23)c1F] | ¹H NMR (400 MHz, METHANOL-d₄) δ 8.52 (s, 1H), 8.35 (s, 1H), 8.20-8.24 (m, 1H), 7.23 (s, 1H), 7.09-7.13 (m, 2H), 6.78 (t, J = 8.4 Hz, 1H), 4.60 (s, 2H), 4.19 (s, 2H), 3.87 (s, 6H), 3.75-3.81 (m, 2H), 3.00 (s, 3H), 2.90-2.95 (m, 4H), 2.45-2.70 (m, 2H). | 480.2 |

Process V

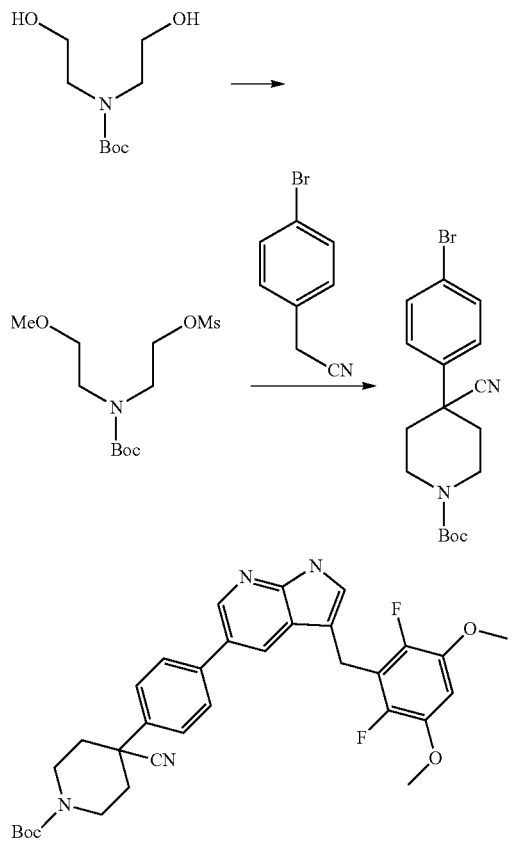

Embodiment 57

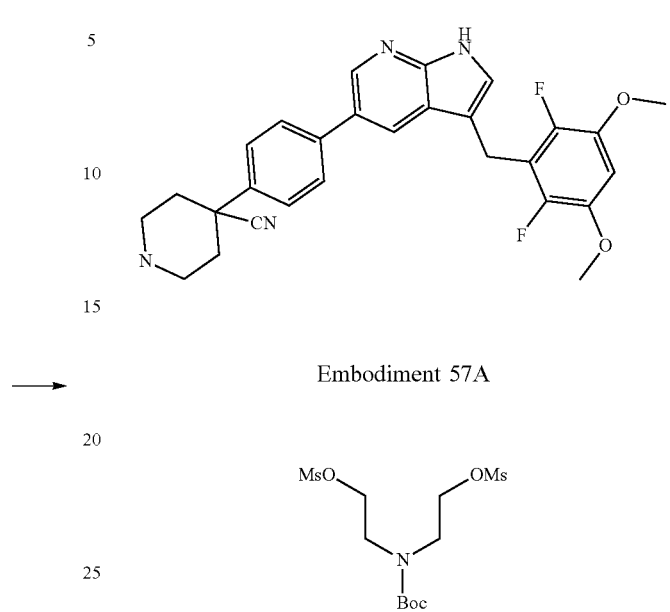

Embodiment 57A

N-Boc-bis(2-hydroxyethyl)amine (1.5 g, 7.31 mmol) was dissolved in dichloromethane (15 mL), and triethylamine (3.70 g, 36.54 mmol, 5.09 mL) was added. Methanesulfonyl chloride (1.84 g, 16.08 mmol) was added dropwise at 0° C. The reaction was allowed to run at 0° C. for 1 hour. The reaction solution was poured into 10 mL of water, extracted with 5 mL of dichloromethane three times. The combined organic phase was dried over anhydrous sodium sulfate, filtered, and concentrated under reduced pressure to obtain the product of embodiment 57A.

Embodiment 57B

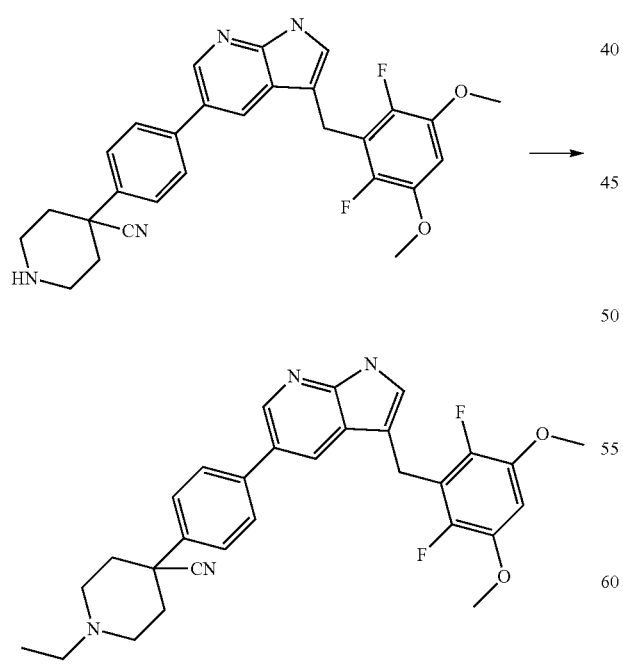

4-Bromophenylacetonitrile (0.9 g, 4.59 mmol) was dissolved in tetrahydrofuran (9 mL), and lithium hexamethyldisilazide (LiHMDS, 1 M, 16.07 mL) was added at −60° C. The reaction solution was heated to 10° C. and stirred for 1 hour, followed by addition of the product of embodiment 57A (1.99 g, 5.51 mmol) at −60° C. The reaction was allowed to run at 10° C. for 16 hours. The reaction solution was poured into 20 mL of water, extracted with ethyl acetate (15 mL×3), washed with saturated brine (50 mL×3) and dried over anhydrous sodium sulfate. The crude product was purified by column chromatography (petroleum ether/ethyl acetate=20/1-3/1) to obtain the product of embodiment 57B.

Embodiment 57C

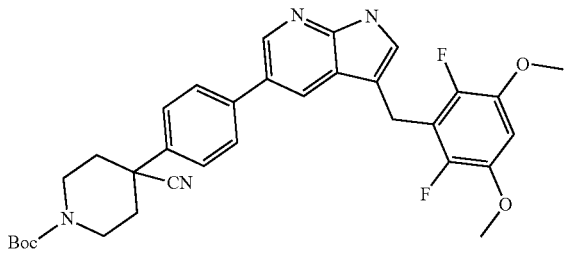 [SMILES: COc1cc(OC)c(F)c(Cc2c[nH]c3ncc(-c4ccc(C5(C#N)CCN(C(=O)OC(C)(C)C)CC5)cc4)cc23)c1F]

The product of embodiment 57B (0.5 g, 1.37 mmol) was dissolved in dioxane (8 mL) and H₂O (2 mL), and then the product of embodiment 27D (706.75 mg, 1.64 mmol), potassium phosphate (1.16 g, 5.48 mmol) and Pd(dppf)Cl₂ (100.16 mg, 136.89 µmol) were added. The reaction was allowed to run at 100° C. for 16 hours. The reaction solution was filtered through diatomaceous earth to remove the inorganic salt and catalyst, then added with 20 mL of water, extracted with 20 mL of ethyl acetate three times, dried over anhydrous sodium sulfate, filtered, and rotary-evaporated to dryness under reduced pressure to obtain a crude product. The crude product was purified by flash chromatograph on a silica gel column (petroleum ether/ethyl acetate=10/1-0/1) to obtain the product of embodiment 57C.

Embodiment 57

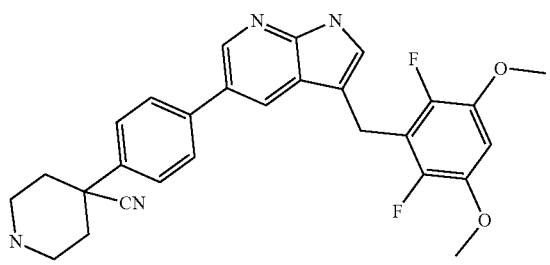 [SMILES: COc1cc(OC)c(F)c(Cc2c[nH]c3ncc(-c4ccc(C5(C#N)CCNCC5)cc4)cc23)c1F]

The product of embodiment 57C (0.5 g, 849.41 µmol) was dissolved in ethyl acetate (1 mL), and hydrogen chloride/ethyl acetate (4 M, 849.41 µL) was added. The reaction solution was stirred at 10° C. for 1 hour. The reaction solution was filtered, washed with ethyl acetate (1 mL) three times to obtain hydrochloride salt of embodiment 57. In embodiment 57, the free base can be obtained by washing a solution of the hydrochloride salt of embodiment 57 in dichloromethane with 1N sodium bicarbonate, followed by separating and concentrating the organic phase.

LCMS (ESI) m/z: 489.1 (M+1)⁺

¹H NMR (400 MHz, METHANOL-d₄) δ 8.99 (d, J=1.5 Hz, 1H), 8.75 (d, J=1.5 Hz, 1H), 7.94 (s, 1H), 7.91 (s, 1H), 7.96-7.90 (m, 1H), 7.84 (s, 1H), 7.82 (s, 1H), 7.53 (s, 1H), 6.86-6.74 (m, 1H), 4.31 (s, 2H), 3.90-3.84 (m, 6H), 3.76-3.65 (m, 2H), 3.52-3.39 (m, 2H), 2.59-2.40 (m, 4H).

Embodiment 58

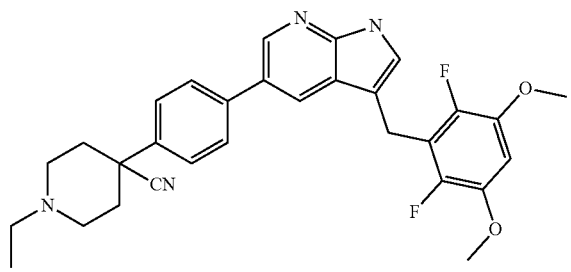 [SMILES: CCN1CCC(C#N)(c2ccc(-c3cnc4[nH]cc(Cc5c(F)c(OC)cc(OC)c5F)c4c3)cc2)CC1]

The product of embodiment 58 was prepared by a method similar to that of embodiment 42 using the product of embodiment 57 (0.05 g, 95.24 µmol) as raw material to obtain trifluoroacetate salt of embodiment 58. In embodiment 58, the free base can be obtained by washing a solution of the trifluoroacetate salt of embodiment 58 in dichloromethane with 1N sodium bicarbonate, followed by separating and concentrating the organic phase.

LCMS (ESI) m/z: 517.1 (M+1)⁺

¹H NMR (400 MHz, METHANOL-d₄) δ 8.54 (br s 2H), 7.86-7.80 (m, 2H), 7.74 (br J=8.0 Hz, 2H), 7.37-7.20 (m, 1H), 6.78 (td J=8.3 Hz, 1H) 4.21 (br s, 2H), 3.91 (br s, 2H), 3.87-3.86 (m, 1H), 3.87 (s, 6H) 3.48-3.35 (H), 4H), 2.66-2.31 (r 4H), 1.46 (t, J=7.2 Hz 3H).

The following embodiments were prepared by referring to the method as described in embodiments 57 and 58.

| Embodiments | Structure | NMR | LCMS (ESI) m/z: (M + 1) |
|---|---|---|---|
| Embodiment 59 | 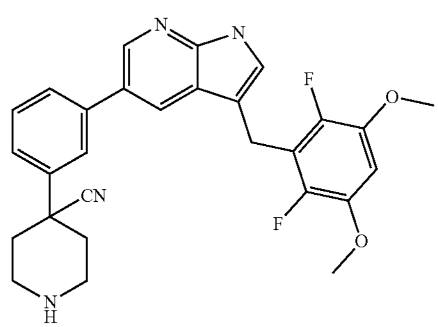 [SMILES: COc1cc(OC)c(F)c(Cc2c[nH]c3ncc(-c4cccc(C5(C#N)CCNCC5)c4)cc23)c1F] | ¹H NMR (400MHz, METHANOL-d₄) δ 9.00-8.92 (m, 1H), 8.77 (br d, J = 1.5 Hz, 1H), 7.98 (br s, 1H), 7.84 (br d, J = 6.5 Hz, 1H), 7.78-7.69 (m, 2H), 7.50 (s, 1H), 6.82 (t, J = 8.3 Hz, 1H), 4.31 (s, 2H), 3.88 (s, 6H), 3.76-3.67 (m, 2H), 3.53-3.42 (m, 2H), 2.65-2.48 (m, 4H). | 489.1 |

| Embodiments | Structure | NMR | LCMS (ESI) m/z: (M + 1) |
|---|---|---|---|
| Embodiment 60 | 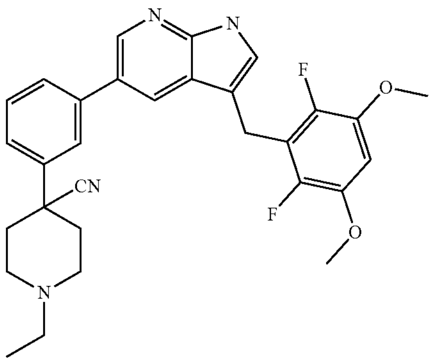 [SMILES: CCN1CCC(C#N)(c2cccc(-c3cnc4[nH]cc(Cc5c(F)c(OC)cc(OC)c5F)c4c3)c2)CC1] | ¹H NMR (400 MHz, METHANOL-d₄) δ 8.59 (br s, 2H), 7.88 (br s, 1H), 7.76 (br d, J = 2.8 Hz, 1H), 7.70-7.58 (m, 2H), 7.38-7.25 (m, 1H), 6.79 (br t, J = 8.2 Hz, 1H), 4.22 (s, 2H), 3.91 (br s, 2H), 3.86 (d, J = 2.0 Hz, 6H), 3.48-3.35 (m, 4H), 2.75-2.37 (m, 4H), 1.45 (br t, J = 7.1 Hz, 3H). | 517.1 |
| Embodiment 61 | 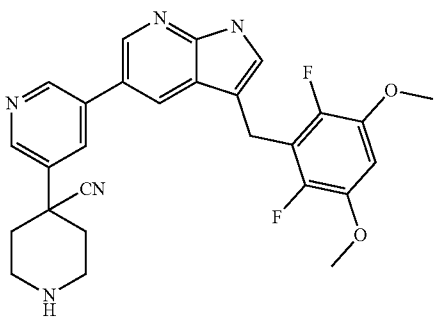 [SMILES: COc1cc(OC)c(F)c(Cc2c[nH]c3ncc(-c4cncc(C5(C#N)CCNCC5)c4)cc23)c1F] | ¹H NMR (400 MHz, METHANOL-d₄) δ 9.26 (s, 1H), 8.90-9.08 (m, 4H), 7.34 (s, 1H), 6.70 (t, J = 8.2 Hz, 1H), 4.21 (s, 2H), 3.76 (s, 6H), 3.62-3.68 (m, 2H), 3.35-3.38 (m, 2H), 2.51-2.65 (m, 4H). | 490.1 |
Process W
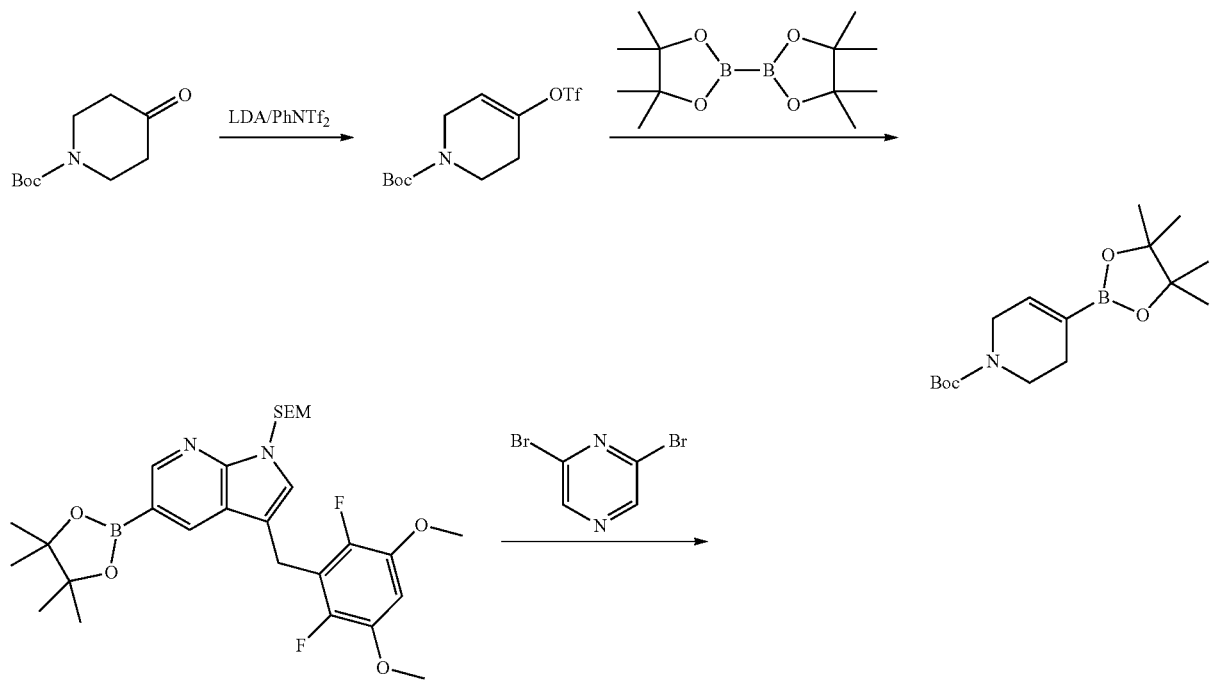

-continued
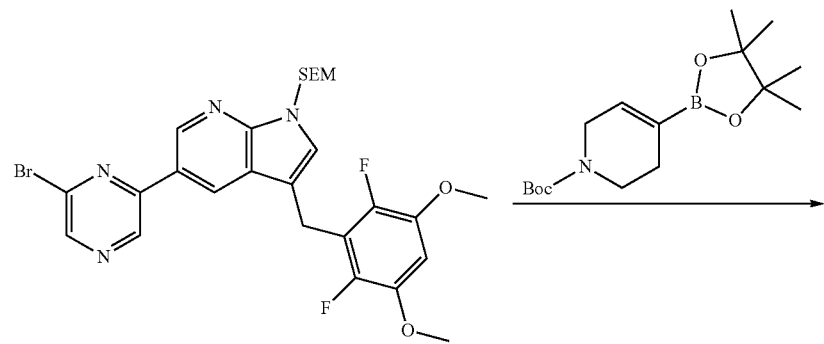
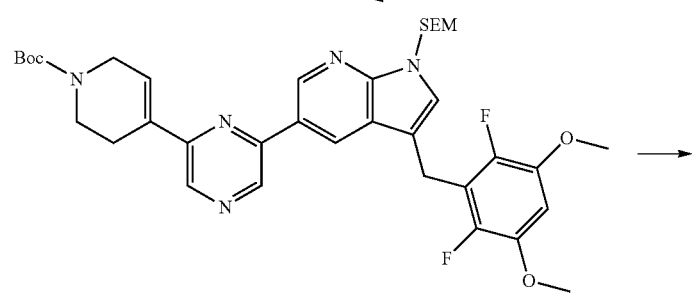
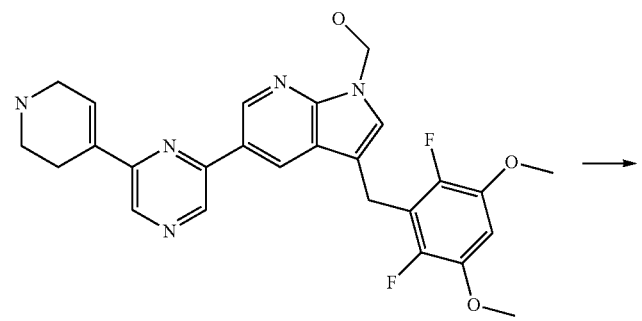
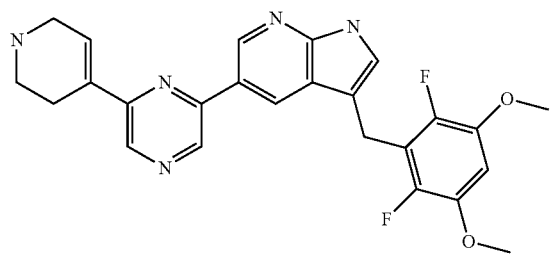
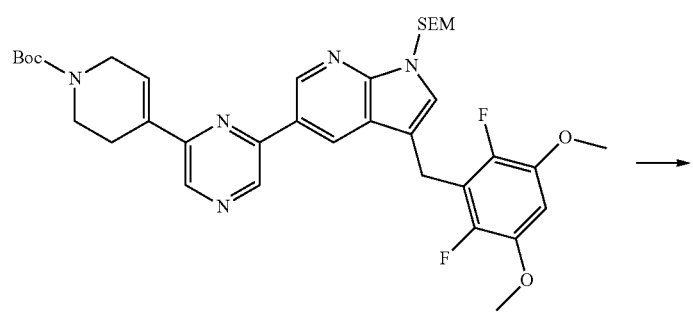

-continued
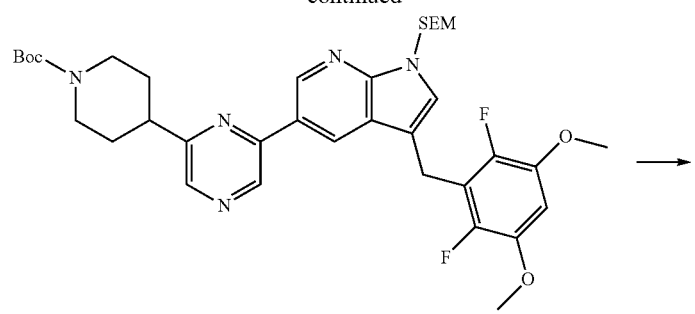
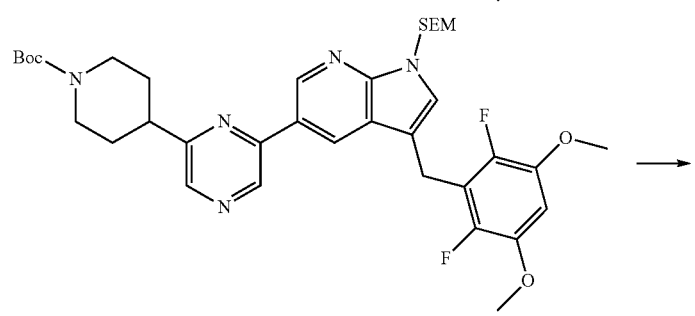
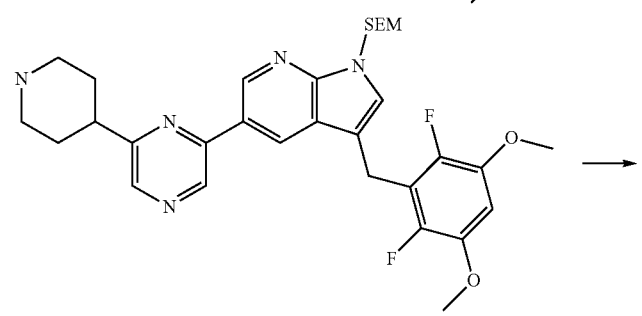
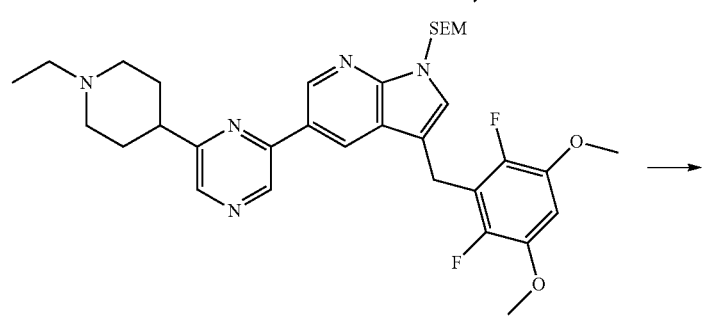
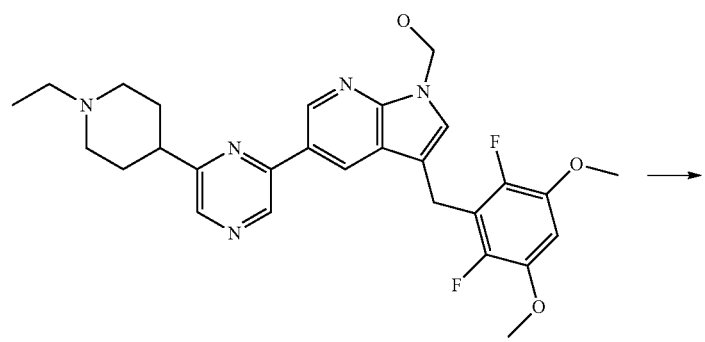

-continued

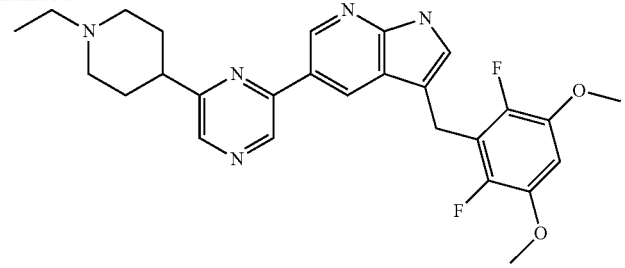

Embodiment 63A

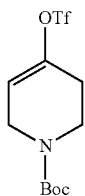

LDA (2 M, 12.55 mL) was added dropwise to a solution of N-Boc-4-piperidone (5 g, 25.09 mmol) in tetrahydrofuran (50 mL) under stirring at −78° C. under nitrogen protection. After the dropwise addition, the reaction solution was still stirred at −78° C. for 0.5 hour. Subsequently. N-phenyltrifluoromethanesulfonamide (10.76 g, 30.11 mmol) dissolved in tetrahydrofuran (100 mL) was added dropwise to the reaction solution under stirring at −78° C. The reaction solution was then slowly warmed to 0° C. and stirred at 0° C. for 3 hours. The reaction solution was quenched with 20 mL of saturated aqueous ammonium chloride, and added with 100 mL of water and 100 mL of ethyl acetate, partitioned. The aqueous phase was then extracted with 100 mL of ethyl acetate. The combined organic phase was dried over anhydrous sodium sulfate and rotary-evaporated to dryness under vacuum to obtain a crude product. The crude product was separated by flash chromatography on a silica gel column to obtain the product of embodiment 63A.

$^1$H NMR (400 MHz, CHLOROFORM-d) δ 5.69 (s, 1H), 3.97 (m, 2H), 3.56 (m, 2H), 3.37 (m, 2H), 1.40 (s, 9H).

Embodiment 63B

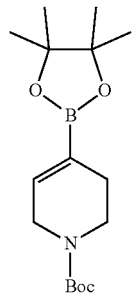

The product of embodiment 63A (1 g, 3.02 mmol), bis(pinacolato)diboron (919.76 mg, 3.62 mmol), Pd(dppf)Cl$_2$ (220.85 mg, 301.83 μmol) and potassium acetate (888.68 mg, 9.06 mmol) were added to dioxane (20 mL) together. The reaction solution was heated to 105° C. and stirred for 16 hours under nitrogen protection. 40 mL of water and 40 mL of ethyl acetate were added to the reaction solution, partitioned, and the aqueous phase was extracted with 40 mL of ethyl acetate. The combined organic phase was dried over anhydrous sodium sulfate, and rotary-evaporated to dryness under vacuum. The crude product was separated by flash chromatography on a silica gel column to obtain the product of embodiment 63B.

$^1$H NMR (400 MHz, CHLOROFORM-d) δ 6.46 (s, 1H), 3.95 (d, J=2.8 Hz, 2H), 3.44 (m, 2H), 2.23 (m, 2H), 1.46 (s, 9H), 1.27 (s, 12H).

Embodiment 63C

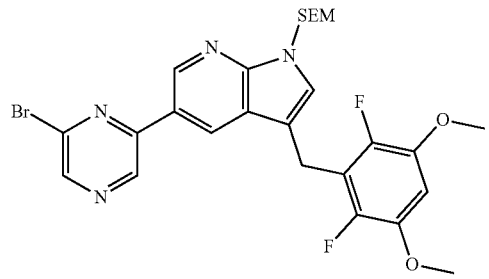 [SMILES: COc1cc(OC)c(F)c(Cc2cn(COCC[Si](C)(C)C)c3ncc(-c4cncc(Br)n4)cc23)c1F]

The product of embodiment 28A (50 mg, 89.20 μmol), 2,6-dibromopyrazine (31.83 mg, 133.81 μmol), Pd(dppf)Cl$_2$ (3.26 mg, 4.46 μmol) and potassium phosphate (56.81 mg, 267.61 μmol) were added together to a microwave tube containing dioxane (1 mL) and water (0.5 mL). The reaction solution was heated to 105° C. subsequently and reacted for 0.5 hour in a microwave synthesizer. 2 mL of water and 2 mL of ethyl acetate were added to the reaction solution, partitioned, and the aqueous phase was extracted with 2 mL of ethyl acetate. The combined organic phase was dried over anhydrous sodium sulfate and purified directly by chromatography on a silica gel plate to obtain the product of embodiment 63C.

$^1$H NMR (400 MHz, CHLOROFORM-d) δ 9.08 (s, 1H), 9.01 (d, J=2.01 Hz, 1H), 8.70 (d, J=2.51 Hz, 1H), 8.69 (s, 1H), 7.31 (s, 1H), 6.62 (t, J=8.03 Hz, 1H), 5.71 (s, 2H), 5.39 (s, 2H), 4.26 (s, 2H), 3.95 (s, 6H), 3.62 (d, J=8.03 Hz, 2H), −0.02-0.01 (m, 9H).

Embodiment 63D

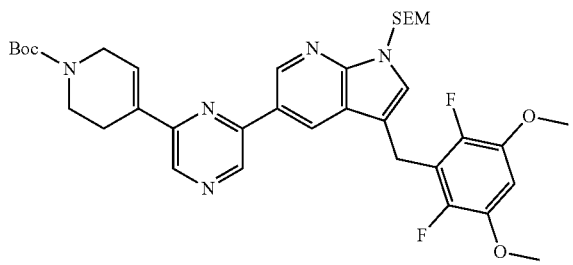 [SMILES: COc1cc(OC)c(F)c(Cc2cn(COCC[Si](C)(C)C)c3ncc(-c4cncc(C5=CCN(C(=O)OC(C)(C)C)CC5)n4)cc23)c1F]

The product of embodiment 63C (15 mg, 25.36 µmol), the product of embodiment 63B (7.84 mg, 25.36 µmol), Pd(dppf)Cl$_2$ (1.86 mg, 2.54 µmol) and potassium phosphate (16.15 mg, 76.08 µmol) were added together to a microwave tube containing dioxane (0.5 mL) and water (0.25 mL). The reaction solution was heated to 105° C. subsequently and reacted for 0.5 hour in a microwave synthesizer. The reaction solution was extracted with 0.5 mL of ethyl acetate, and the aqueous phase was extracted again with 0.5 mL of ethyl acetate. The combined organic phase was dried over anhydrous sodium sulfate and purified directly by chromatography on a silica gel plate to obtain the product of embodiment 63D.

LCMS (ESI) m/z: 694.3 (M+1)$^+$

Embodiment 63E

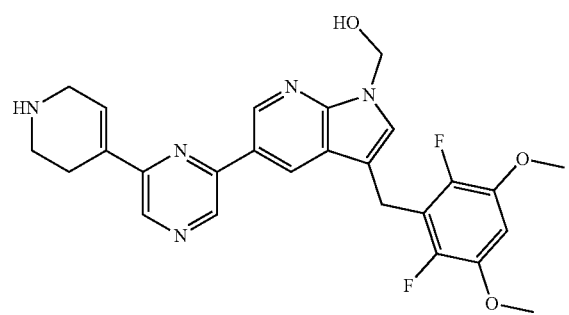 [SMILES: COc1cc(OC)c(F)c(Cc2cn(CO)c3ncc(-c4cncc(C5=CCNCC5)n4)cc23)c1F]

The product of embodiment 63D (10 mg, 14.41 µmol) was added to a thumb flask (1 mL) containing dichloromethane (1 mL), and then trifluoroacetic acid (16.43 mg, 144.12 µmol, 10.67 µL) was added. The reaction solution was stirred at 10-20° C. for 1 hour. The reaction solution was directly concentrated by rotary evaporation to obtain a crude product. The reaction solution was directly concentrated to obtain a crude product. The crude product was directly used in the next step without further purification to obtain the product of embodiment 63E as a yellow oil.

LCMS (ESI) m/z: 494.2 (M+1)$^+$

Embodiment 63

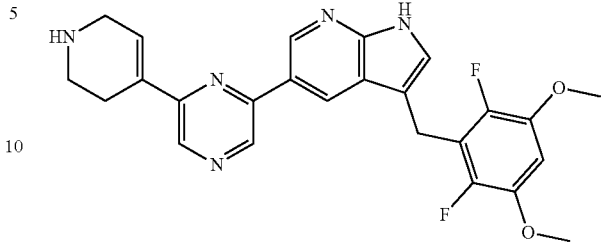

The product of embodiment 63E (7 mg, 14.18 µmol) was added to a thumb flask (10 mL) containing methanol (1 mL), and potassium carbonate (5.88 mg, 42.55 µmol) was added to the reaction solution in one portion. The reaction solution was stirred at 15-20° C. for 1 hour under nitrogen protection. LCMS showed that the reaction completed and the product appeared. The reaction solution was directly rotary-evaporated to dryness under vacuum to obtain a crude product. The crude product was directly separated by preparative HPLC (HCl system) to obtain hydrochloride salt of embodiment 63. In embodiment 63, the free base can be obtained by washing a solution of the hydrochloride salt of embodiment 63 in dichloromethane with 1N sodium bicarbonate, followed by separating and concentrating the organic phase.

LCMS (ESI) m/z: 464.2 (M+1)$^+$ $^1$H NMR (400 MHz, METHANOL-d$_4$) δ 9.20-9.25 (m, 1H), 8.91 (s, 1H), 7.87 (s, 1H), 7.49 (s, 1H), 7.05 (br s, 1H), 6.78 (br s, 1H), 5.35 (br s, 1H), 4.26 (s, 2H), 4.05 (br s, 1H), 3.87 (s, 6H), 3.61 (br t, J=6.02 Hz, 2H), 3.15 (br s, 1H), 2.21 (br s, 1H), 2.03-2.05 (m, 1H).

Embodiment 63F

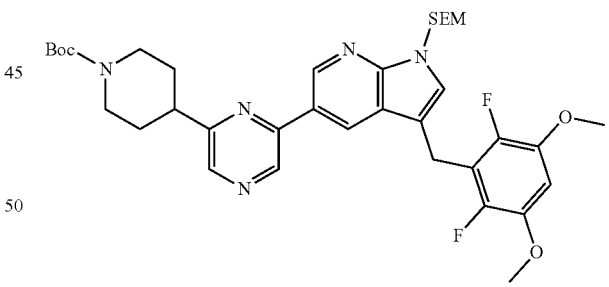

The product of embodiment 63D (50 mg, 72.06 µmol) was added to a thumb flask (10 mL) containing methanol (2 mL), and then PtO$_2$ (9.82 mg, 43.24 µmol) was added to the reaction solution. The reaction solution was purged with hydrogen three times, and then stirred at 20° C. for 16 hours under hydrogen protection (15 psi). The reaction solution was filtered to obtain the filtrate. The filtrate was rotary-evaporated to dryness under vacuum to obtain the crude product. The crude product was purified by chromatography on a silica gel plate to obtain the product of embodiment 63F.

LCMS (ESI) m/z [M+H]$^+$: 696.3

Embodiment 63G

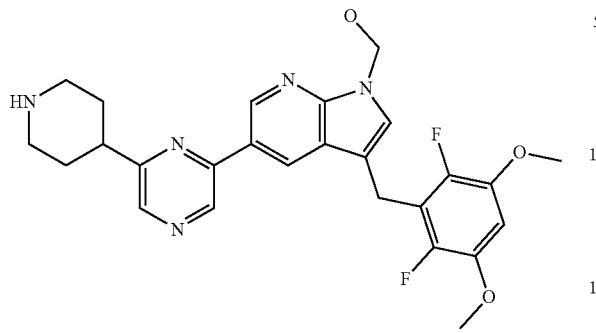

The product of embodiment 63F (40 mg, 57.48 µmol) was dissolved in dichloromethane (2 mL) in a thumb flask (10 mL), then trifluoroacetic acid (65.54 mg, 574.82 µmol, 42.56 µL) was added to the reaction solution. The reaction solution was stirred at 10-20° C. for 16 hours under nitrogen protection. The reaction solution was directly rotary-evaporated to dryness under vacuum to obtain a crude product. The crude product was directly used in the next reaction without further purification. Finally the product of embodiment 63G was obtained.

LCMS (ESI) m/z [M+H]$^+$: 496.2

Embodiment 63H

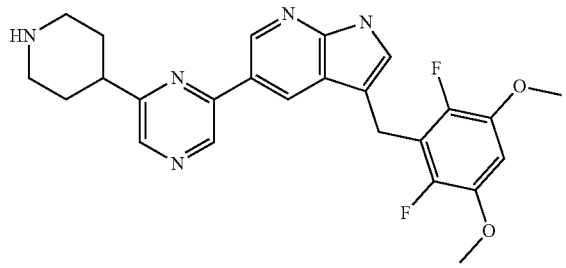 [SMILES: COc1cc(OC)c(F)c(Cc2c[nH]c3ncc(-c4cncc(C5CCNCC5)n4)cc23)c1F]

The product of embodiment 63G (25 mg, 50.45 µmol) was added to a thumb flask (10 mL) containing methanol (1 mL), and then potassium carbonate (20.92 mg, 151.36 µmol) was added to the reaction solution in one portion. The reaction solution was stirred at 15-20° C. for 16 hours under nitrogen protection. The reaction solution was filtered directly, and the filtrate was collected and rotary-evaporated to dryness under vacuum to obtain a crude product. The crude product was used directly in the next step without further purification. Finally the product of embodiment 63H was obtained.

LCMS (ESI) m/z [M+H]$^+$: 466.2

Embodiment 65

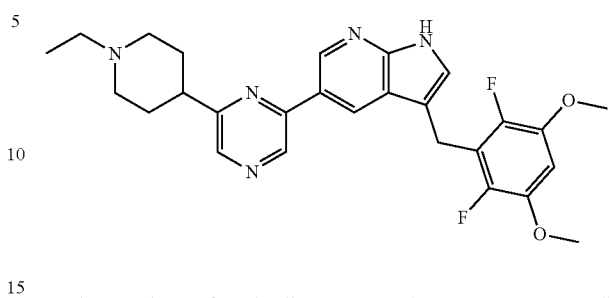

The product of embodiment 63H (20 mg, 42.97 µmol) was added to a thumb flask (10 mL) containing dichloromethane (4 mL) and methanol (2 mL), then acetaldehyde (11.36 mg, 257.79 µmol, 14.47 µL) and acetic acid (2.58 mg, 42.97 µmol, 2.46 µL) were added, and subsequently sodium triacetoxyborohydride (13.66 mg, 64.45 µmol) was added. The reaction was allowed to run at 15-20° C. for 2 hours. LCMS showed the disappearance of the raw material and the appearance of the product. The reaction solution was directly rotary-evaporated to dryness under vacuum to obtain a crude product. The crude product was separated by liquid phase chromatography (HCl system) to obtain hydrochloride salt of embodiment 65. In embodiment 65, the free base can be obtained by washing a solution of the hydrochloride salt of embodiment 65 in dichloromethane with 1N sodium bicarbonate, followed by separating and concentrating the organic phase.

LCMS (ESI) m/z [M+H]$^+$: 494.2

$^1$H NMR (400 MHz, METHANOL-d$_4$) δ 9.51 (s, 1H), 9.26 (d, J=2.01 Hz, 1H), 9.25-9.28 (m, 1H), 8.72 (s, 1H), 7.55 (s, 1H), 6.83 (t, J=8.28 Hz, 1H), 4.33 (s, 2H), 3.88 (br d, J=11.80 Hz, 2H), 3.81 (br d, J=11.80 Hz, 2H), 3.81 (br d, J=11.80 Hz, 2H), 8.28 Hz, 1H), 4.33 (s, 2H), 3.88 (s, 6H), 3.81 (br d, J=11.80 Hz, 2H), 3.35-3.44 (m, 2H), 3.19-3.28 (m, 2H), 2.37-2.43 (m, 4H), 1.47 (t, J=7.15 Hz, 3H)

Process X

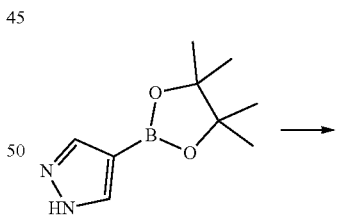

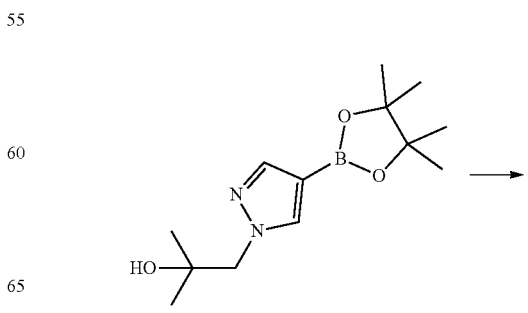

Embodiment 66A

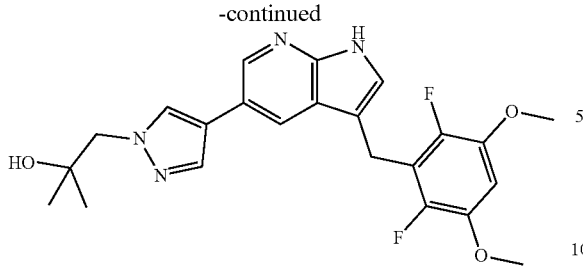

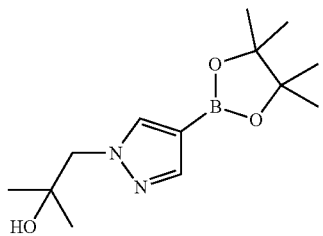 [SMILES: CC(C)(O)Cn1cc(B2OC(C)(C)C(C)(C)O2)cn1]

Sodium hydride (61.84 mg, 1.55 mmol, 60% purity) was slowly added to a solution of pyrazole-4-boronic acid pinacol ester (200 mg, 1.03 mmol) in DMF (5 mL) at 0° C. The reaction solution was stirred at that temperature for 30 min, followed by addition of 2,2-dimethyloxirane (297.28 mg, 4.12 mmol, 366.11 μL) was added to the above reaction solution. The reaction solution was heated to 80° C. and reacted for 5.5 hours. The reaction solution was quenched with water (5 mL), extracted with ethyl acetate (5 mL*2), washed with saturated brine (6 mL), dried over anhydrous sodium sulfate, filtered, and the filtrate was rotary-evaporated to dryness under vacuum. The residue was purified by flash chromatography on a silica gel column (petroleum ether:ethyl acetate=3:1) to obtain the product of embodiment 66A.

$^1$H NMR (400 MHz, CHLOROFORM-d) δ 7.83 (s, 1H), 7.70 (s, 1H), 4.05-4.11 (m, 2H), 1.33 (s, 12H), 1.16 (s, 6H)

Embodiment 66

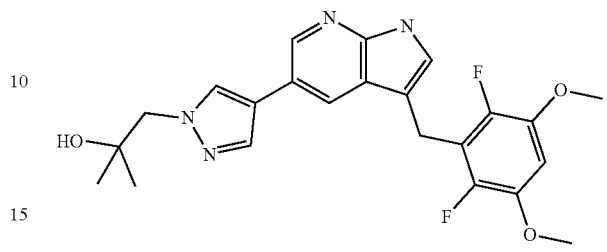

Under nitrogen protection, a suspension of the product of embodiment 22C (80 mg, 208.78 μmol, 1 eq), the product of embodiment 66A (55.56 mg, 208.78 μmol), Pd(dppf)Cl$_2$ (7.64 mg, 10.44 μmol) and potassium phosphate (57.71 mg, 417.55 μmol) in dioxane (2 mL) and water (0.5 mL) was heated to 100° C. under microwave conditions and the reaction was allowed to run for 20 min. The upper layer of the reaction solution was purified by flash chromatography on a preparative plate (petroleum ether:ethyl acetate=0:1) to obtain the product of embodiment 66. The product of embodiment 66 was dissolved in dichloromethane, followed by addition of acid in 2 equivalents dropwise, and the salt of embodiment 66 was precipitated and obtained.

LCMS (ESI) m/z [M+H]$^+$: 443.5

$^1$H NMR (400 MHz, METHANOL-d$_4$) δ 8.39 (d, J=1.76 Hz, 1H), 8.15 (d, J=2.01 Hz, 1H), 8.01 (s, 1H), 7.84 (s, 1H), 7.12 (s, 1H), 6.75 (t, J=8.28 Hz, 1H), 4.16 (s, 2H), 4.12 (s, 2H), 3.85 (s, 6H), 1.23 (s, 7H).

The following embodiments and salts thereof were prepared by referring to the method as described in embodiment 66.

| Embodiments | Structure | NMR | LCMS (ESI) m/z: (M + 1) |
|---|---|---|---|
| Embodiment 67 | 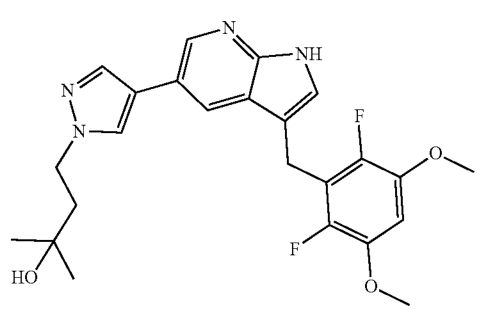 [SMILES: COc1cc(OC)c(F)c(Cc2c[nH]c3ncc(-c4cnn(CCC(C)(C)O)c4)cc23)c1F] | $^1$H NMR (400 MHz, METHANOL-d$_4$) δ 8.88 (d, J = 1.51 Hz, 1H), 8.65 (d, J = 1.51 Hz, 1H), 8.27 (s, 1H), 8.03 (s, 1H), 7.41 (s, 1H), 6.81 (t, J = 8.28 Hz, 1H), 4.34-4.42 (m, 2H), 4.25 (s, 2H), 3.82-3.89 (m, 6H), 2.06-2.14 (m, 2H), 1.28 (s, 6H) | 456.3 |

-continued

| Embodiments | Structure | NMR | LCMS (ESI) m/z: (M + 1) |
|---|---|---|---|
| Embodiment 68 | | $^1$H NMR (400 MHz, METHANOL-d$_4$) δ 8.83 (d, J = 1.25 Hz, 1H), 8.66 (s, 1H), 8.34 (s, 1H), 8.09 (s, 1H), 7.41 (s, 1H), 6.80 (t, J = 8.32 Hz, 1H), 4.63 (t, J = 5.82 Hz, 2H), 4.23 (s, 2H), 3.86 (s, 6H), 3.61 (br t, J = 5.82 Hz, 2H), 3.51 (td, J = 6.50, 13.01 Hz, 1H), 1.39 (d, J = 6.50 Hz, 6H) | 456.5 |
| Embodiment 69 | | $^1$H NMR (400 MHz, METHANOL-d$_4$) δ 8.87 (s, 1H), 8.68 (s, 1H), 8.40 (s, 1H), 8.11 (s, 1H), 7.42 (s, 1H), 6.80 (t, J = 8.25 Hz, 1H), 4.73 (t, J = 5.88 Hz, 2H), 4.25 (s, 2H), 3.86 (s, 6H), 3.78 (t, J = 5.88 Hz, 2H), 3.35 (q, J = 7.34 Hz, 4H), 1.37 (t, J = 7.25 Hz, 6H) | 470.5 |
| Embodiment 70 | | $^1$H NMR (400 MHz, METHANOL-d$_4$) δ 8.88 (s, 1H), 8.68 (s, 1H), 8.35 (s, 1H), 8.10 (s, 1H), 7.42 (s, 1H), 6.80 (t, J = 8.32 Hz, 1H), 4.65 (t, J = 5.63 Hz, 2H), 4.24 (s, 2H), 3.83-3.88 (s, 6H), 3.61-3.73 (m, 4H), 3.42-3.46 (s, 3H), 3.34 (t, J = 4.88 Hz, 2H) | 472.5 |
| Embodiment 71 | | $^1$H NMR (400 MHz, METHANOL-d$_4$) δ ppm 8.92 (d, J = 1.51 Hz, 1 H) 8.71 (d, J = 1.51 Hz, 1 H) 8.33 (s, 1 H) 8.10 (s, 1 H) 7.44 (s, 1 H) 6.83 (t, J = 8.28 Hz, 1 H) 4.31-4.46 (m, 3 H) 4.27 (s, 2 H) 3.88 (s, 6 H) 3.46 (dt, J = 13.05, 6.53 Hz, 1 H) 3.20-3.28 (m, 1 H) 2.99-3.08 (m, 1 H) 1.38 (dd, J = 6.53, 4.77 Hz, 6 H) | 486.3 |
| Embodiment 72 | | $^1$H NMR (400 MHz, METHANOL-d$_4$) δ ppm 8.79 (s, 1 H) 8.64 (s, 1 H) 8.29 (s, 1 H) 8.06 (s, 1 H) 7.37-7.45 (m, 1 H) 6.82 (t, J = 8.28 Hz, 1 H) 4.42 (t, J = 6.53 Hz, 2 H) 4.25 (s, 2 H) 4.12 (q, J = 7.28 Hz, 4 H) 3.88 (s, 6 H) 2.29-2.33 (m, 1 H) 1.36 (d, J = 6.53 Hz, 6 H) H) | 470.3 |

-continued
| Embodiments | Structure | NMR | LCMS (ESI) m/z: (M + 1) |
|---|---|---|---|
| Embodiment 73 | 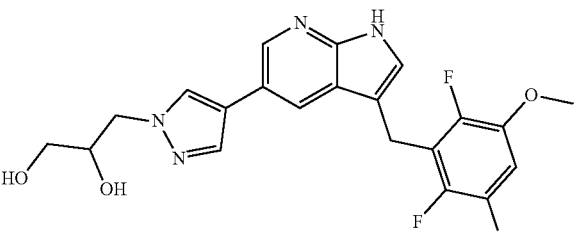 | $^1$H NMR (400 MHz, METHANOL-d$_4$) δ ppm 8.90 (d, J = 1.51 Hz, 1 H) 8.67 (d, J = 1.51 Hz, 1 H) 8.26 (s, 1 H) 8.06 (s, 1 H) 7.43 (s, 1 H) 6.83 (t, J = 8.41 Hz, 1 H) 4.43 (dd, J = 14.05, 4.02 Hz, 1 H) 4.22-4.29 (m, 3 H) 4.03-4.12 (m, 1 H) 3.88 (s, 6 H) 3.58 (d, J = 5.52 Hz, 2 H) | 445.2 |
| Embodiment 76 | 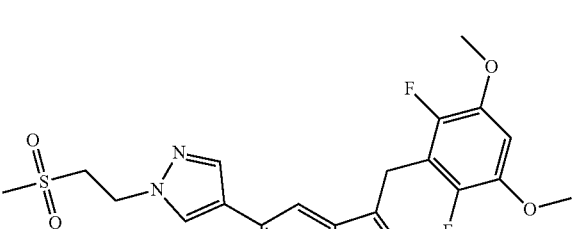 | $^1$H NMR (400 MHz, METHANOL-d$_4$) δ ppm 8.68 (s, 1 H) 8.58 (s, 1 H) 8.25 (s, 1 H) 8.04 (s, 1 H) 7.35 (s, 1 H) 6.82 (t, J = 8.0 Hz, 1 H) 4.75 (t, J = 6.0 Hz, 2 H) 4.23 (s, 2 H) 3.88 (s, 6 H) 3.80 (t, J = 6.40 Hz, 2 H) 2.87 (s, 3 H). | 477.0 |
Process Y
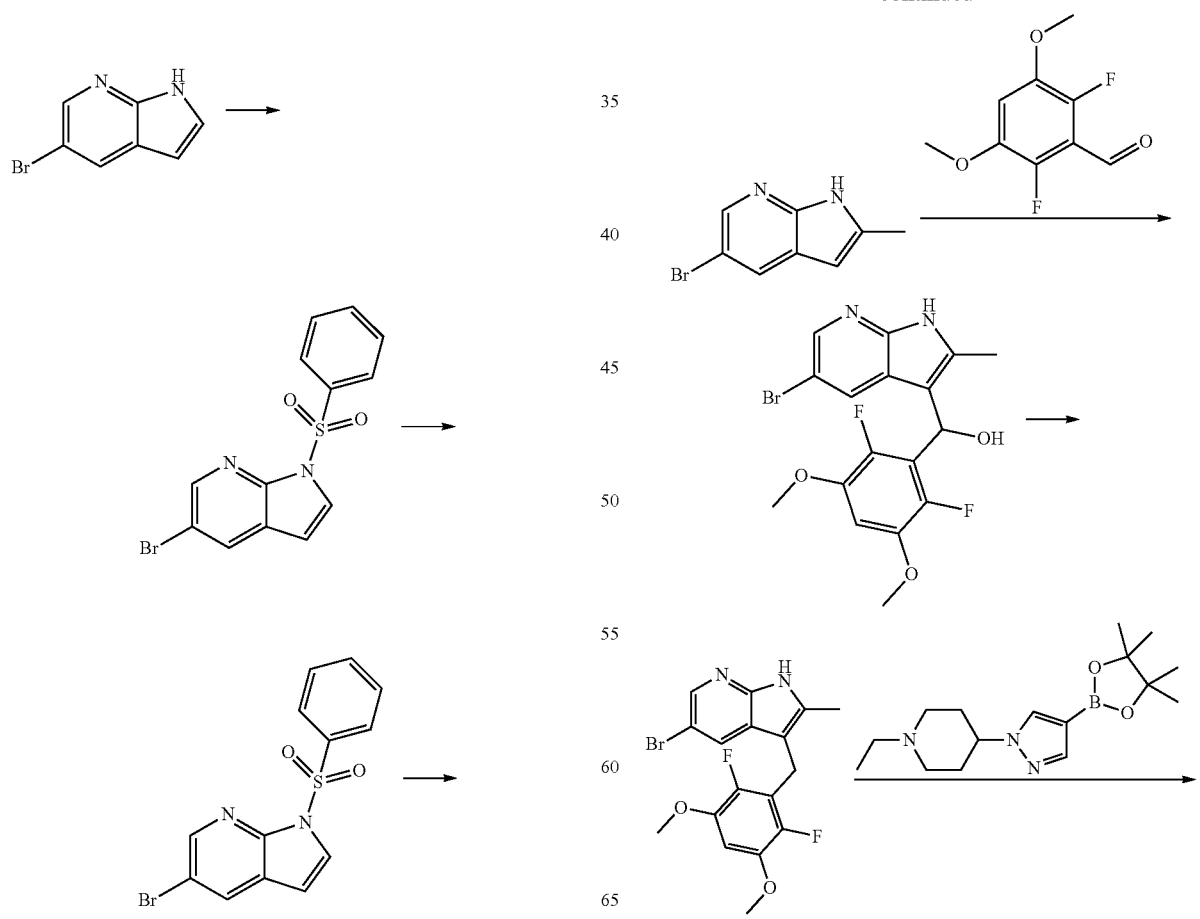

Embodiment 74

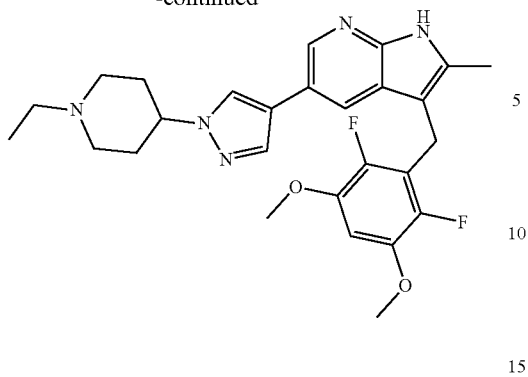

Embodiment 74A

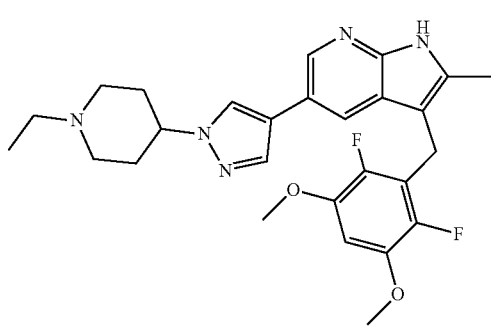 [SMILES: CCN1CCC(n2cc(-c3cnc4[nH]c(C)c(Cc5c(F)c(OC)cc(OC)c5F)c4c3)cn2)CC1]

5-Bromo-7-azaindole (5 g, 25.38 mmol) was dissolved in DMF (50 mL) in a round bottom flask (100 mL), and then ☐☐☐(1.52 g, 38.06 mmol, 60% purity) was slowly added at 0° C. The reaction solution was stirred at 10-15° C. for 0.5 hour. Benzenesulfonyl chloride (5.38 g, 30.45 mmol) was added to the reaction solution under stirring finally, and the reaction solution was stirred for 16 hours at 10-15° C. under nitrogen protection. The reaction solution was quenched with 10 mL of saturated aqueous ammonium chloride, extracted with 50 mL of water and 50 mL of dichloromethane. The aqueous phase was then extracted with 50 mL of dichloromethane. The combined organic phase was dried over anhydrous sodium sulfate, and rotary-evaporated to dryness to obtain the product of embodiment 74A.

Embodiment 74B

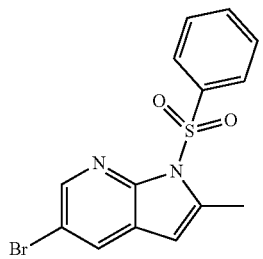

The product of embodiment 74A (4 g, 11.86 mmol) was dissolved in ☐☐☐(20 mL) in a 100 mL round bottom flask, and then LDA (2 M, 17.79 mL) was added dropwise to the reaction solution under stirring at −78° C. for 0.5 hour. Iodomethane (5.05 g, 35.59 mmol, 2.22 mL) was added dropwise to the reaction solution under stirring at −78° C. The reaction solution was stirred for 16 hours at 15° C. under nitrogen protection. The reaction solution was quenched with 5 mL of saturated aqueous ammonium chloride, extracted with 50 mL of water and 50 mL of ethyl acetate. The aqueous phase was then extracted with 20 mL of ethyl acetate. The combined organic phase was dried over anhydrous sodium sulfate, and rotary-evaporated to dryness to obtain a crude product. The crude product was separated by flash chromatography on a silica gel column (petroleum ether/ethyl acetate=10/1 to 5/1) to obtain the product of embodiment 74B.

LCMS (ESI) m/z: 352.8 (M+1)$^+$

Embodiment 74C

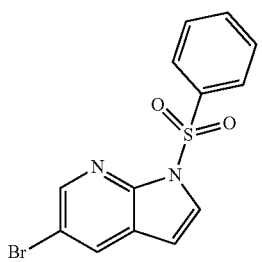 [SMILES: O=S(=O)(c1ccccc1)n1ccc2cc(Br)cnc21]

The product of embodiment 74B (3.5 g, 9.97 mmol) and ☐☐☐☐ (2 M, 70.00 mL) were added together to a thumb flask containing ☐☐ (70 mL). The reaction solution was stirred at 65° C. for 2 hours under nitrogen protection. The reaction solution was extracted with 100 mL of ethyl acetate and partitioned. The aqueous phase was then extracted with 100 mL of ethyl acetate. The combined organic phase was washed with 100 mL of saturated brine, dried over anhydrous sodium sulfate and rotary-evaporated to dryness to obtain the product of embodiment 74C.

LCMS (ESI) m/z: 212.9 (M+1)$^+$

Embodiment 74D

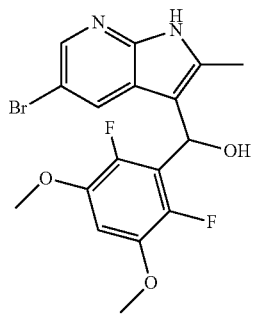

The product of embodiment 74C (1 g, 4.74 mmol), 2,6-difluoro-3,5-dimethoxybenzaldehyde (1.05 g, 5.21 mmol) and ☐☐☐☐ (531.70 mg, 9.48 mmol) were added together to a thumb flask (10 mL) containing MeOH (10 mL). The reaction solution was stirred for 16 hours at 10-15° C. under nitrogen protection. The reaction solution was rotary-evaporated to dryness to obtain a crude product. The crude product was purified by flash chromatography on a silica gel column (petroleum ether/ethyl acetate=3/1) to obtain the product of embodiment 74D.

LCMS (ESI) m/z: 415.1 (M+1)$^+$

Embodiment 74E

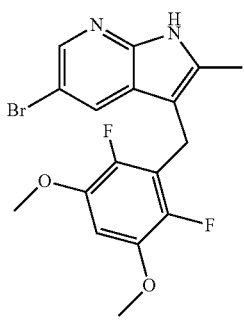

The product of embodiment 74D (320 mg, 774.42 μmol), triethylsilane (450.23 mg, 3.87 mmol) and trifluoroacetic acid (441.51 mg, 3.87 mmol) were added together to a reaction flask (100 mL) containing DCM (5 mL). The reaction solution was stirred at 10-15° C. for 16 hours under nitrogen protection. The reaction solution was directly rotary-evaporated to dryness to obtain the product of embodiment 74E.

LCMS (ESI)$_m$/z: 398.9 (M+1)$^+$

Embodiment 74

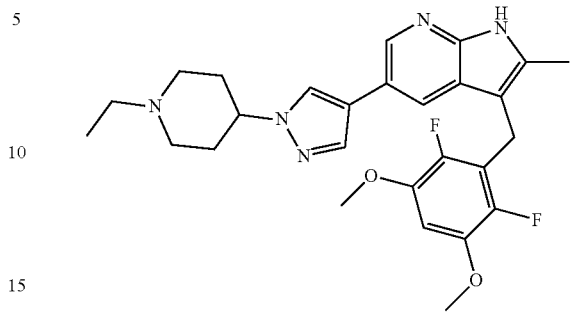

The product of embodiment 74E (200 mg, 503.51 μmol), 1-ethyl-(4-boronic acid pinacol ester-1H-pyrazol-1-yl)piperidine (184.42 mg, 604.21 μmol), Pd(dppf)Cl$_2$ (36.84 mg, 50.35 μmol) and potassium phosphate (347.84 mg, 1.51 mmol) were added together to dioxane (2 mL) and H$_2$O (1 mL) together. The reaction solution was heated to 100° C. and reacted for 0.5 hour under nitrogen protection in a microwave synthesizer. To the reaction solution were added 10 mL of water and 10 mL of ethyl acetate for extraction. The aqueous phase was then extracted with 10 mL of ethyl acetate. The combined organic phase was dried over anhydrous sodium sulfate and rotary-evaporated to dryness to obtain a crude product. The crude product was separated by preparative chromatography (HCl system) to finally obtain hydrochloride salt of embodiment 74. In embodiment 74, the free base can be obtained by washing a solution of the hydrochloride salt of embodiment 74 in dichloromethane with 1N sodium bicarbonate, followed by separating and concentrating the organic phase.

LCMS (ESI) m/z: 496.3 (M+1)$^+$
$^1$H NMR (400 MHz, METHANOL-d$_4$) δ 8.64-8.66 (m, 1H), 8.54 (s, 1H), 8.37-8.41 (m, 1H), 8.00-8.01 (m, 1H), 6.77-6.83 (m, 1H), 4.73 (s, 1H), 4.16 (s, 2H), 3.73 (s, 2H), 3.85 (s, 6H), 3.79-3.82 (m, 2H), 3.28-3.30 (m, 2H), 2.17 (s, 3H), 2.45 (s, 4H), 1.45 (t, =7.2 Hz, 3H).

Experimental Embodiment 1: In Vitro Enzyme Activity Test of the Compounds of the Present Disclosure The inhibitory activities of the tested compounds on human FGFR1, FGFR4, and c-Met were evaluated by the IC$_{50}$ values measured using $^{33}$P isotope-labeled kinase activity test (Reaction Biology Corp).

Buffer condition: 20 mM Hepes (pH 7.5), 10 mM MgCl$_2$, 1 mM EGTA, 0.02% Brij35, 0.02 mg/mL BSA, 0.1 mM Na$_3$VO$_4$, 2 mM DTT, 1% DMSO.

Test procedure: The test compounds were dissolved in DMSO at room temperature and formulated to be 10 mM solutions for later use. The substrates were dissolved in freshly prepared buffer, and kinases to be tested were added and mixed well. The test compounds dissolved in DMSO were added to the above mixed reaction solutions by acoustic technique (Echo 550). The concentration of the compound in reaction solution was 1 μM, 0.25 μM, 0.156 μM, 3.91 nM, 0.977 nM, 0.244 nM, 0.061 nM, 0.0153 nM, 0.00381 nM or 10 μM, 2.50 μM, 0.62 μM, 0.156 μM, 39.1 nM, 9.8 nM, 2.4 nM, 0.61 nM, 0.15 nM, 0.038 nM. After incubation for 15 min, $^{33}$P-ATP (activity 0.01 μCi/μL, corresponding concentrations are listed in Table 1) was added to start the reaction. Supplier item number, batch number, as well as the concentration information in the reaction solution of FGFR1, FGFR4, c-Met and substrates thereof are listed in Table 1. After 120 minutes of reaction at room temperature, the reaction solution was spotted on P81 ion exchange filter paper (Whatman #3698-915). The filter paper was washed with 0.75% phosphoric acid solution repeatedly, and the radioactivity of the phosphorylated substrate remained on the filter paper was determined. The kinase activity data are expressed by comparison between the kinase activity in the test compound group and the kinase activity in the blank group (containing DMSO only). $IC_{50}$ values were obtained by curve fitting with Prism4 software (GraphPad). The experimental results are shown in Table 2.

TABLE 1

Information of kinases, substrates and ATP in in vitro tests.

| Kinase | Kinase concentration in reaction solution (nM) | Substrate | Substrate concentration in reaction solution (mg/mL) | ATP concentration (μM) |
|---|---|---|---|---|
| FGFR1 Supplier: Invitrogen Cat#: PV3146 Lot #: 28427Q | 1.75 | pEY (mg/ml) + Mn Supplier: Sigma Cat#: P7244-250MG Lot #: 062K5104V | 0.2 mg/mL | 5 |
| FGFR4 Supplier: Invitrogen Cat#: P3054 Lot #: 26967J | 2.5 | pEY (mg/mL) + Mn Supplier: Sigma Cat#: P7244-250MG Lot #: 062K5104V | 0.2 mg/mL | 100 |
| c-Met Supplier: Invitrogen Cat#: PV3143 Lot #: 464006A | 8 | MBP Supplier: Active Motif Cat#: 102641 Lot #: 04811001 | 20 μm | 10 |

TABLE 2

Results of $IC_{50}$ of the embodiments on kinases

| Test sample (title compound) | FGFR1 | FGFR4 | c-Met |
|---|---|---|---|
| Comparative Compound 1a | 2419 | >10000 | 758.3 |
| Comparative Compound 1b | 709.1 | 5092.0 | 11.1 |
| Trifluoroacetate salt of embodiment 1 | 2.0 | 39.7 | 1288 |
| Hydrochloride of embodiment 2 | 1.3 | 137.1 | 7.8 |
| Hydrochloride of embodiment 3 | 0.13 | 147.7 | 76.1 |
| Hydrochloride of embodiment 4 | 66.2 | 798.7 | 177 |
| Trifluoroacetate salt of embodiment 5 | 0.6 | 20.3 | 47.2 |
| Trifluoroacetate salt of embodiment 6 | 0.04 | 15.2 | 74.3 |
| Embodiment 7 | 85.9 | >10,000 | 41.5 |
| Trifluoroacetate salt of embodiment 8 | 0.43 | 20.7 | 496 |
| Embodiment 9 | 0.8 | 18.3 | 11.3 |
| Trifluoroacetate salt of embodiment 10 | 80.6 | 1707.0 | 8.7 |
| Trifluoroacetate salt of embodiment 11 | 17.1 | 549.9 | N/A |
| Trifluoroacetate salt of embodiment 12 | 0.13 | 36 | 3.17 |
| Trifluoroacetate salt of embodiment 13 | 0.04 | 9.0 | 7.62 |
| Trifluoroacetate salt of embodiment 14 | 1.34 | 27.5 | 14 |
| Trifluoroacetate salt of embodiment 15 | 1.94 | 25.9 | 16 |
| Embodiment 16 | 0.73 | 16.1 | 10.5 |
| Trifluoroacetate salt of embodiment 17 | 2.17 | 7.5 | 11.64 |
| Trifluoroacetate salt of embodiment 18 | 3.0 | 29.7 | 16.1 |
| Trifluoroacetate salt of embodiment 19 | 13.7 | 262.2 | 5.7 |
| Trifluoroacetate salt of embodiment 20 | 1.1 | 158.0 | 12 |
| Trifluoroacetate salt of embodiment 21 | 2 | 25.2 | 55.9 |
| Trifluoroacetate salt of embodiment 22 | 2.8 | 29.2 | 23.8 |
| Trifluoroacetate salt of embodiment 23 | 4.85 | 43.9 | 21.0 |
| Trifluoroacetate salt of embodiment 24 | 6.3 | 252.0 | 76.5 |
| Trifluoroacetate salt of embodiment 25 | 2.1 | 31.9 | 16.9 |
| Trifluoroacetate salt of embodiment 26 | 1.1 | 35.3 | 13.8 |
| Trifluoroacetate salt of embodiment 27 | 0.8 | 13.1 | 6.7 |
| Hydrochloride of embodiment 28 | 0.55 | 20.2 | 25.9 |
| Trifluoroacetate salt of embodiment 29 | 1.9 | 24.6 | 35.6 |
| Trifluoroacetate salt of embodiment 30 | 2.1 | 28.2 | 169,1 |
| Trifluoroacetate salt of embodiment 31 | 0.9 | 9.9 | 6.9 |
| Embodiment 32 | 0.75 | 13.5 | 6.2 |
| Embodiment 33 | 0.55 | 20.8 | 7.4 |
| Hydrochloride of embodiment 34 | 8.9 | 126.0 | 86.7 |
| Trifluoroacetate salt of embodiment 35 | 1.1 | 23.5 | 14.0 |
| Hydrochloride of embodiment 36 | 34.3 | 684.4 | 27.3 |
| Hydrochloride of embodiment 37 | 2.1 | 52.4 | 33.0 |
| Embodiment 38 | 7.9 | 599.1 | 9.1 |
| Trifluoroacetate salt of embodiment 39 | 29.0 | 752 | 24.5 |
| Hydrochloride of embodiment 40 | 0.4 | 21.5 | 14.6 |
| Hydrochloride of embodiment 42 | 1.4 | 10.2 | 7.1 |
| Hydrochloride of embodiment 43 | 0.4 | 61.7 | 57.1 |
| Trifluoroacetate salt of embodiment 44 | 1.8 | 32.3 | 191.1 |
| Embodiment 45 | 14.2 | 351 | 9.1 |
| Hydrochloride of embodiment 46 | 0.42 | 2.9 | 8.9 |
| Hydrochloride of embodiment 47 | 1.2 | 25.2 | 58.9 |
| Embodiment 48 | 0.3 | 1.7 | 6.3 |
| Trifluoroacetate salt of embodiment 49 | 5.4 | 529.0 | 8.8 |
| Trifluoroacetate salt of embodiment 50 | 0.12 | 4.4 | 135.9 |
| Trifluoroacetate salt of embodiment 51 | 0.27 | 3.0 | 84.1 |
| Trifluoroacetate salt of embodiment 52 | 0.06 | 13.7 | 137.2 |
| Trifluoroacetate salt of embodiment 53 | 0.32 | 2.9 | 107.3 |
| Trifluoroacetate salt of embodiment 54 | 2.7 | 58.5 | 16.5 |
| Trifluoroacetate salt of embodiment 55 | 2.2 | 44.9 | 22.8 |
| Trifluoroacetate salt of embodiment 56 | 1.9 | 53.2 | 7.8 |
| Hydrochloride of embodiment 57 | 1.1 | 21.4 | 49.4 |
| Trifluoroacetate salt of embodiment 58 | 1.2 | 23.5 | 161.9 |
| Trifluoroacetate salt of embodiment 59 | 0.8 | 14.7 | 126,9 |
| Trifluoroacetate salt of embodiment 60 | 2.2 | 33.4 | 319.6 |
| Trifluoroacetate salt of embodiment 61 | 0.7 | 4.5 | 243.4 |
| Trifluoroacetate salt of embodiment 62 | 0.4 | 8.6 | 131.8 |
| Hydrochloride of embodiment 63 | 9.41 | N/A | N/A |
| Hydrochloride of embodiment 65 | 0.04 | 2.7 | 135 |
| Trifluoroacetate salt of embodiment 66 | 0.5 | 9.0 | 28 |

TABLE 2-continued

Results of IC$_{50}$ of the embodiments on kinases

| Test sample (title compound) | FGFR1 | FGFR4 | c-Met |
|---|---|---|---|
| Hydrochloride of embodiment 67 | 0.8 | 14.3 | 7.0 |
| Hydrochloride of embodiment 68 | 0.7 | 10.0 | 53.5 |
| Hydrochloride of embodiment 69 | 0.6 | 8.4 | 35.3 |
| Hydrochloride of embodiment 70 | 0.5 | 5.0 | 31.4 |
| Hydrochloride of embodiment 71 | 0.4 | 4.9 | 32.8 |
| Hydrochloride of embodiment 72 | 2.1 | 53.1 | 70.8 |
| Hydrochloride of embodiment 73 | 0.6 | 2.5 | 32.4 |
| Hydrochloride of embodiment 74 | 1.6 | 56.45 | 4.2 |
| Embodiment 75 | 0.64 | 10.59 | 3.26 |
| Trifluoroacetate salt of embodiment 76 | 0.60 | 3.87 | N/A |
| Trifluoroacetate salt of embodiment 77 | 0.69 | 3.41 | N/A |
| Embodiment 78 | 0.34 | 9.8 | 141.1 |

Note:
IC$_{50}$ unit is nM; N/A, indicates not measured.

CONCLUSION: Compared to the comparative compounds, the compounds of the present disclosure significantly increase the activities on both FGFR1 and FGFR4, while still maintaining excellent c-Met activity, which is unexpected. The compounds of the present disclosure were based on the structural analysis of c-Met and FGFR dual kinase proteins by which a highly active small molecule parent nucleus capable of inhibiting both c-Met and FGFR was found. In such dual-target inhibitors, the FGFR target and c-Met target can synergistically complement each other; FGFR mutation and c-Met mutation are prone to play a signaling compensatory role when one of them is inhibited, thus making tumor cells resistant to an inhibitor of only one of them; this dual-target inhibition will potentially reduce tumor cell-dependent escape and greatly improve the effectiveness of tumor therapy.

Experimental Embodiment 2: Pharmacokinetic Evaluation of the Compounds of the Present Disclosure Experimental Procedure: 0.4 mg/mL clear solution of the test compounds in a specific menstruum was injected intravenously into male CD-1 nude mice (overnight fasting, aged 7-9 weeks) via caudal vein at a dose of 2 mg/kg. About 30 μL of blood was collected from jugular or caudal vein at 0.0833, 0.25, 0.5, 1.0, 2.0, 4.0, 8.0 and 24 h after intravenous administration. 2.0 mg/mL suspension of the test compounds in a specific menstruum was administered intragastrically to male CD-1 mice (overnight fasting, aged 7-9 weeks) at a dose of 10 mg/mL. The experimental conditions are listed in Table 3 in detail. About 30 μL of blood was collected from jugular or caudal vein of the male CD-1 mice at 0.0833, 0.25, 0.5, 1.0, 2.0, 4.0, 8.0 and 24 h after oral administration. The blood samples were added into anticoagulant tubes containing EDTA-K2, and then centrifuged to separate the plasma. LC-MS/MS method was used to determine the drug concentration in blood, and WinNonlin™ Version 6.3 (Pharsight, Mountain View, CA) pharmacokinetic software was used to calculate the relevant pharmacokinetic parameters by non-compartment model linear logarithmic trapezoidal method. The results of the experiments are shown in Table 4.

TABLE 3

Pharmacokinetics experimental conditions of each compound in mice

| | IV (injection) | | PO (oral) | |
|---|---|---|---|---|
| | Dose | Menstruum | Dose | Menstruum |
| Embodiment 46 | 2 mg/kg | 0.4 mg/mL in 10% DMSO + 50% PEG400 + 40% water, clear solution | 10 mg/kg | 2.0 mg/mL in 10% DMSO + 50% PEG400 + 40% water, clear solution |
| Embodiment 48 | 2 mg/kg | 0.4 mg/mL in 10% DMSO + 50% PEG400 + 40% water, clear solution | 10 mg/kg | 20 mg/mL in 0.5% MC + 0.2% Tween80, homogeneous suspension |

TABLE 4

Results of pharmacokinetic experiments of each compound in mice

| Dose | IV 2 mg/kg | | | | PO 10 mg/kg | | | |
|---|---|---|---|---|---|---|---|---|
| | Cl (mL/min/kg) | V$_{dss}$ (L/kg) | T$_{1/2}$ (h) | AUC$_{0-last}$ (nM · h) | C$_{max}$ (nM) | T$_{max}$ (h) | AUC$_{0-last}$ (nM · h) | F (%) |
| Embodiment 46 | 21.2 | 1.7 | 1.1 | 3790 | 5045 | 1.0 | 16569 | 86.6 |
| Embodiment 48 | 25.3 | 2.1 | 1.1 | 3149 | 877 | 1.3 | 3226 | 21.5 |

Note: Plasma clearance (Cl) mL/min/kg, steady-state apparent volume of distribution (V$_{dss}$) L/kg, elimination half-life (T$_{1/2}$) and area under the plasma concentration curve from point 0 to the last measurable time point (AUC$_{0-last}$), bioavailability F %, peak concentration (C$_{max}$), time to peak T$_{max}$ CONCLUSION; From the experimental results, both compounds exhibit moderately low clearance, high volume of distribution, moderate half-life, and high drug exposure in the case of intravenous administration. Both compounds exhibit rapid peak concentration and high oral exposure in the case of oral administration. Embodiment 46 exhibit high oral bioavailability and embodiment 48 exhibit moderate bioavailability. This series of compounds have excellent pharmacokinetic properties.

Experimental Embodiment 3: In Vivo Pharmacodynamic Evaluation of the Compounds of the Present Disclosure Method of establishing SNU-16 gastric cancer model: SNU-16 cells in logarithmic growth phase were collected, and the cells were resuspended in 50% PBS (pH 7.4, 0.01 M) and 50% Matrigel after cell counting. The cell concentration was adjusted to 4×107 cells/mL; the cells were placed in an ice box, and the cell suspension was aspirated with a 1-mL syringe and subcutaneously injected into nude mice via the anterior right armpit. Each animal was inoculated with 200 μL (8×106 cells/each) to establish the SNU-16 transplantation tumor model. The animals were observed regularly, and the tumor diameters were measured using an electronic vernier caliper. The data were inputted an Excel spreadsheet to calculate the tumor volume and monitor the tumor growth. When the tumor volume reached 100-300 mm³, mice bearing similar tumor volume and in good health condition were selected. Randomization method was used for animal grouping; the number of animals in each group was n=7, and the average tumor volume of each group was about 145 mm³. After the experiment started, tumor diameters were measured and tumor volume was calculated twice a week, and the weight of animals was weighed and recorded.

Tumor growth inhibition (TGI) was used to analyze the tumor growth trend and evaluated by tumor volume over time. The long axis (L) and short axis (W) of the subcutaneous tumors were measured twice a week by a caliper, and the tumor volume (TV) was calculated by the formula ((L×W²)/2). TGI was calculated by the difference between the median tumor volume of mice in the solvent control group and the median tumor volume of mice in the treatment group, showed as a percentage of the median tumor volume in the solvent control group.

The calculation is performed by the following equation:

% TGI=((median tumor volume (control)−median tumor volume (treatment group))/median tumor volume (control))×100%

The experimental data were calculated and statistically processed by SPSS 19.0. Unless otherwise stated, data were expressed as mean f standard error (Mean±SE), and comparisons between two groups were analyzed by t-test. p<0.05 indicates a significant difference. The solvent 30% PEG400 (containing 70% deionized water, v/v) was used as negative control. The results of the experiments are shown in Table 5.

TABLE 5

Results of in vivo anti-tumor activity

| | SNU-16 transplantation model | TGI % (the last administration on the 21ᵗʰ day) | P-value |
|---|---|---|---|
| Embodiment 46 | 5 mg/KG BID | 98 | <0.005 |
| Embodiment 46 | 10 mg/KG QD | 80 | <0.005 |
| Embodiment 48 | 10 mg/KG QD | 77 | <0.005 |

Note:
BID: twice a day, QD: once a day, TGI %; tumor growth inhibition rate

CONCLUSION: The compounds of the present disclosure show excellent tumor suppressive effects in the tumor model SNU-16.

What is claimed is:
1. A compound represented by formula (I), a tautomer thereof or a pharmaceutically acceptable salt thereof,

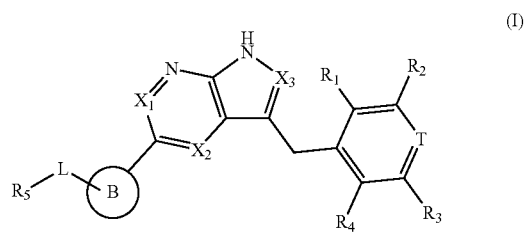

wherein,
$X_1$, $X_2$ and $X_3$ are respectively independently selected from CH, C(CH$_3$) and N;
T is selected from CH and N;
$R_1$ and $R_4$ are F;
$R_2$ is

$R_3$ is H or

$R_5$ is selected from H, $C_{1-6}$ alkyl, $C_{1-6}$ heteroalkyl, $C_{3-6}$ cycloalkyl, 4-6 membered heterocycloalkyl and 5-6 membered heterocycloalkenyl, wherein the $C_{1-6}$ alkyl, $C_{1-6}$ heteroalkyl, $C_{3-6}$ cycloalkyl, 4-6 membered heterocycloalkyl and 5-6 membered heterocycloalkenyl are optionally substituted by 1, 2 or 3 $R_b$;
ring B is selected from phenyl and 5-6 membered heteroaryl, wherein the phenyl and 5-6 membered heteroaryl are optionally substituted by 1, 2 or 3 $R_6$;
$R_6$ is selected from H, F, Cl, Br, I, OH, NH$_2$, CN, COOH, $C_{1-3}$ alkyl and $C_{1-3}$ heteroalkyl, wherein the $C_{1-3}$ alkyl and $C_{1-3}$ heteroalkyl are optionally substituted by 1, 2 or 3 $R_c$;
alternatively, two $R_6$ connected to adjacent carbon atoms and the C atoms to which they are connected together form a 4-6 membered heterocycloalkyl, which is optionally substituted by 1, 2 or 3 $R_c$;
L is selected from single bond and —(CR$_d$R$_e$)$_m$—;
m is selected from 1, 2, 3 and 4;
$R_b$ is respectively independently selected from H, F, Cl, Br, I, OH, NH$_2$, CN, COOH, $C_{1-3}$ alkyl, $C_{1-3}$ heteroalkyl and 4-6 membered heterocycloalkyl, wherein the $C_{1-3}$ alkyl, $C_{1-3}$ heteroalkyl and 4-6 membered heterocycloalkyl are optionally substituted by 1, 2 or 3 R;
$R_c$ is respectively independently selected from H, F, Cl, Br, I, OH, NH$_2$, CH$_3$ and CH$_3$CH$_2$;
alternatively, two $R_c$ connected to the same carbon atom and the C atom to which they are connected together form a 4-6 membered heterocycloalkyl, which is optionally substituted by 1, 2 or 3 R;
$R_d$ and $R_e$ are respectively independently selected from H, F, Cl, Br, I, OH, NH$_2$, CH$_3$ and CH$_3$CH$_2$;
R is selected from F, Cl, Br, I, OH, CN, NH$_2$, CN, COOH, CH$_3$, CH$_3$CH$_2$, CH$_3$CH$_2$CH$_2$, (CH$_3$)$_2$CH, CF$_3$, CHF$_2$, CH$_2$F, CH$_3$O and

wherein the $C_{1-6}$ heteroalkyl, $C_{1-3}$ heteroalkyl, 5-6 membered heteroaryl, 4-6 membered heterocycloalkyl and 5-6 membered heterocycloalkenyl respectively independently contain 1, 2, 3 or 4 heteroatoms or heteroatom groups independently selected from —NH—, —O—, —S—, —C(=O)—, S(=O)—, S(=O)$_2$—, and N;

or a compound having any of the following structures, a tautomer thereof or a pharmaceutically acceptable salt thereof,

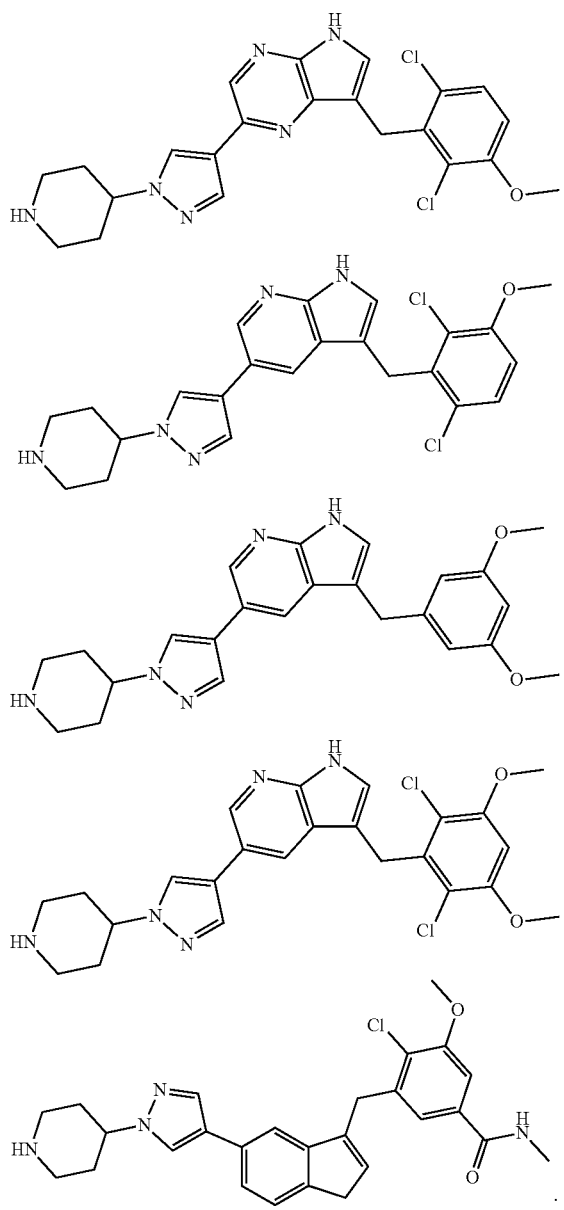 [SMILES: COc1ccc(Cl)c(Cc2c[nH]c3ncc(-c4cnn(C5CCNCC5)c4)nc23)c1Cl ; COc1ccc(Cl)c(Cc2c[nH]c3ncc(-c4cnn(C5CCNCC5)c4)cc23)c1Cl ; COc1cc(Cc2c[nH]c3ncc(-c4cnn(C5CCNCC5)c4)cc23)cc(OC)c1 ; COc1cc(OC)c(Cl)c(Cc2c[nH]c3ncc(-c4cnn(C5CCNCC5)c4)cc23)c1Cl ; CNC(=O)c1cc(CC2=CCc3ccc(-c4cnn(C5CCNCC5)c4)cc32)c(Cl)c(OC)c1]

2. The compound the, tautomer thereof or the pharmaceutically acceptable salt thereof as defined in claim 1, wherein $R_b$ is respectively independently selected from H, F, Cl, Br, I, OH, NH$_2$, CN, COOH, CH$_3$, CH$_3$CH$_2$, CH$_3$CH$_2$CH$_2$, (CH$_3$)$_2$CH, CF$_3$, CHF$_2$, CH$_2$F,

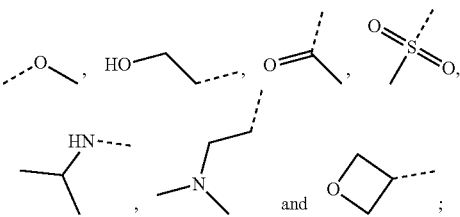

or, the L is selected from a single bond, —CH$_2$—, —CH$_2$CH$_2$.

3. The compound, the tautomer thereof or the pharmaceutically acceptable salt thereof as defined in claim 1, wherein $R_5$ is selected from H, $C_{1-3}$ alkyl, $C_{1-3}$ alkoxy, $C_{1-3}$ alkyl-C(=O)—, $C_{1-3}$ alkyl-S(=O)$_2$—, $C_{1-3}$ alkyl-S(=O)$_2$—$C_{1-3}$ alkyl-, $C_{1-3}$ alkylamino, cyclohexyl, piperidinyl, morpholinyl, tetrahydropyranyl, tetrahydrofuranyl, 1,2,3,6-tetrahydropyridyl, azetidinyl, oxebutanyl, pyrrolidinyl and piperazinyl, wherein $C_{1-3}$ alkyl, $C_{1-3}$ alkoxy, $C_{1-3}$ alkyl-C(=O)—, $C_{1-3}$ alkyl-S(=O)$_2$—, $C_{1-3}$ alkyl-S(=O)$_2$—$C_{1-3}$ alkyl-, $C_{1-3}$ alkylamino, cyclohexyl, piperidinyl, morpholinyl, tetrahydropyranyl, tetrahydrofuranyl, 1,2,3,6-tetrahydropyridyl, azetidinyl, oxebutanyl, pyrrolidinyl and piperazinyl are optionally substituted by 1, 2 or 3 $R_b$.

4. The compound, the tautomer thereof or the pharmaceutically acceptable salt thereof as defined in claim 1, wherein, $R_2$ and $R_3$ are respectively independently

or, $R_5$ is selected from H, CH$_3$, CH$_3$CH$_2$, CH$_3$CH$_2$CH$_2$, (CH$_3$)$_2$CH, C(R$_b$)$_3$, CH(R$_b$)$_2$, CH$_2$(R$_b$),

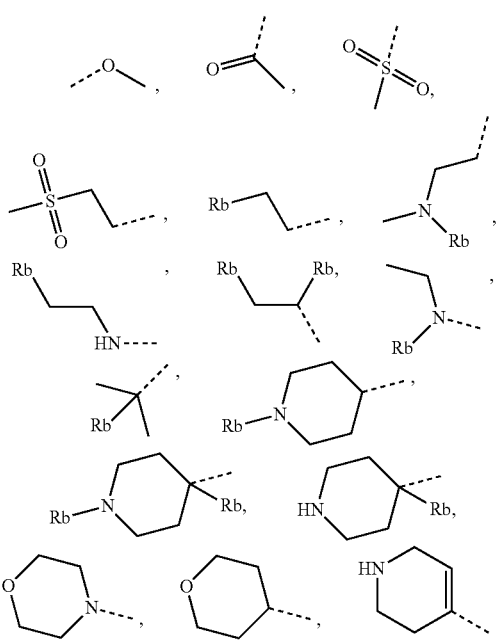

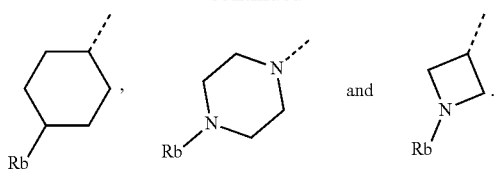

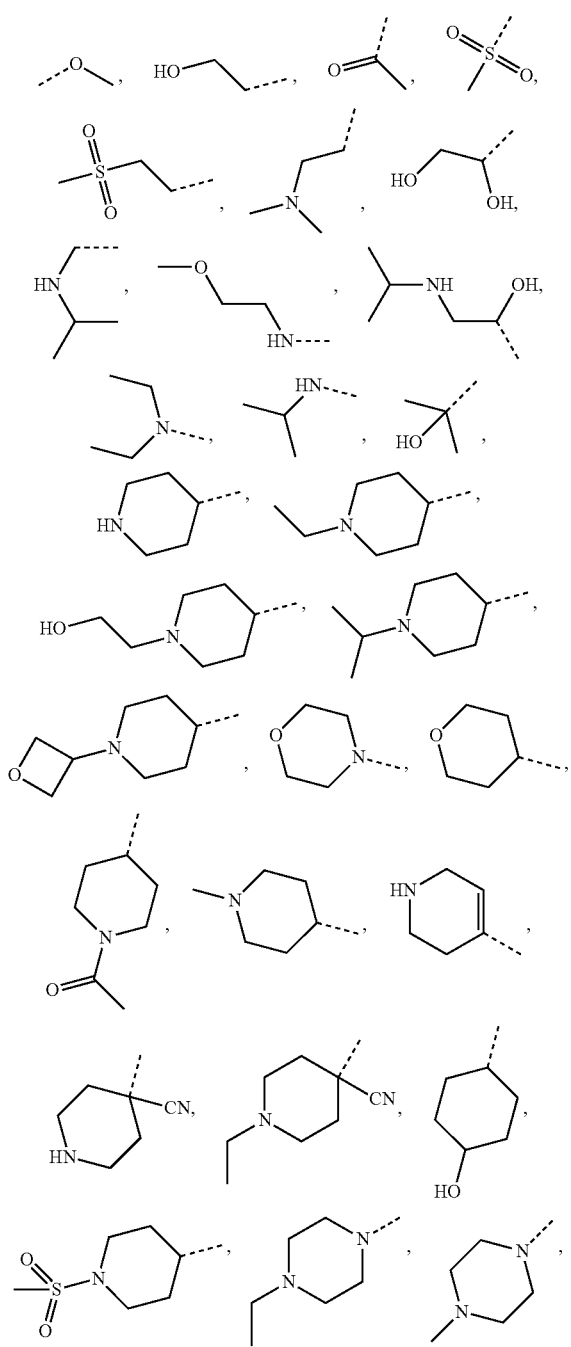

5. The compound, the tautomer thereof or the pharmaceutically acceptable salt thereof as defined in claim 1, wherein $R_5$ is selected from H, $CH_3$, $CH_3CH_2$, $CH_3CH_2CH_2$, $(CH_3)_2CH$, $CF_3$, $CHF_2$, $CH_2F$,

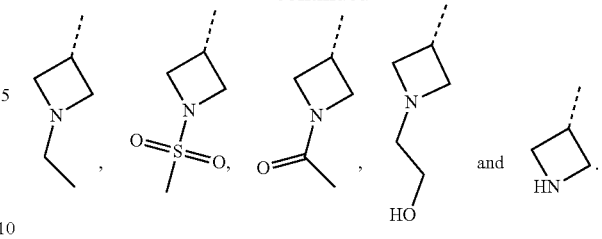

6. The compound, the tautomer thereof or the pharmaceutically acceptable salt thereof as defined in claim 1, wherein the $R_6$ is respectively independently selected from H, F, Cl, Br, I, OH, $NH_2$, CN, COOH, $CH_3$, $CH_2CH_3$, $CH_3CH_2CH_2$, $(CH_3)_2CH$ and

wherein the $CH_3$, $CH_2CH_3$, $CH_3CH_2CH_2$, $(CH_3)_2CH$ and

are optionally substituted by 1, 2 or 3 $R_e$.

7. The compound, the tautomer thereof or the pharmaceutically acceptable salt thereof as defined in claim 6, wherein the $R_6$ is respectively independently selected from H, F, Cl, Br, I, OH, $NH_2$, CN, COOH, $CH_3$, $CH_3CH_2$, $CH_3CH_2CH_2$, $(CH_3)_2CH$, $CF_3$, $CHF_2$, $CH_2F$ and

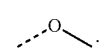

8. The compound, the tautomer thereof or the pharmaceutically acceptable salt thereof as defined in claim 1, wherein the two $R_c$ connected to the same carbon atom are linked together to form piperidinyl optionally substituted by 1, 2 or 3 R.

9. The compound, the tautomer thereof or the pharmaceutically acceptable salt thereof as defined in claim 8, wherein the two $R_c$ connected to the same carbon atom are linked together to form

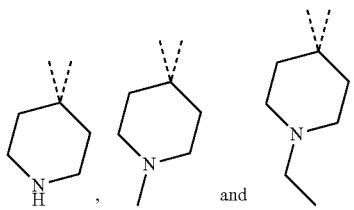

10. The compound, the tautomer thereof or the pharmaceutically acceptable salt thereof as defined in claim 1, wherein the ring B is selected from phenyl, pyrazolyl, imidazolyl, pyridyl and pyrazinyl, wherein the phenyl, pyrazolyl, imidazolyl, pyridyl and pyrazinyl are optionally substituted by $R_6$, and the number of $R_6$ is 1, 2 or 3.

11. The compound, the tautomer thereof or the pharmaceutically acceptable salt thereof as defined in claim 10, wherein the ring B is selected from

12. The compound, the tautomer thereof or the pharmaceutically acceptable salt thereof as defined in claim 1, wherein the ring B is selected from
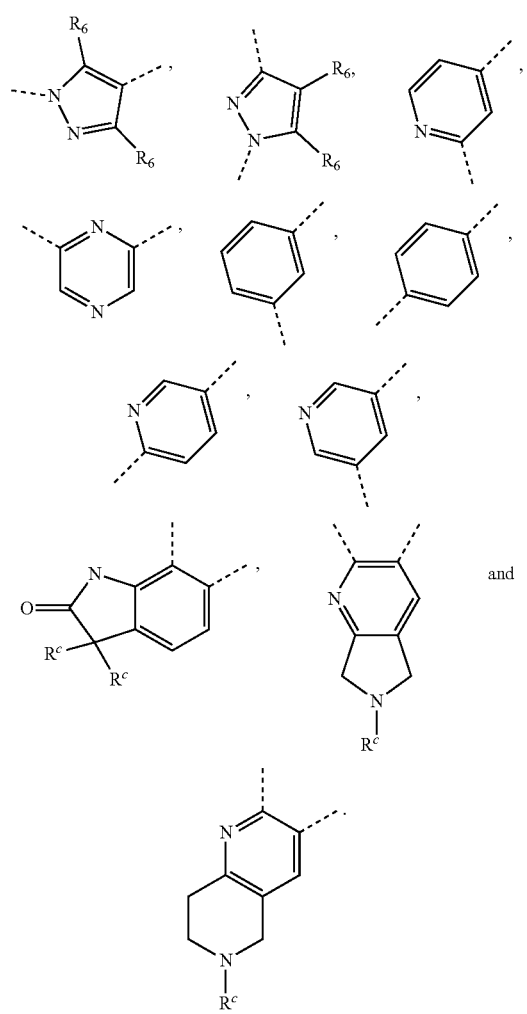
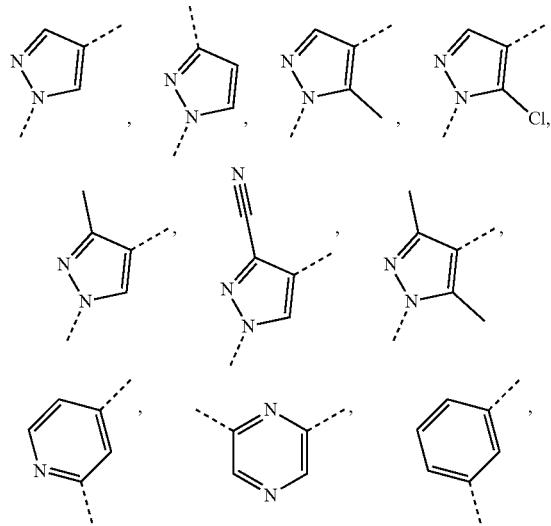
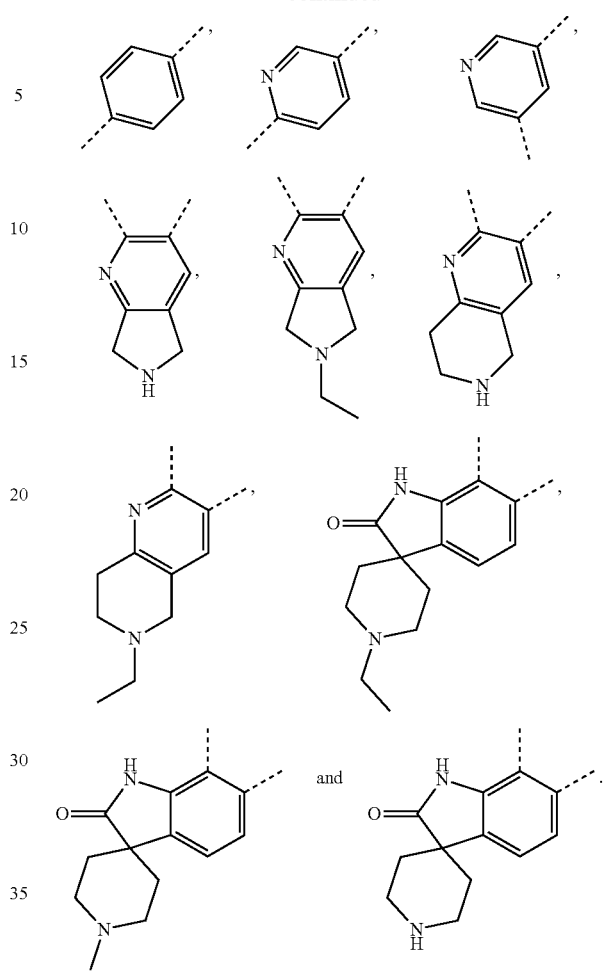
and
13. The compound, the tautomer thereof or the pharmaceutically acceptable salt thereof as defined in claim 1, wherein the moiety
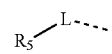
is selected from H, $CH_3$, $CH_3CH_2$, $CH_3CH_2CH_2$, $(CH_3)_2CH$, $CF_3$, $CHF_2$, $CH_2F$,
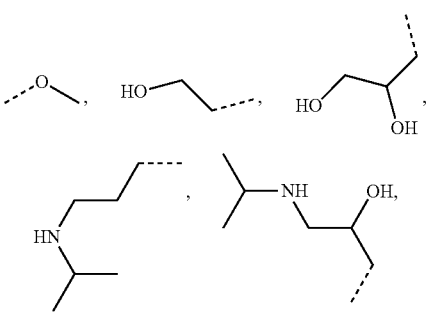

-continued
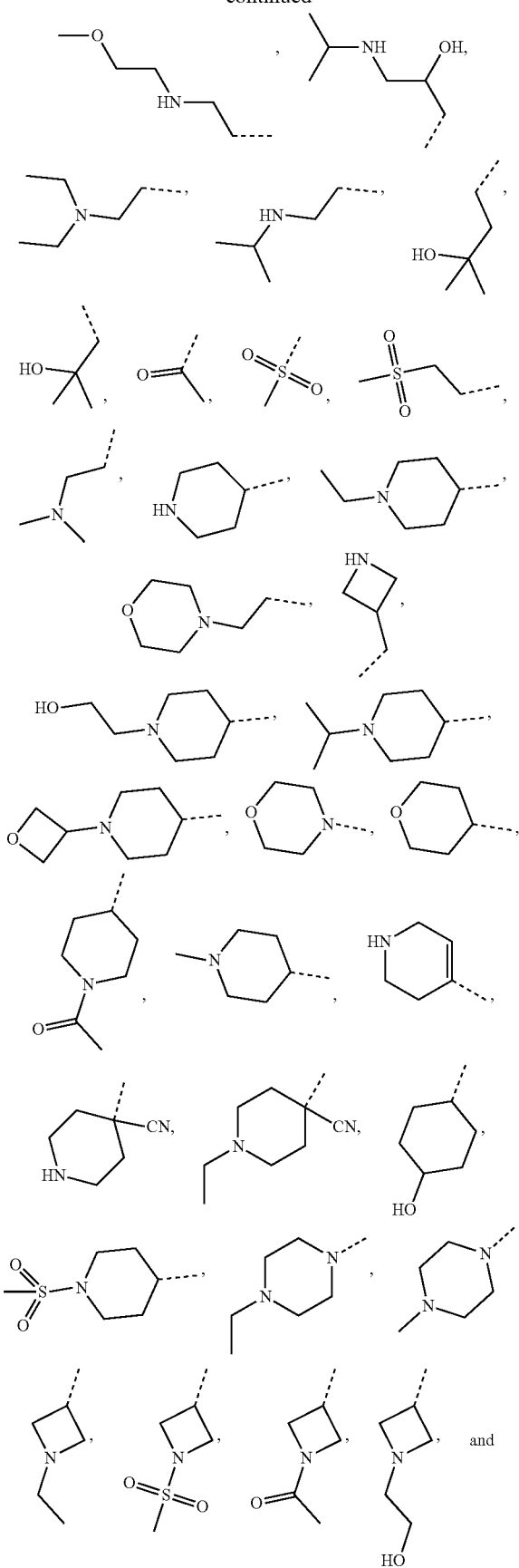
-continued
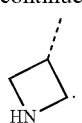
14. The compound, the tautomer thereof or the pharmaceutically acceptable salt thereof as defined in claim 1, wherein the moiety
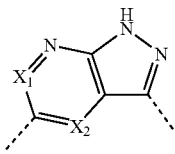
is selected from
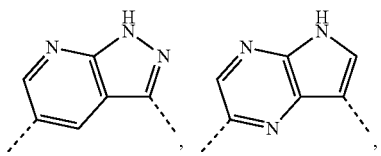
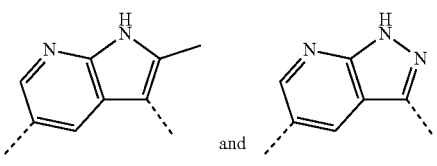
15. The compound, the tautomer thereof or the pharmaceutically acceptable salt thereof as defined in claim 1, which is selected from
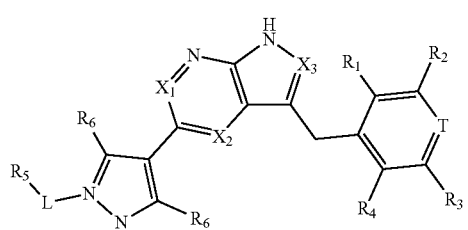
(I-1)
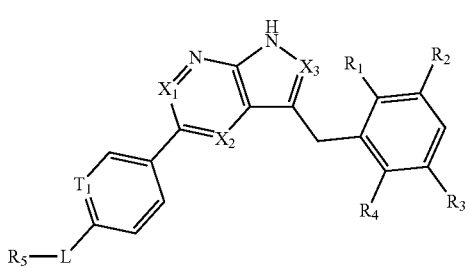
(I-2)

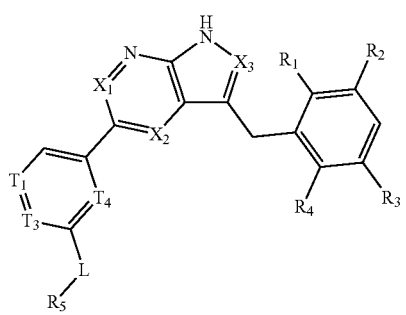
(I-3)
wherein,
$T_1$, $T_2$, $T_3$ and $T_4$ are respectively independently selected from $C(R_6)$ and N;
T, $X_1$, $X_2$, $X_3$, $R_1$, $R_2$, $R_3$, $R_4$, $R_5$, $R_6$ and L are as defined in claim 1.
16. The compound, the tautomer thereof or the pharmaceutically acceptable salt thereof as defined in claim 15, which is selected from
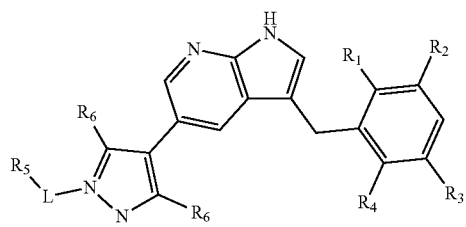
(I-1a)
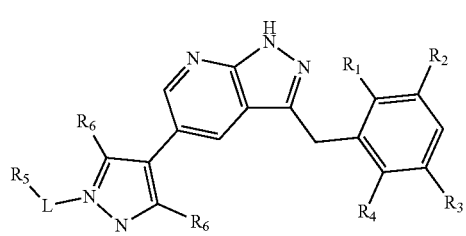
(I-1b)
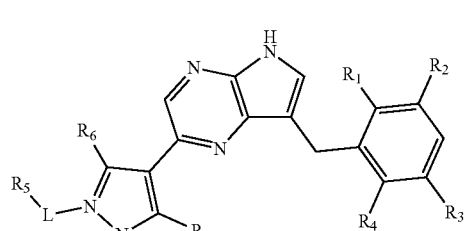
(I-1c)
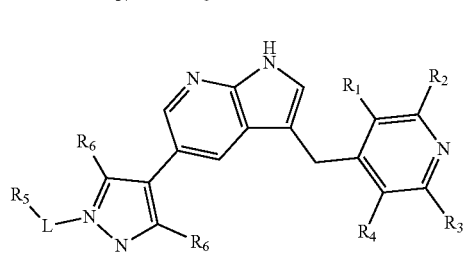
(I-1d)
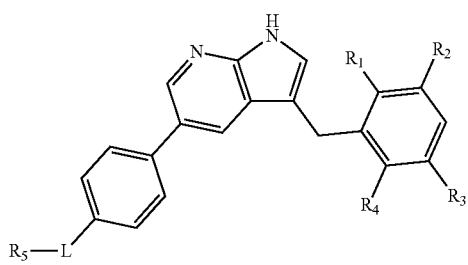
(I-2a)
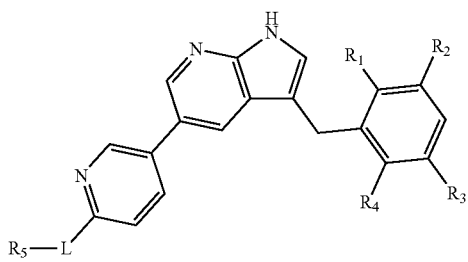
(I-2b)
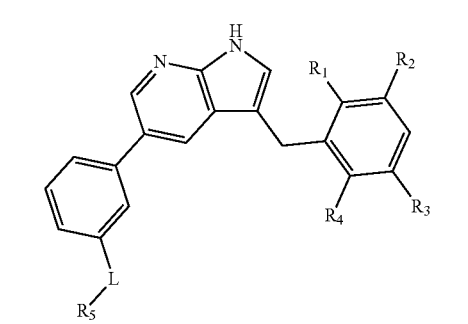
(I-3a)
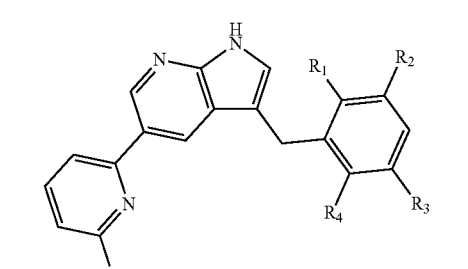
(I-3b)
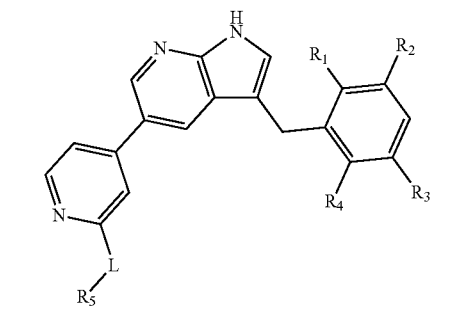
(I-3c)

(I-3d)
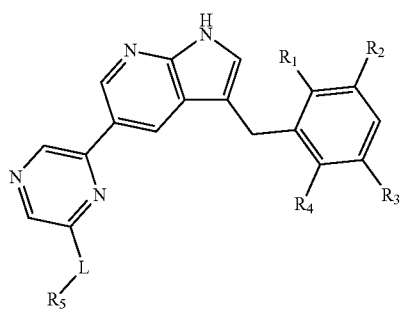
(I-3e)
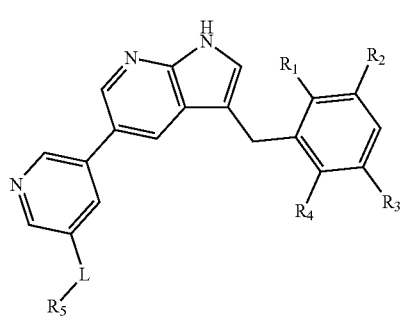
wherein,
R₁, R₂, R₃, R₄, R₅ and L are as defined in claim 15.
17. A compound, tautomer thereof or a pharmaceutically acceptable salt thereof, wherein the compound is selected from
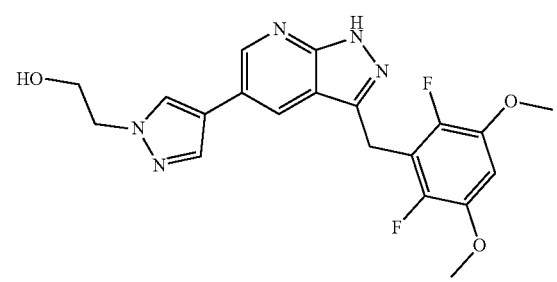
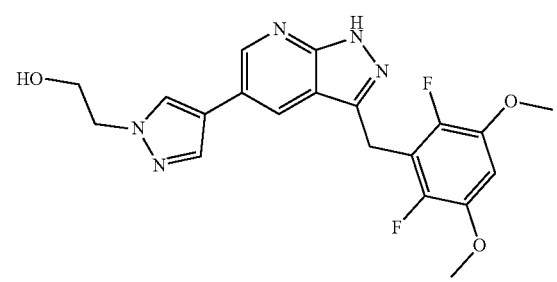
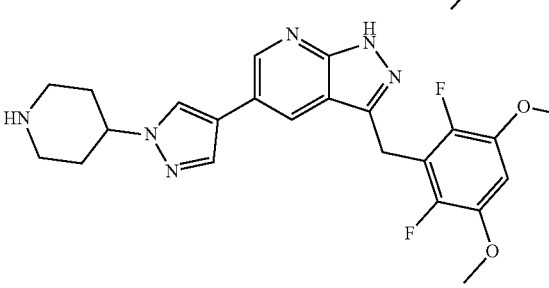
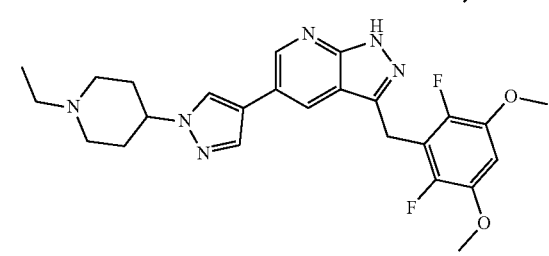
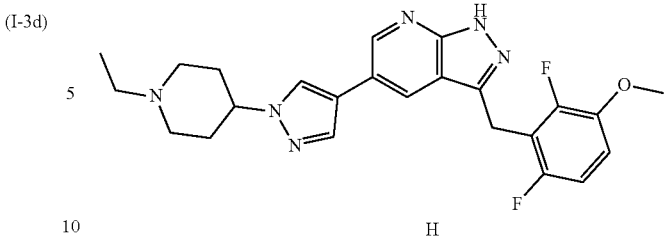
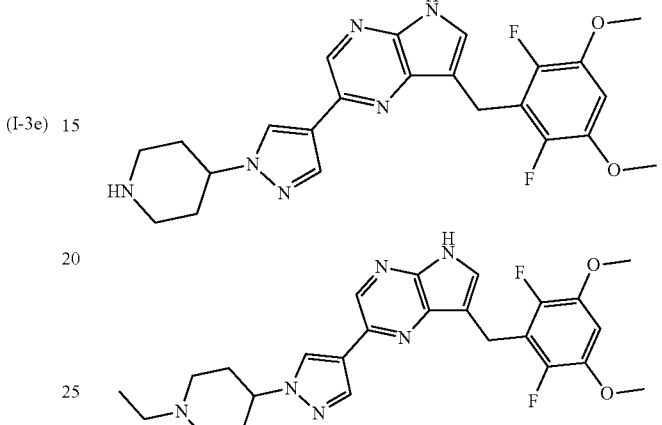
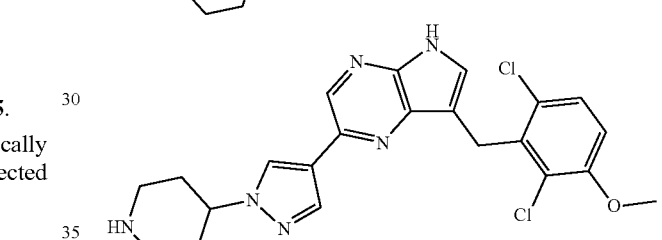
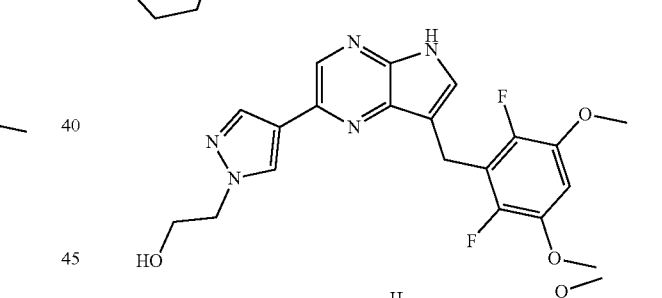
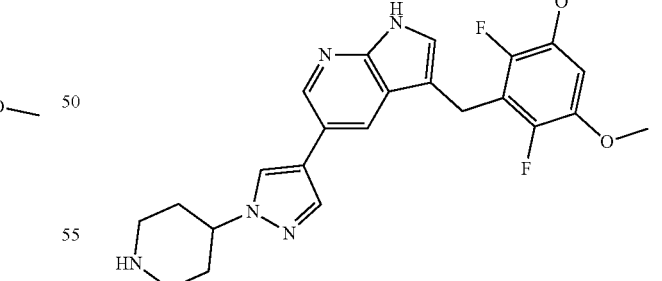
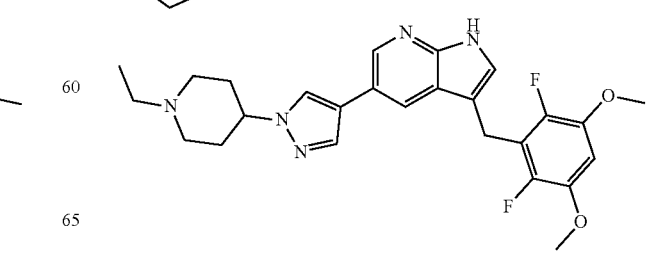
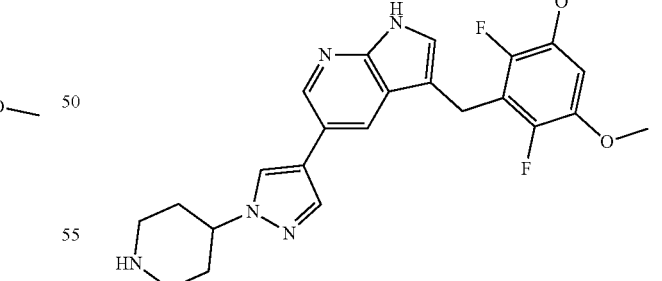
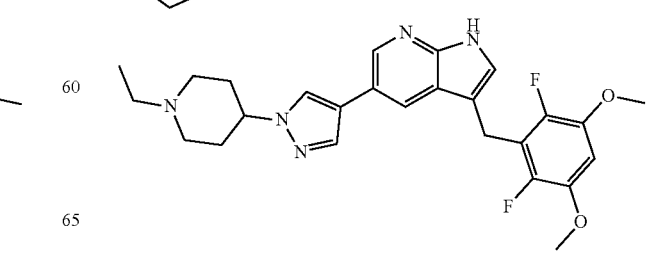
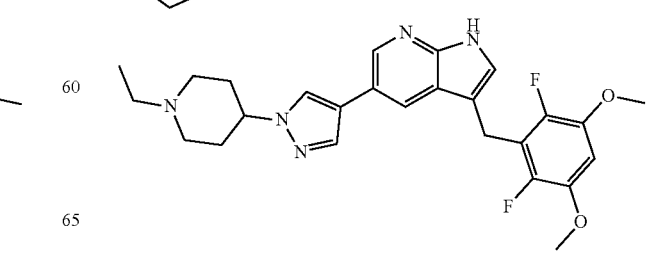

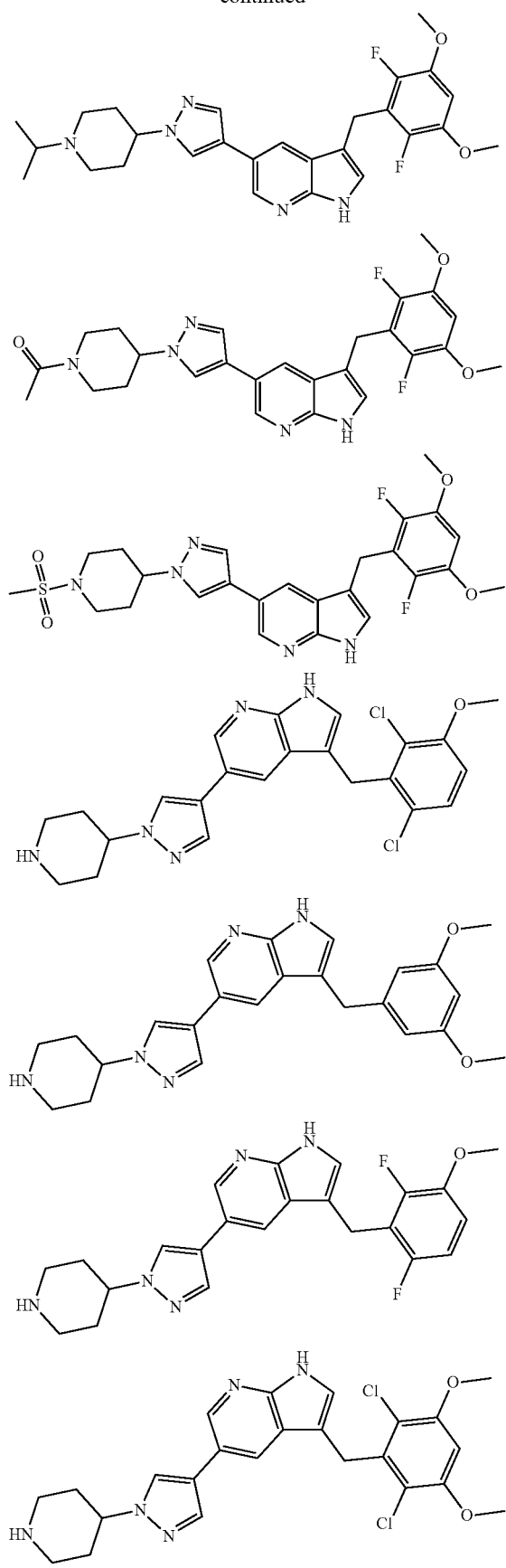
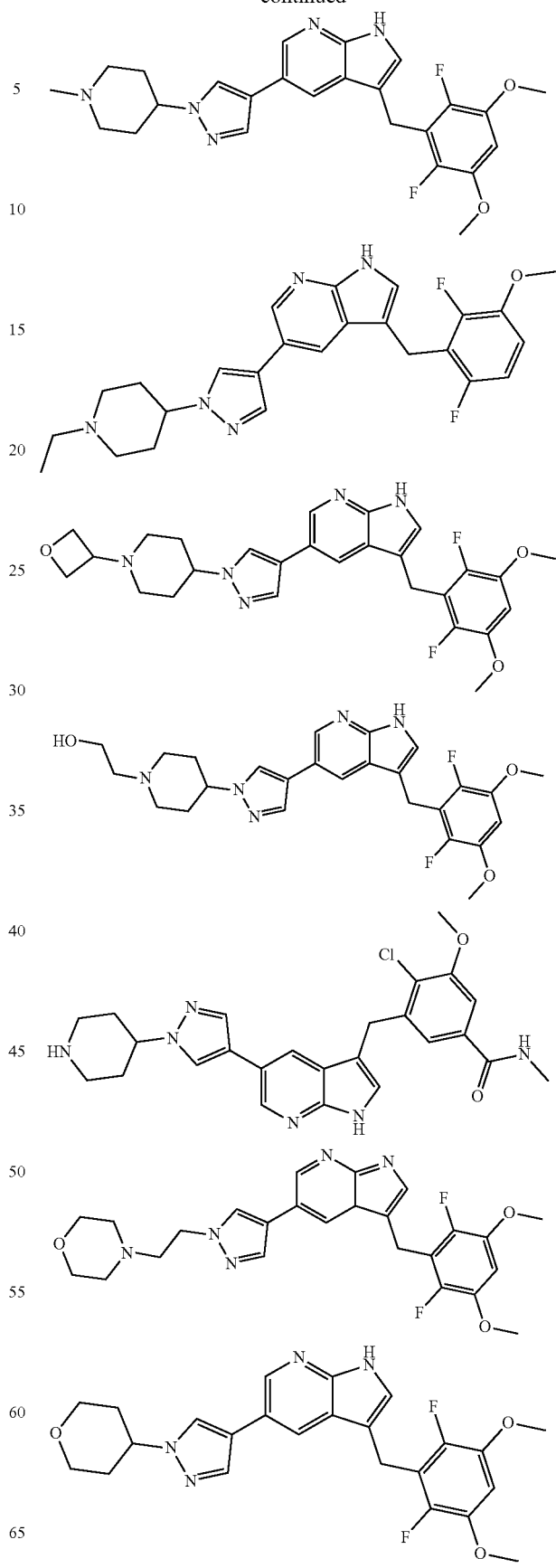

177
-continued
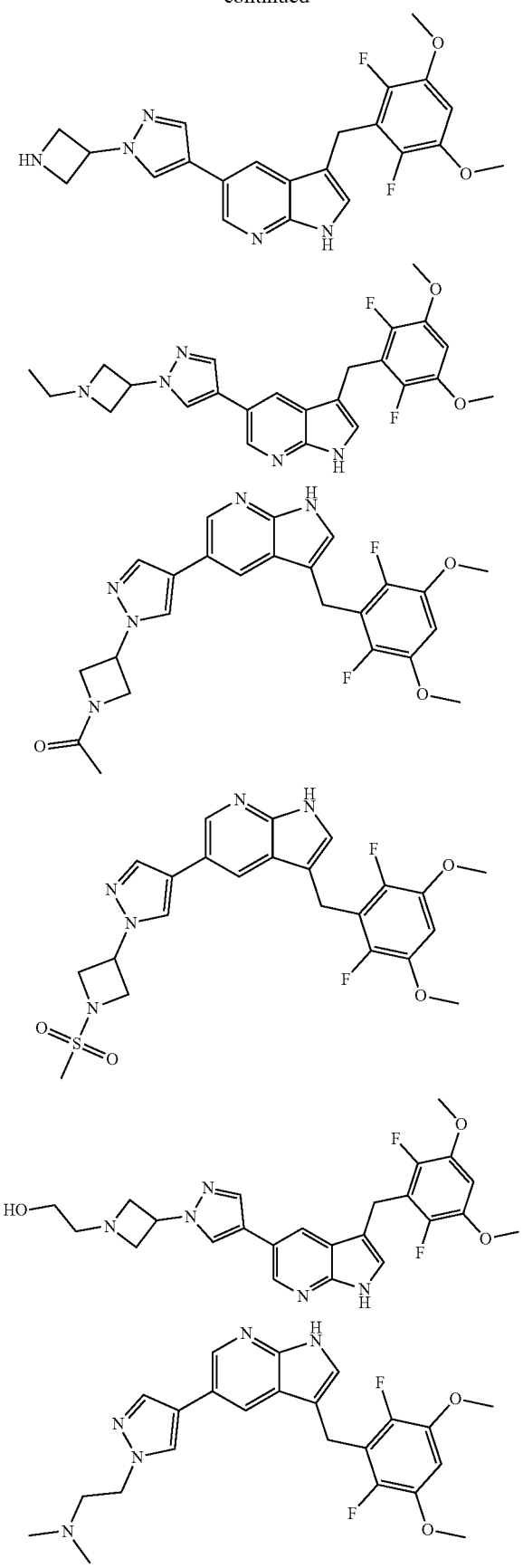
178
-continued
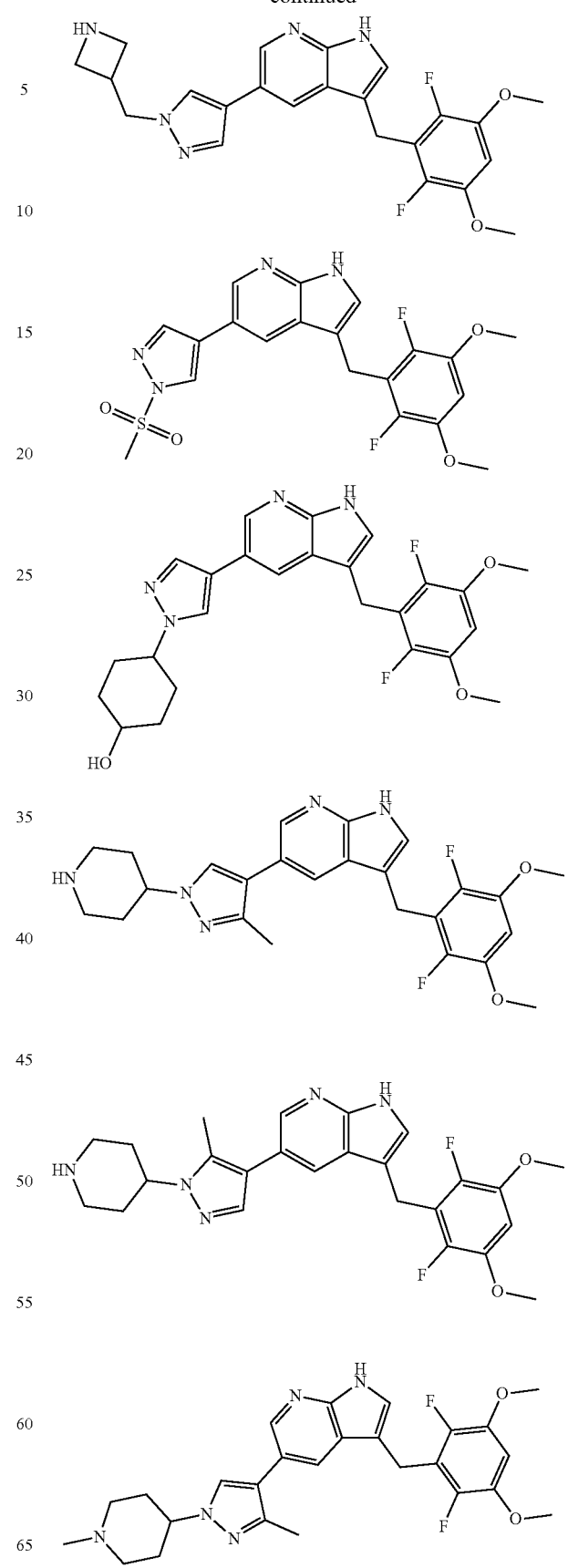

179
-continued
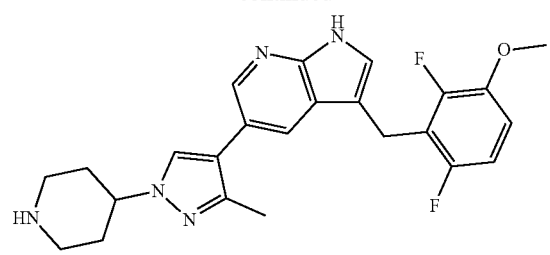
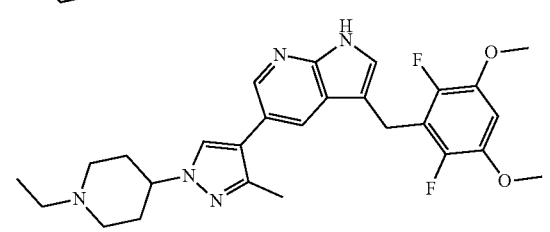
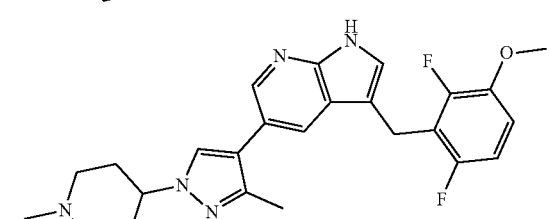
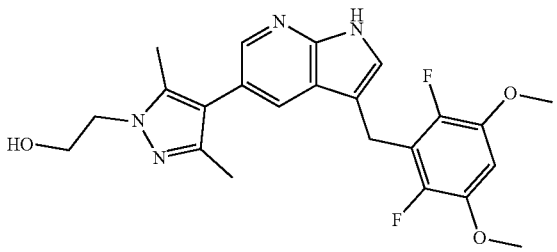
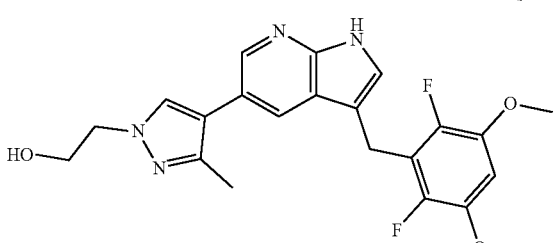
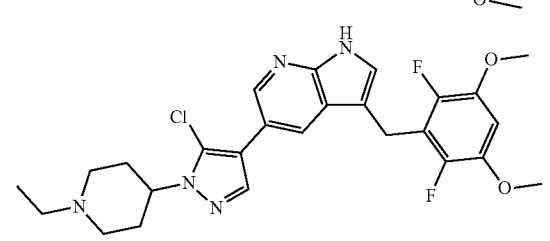
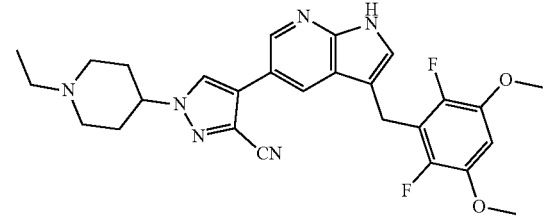
180
-continued
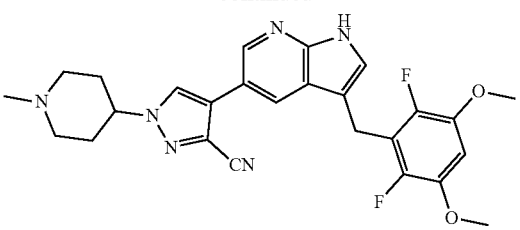
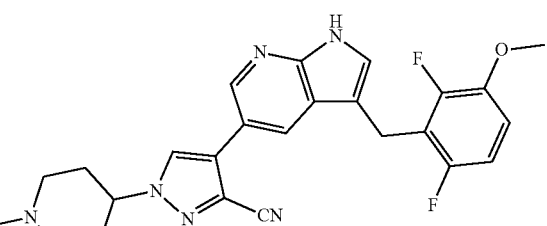
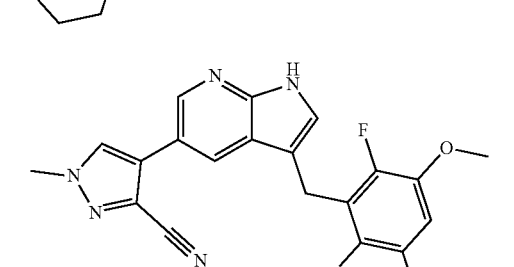
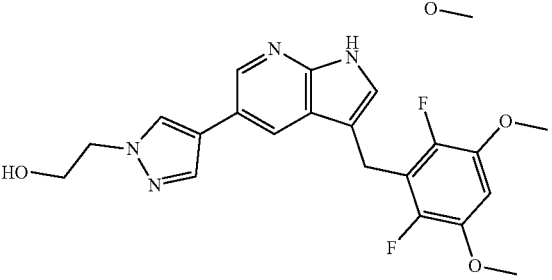
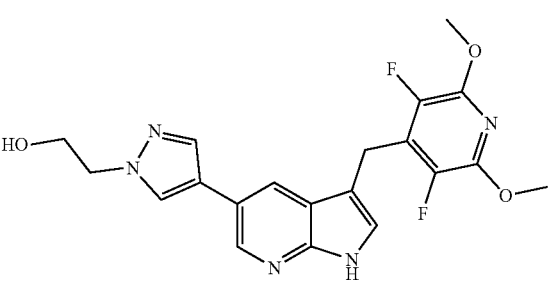
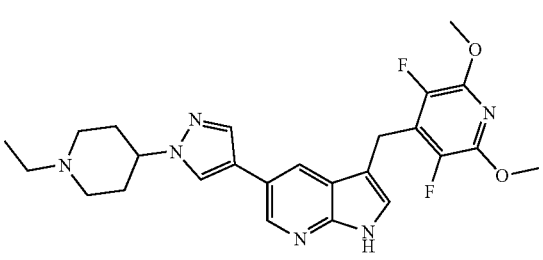

181
-continued
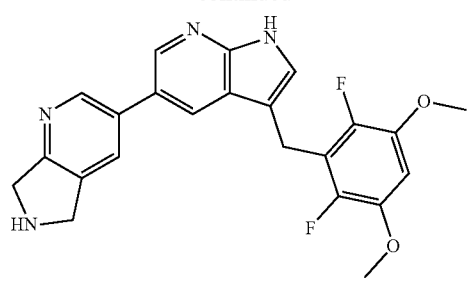
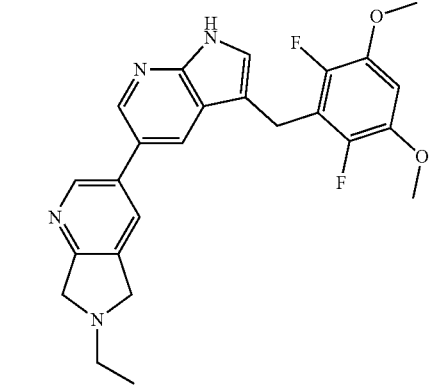
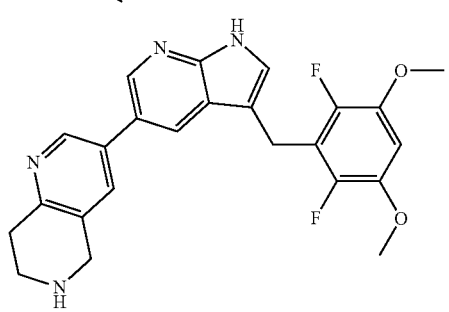
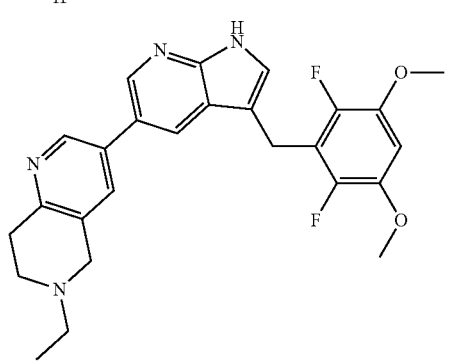
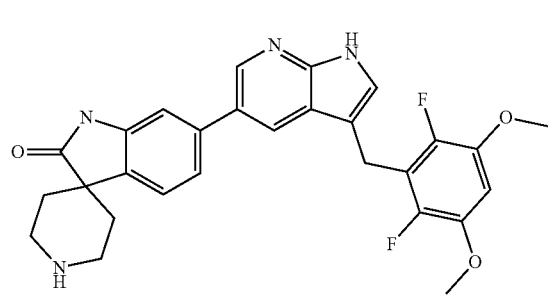
182
-continued
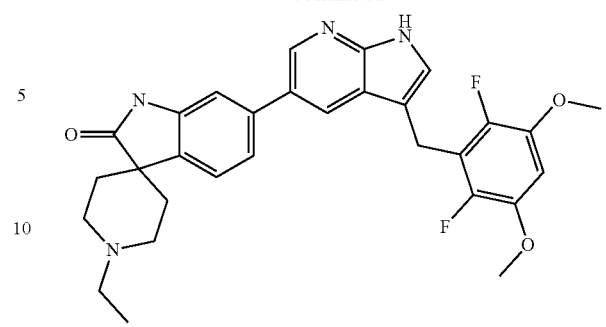
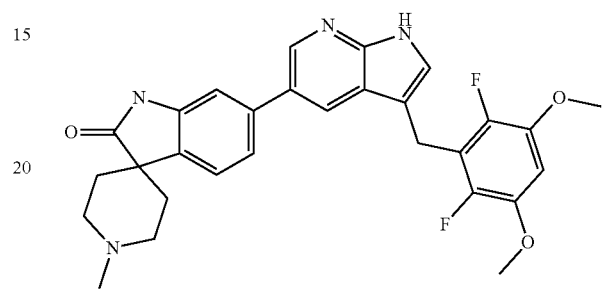
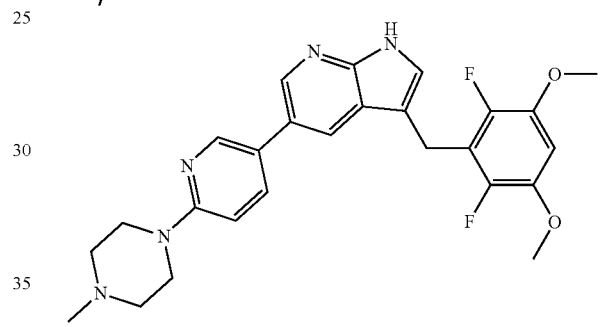
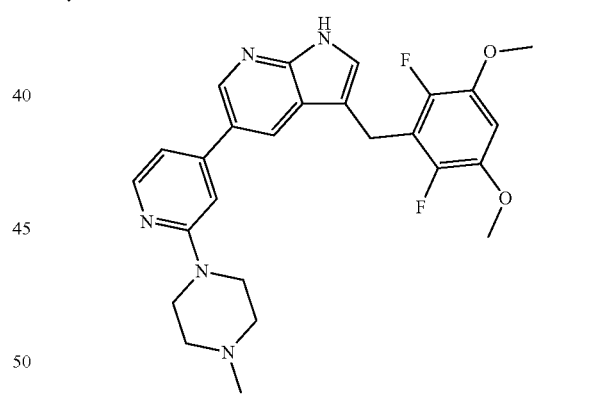
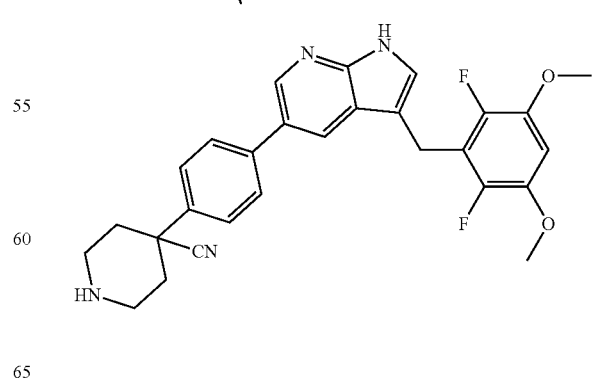

-continued

-continued

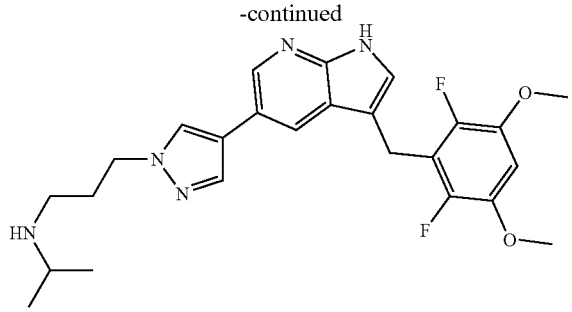

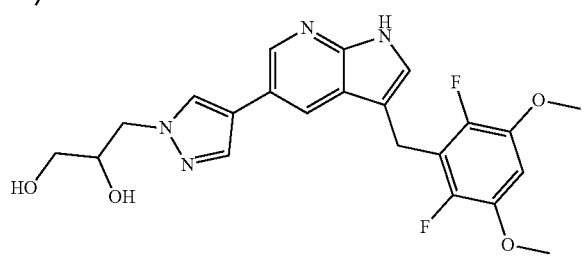

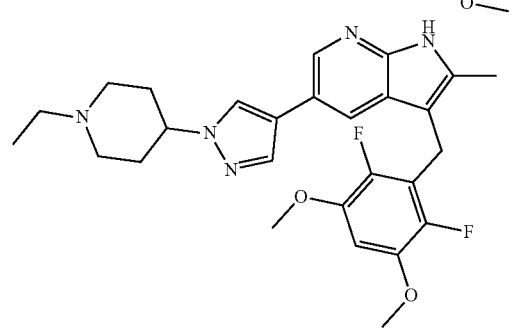

-continued

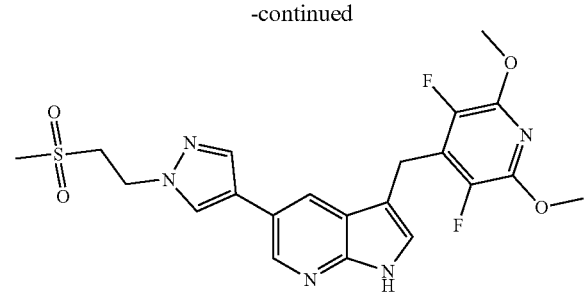

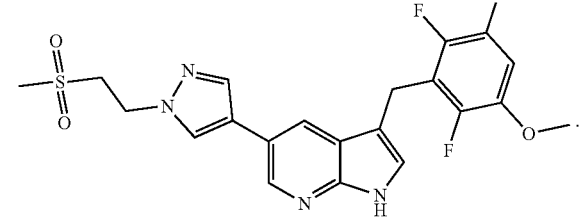

18. A method of treating a disease associated with FGFR and c-Met in a subject, comprising administering the compound, the tautomer thereof or the pharmaceutically acceptable salt thereof as defined in claim 1 to the subject; wherein the disease associated with FGFR and c-Met is non-small cell lung cancer, multiple myeloma, renal cell carcinoma, breast cancer, liver cancer, bile duct epithelial cancer, thyroid cancer, brain cancer, bladder cancer, hemangioma, biliary tract cancer or gastric cancer.

\* \* \* \* \*

UNITED STATES PATENT AND TRADEMARK OFFICE
CERTIFICATE OF CORRECTION

PATENT NO. : 12,312,347 B2  
APPLICATION NO. : 17/261460  
DATED : May 27, 2025  
INVENTOR(S) : Yang Zhang et al.

Page 1 of 2

It is certified that error appears in the above-identified patent and that said Letters Patent is hereby corrected as shown below:

In the Claims

In Claim 1:
At Column 163, Line 60,

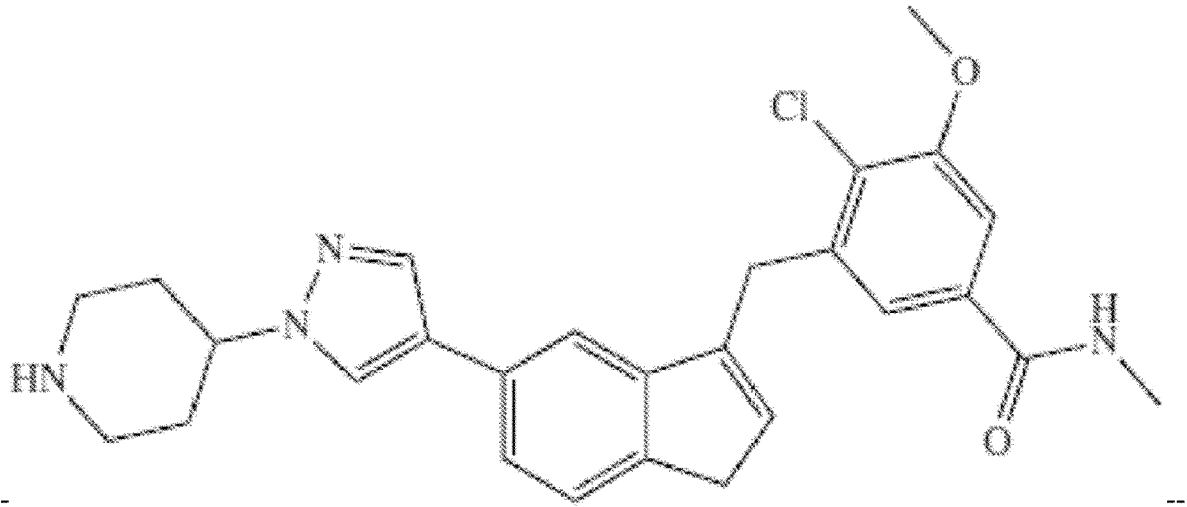

-- -- should be

Signed and Sealed this  
Twenty-first Day of October, 2025

John A. Squires  
*Director of the United States Patent and Trademark Office*

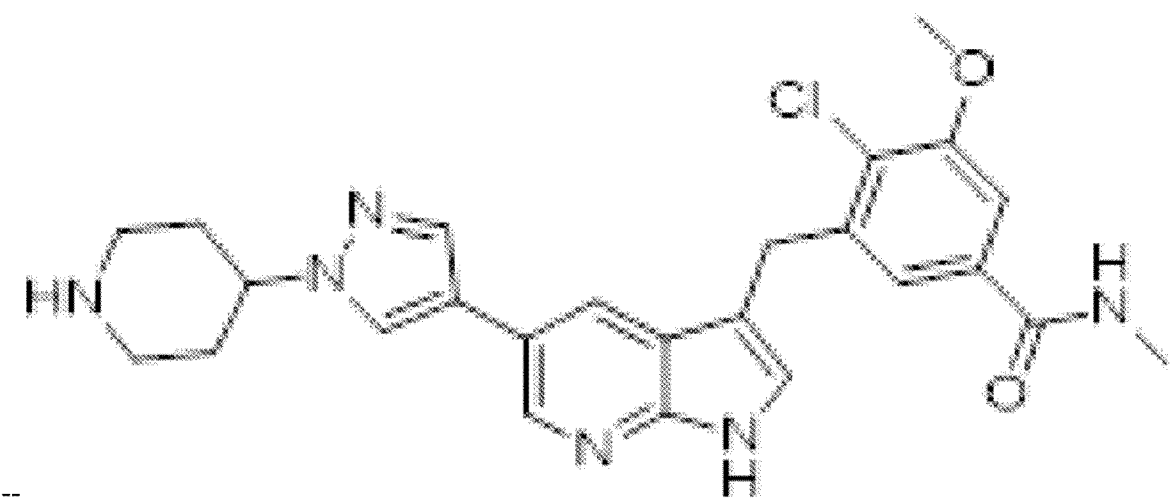
--  --
In Claim 6:
At Column 166, Line 28, "$R_e$." should be --$R_c$.--
In Claim 14:
At Column 170, Line 15, " 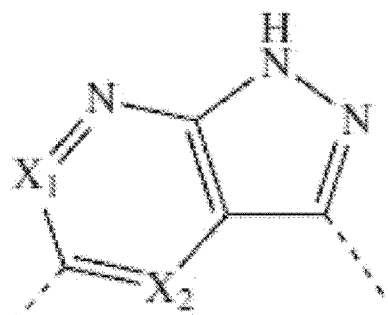 " should be 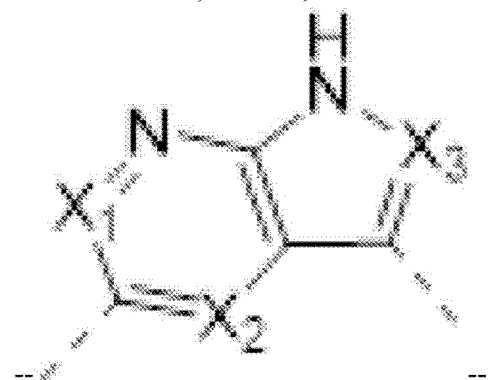
--  --